US008415151B2

(12) United States Patent
Wei et al.

(10) Patent No.: US 8,415,151 B2
(45) Date of Patent: Apr. 9, 2013

(54) CRYSTALLINE RECOMBINANT INTERFERON WITH ALTERED SPATIAL CONFIGURATION, THREE-DIMENSIONAL STRUCTURE AND USES THEREOF

(76) Inventors: Guangwen Wei, Chengdu (CN); Dacheng Wang, Beijing (CN)

(*) Notice: Subject to any disclaimer, the term of this patent is extended or adjusted under 35 U.S.C. 154(b) by 70 days.

(21) Appl. No.: 12/971,956

(22) Filed: Dec. 17, 2010

(65) Prior Publication Data

US 2011/0158941 A1 Jun. 30, 2011

Related U.S. Application Data

(60) Provisional application No. 61/289,494, filed on Dec. 23, 2009.

(30) Foreign Application Priority Data

Dec. 18, 2009 (CN) .......................... 2009 1 0259339

(51) Int. Cl.
*C07K 14/555* (2006.01)

(52) U.S. Cl.
USPC ........................................................ 435/351

(58) Field of Classification Search ................... None
See application file for complete search history.

(56) References Cited

U.S. PATENT DOCUMENTS

| 4,695,623 A | 9/1987 | Stabinsky |
| 4,897,471 A | 1/1990 | Stabinsky |
| 5,372,808 A | 12/1994 | Blatt et al. |
| 6,297,021 B1 | 10/2001 | Nienaber et al. |
| 7,364,724 B2 | 4/2008 | Wei et al. |
| 7,585,647 B2 * | 9/2009 | Wei ............................ 435/69.51 |

FOREIGN PATENT DOCUMENTS

| CN | 1311035 A | 9/2001 |
| CN | 1740197 A | 3/2006 |
| EP | 1371373 A1 | 12/2003 |
| WO | WO 2011/072487 | 6/2011 |

OTHER PUBLICATIONS

Wiencek, J. M. Ann. Rev. Biomed. Eng. 1999, 1, 505-534.*
International Search Report, Mar. 24, 2011,Sichuan Huiyang Life Science & Technology Corp. , PCT Application No. PCT/CN2010/002055,Filed Dec. 16, 2010.
Written Opinion of the International Searching Authority, Mar. 24, 2011, Sichuan Huiyang Life Science & Technology Corp., PCT Application No. PCT/CN2010/002055,Filed Dec. 16, 2010.
International Preliminary Report on Patentability, Feb. 13, 2012, Sichuan Huiyang Life Science & Technology Corp., PCT Application No. PCT/CN2010/002055,Filed Dec. 16, 2010.
Korn, AP et al., Journal of Interferon Research 1994, 14: 1-9.
Klein ML, et al., Structural characterization of recombinant consensus interferon-alpha. Journal of Chromatography, 1988; 454: 205-215.

* cited by examiner

*Primary Examiner* — Nashaat Nashed
(74) *Attorney, Agent, or Firm* — Law Offices of Albert Wai-Kit Chan, PLLC

(57) ABSTRACT

This invention provides a crystalline recombinant interferon (rSIFN-co (SEQ ID NO: 1)) having (i) the same amino acid sequence as that of human consensus interferon, and (ii) altered three-dimensional structure as compared to IFN-$\alpha$2b. The interferon of the present invention exhibits enhanced biological activities. The present invention also provides a structure model of said interferon useful for drug screening and/or drug design and the mimetic of said interferon.

6 Claims, 16 Drawing Sheets

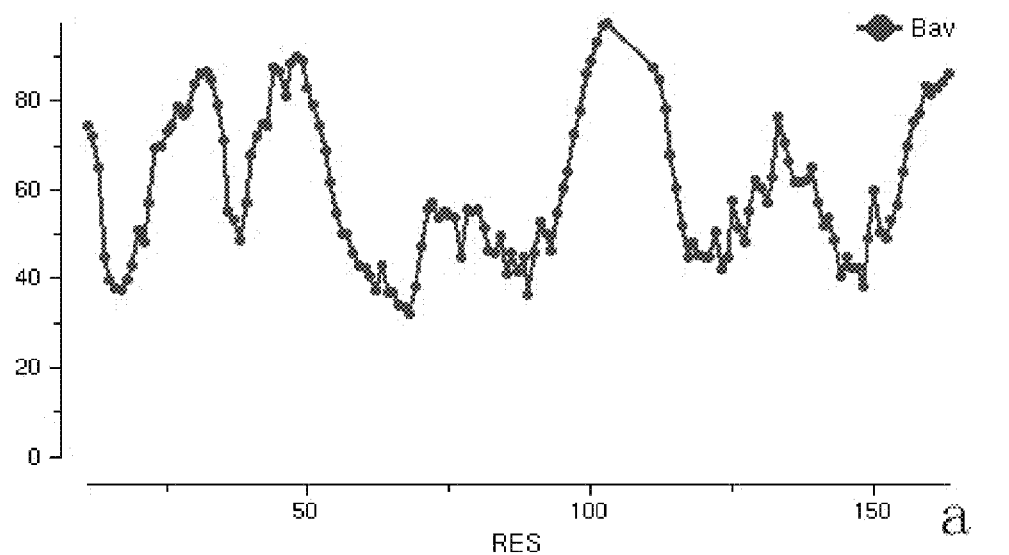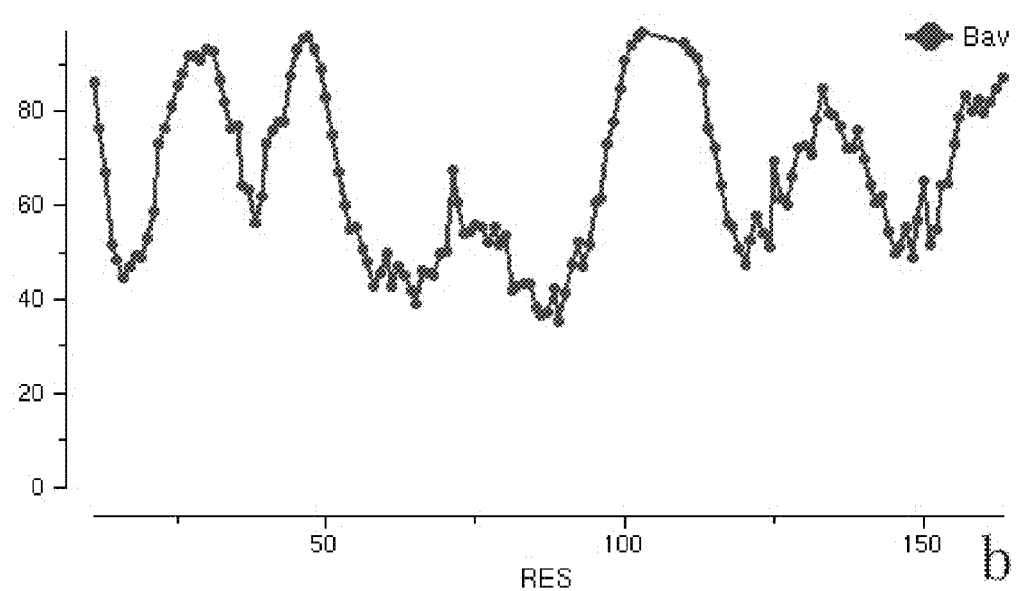
Figure 4

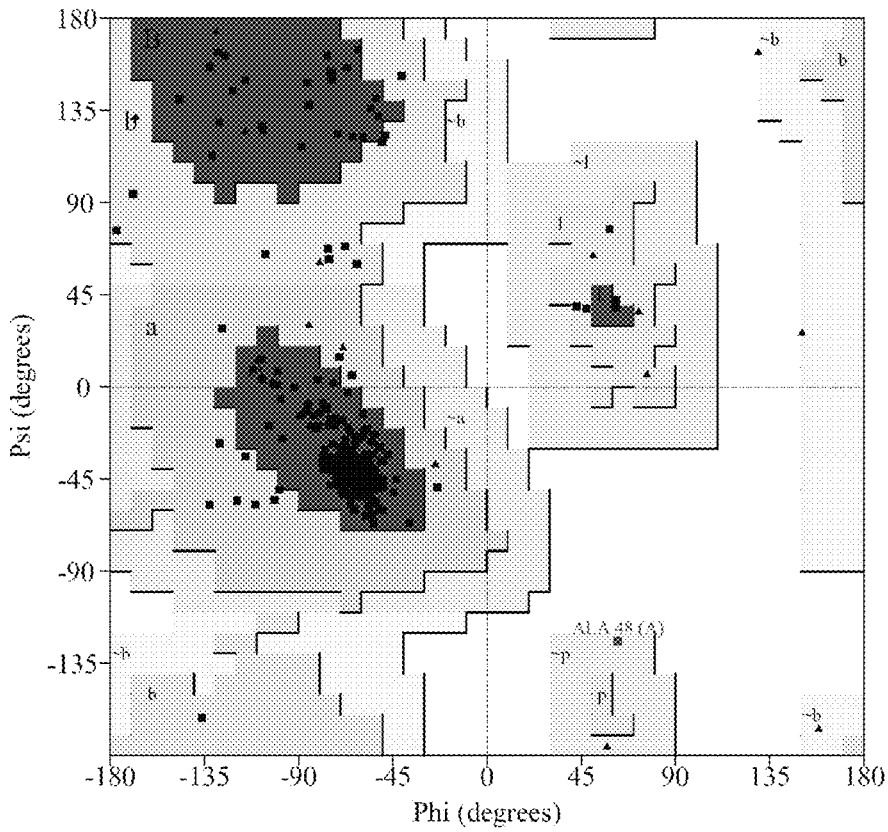

PROCHECK

Ramachandran Plot
rSIFN-co

Plot statistics

| | | |
|---|---|---|
| Residues in most favoured regions [A, B, L] | 240 | 90.6% |
| Residues in additional allowed regions [a, b, l, p] | 24 | 9.1% |
| Residues in generously allowed regions [~a, ~b, ~l, ~p] | 1 | 0.4% |
| Residues in disallowed regions | 0 | 0.0% |
| Number of non-glycine and non-proline residues | 265 | 100.0% |
| Number of end-residues (excl. Gly and Pro) | 127 | |
| Number of glycine residues | 18 | |
| Number of proline residues | 6 | |
| Total number of residues | 416 | |

Based on an analysis of 118 structures of resolution of at least 2.0 Angstroms and R-factor no greater than 20%, a good quality model would be expected to have over 90% in the most favoured regions.

CRYSTALLINE RECOMBINANT INTERFERON WITH ALTERED SPATIAL CONFIGURATION, THREE-DIMENSIONAL STRUCTURE AND USES THEREOF

CROSS-REFERENCE TO RELATED APPLICATIONS

This application claims the priority of U.S. Ser. No. 61/289,494, filed Dec. 23, 2009. This application also claims priority of Chinese Application No. 200910259339.2, filed Dec. 18, 2009. The entire contents and disclosures of the preceding applications are incorporated by reference into this application.

FIELD OF THE INVENTION

This invention relates in general to the crystal of recombinant interferon with altered spatial configuration, crystallization method and three-dimensional structure thereof, which also relates to uses of said crystal and three-dimensional structure, and mimetics of said recombinant interferon.

BACKGROUND OF THE INVENTION

Interferon (IFN) is a kind of soluble protein produced by a variety of cells, which has many important biological functions, including anti-viral, anti-tumor, and immunoregulatory functions. Interferons can be divided into type I, type II, and type III interferons according to the types of producing cells, receptors and biological activities etc. Type I IFNs, which are mostly induced by viruses and synthetic double-stranded RNA, are also known as anti-viral interferons. There are three forms of type I interferons: IFN$\alpha$, INF$\beta$, IFN$\omega$. Type II IFN, also known as immune interferon or IFN$\gamma$, is produced by T cells, and is an important immunoregulatory factor in vivo. Type III interferon is made up of IFN-$\lambda$ molecules.

In recent years, companies throughout the world have engaged in interferon research, as exemplified by a number of pertinent patents and disclosure documents. For example, U.S. Pat. Nos. 4,695,623 and 4,897,471 disclosed new types of human interferon polypeptides, the amino acid sequence of which contains the common or predominant amino acids found in naturally occurring $\alpha$-interferon polypeptides. That new type of interferon was named IFN-con (consensus interferon $\alpha$). The disclosed amino acid sequences were named IFN-con1, IFN-con2 and IFN-con3. Genes encoding consensus interferon sequences, i.e. 'IFN-cons,' as well as means of gene expression in *Escherichia coli* were also disclosed. Compared with leukocyte interferon or other type I interferons, studies have shown that recombinant IFN-con has higher anti-viral, anti-proliferative and natural killer cell activity in vitro.

U.S. Pat. No. 5,372,808 disclosed using human IFN-con in the treatment of disease. Compared with previous clinically approved $\alpha$-interferon such as INTRONA® (IFN-$\alpha$2b, SGP), recombinant human IFN-con has been shown to have lower side-effects. By the end of 1997, the FDA had approved the use of human IFN-con, which was produced by Amgen and sold under the brand name INFERGEN® (interferon alfacon-1) (SEQ ID NO: 1), for clinical treatment of hepatitis C.

U.S. Pat. No. 7,364,724 disclosed a novel recombinant interferon (hereafter referred to as "rSIFN-co" (SEQ ID NO: 1)) that has enhanced efficacy, fewer side-effects and can be used in high doses. The recombinant interferon disclosed in the '724 patent has the same amino acid sequence as INFERGEN® (SEQ ID NO: 1), but has different spatial structure and biological efficacy. It is of interest to determine the three-dimensional structure of the recombinant interferon with altered structure and functions, establish its model, and take advantage of these structures and models to conduct drug design and to improve the efficacy of known interferons.

SUMMARY OF THE INVENTION

This invention relates to the crystal of a novel recombinant interferon having the amino acid sequence of SEQ ID NO: 1. Further, this invention provides the crystallization method of this recombinant interferon and the composition comprising said crystal. In addition, this invention provides three-dimensional structure of this recombinant interferon, which is different from the three-dimensional structure of IFN-$\alpha$2b published in the art and the three-dimensional structure of INFERGEN® (SEQ ID NO: 1) based on computational model structure. Also provided are uses of said three-dimensional structure for identifying candidate compounds interacting with said interferon, designing mimetics of said interferon and performing rational drug design based on computer modeling.

BRIEF DESCRIPTION OF THE DRAWINGS

FIG. 4 shows a scatter diagram of the average temperature factors for all the atoms of rSIFN-co (SEQ ID NO: 1). (A) A chain; (B) B chain.

FIG. 5 shows ($\Phi$, $\Psi$) value distribution on the Ramachandran Diagram of all the amino acid residues in the molecular structure of rSIFN-co (SEQ ID NO: 1).

FIG. 10 shows sequence alignment between the secondary structure of rSIFN-co (SEQ ID NO: 1) and its amino acid sequence; the light colored boxes represent residues that were not set up in the structure; the dark colored boxes represent residues which were set up as Ala or Gly. The solid lines represent two pairs of disulfide linkages and the subscripts represent one disulfide linkage that has been constructed in the structure.

FIG. 11 shows sequence alignment of rSIFN-co (SEQ ID NO: 1) protein and homologous IFN polypeptides.

DETAILED DESCRIPTION OF THE INVENTION

Recombinant Interferon (rSIFN-co (SEQ ID NO: 1))

In one embodiment, the amino acid sequence of the present recombinant interferon, as well as the nucleotide sequence encoding the same, are shown below:

```
     M   C   D   L   P   Q   T   H   S   L   G   N   R   R   A   L   I   L   L   A
   1 ATGTGCGACC TGCCGCAGAC CCACTCCCTG GGTAACCGTC GTGCTCTGAT CCTGCTGGCT
     TACACGCTGG ACGGCGTCTG GGTGAGGGAC CCATTGGCAG CACGAGACTA GGACGACCGA

Q   M   R   R   I   S   P   F   S   C   L   K   D   R   H   D   F   G   F   P
  61 CAGATGCGTC GTATCTCCCC GTTCTCCTGC CTGAAAGACC GTCACGACTT CGGTTTCCCG
     GTCTACGCAG CATAGAGGGG CAAGAGGACG GACTTTCTGG CAGTGCTGAA GCCAAAGGGC

Q   E   E   F   D   G   N   Q   F   Q   K   A   Q   A   I   S   V   L   H   E
 121 CAGGAAGAAT TCGACGGTAA CCAGTTCCAG AAAGCTCAGG CTATCTCCGT TCTGCACGAA
     GTCCTTCTTA AGCTGCCATT GGTCAAGGTC TTTCGAGTCC GATAGAGGCA AGACGTGCTT

M   I   Q   Q   T   F   N   L   F   S   T   K   D   S   S   A   A   W   D   E
 181 ATGATCCAGC AGACCTTCAA CCTGTTCTCC ACCAAAGACT CCTCCGCTGC TTGGGACGAA
     TACTAGGTCG TCTGGAAGTT GGACAAGAGG TGGTTTCTGA GGAGGCGACG AACCCTGCTT

S   L   L   E   K   F   Y   T   E   L   Y   Q   Q   L   N   D   L   E   A   C
 241 TCCCTGCTGG AAAAATTCTA CACCGAACTG TACCAGCAGC TGAACGACCT GGAAGCTTGC
     AGGGACGACC TTTTTAAGAT GTGGCTTGAC ATGGTCGTCG ACTTGCTGGA CCTTCGAACG

V   I   Q   E   V   G   V   E   E   T   P   L   M   N   V   D   S   I   L   A
 301 GTTATCCAGG AAGTTGGTGT TGAAGAAACC CCGCTGATGA ACGTTGACTC CATCCTGGCT
     CAATAGGTCC TTCAACCACA ACTTCTTTGG GGCGACTACT TGCAACTGAG GTAGGACCGA

V   K   K   Y   F   Q   R   I   T   L   Y   L   T   E   K   K   Y   S   P   C
 361 GTTAAAAAAT ACTTCCAGCG TATCACCCTG TACCTGACCG AAAAAAAATA CTCCCCGTGC
     CAATTTTTTA TGAAGGTCGC ATAGTGGGAC ATGGACTGGC TTTTTTTTAT GAGGGGCACG

A   W   E   V   V   R   A   E   I   M   R   S   F   S   L   S   T   N   L   Q
 421 GCTTGGGAAG TTGTTCGTGC TGAAATCATG CGTTCCTTCT CCCTGTCCAC CAACCTGCAG
     CGAACCCTTC AACAAGCACG ACTTTAGTAC GCAAGGAAGA GGGACAGGTG GTTGGACGTC

E   R   L   R   R   K   E
 481 GAACGTCTGC GTCGTAAAGA ATAA          (SEQ ID NO: 1)
     CTTGCAGACG CAGCATTTCT TATT          (SEQ ID NO: 2)
                                         (SEQ ID NO: 3)
```

Figure 12:
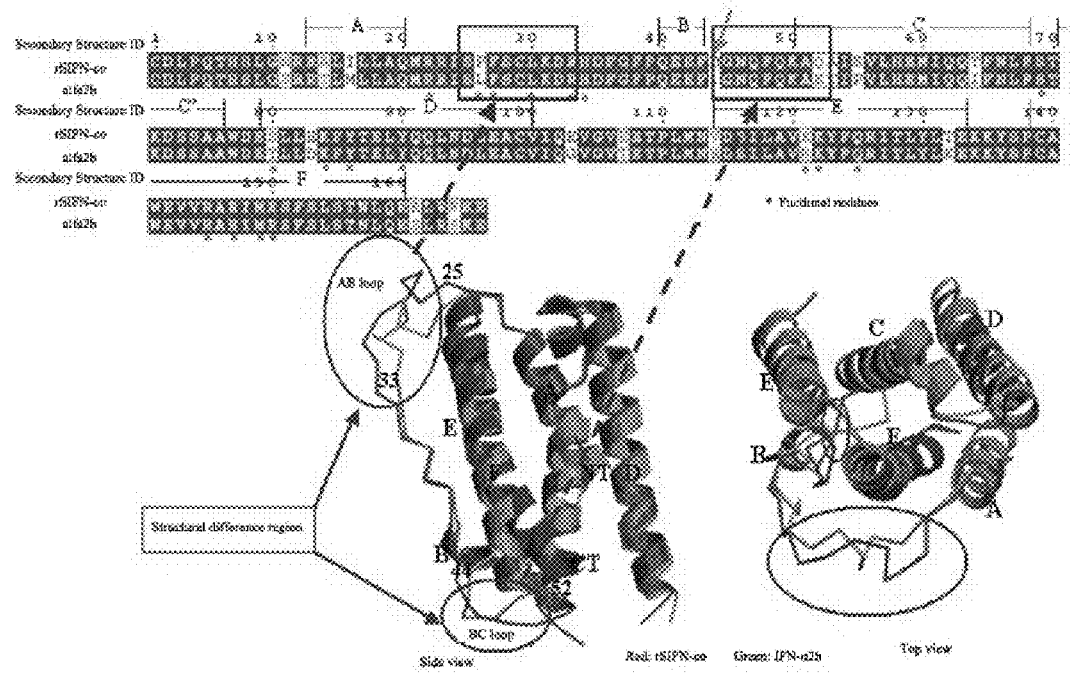
FIG. 12 shows a comparative diagram of rSIFN-co (SEQ ID NO: 1) and IFN-$\alpha$2b in three-dimensional structure.
Figure 14:
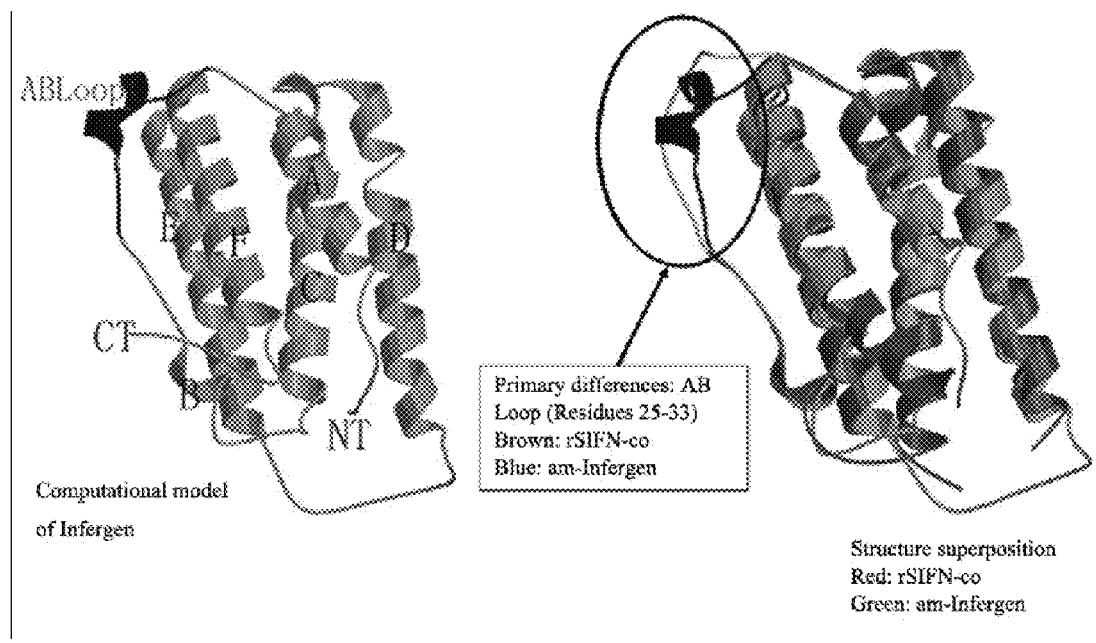
FIG. 14 shows the comparative differences between three-dimensional structure of rSIFN-co (SEQ ID NO: 1) and the computational model structure of INFERGEN® (SEQ ID NO: 1).

The circular dichroism spectrum (CD) of the present recombinant interferon in ranges of 190-250 nm and 250-320 nm is different from the corresponding CD of INFERGEN® (SEQ ID NO: 1) when determined under the same conditions. In addition, the three-dimensional structure of the present recombinant interferon is also different from the three-dimensional structure of IFN-α2b published in the art (see FIG. 12) and the three-dimensional structure of INFERGEN® (SEQ ID NO: 1) based on computational model structure (see KORN, A P et al., Journal of Interferon Research 1994, 14: 1-9). There are obvious differences between AB loops of each from comparison, and BC loops cannot coincide completely (see FIG. 14).

Several subjects whose BMI ranged from 18 to 23 were chosen to receive this recombinant interferon by intramuscular injection, then graphical charts plotting time of blood collection versus concentration of 2-5 A oligonucleotidase (also referred to as 2',5'-OAS) in the serum of the subjects were made. The charts shows general two-peak pattern, and the resulting peak area of this chart is greater than that of INFERGEN® (SEQ ID NO: 1) after injection under the same conditions. The half-life period of this recombinant interferon in the body is longer than that of INFERGEN® (SEQ ID NO: 1) after injection into the body.

The experimental results have also confirmed that the present recombinant interferon is more effective than any interferon used clinically at present (including INFERGEN® (SEQ ID NO: 1)). For example, the recombined interferon from this invention is not only capable of restraining DNA replication of HBV, but also of inhibiting secretions of both HBsAg and HBeAg. The efficiency of restraining DNA replication of HBcAg in this interferon is as much as twice of INFERGEN® (SEQ ID NO: 1). The cytotoxicity of the present recombinant interferon is only 1/8 that of currently used interferons, but its antiviral activity is as much as 5-20 times greater than said clinical interferons; meanwhile, the present recombinant interferon is more effective, more broad-spectrum and more lasting in biological responses in human body.

Thus, the present recombinant interferon has different spatial configuration, enhanced biologic activities and different pharmacokinetics characteristics as compared with INFERGEN® (SEQ ID NO: 1).

As used herein, terms 'spatial configuration', 'spatial structure', 'three-dimensional structure' and 'three-dimensional configuration' can be used interchangeably.

Therefore, in one embodiment, the present recombinant interferon comprises the amino acid sequence of SEQ ID NO: 1 and is encoded by the nucleotide sequence comprising SEQ ID NO: 2. Further, the present recombinant interferon has the amino acid sequence of SEQ ID NO: 1, and is encoded by the nucleotide sequence of SEQ ID NO: 2. In comparison with an interferon which has the same amino acid sequence with SEQ ID NO: 1, but is not encoded by the nucleotide sequence of SEQ ID NO: 2, such as INFERGEN® (SEQ ID NO: 1), the present recombinant interferon has different spatial configuration and/or enhanced biologic activities and/or different pharmacokinetics characteristics. For example, the present recombinant interferon has different spatial configuration and enhanced biologic activities, different spatial configuration and different pharmacokinetics characteristics, or enhanced biologic activities and different pharmacokinetics characteristics. Further, said different spatial configuration includes: the circular dichroism spectrum (CD) of the present recombinant interferon in ranges of 190-250 nm and/or 250-320 nm is different from the corresponding CD of INFERGEN® (SEQ ID NO: 1) when determined under the same conditions. The enhanced biologic activities include: this recombinant interferon has enhanced antiviral activity, greatly reduced toxic side effects and/or could be used in large dosages (each dose >10 million IU). The different pharmacokinetics characteristics include: several subjects whose BMI ranged from 18 to 23 are chosen to receive this recombinant interferon by intramuscular injection, then graphical charts plotting time of blood collection versus concentration of 2-5 A oligonucleotidase in the serum of the subjects are made, and the resulting peak area of this chart is greater than that of INFERGEN® (SEQ ID NO: 1) after injection under the same conditions and/or the half-life period of this recombinant interferon in the body is longer than that of INFERGEN® (SEQ ID NO: 1) after injection into the body.

In another embodiment, the present recombinant interferon can be produced by the method comprising the following steps: introducing into an isolated host cell a nucleotide sequence comprising SEQ ID NO: 2 that encodes a recombinant interferon; culturing the host cell in an appropriate condition for the expression of the recombinant interferon; and harvesting the recombinant interferon, wherein the recombinant interferon has an amino acid sequence of SEQ ID NO: 1, and the recombinant interferon inhibits secretion of HBsAg and HBeAg of Hepatitis B Virus. Further, said host cell is *Escherichia coli*, such as *Escherichia coli* LGM 194. In some embodiments, the nucleotide sequence comprising SEQ ID NO.2 is under the control of promoter $P_{BAD}$. In some embodiments, the harvesting step comprises extraction of interferon from fermentation broth, collection of inclusion body, denaturation and renaturation of the harvested protein. In some embodiments, the harvesting step comprises separation and purification of the recombinant interferon.

Crystal of Recombinant Interferon and Crystallization Method Thereof

Crystal of Recombinant Interferon

In one embodiment, this invention provides a crystal of recombinant interferon comprising the amino acid sequence of SEQ ID NO: 1. Further, this crystal belongs to the trigonal system. In one embodiment, the space group of this crystal is $P3_121$. In some embodiments, the unit cell parameters of this crystal are a=b=77.92 Å, c=125.935 Å, $\alpha=\beta=90°$, $\gamma=120°$, with a variability of at most 5% in all cell parameters. In some embodiments, said crystal contains two molecules in the asymmetric unit. In some embodiments, this crystal further comprises covalently or non-covalently bound metal ions. Further, said mental ions can be magnesium ion, zinc ion and the like, these mental ions can mediate the formation of the interferon dimers in the crystal. In some embodiments, said recombinant interferon is encoded by the nucleotide sequence comprising SEQ ID NO: 2.

In a still further embodiment, this invention provides a crystal of recombinant interferon comprising the amino acid sequence of SEQ ID NO: 1, preferably the recombinant interferon having the amino acid sequence of SEQ ID NO: 1, in which the space group of this crystal is $P3_121$, with two molecules in the asymmetric unit, and the unit cell parameters are a=b=77.92 Å, c=125.935 Å, $\alpha=\beta=90°$, $\gamma=120°$, with a variability of at most 5% in all cell parameters. Further, such recombinant interferon is encoded by the nucleotide sequence comprising SEQ ID NO: 2, preferably encoded by the nucleotide sequence of SEQ ID NO: 2.

Crystallization Method

In one embodiment, this invention provides a method for preparing or culturing a crystal of present recombinant interferon, comprising the steps of: concentrating the recombinant interferon to about 3-3.5 mg/ml, and leaving it in the crystallizable solution containing $Li_2SO_4$, CAPS (3-(cyclohexylamino)-1-propanesulfonic acid) and $MgCl_2$ for an appropriate period of time to obtain the crystal. Further, said method for preparing or culturing the crystal is performed at room temperature such as about 293K. In some embodiments, this crystal can be cultured via hanging drop method or sitting drop method, preferably the hanging drop method (also referred to as the hanging drop vapor diffusion method). In some embodiments, said crystallizable solution contains about 1.0-about 1.5M $Li_2SO_4$, about 0.05-about 0.15M CAPS and about 0.01-about 0.03 M $MgCl_2$. In some embodiments, the pH value of the crystallizable solution is in the range of about 10.5-about 12.0, preferably about 11.1. In some embodiments, said crystallizable solution contains 1.2M $Li_2SO_4$, 0.1M CAPS, pH 11.1, 0.02 M $MgCl_2$. In some embodiments, the method for preparing or culturing the crystal includes leaving the crystallizable solution which further contains said recombinant interferon for about 1 day to about 2 weeks, preferably about 2 days to about 10 days, more preferably about 3 days to about 1 week, such as 3 days to 1 week.

X-Ray Crystallographic Analysis

Each of the constituent amino acids of interferon disclosed herein is defined by a set of structure coordinates. The term "structure coordinates" refers to Cartesian coordinates derived from mathematical equations related to the patterns obtained on diffraction of a monochromatic beam of x-rays by the atoms (scattering centers) of the present interferon in crystal form. The diffraction data are used to calculate an electron density map of the repeating unit of the crystal. The electron density maps are then used to establish the positions of the individual atoms of the interferon protein or protein/ligand complex.

Slight variations in structure coordinates can be generated by mathematically manipulating the interferon or interferon/ligand structure coordinates. For example, the structure coordinates disclosed herein could be manipulated by crystallographic permutations of the structure coordinates, fractionalization of the structure coordinates, integer additions or subtractions to sets of the structure coordinates, inversion of the structure coordinates or any combination of the above. Alternatively, modifications in the crystal structure due to mutations, additions, substitutions, and/or deletions of amino acids, or other changes in any of the components that make up the crystal, could also yield variations in structure coordinates. Such slight variations in the individual coordinates will have little effect on overall shape. If such variations are within an acceptable standard error as compared to the original coordinates, the resulting three-dimensional shape is considered to be structurally equivalent.

It should be noted that slight variations in individual structure coordinates of the interferon of the present invention would not be expected to significantly alter the nature of the entities such as ligands that could associate with the interferon or portion thereof (e.g. the AB or the BC loop). As used herein, the "AB loop" of present recombinant interferon means the amino acid residues 25-33 of the present recombinant interferon, which has amino acid sequence SPFS- CLKDR as shown in SEQ ID NO: 4, and "BC loop" of the present recombinant interferon means the amino acid residues 44-52 of present recombinant interferon, which has amino acid sequence DGNQFQKAQ as shown in SEQ ID NO: 5. In the context, the phrase "associating with" refers to a condition of proximity between a ligand, or portions thereof, and an interferon molecule or portions thereof. The association may be non-covalent, wherein the juxtaposition is energetically favored by hydrogen bonding, van der Waals forces, or electrostatic interactions, or it may be covalent. Thus, for example, a ligand that binds to a binding pocket or region of interferon would also be expected to bind to or interfere with a structurally equivalent binding pocket or region.

For the purpose of this invention, any molecule or molecular complex, or any portion thereof, that has a root mean square deviation of conserved residue backbone atoms (e.g. N, Cα, C, O, preferably Cα) of less than about 0.65 Å, when superimposed on the relevant backbone atoms described herein, is considered "structurally equivalent". That is to say, the crystal structures of those portions of the two molecules are substantially identical, within acceptable error. Particularly preferred structurally equivalent molecules or molecular complexes are those that are defined by the entire set of structure coordinates disclosed herein ±a root mean square deviation from the conserved backbone atoms of those amino acids of less than about 0.65 Å. More preferably, the root mean square deviation is at most about 0.5 Å, and even more preferably, at most about 0.35 Å. Other embodiments of this invention include a molecular complex defined by the structure coordinates for the AB or the BC loop disclosed herein ±a root mean square deviation of less than about 0.65 Å, preferably at most about 0.5 Å, and more preferably at most about 0.35 Å.

The term "root mean square deviation" means the square root of the arithmetic mean of the squares of the deviations. It is a way to express the deviation or variation from a trend or object. In one embodiment, the "root mean square deviation" defines the variation in the backbone of a protein from the backbone of interferon or a portion thereof as defined by the structure coordinates described herein.

X-ray structure coordinates define a unique configuration of points in space. Those of skill in the art understand that a set of structure coordinates for a protein or a protein/ligand complex, or a portion thereof, define a relative set of points that, in turn, define a configuration in three dimensions. A similar or identical configuration can be defined by an entirely different set of coordinates, provided the distances and angles between coordinates remain essentially the same. In addition, a scalable configuration of points can be defined by increasing or decreasing the distances between coordinates by a scalar factor while keeping the angles essentially the same.

Various computational analyses can be used to determine whether a molecule or a portion thereof is "structurally equivalent," defined in terms of its three-dimensional structure, to all or part of the interferon disclosed herein. For example, comparisons between different structures, different conformations of the same structure, or different parts of the same structure can be made by various computational analyses. In one embodiment, such analysis can be divided into four steps: (1) load the structures to be compared; (2) define the atom equivalences in these structures; (3) perform a fitting operation; and (4) analyze the results.

Three-Dimensional Structure of rSIFN-Co (SEQ ID NO: 1)

This invention provides a three-dimensional structure of present recombinant interferon. This three-dimensional structure is different from the three-dimensional structure of IFN-α2b published in the art (see FIG. 12) and the computational model structure of INFERGEN® (SEQ ID NO: 1) (see FIG. 14), especially in the AB and BC loops.

In one embodiment, the three-dimensional structure of said recombinant interferon contains the atomic coordinates of as shown in Table 5, said atomic coordinates optionally have the variability of root mean square deviation from the conserved backbone atoms (preferably Cα, which also referred to as 'α carbon atom') less than about 0.65 Å, preferably at most about 0.5 Å, and more preferably at most about 0.35 Å.

In one embodiment, in the above-mentioned three-dimensional structure of recombinant interferon, each monomer of said recombinant interferon is composed of 6 segments of α-helix, a segment of $3_{10}$ helix, and the connecting peptides between them. The corresponding amino acid residue locations of said 6 segments of the α-helices are 13-20, 50-68, 70-76, 79-100, 114-133, and 138-160; the corresponding amino acid residue location of said segment of $3_{10}$ helix is 40-43. The folding of the monomer structure belongs to the helical cytokine type, of which the characteristic is that after superimposition of the Cα-backbone of said recombinant interferon and the Cα-backbone of IFN-α2b protein using least squares method, the location root-mean-square deviation of Cα in the 25-33 residues (AB loop) of said recombinant interferon and Cα in the corresponding residues of IFN-α2b protein is 3.63 Å±5%.

In one embodiment, the location root-mean-square deviation of Cα in the 25 residue of both said recombinant interferon and IFN-α2b protein is 3.291 Å±5%, the location root-mean-square deviation of Cα in the 26 residue of them is 4.779 Å±5%; the location root-mean-square deviation of Cα in the 27 residue of them is 5.090 Å±5%; the location root-mean-square deviation of Cα in the 28 residue of them is 3.588 Å±5%; the location root-mean-square deviation of Cα in the 29 residue of them is 2.567 Å±5%, the location root-mean-square deviation of Cα in the 30 residue of them is 2.437 Å±5%; the location root-mean-square deviation of Cα in the 31 residue of them is 3.526 Å±5%; the location root-mean-square deviation of Cα in the 32 residue of them is 4.820 Å±5%; and the location root-mean-square deviation of Cα in the 33 residue of them is 2.756 Å±5%.

In one embodiment, the location root-mean-square deviation of Cα in the 44-52 residues (BC loop) of said recombinant interferon and Cα in the corresponding residues of IFN-α2b protein is 2.90 Å±5%. Thereinto, the location root-mean-square deviation of Cα in the 44 residue of both said recombinant interferon and IFN-α2b protein is 1.614 Å±5%; the location root-mean-square deviation of Cα in the 45 residue of them is 1.383 Å±5%; the location root-mean-square deviation of Cα in the 46 residue of them is 2.735 Å±5%; the location root-mean-square deviation of Cα in the 47 residue of them is 2.709 Å±5%; the location root-mean-square deviation of Cα in the 48 residue of them is 5.018 Å±5%; the location root-mean-square deviation of Cα in the 49 residue of them is 4.140 Å±5%; the location root-mean-square deviation of Cα in the 50 residue of them is 3.809 Å±5%; the location root-mean-square deviation of Cα in the 51 residue of them is 2.970 Å±5%; and the location root-mean-square deviation of Cα in the 52 residue of them is 0.881 Å±5%. (The "location root-mean-square deviation" listed above are all root-mean-square deviations of coordinate positions.)

In another aspect, this invention provides the selected portion of the three-dimensional structure of present recombinant interferon, which contains atomic coordinates of one or more amino acid residues of the amino acid residues 25-33 and/or 45-52 in Table 5. In some embodiments, the "one or more amino acid residues" described herein include 1, 2, 3, 4, 5, 6, 7, 8, 9, 10, 11, 12, 13, 14, 15, 16, 17 or 18 amino acid residues. In some embodiments, the "selected portion of said three-dimensional structure" contains the atomic coordinates of the amino acid residues 25-33 and/or 44-52 in Table 5. In some embodiments, the "selected portion of the three-dimensional structure" contains atomic coordinates of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 amino acid residues in Table 5. In some embodiments, said atomic coordinates have the variability of root mean square deviation from the conserved backbone atoms (preferably Cα) less than about 0.65 Å, preferably at most about 0.5 Å, and more preferably at most about 0.35 Å.

In another aspect, this invention provides the protein spatial structure model comprising three-dimensional structure of present recombinant interferon. In one embodiment, said protein spatial structure model could be an electron density map, a wire-frame model, a chicken-wire model, a space-filling model, a stick-model, a ribbon model and molecular surface model and the like.

In still another aspect, the present invention provides a scalable three-dimensional configuration of points, wherein at least a portion of said points are derived from structure coordinates disclosed herein, or from peptides comprising the AB loop or the BC loop of the recombinant interferon of the present invention. In one embodiment, the scalable three-dimensional configuration of points is displayed as a holographic image, a stereodiagram, a model, or a computer-displayed image.

The Application of Three-Dimensional Structure Screening/Designing Candidate Compound that could Interact with Recombinant Interferon In one aspect, this invention provides a method for screening/designing candidate compounds that could interact with present recombinant interferon. Further, said method utilizes the three-dimensional structure of present recombinant interferon, and is based on computer methods. In one embodiment, this invention provides a computer-based method for identifying candidate compounds that could interact with recombinant interferon, said method comprising the steps of: (a) providing the three-dimensional structure comprising atomic coordinate of recombinant interferon as shown in Table 5, where said atomic coordinates optionally have the variability of root mean square deviation from the conserved backbone atoms (preferably Cα) of less than about 0.65 Å, preferably at most about 0.5 Å, and more preferably at most about 0.35 Å; and (b) selecting a candidate compound that comprises structural features capable of interacting with said three-dimensional structure or selected portion thereof, thereby identifying a candidate compound that could interact with said recombinant interferon. In some embodiments, said structural features are selected from the group consisting of antigenic sites, hydrophathy profiles, surface accessibility, and structural motifs. In some embodiments, the selection and identification of a candidate compound in step (b) comprises: (i) generating three-dimensional structures for a plurality of candidate compounds; and (ii) fitting each of the three-dimensional structures of (i) against the three-dimensional structure of step (a) or a selected portion thereof to find the most energetically favorable interaction, thereby identifying a candidate compound that could interact with the recombinant interferon. In some embodiments, said method further comprises the steps of: (c) obtaining or synthesizing the candidate compound; and (d) contacting the candidate compound with said recombinant interferon to determine the ability of the candidate compound to interact with said recombinant interferon. Further, the step of determining the ability of the candidate compound to interact with said recombinant interferon may further comprise measuring an activity of said recombinant interferon when contacted with the candidate compound. Interferon activities to be measured include, for example, antivirus activity, anti-tumor activity, anti-proliferation activity, natural killer cell activation, and immunomodulatory activity. In some embodiments, said candidate compound is a ligand bound to said recombinant interferon or a selected portion thereof. For example, said ligand is selected from the group consisting of receptor, modifier, agonist and antagonist, such receptor could be IFNAR1, 2 or their complex, and said selected portion comprises one or more amino acid residues of amino acid residues 25-33 (AB loop) and/or 45-52 (BC loop) of said recombinant interferon. Further, said selected portion comprises amino acid residues 25-33 and/or 44-52 of said recombinant interferon.

In another aspect, the present invention provides a method of identifying the ability of a potential ligand to bind to the present recombinant interferon. In one embodiment, the method includes exposing a crystal disclosed herein to one or more samples including a potential ligand, and determining whether a ligand-interferon molecular complex is formed.

In another aspect, the present invention provides a method of acquiring structural information for designing potential ligands for forming molecular complexes with interferon. In one embodiment, the method includes exposing a crystal disclosed herein to a library of potential ligands, and determining whether a ligand-interferon molecular complex is formed.

In another aspect, the present invention provides computer-assisted methods for identifying, designing, or making a potential modifier of interferon activity. In one embodiment, the methods include screening a library of chemical or biological entities.

One of skill in the art would utilize crystallography to screen and identify chemical or biological entities that may become ligands of interferon (see e.g. in U.S. Pat. No. 6,297,021). For example, a preferred method may include obtaining a crystal of unliganded interferon; exposing the unliganded interferon to one or more test samples that include a potential ligand of interferon; and determining whether a ligand-interferon molecular complex is formed. The interferon may be exposed to potential ligands by various methods including, for example, soaking an interferon crystal in a solution of one or more potential ligands, or co-crystallizing interferon in the presence of one or more potential ligands.

Structural information from the ligand-interferon complexes found may preferably be used to design new ligands that bind tighter, bind more specifically, have desired biological activity properties, have better safety profiles than known ligands, or combinations thereof. For example, the calculated electron density directly reveals the binding event, identifies the bound chemical or biological entity, and provides a detailed three-dimensional structure of the ligand-interferon complex. Once a hit is found, preferably a number of analogs or derivatives of the hit may be screened for tighter binding or desired biological activity by traditional screening methods. Optionally, the ligand-interferon complex may be exposed to additional iterations of potential ligands so that two or more hits may preferably be linked together to identify or design a more potent ligand.

Obtaining of Structurally Homologous Molecules/Designing of Interferon Mimetics

The structure coordinates disclosed herein can be used to aid in obtaining structural information about another crystallized molecule or molecular complex. The method of the invention allows determination of at least a portion of the three-dimensional structure of molecules or molecular complexes which contain one or more structural features that are similar to the structural features of the interferon disclosed herein. These molecules are referred to herein as "structurally homologous". Similar structural features can include, for example, regions of amino acid identity, conserved active site or binding site motifs, and similarly arranged secondary structural elements (e.g., a helices and (3 sheets). In another embodiment, structural homology is determined by aligning the residues of the two amino acid sequences to optimize the number of identical amino acids along the lengths of their sequences; gaps in either or both sequences are permitted in making the alignment in order to optimize the number of identical amino acids, although the amino acids in each sequence must nonetheless remain in their proper order. Preferably, a structurally homologous molecule is a protein that has an amino acid sequence sharing at least 65% identity with SEQ ID NO:1. More preferably, a protein that is structurally homologous to the interferon of the present invention includes a contiguous stretch of at least 50 amino acids that shares at least 80% amino acid sequence identity with the analogous portion of SEQ ID NO:1. Methods for generating structural information about the structurally homologous molecule or molecular complex are well-known in the art.

The structure coordinates disclosed herein are also useful to solve the structure of crystals of related interferons, interferon mutants or interferon homologs co-complexed with a variety of ligands. This approach enables the determination of the optimal sites for interaction between the ligand and interferon, e.g. between candidate interferon modifiers and interferon. Potential sites for modification within the various binding sites of the molecule can also be identified. This information provides an additional tool for determining the most efficient binding interactions, for example, increased hydrophobic interactions, between an interferon and a ligand.

In one embodiment, the present invention also provides a computer-based method for designing a mimetic of the recombinant interferon, comprising the steps of: (a) generating three-dimensional structures for a plurality of mimetics; and (b) fitting each of the three-dimensional structures of step (a) against the three-dimensional structure comprising atomic coordinate of recombinant interferon as shown in Table 5 or selected portion thereof to find the best fitting mimetic of said recombinant interferon, said atomic coordinates optionally have the variability of root mean square deviation from the conserved backbone atoms (preferably Cα) less than about 0.65 Å, preferably at most about 0.5 Å, and more preferably at most about 0.35 Å.

Rational Drug Design

Computational techniques can be used to screen, identify, select and/or design chemical entities or ligands capable of associating with interferon or structurally homologous molecules. Knowledge of the structure coordinates for interferon disclosed herein permits the design and/or identification of synthetic compounds and/or other molecules which have a shape complementary to the conformation of the interferon disclosed herein. In particular, computational techniques can be used to identify or design chemical entities or ligands, such as receptors, modifiers, agonists and antagonists, that associate with the interferon or a portion thereof (e.g. the AB or the BC loop). Potential modifiers may bind to or interfere with all or a portion of an active site of interferon, and can be competitive, non-competitive, or uncompetitive inhibitors; or interfere with dimerization by binding at the interface between the two monomers. Once identified and screened for biological activity, these inhibitors/agonists/antagonists may be used therapeutically or prophylactically to block or enhance interferon activity. Structure-activity data for analogues of ligands that bind to or interfere with interferon can also be obtained computationally.

The term "chemical entity", as used herein, refers to chemical compounds, complexes of two or more chemical compounds, and fragments of such compounds or complexes. Chemical entities that are determined to associate with the interferon of the present invention are potential drug candidates. A graphical three-dimensional representation of the structure of the present interferon or a structurally homologous molecule, as identified herein, or portions thereof may thus be advantageously used for drug discovery. The structure coordinates of the chemical entity are used to generate a three-dimensional image that can be computationally fit to the three-dimensional image of the interferon or a structurally homologous molecule by one of many computation methods and techniques available in the art.

One embodiment of the method of drug design involves evaluating the potential association of a known chemical entity or ligand with the interferon or a structurally homologous molecule. The method of drug design thus includes computationally evaluating the potential of a selected chemical entity or ligand to associate with any of the molecules or molecular complexes set forth herein. In another embodiment, the method of drug design involves computer-assisted design of chemical entities or ligands that associate with the present interferon, its homologs, or portions thereof. Chemical entities or ligands can be designed in a step-wise fashion, one fragment at a time, or may be designed as a whole or "de novo".

Thus, in one embodiment, the present invention provides a computer-based method of rational drug design, comprising the steps of: (a) providing the three-dimensional structure comprising atomic coordinate of recombinant interferon as shown in Table 5, said atomic coordinates optionally have the variability of root mean square deviation from the conserved backbone atoms (preferably Cα) less than about 0.65 Å, preferably at most about 0.5 Å, and more preferably at most about 0.35 Å; (b) providing a plurality of molecular fragments, and generating three-dimensional structures thereof; (c) fitting each of the three-dimensional structures of (b) against the three-dimensional structure of step (a) or selected portion thereof; and (d) assembling the selected molecular fragments into a molecule to form a candidate drug. In one embodiment, said method may further comprise the steps of: (e) obtaining or synthesizing the candidate drug; and (f) contacting the candidate drug with said recombinant interferon to determine the ability of the candidate drug to interact with said recombinant interferon.

In some embodiments of the invention, the selected portion of said three-dimensional structure comprises the atomic coordinates of one or more amino acid residues of the amino acid residues 25-33 (amino acid sequence as shown in SEQ ID NO: 4) and/or 45-52 (amino acid sequence as shown in SEQ ID NO: 5) in Table 5. Further, the selected portion of said three-dimensional structure comprises the atomic coordinates of the amino acid residues 25-33 and/or 45-52 in Table 5, said atomic coordinates optionally have the variability of root mean square deviation from the conserved backbone atoms (preferably Cα) less than about 0.65 Å, preferably at most about 0.5 Å, and more preferably at most about 0.35 Å.

Homology Modeling

In one aspect, using homology modeling, a computer model of an interferon homolog can be built or refined without crystallizing the homolog. First, a preliminary model of an interferon homolog is created by sequence alignment, secondary structure prediction, screening of structural libraries, or any combination of those techniques. Computational software may be used to carry out the sequence alignments and the secondary structure predictions. Structural incoherences, e.g., structural fragments around insertions and deletions, can be modeled by screening a structural library for peptides of the desired length and with a suitable conformation. If the interferon homolog has been crystallized, the final homology model can be used to solve the crystal structure of the homolog by techniques known in the art. Next, the preliminary model is subjected to energy minimization to yield an energy minimized model. The energy minimized model may contain regions where stereochemistry restraints are violated, in which case such regions are remodeled to obtain a final homology model using one of many techniques known in the art.

In another aspect, the present invention provides a method for obtaining structural information about a molecule or a molecular complex of unknown structure. In one embodiment, the method includes crystallizing the molecule or molecular complex; generating an x-ray diffraction pattern from the crystallized molecule or molecular complex; and applying to the x-ray diffraction pattern at least a portion of the structure coordinates for interferon disclosed herein to generate a three-dimensional electron density map of at least a portion of the molecule or molecular complex whose structure is unknown.

In another aspect, the present invention provides a method for modeling an interferon homolog. In one embodiment, the method includes aligning the amino acid sequence of a putative interferon homolog with the amino acid sequence of the present interferon and incorporating the sequence of the putative homolog into a model of interferon formed from structure coordinates disclosed herein to yield a preliminary model of interferon homolog; subjecting the preliminary model to energy minimization to yield an energy minimized model; and remodeling regions of the energy minimized model where stereochemistry restraints are violated to yield a final model of interferon homolog.

Interferon Mimetics

The present invention provides interferon mimetics. In one aspect, the present invention provides a peptide comprising a sequence as disclosed herein, or a derivative, active portion, analogue, variant or mimetic, and uses thereof. Thus, in one embodiment, the present invention provides a mimetic of the interferon which comprises the amino acid sequence as shown in SEQ ID NO: 4 and/or SEQ ID NO: 5. In one embodiment, after superimposition of the Cα-backbone of three-dimensional structure of said recombinant interferon and the Cα-backbone of three-dimensional structure of IFN-α2b protein using least squares method, the location root-mean-square deviation of Cα in the 25-33 residues of said recombinant interferon and Cα in the corresponding residues of IFN-α2b protein is 3.63 Å±5%. In some embodiments, in comparison with the corresponding residues of IFN-α2b, the deviations of α carbons of residues 25-33 of said recombinant interferon are 3.291 Å±5%, 4.779 Å±5%, 5.090 Å±5%, 3.588 Å±5%, 2.567 Å±5%, 2.437 Å±5%, 3.526 Å±5%, 4.820 Å±5% and 2.756 Å±5% respectively. In some embodiments, after superimposition of the Cα-backbone of three-dimensional structure of said recombinant interferon and the Cα-backbone of three-dimensional structure of IFN-α2b protein using least squares method, the location root-mean-square deviation of Cα in the 44-52 residues of said recombinant interferon and Cα in the corresponding residues of IFN-α2b protein is 2.90 Å±5%. In some embodiments, in comparison with the corresponding residues of IFN-α2b, the deviations of α carbons of residues 44-52 of said recombinant interferon are 1.614 Å±5%, 1.383 Å±5%, 2.735 Å±5%, 2.709 Å±5%, 5.018 Å±5%, 4.140 Å±5%, 3.809 Å±5%, 2.970 Å±5%, and 0.881 Å±5% respectively. In some embodiments, the mimetic is a functional mimetic or a structural mimetic. In some embodiments, the mimetic is mimetic of present recombinant interferon (rSIFN-co (SEQ ID NO: 1)). Further, the mimetics do not comprise INFERGEN® (SEQ ID NO: 1). In some embodiments, the three-dimensional structure of said interferon mimetic is similar to that of the present recombinant interferon (rSIFN-co (SEQ ID NO: 1)). In particular, both three-dimensional structures can be the same or essentially same at the AB and BC loops. Further, the three-dimensional structure of said interferon mimetic comprises the atomic coordinates of amino acid residues 25-33 (AB loop) and/or 44-52 (BC loop) in Table 5, said atomic coordinates optionally have the variability of root mean square deviation from the conserved backbone atoms (preferably Cα) less than about 0.65 Å, preferably at most about 0.5 Å, and more preferably at most about 0.35 Å.

The present invention comprises variant peptides in which individual amino acids can be substituted by other amino acids which are closely related as is understood in the art. For example, individual amino acid may be substituted as follows: any hydrophobic aliphatic amino acid may be substituted in place of any other hydrophobic aliphatic amino acid; any hydrophobic aromatic amino acid may be substituted in place of any other hydrophobic aromatic amino acid; any neutral amino acid with a polar side chain may be substituted in place of any other neutral amino acid with a polar side chain; an acidic amino acid may be substituted in place of an acidic amino acid; and a basic amino acid may be substituted in place of a basic amino acid. As used herein, "mimetic", "functional/structural mimetic" relate to peptide variants or organic compounds having the same functional/structural activity as the polypeptide disclosed herein. Examples of such mimetics or analogues include chemical compounds or peptides which are modeled to resemble the three-dimensional structure of the interferon disclosed herein which can comprise the atomic coordinates of recombinant interferon as shown in Table 5, and in particular the arrangement of the amino acid residues as described above.

Thus, as used herein, "mimetic of present recombinant interferon" refers to a peptide variant or organic compound which has the same function/structure-activity with present recombinant interferon (rSIFN-co (SEQ ID NO: 1)), but it is different from present recombinant interferon, and which especially has the same AB loop and/or BC loop spatial structure with present recombinant interferon. When the "mimetic" is peptide variant, the length of its amino acid sequence is generally similar to that of the present recombinant interferon. For example, said amino acid sequence of the mimetic can comprise about 120-200 amino acid residues, preferably about 140-180 amino acid residues, more preferably about 150-175 amino acid residues, still more preferably about 160-170 amino acid residues, for example, about 164, 165, 166 or 167 amino acid residues. Alternatively, such "mimetic" can be the peptide variants having short length of the amino acid sequence but comprising AB loop and/or BC loop of present recombinant interferon, for example, it can comprise about 10-100 amino acid residues, preferably about 15-80 amino acid residues.

Suitable mimetics or analogues can be generated by modeling techniques generally known in the art. This includes the design of "mimetics" which involves the study of the functional interactions and the design of compounds which contain functional groups arranged in such a manner that they could reproduce those interactions.

The design of mimetics to a known pharmaceutically active compound is a known approach to the development of pharmaceuticals based on a "lead" compound. This might be desirable where the active compound is difficult or expensive to synthesize or where it is unsuitable for a particular method of administration, e.g. peptides are not well suited as active agents for oral compositions as they tend to be quickly degraded by proteases in the alimentary canal. Mimetic design, synthesis and testing may be used to avoid randomly screening large number of molecules for a target property.

There are several steps commonly taken in the design of a mimetic from a compound/peptide having a given target property. Firstly, the particular parts of the compound/peptide that are critical and/or important in determining the target property are determined. In the case of a peptide, this can be done by systematically varying the amino acid residues in the peptide, e.g. by substituting each residue in turn. These parts or residues constituting the active region of the compound are known as its "pharmacophore".

Once the pharmacophore has been found, its structure is modeled according to its physical properties, e.g. stereochemistry, bonding, size and/or charge, using data from a range of sources, e.g. spectroscopic techniques, X-ray diffraction data and NMR. Computational analysis, similarity mapping (which models the charge and/or volume of a pharmacophore, rather than the bonding between atoms) and other techniques can be used in this modeling process. In a variant of this approach, the three-dimensional structure of the ligand and its binding partner are modeled. This can be especially useful where the ligand and/or binding partner change conformation on binding, allowing the model to take account of the design of the mimetic A template molecule is then selected onto which chemical groups which mimic the pharmacophore can be grafted. The template molecule and the chemical groups grafted on to it can conveniently be selected so that the mimetic is easy to synthesize, is likely to be pharmacologically acceptable, and does not degrade in vivo, while retaining the biological activity of the lead compound. The mimetic or mimetics found by this approach can then be screened to see whether they have the target property, or to what extent they exhibit it. Further optimization or modification can then be carried out to arrive at one or more final mimetics for in vivo or clinical testing.

In another aspect, the present invention provides an unliganded molecule including at least a portion of the interferon disclosed herein, e.g. the unliganded molecule may comprise SEQ ID NO:4 or SEQ ID NO:5 (the sequence of the AB loop and the BC loop respectively of the interferon described herein). Further, the unliganded molecule has sequence as shown in SEQ ID NO:4 or SEQ ID NO:5.

Composition and Therapeutic Application

The present invention provides the composition comprising the crystal of the present recombinant interferon or mimetic of the present recombinant interferon. In one embodiment, the composition is a pharmaceutical composition. In one embodiment, said pharmaceutical composition further comprises a pharmaceutically acceptable carrier.

Whether it is a polypeptide, antibody, peptide, nucleic acid molecule, small molecule, mimetic or other pharmaceutically useful compound according to the present invention that is to be given to an individual, administration is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc., is within the responsibility of general practitioners and other medical doctors. A composition may be administered alone or in combination with other treatments, either simultaneously or sequentially dependent upon the condition to be treated.

Pharmaceutical compositions according to the present invention, and for use in accordance with the present invention, may include, in addition to the active ingredient, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. cutaneous, subcutaneous or intravenous. Examples of techniques and protocols mentioned above can be found in Remington's Pharmaceutical Sciences, 16th edition, Osol, A. (ed.), 1980.

In some embodiments, said pharmaceutical composition can be formulated into the following dosage forms, including: tablets, capsules, liquids for oral consumption, pastes, injections, sprays, suppositories, and solutions. The recommended dosage form is injection. Subcutaneous or intravenous administration can be adapt, and the carrier in the pharmaceutical composition may be any acceptable drug carrier, including binders, disintegrating agents, lubricants, fillers, solubilizer, buffer, preservatives, thickener, chelating agent and other adjuvants.

For the purposes of this invention, "pharmaceutically acceptable carriers" means any of the standard pharmaceutical carriers. For example, known appropriate carrier includes but not limited to phosphate buffered saline and various wetting agents. Other carriers may include additive agents used for tablets, particles, and capsules. Typical carriers often contain: starch, latex, sugar, certain types of clay, gelatin, stearic acid and its salts such as magnesium stearate or calcium stearate, talc, plant oils, gums, glycol or other known excipients. Such carriers may also include flavor and color additives or other ingredients. The composition of these carriers can be formulated using known methods.

The invention being generally described, will be more readily understood by reference to the following examples which are included merely for purposes of illustration of certain aspects and embodiments of the present invention, and are not intended to limit the invention. Modifications may be made in the design and arrangement of the elements described herein without departing from the scope of the invention as expressed in the appended claims.

Throughout this application, various references or publications are cited. Disclosures of these references or publications in their entireties are hereby incorporated by reference into this application in order to more fully describe the state of the art to which this invention pertains.

Example 1

Production of Recombinant Interferon rSIFN-co (SEQ ID NO: 1)

This example is the preparation method of recombinant super-compound interferon, rSIFN-co (SEQ ID NO: 1).

1. Gene Cloning

The design of rsIFN-co (SEQ ID NO: 1) cDNA was strictly based on the published primitive amino acid sequence of INFERGEN (SEQ ID NO: 1) (Klein M L, et al., Structural characterization of recombinant consensus interferon-alpha. Journal of Chromatography, 1988; 454: 205-215) with some modification on DNA sequence according to codon usage of *E. coli* to achieve high expression. (The *E. coli* codon usage frequency is refer to The Wisconsin Package, by Genetics Computer Group, Inc. Copyright 1992, Madison, Wis., USA).

rSIFN-co (SEQ ID NO: 1) cDNA Sequence Synthesis
Synthesis of Two Semi-Sequences

Two semi-sequences can be directly synthesized by PCR: rSIFN-co (SEQ ID NO: 1) cDNA 5'-terminus 280 bp (fragment I) and 3'-terminus 268 bp (fragment II). There is a 41-bp overlap among fragment I and fragment II.

(1) Chemical Synthesis of Oligodeoxynucleotide Fragment:

```
Oligomer A:
5'ATGTGCGACCTGCCGCAGACCCACTCCCTGGGTAACCGTCGTGCTCT

GATCCTGCTGGCTCAGATGCGTCGTATCTCCCCGTTCTCCTGCCTGAAA

GACCGTCACGAC3' (SEQ ID NO: 6)

Oligomer B:
5'CTGAAAGACCGTCACGACTTCGGTTTCCCGCAGGAGAGGTTCGACGG

TAACCAGTTCCAGAAAGCTCAGGCTATCTCCGTTCTGCACGAAATGATC

CAGCAGACCTTC3' (SEQ ID NO: 7)

Oligomer C:
5'GCTGCTGGTACAGTTCGGTGTAGAATTTTTCCAGCAGGGATTCGTCC

CAAGCAGCGGAGGAGTCTTTGGTGGAGAACAGGTTGAAGGTCTGCTGGA

TCATTTC3' (SEQ ID NO: 8)

Oligomer D:
5'ATCCCTGCTGGAAAAATTCTACACCGAACTGTACCAGCAGCTGAACG

ACCTGGAAGCTTGCGTTATCCAGGAAGTTGGTGTTGAAGAAACCCCGCT

GATGAAC3' (SEQ ID NO: 9)

Oligomer E:
5'GAAGAAACCCCGCTGATGAACGTTGACTCCATCCTGGCTGTTAAAAA

ATACTTCCAGCGTATCACCCTGTACCTGACCGAAAAAAAATACTCCCCG

TGCGCTTGGG3' (SEQ ID NO: 10)

Oligomer F:
5'TTATTCTTTACGACGCAGACGTTCCTGCAGGTTGGTGGACAGGGAGA

AGGAACGCATGATTTCAGCACGAACAACTTCCCAAGCGCACGGGAGTA

TTTTTTTTCGGTCAGG3' (SEQ ID NO: 11)
```

Polymerase Chain Reaction (PCR)

PCR I for 280-bp fragment I: using oligodeoxynucleotide fragment B (SEQ ID NO: 7) as a template, oligodeoxynucleotide fragments A (SEQ ID NO: 6) and C (SEQ ID NO: 8) as primers.

The PCR I mixture is as follows:

| PCR I mixture | |
|---|---|
| (units: μl) (Total volume 50 μl) | |
| sterilized distilled water | 39 |
| 10 × Pfu buffer (Stratagen American Ltd.) | 5 |
| dNTP mixture (2.5 mmol/L for each dNTP) | 2 |
| Oligomer A primer (25 μmol/L) (SEQ ID NO: 6) | 1 |

| PCR I mixture (continued) | |
|---|---|
| (units: μl) (Total volume 50 μl) | |
| Oligomer C primer (25 μmol/L) (SEQ ID NO: 8) | 1 |
| Oligomer B template (1 μmol/L) (SEQ ID NO: 7) | 1 |
| Pfu DNA polymerase (Stratagen American Ltd.) (25 U/μl) | 1 |

PCR I reaction cycle: 95° C. 2 m→(95° C. 45 s→65° C. 1 m→72° C. 1 m)×25 cycle→72° C. 10 m→4° C.

PCR II for 268-bp fragment II: using oligodeoxynucleotide fragment E (SEQ ID NO: 10) as template, oligodeoxynucleotide fragments D (SEQ ID NO: 9) and F (SEQ ID NO: 11) as primers.

| The PCR II mixture is as follows: | |
|---|---|
| (units: μl) (Total volume 50 μl) | |
| sterilized distilled water | 39 |
| 10 × Pfu buffer (Stratagen American Ltd.) | 5 |
| dNTP mixture (2.5 mmol/L for each dNTP) | 2 |
| Oligomer D primer (25 μmol/L) (SEQ ID NO: 9) | 1 |
| Oligomer E primer (25 μmol/L) (SEQ ID NO: 10) | 1 |
| Oligomer F template (1 μmol/L) (SEQ ID NO: 11) | 1 |
| Pfu DNA polymerase (Stratagen American Ltd.) (25 U/μl) | 1 |

PCR reaction cycle: the same as PCR I

Assembling of Full-Length rSIFN-co (SEQ ID NO: 1) cDNA

Fragments I and II were assembled together to get the complete cDNA molecular sequence of rSIFN-co (SEQ ID NO: 1) using the overlapping and extending PCR method. Restriction enzyme sites Nde I and Pst I were introduced to the plasmid.

(1) Chemical Synthesis Primers

```
Oligomer G:
5'ATCGGCCATATGTGCGACCTGCCGCAGACCC3' (SEQ ID NO: 12)

Oligomer H:
5'ACTGCCAGGCTGCAGTTATTCTTTACGACGCA

GACGTTCC3' (SEQ ID NO: 13)
```

(2) Overlapping and Extending PCR

| PCR mixture | |
|---|---|
| (units: μl) (Total volume 50 μl) | |
| sterilized distilled water | 38 |
| 10 × Pfu buffer (Stratagen American Ltd.) | 5 |
| dNTP mixture (2.5 mmol/L for each dNTP) | 2 |
| primerG (25 μmol/L) (SEQ ID NO: 12) | 1 |
| primerH (25 μmol/L) (SEQ ID NO: 13) | 1 |
| *fragment I PCR product (1 μmol/L) | 1 |
| *fragment II PCR product (1 μmol/L) | 1 |
| Pfu DNA polymerase (Stratagen American Ltd.) (25 U/μl) | 1 |

*Separate and purify PCR product with STRATAPREP PCR purification kit produced by Stratagen American Ltd. And dissolve it into sterilized distilled water.

PCR reaction condition and cycle: the same as PCR I.

rSIFN-co (SEQ ID NO: 1) Gene Clone and Sequence Analysis pLac T7 plasmid, which is reconstructed from pBluescript II KS(+) plasmid produced by Stratagen, was used as cloning vector.

Purify PCR product of rSIFN-co (SEQ ID NO: 1) cDNA with StrataPrep PCR purification kit. Digest the cDNA and pLac T7 plasmid with Nde I and Pst I. Run 1% agarose gel electrophoresis to separate these double-digested DNA fragments. Recover and purify a 507-bp rSIFN-co (SEQ ID NO: 1) DNA fragment and a 2.9-kb plasmid DNA fragment with Winzard DNA purification kit produced by Promoga American Ltd. Ligate these fragments by T4 DNA ligase to form a recombinant plasmid. Transform DH5a competent cells (Gibco) with the recombinant plasmid, culture at 37° C. overnight. Identify the positive recombinant colony, named pHY-1.

Run DNA sequencing on DNA sequencer L1-COR Model 4000L with SequiTherm™ Cycle Sequencing Kit following instruction provided by producer (American Epicentre Technologies Ltd). Universal primer T7 and T3 were used. The result of DNA sequencing matches theoretic design.

Purify the rSIFN-co (SEQ ID NO: 1), and sequence sixteen N-terminus amino acids and four C-terminus amino acids. The results were shown below:

```
N-Cys-Asp-Leu-Pro-Gln-Thr-His-Ser-Leu-Gly-Asn-

Arg-Arg-Ala-Leu- (SEQ ID NO: 14)
```

MET at N-terminus is resected in mature protein.

```
C-Arg-Arg-Lys-Glu-COOH (SEQ ID NO: 15)
```

Full-length nucleotide sequence of rSIFN-co (SEQ ID NO: 1) is shown as SEQ ID NO:2 and the amino sequence is shown as SEQ ID NO: 1.

Construction, Transformation, Identification, and Hereditary Stability of Expression Vector Linearize *E. Coli* expression vector pBAD18 by digestion with Nde I and subsequently fully digest it with Xba I. Run 1% agarose gel electrophoresis and purify with QIAEX II kit (QIAGEN Germany Ltd) to get a 4.8-kb fragment digested from pBAD 18.

At the same time, the pHY-1 plasmid is double digested with NdeI and Xba I and purified by 1% agarose gel electrophoresis to get a 715-bp fragment. Ligate this fragment with the 4.8-kb fragment digested from pBAD18 by T4 DNA ligase to construct the recombinant plasmid, and transform DH5α-competent cells. Spread the transformed cells on LB plate with Amp, culture overnight at 37° C.

Screening Positive Clone

Randomly choose *E. Coli*. colonies from above LB-plate, and screen positive clones containing recombinant plasmid with full length rsIFN-co (SEQ ID NO: 1) cDNA by endonuclease digesting and PCR analysis. One of the positive recombinant plasmid was named pHY-5, and the strain containing pHY-5 plasmid was named PVIII. Amplify PVIII and store at −80° C. with glycerol.

High Expression of rSIFN-co (SEQ ID NO: 1) Gene in *E. Coli* LMG194

In pHY-5 plasmid, rSIFN-co (SEQ ID NO: 1) gene is under control of the strong promoter $P_{BAD}$. This promoter is positively and negatively regulated by the product of the gene ara C: Ara C. AraC is a transcriptional regulator that can forms a complex with arabinose. In the absence of arabinose, the dimer of Ara C binds to $O_2$ and $I_2$ forming a 210-bp loop. This conformation leads to a complete inhibition of transcription. In the presence of arabinose, the dimer is released from $O_2$ and binds to $I_1$ and $I_2$ leading to transcription. Therefore, Arabinose can activate $P_{BAD}$ promoter and inducing a high expression of rSIFN-co (SEQ ID NO: 1). rSIFN-co (SEQ ID NO: 1) expression level is more than 50% of the total *E. Coli* protein.

2. Separation and Purification (1) Preparation of Producing Strains

The *E. coli* engineering strain LMG194 with expression vector pHY-5 is inoculated in LB culture medium, then shake at 200 rpm overnight (about 18 h) at 37° C. Add 50% of glycerine with the concentration of 30% into bacterium culture solution, fully mixed and stored at −20° C. in 1 ml aliquot as producing strain.

(2) Preparation of Seed Strain Level-I

The producing strain was inoculated in LB culture medium (including Tryptone 10 g, Yeast extracts 5 g and NaCl 10 g per 1 L), then shake at 200 rpm overnight (about 18 h) at 37° C. And this is regarded as seed strain level-I.

(3) Fermentation and Collect the Strain

% v/v of seed strain level-I was inoculated in RM culture medium (including Casein 20 g, $MgCl_2$ 1 mmol/L (0.203 g), $Na_2HPO_4$ 4 g, $KH_2PO_4$ 3 g, NaCl 0.5 g and $NH_4Cl$ 1 g per 1 L). Let it ferment under the condition of 37° C. and pH 7.0 until OD reaches about 2.0. Induce by adding 20% arabinose (terminal concentration: 0.02%) and collected bacteria 4 hours later. Get the pellet after centrifugation.

(4) Preparation of Inclusion Bodies

The pellet is resuspended with appropriate amount of buffer A (100 mmol/L Tris-HCl, pH 7.5, 10 mmol/L EDTA, 100 mmol/L NaCl) and stored at −20° C. overnight. Break and homogenize by homogenizer after thawing, centrifuge, wash the pellet with buffer B (50 mmol/L Tris-HCl pH 7.5, 1 mol/L urea, 10 mmol/L EDTA, 0.5% Triton X-100) and buffer C (50 mmol/L Tris-HCl pH 7.5, 2 mol/L urea, 10 mmol/L EDTA, 0.5% Triton X-100) respectively for two times, and wash with distilled water for the last time. Then the pellet is the inclusion bodies.

(5) Renaturation Treatment

The inclusion body was dissolved in 6 mol/L Guanidine-HCl or urea and subsequently centrifuged at the speed of 10000 rpm. The supernatant was collected and used to analyze the contents of protein. Add denatured solution separately in three times into renaturation buffer (0.5 mol/L Arg, 150 mmol/L Tris-HCl, pH 7.5, 0.2 mmol/L EDTA) until the final concentration of protein reached 0.3 mg/ml and stirring at 4° C. overnight (about 18 h). After that, dialyze with 10 times volume of 10 mol/L PB buffer, 5 mol/L PB buffer and distilled water in turn and subsequently adjust its pH by 2 mol/L HAc—NaAc (pH 5.0). Let it stand, then filtrate.

(6) POROS HS/M Anion Exchange Chromatography

Equilibrate column with 20 mmol/L HAc—NaAc (pH 5.0) before loading samples (obtained from step (5)) at speed of 30 ml/min. Then wash the column with 20 column volumes (CV) of 20 mmol/L HAc—NaAc (pH 5.0), 5 CV of 20 mmol/L HAc—NaAc (pH 5.0)-0.15 mol/L NaCl and 3 CV of 20 mmol/L HAc—NaAc (pH 5.0)—0.18 mmol/L NaCl subsequently. Elute the target protein with buffer containing 20 mmol/L HAc—NaAc (pH 5.0) and 0.25 mol/L NaCl.

(7) Copper Ion Affinity Chromatography (Chelating Sepharose™ Fast Flow)

Prepare loading sample by adding protein solution eluted from HS column into buffer of 0.2 mol/L PB, pH 6.6 and adjusting concentration of NaCl to 1 mol/L and pH 6.0 by 4 mol/L NaCl. Equilibrate column with 50 mmol/L $Na_2HPO_4$ (pH 5.5) containing 1 mol/L NaCl, and load sample at rate of 1 ml/min. Wash column with buffers of 1 mol/L NaCl-50 mmol/L $Na_2HPO_4$ (pH 5.0) and 1 mol/L NaCl-50 mmol/L $Na_2HPO_4$ (pH 4.0) subsequently. Elute target protein with 1 mol/L NaCl-50 mmol/L $Na_2HPO_4$ (pH 3.6).

(8). HS Column Chromatography Dilute protein solution eluted from the chelating column 30 times and adjust pH to pH 5.0, then loading samples and elute with PB buffer, pH 7.0, containing 0.5 mol/L NaCl. Pool the eluate as protein stock solution of rsIFN-co (SEQ ID NO: 1).

Example 2

Preparation of Recombinant Interferon

Formula of Lyophilized Injection:

| | |
|---|---|
| the present invention rSIFN-co (SEQ ID NO: 1)stock solution | 34.5 µg/ml |
| phosphate buffer, pH 7.0 | 10 mmol/L |
| glycine | 0.4 mol/L |

Preparation Technology:

Materials were weighed according to the prescription, dissolved in sterile and pyrogen-free water for injection and filter sterilized using a membrane with 0.22 µm aperture, The prepared solution was then preserved at 6-10° C. until it was qualified by sterility test and pyrogen-free test, before subpackaged to vials. Every single dose is 0.3 ml or 0.5 ml. All the subpackaged samples were lyophilized in lyophilization machine.

Formula of Aqueous Injection:

| | |
|---|---|
| the present invention rSIFN-co (SEQ ID NO: 1)_stock solution | 34.5 µg/ml |
| phosphate buffer, pH 7.0 | 25 mmol/L |
| NaCl | 0.4 mol/L |

Materials were weighed according to the prescription and dissolved in sterile and pyrogen-free water for injection, filter sterilized using a membrane with 0.22 µm aperture, preserved at 6-10° C., and sampled to do a sterile and heat source test. The prepared solution was then preserved at 6-10° C. until it was qualified by sterility test and pyrogen-free test, before subpackaged to vials. Every single dose is 0.3 ml or 0.5 ml. Final products were stored in a dark place at 2-10° C.

Example 3

Pharmacokinetics and Bioequivalence Comparative Study Between rsIFN-Co (SEQ ID NO: 1) and INFERGEN (SEQ ID NO: 1)

The example relates a research of pharmacokinetics and bioequivalence comparative study between rSIFN-co (SEQ ID NO: 1) and INFERGEN (SEQ ID NO: 1). Take the present recombinant interferon rSIFN-co (SEQ ID NO: 1) and INFERGEN (SEQ ID NO: 1) produced by U.S. Amgen as trial drugs respectively, so as to compare their pharmacokinetics and bioequivalence.

A pharmacokinetics study of interferon in a healthy body is difficult in interferon research. Due to the fact that medicinal interferon levels in plasma are tiny after infection, Enzyme-linked immunosorbent assay (ELISA) or virus cytopathic inhibition assay can hardly measure it directly in the serum of healthy adults. Recently, the detection index used for a pharmacokinetics study of interferon is generally 2',5'-OAS (2-5 A oligonucleotidase): it is an object induced by production of interferon, but also is representative of interferon's efficaciousness.

Object and Method

1. Object

There were 18 healthy male volunteers, average age is 22.8±1.4, height is 170±5.0 cm, BMI is 20.5±2.4, and body weight is 59.4±7.2 kg. Subjects are ensured normal by a comprehensive physical examination, laboratory tests (including hematology, urine, liver and kidney function) and electrocardiogram. These subjects have not participated in drug trials within four weeks and have not used known drugs which can damage some organs within three months. These subjects have no the allergic history of test drug and must take part voluntarily and sign an information consent form.

2. Method

The experimental scheme is approved by Medical Ethics Committee of West China Hospital, Sichuan University, operated in accordance with relevant guidelines of GCP of the PRC.

(1) Reagents

Test preparation: Efficient recombinant interferon Lyophilized powder for injection (Experimental preparations, i.e. the recombinant interferon rSIFN-co (SEQ ID NO: 1), 9 g/bottle).

Control preparation: INFERGEN (SEQ ID NO: 1) injection (Control reagent, 9 g/bottle) produced by U.S. Amgen.

2-5 A Kit: Eiken' Radioimmunoassay Kit was supplied by Eiken Chemical Co., LTD. The Kit includes: (1) $I_{125}$-labelled 2',5'-OAS, (2) Anti-2',5'-OAS serum, (3) 2',5'-OAS Standard liquid (each contains 0, 10, 30, 90, 270 or 810 µmol/dL 2',5'-OAS), (4) Buffer, (5) Blank serum, (6) Poly(I)-poly(C) agarose gel, (7) ATP, (8) Mercaptoethanol, (9) Quality control serum.

(2) Experimental Design and Dose Methods

In a random crossover controlled trial, 18 subjects were randomly divided into A and B groups, each group comprising nine people, with cross subcutaneous injection respectively with 9 µg rSIFN-co (SEQ ID NO: 1) and 9 µg INFERGEN (SEQ ID NO: 1) in two cycles, one week of wash period.

Fasting from eight o'clock at night the day before the test day to 2 h after dose the next morning, subcutaneous injections were taken in the brachial deltoid muscle at 7:00 in the morning. All the subjects were required to have unified meals (food without high fat), and forbidden to smoke, drink, take tea, coffee beverages, and exercise intensely. All drugs were banned during the tests.

(3) Blood Collection and Detection 4 ml blood samples was drawn before dose, while 3.5 ml blood samples were respectively drawn at 2, 6, 12, 18, 22, 24, 26, 30, 34, 38, 42 and 48 hours after injection from the elbow vein which was opposite the injection position, centrifuged immediately; the serum was preserved at −20° C. until the test. The serum 2',5'-OAS concentration was thereafter detected.

3. Statistical Methods

Using the DAS ver1.0 statistical software, test preparation and reference preparation were compared with paired t test.

Results

Figure 16:
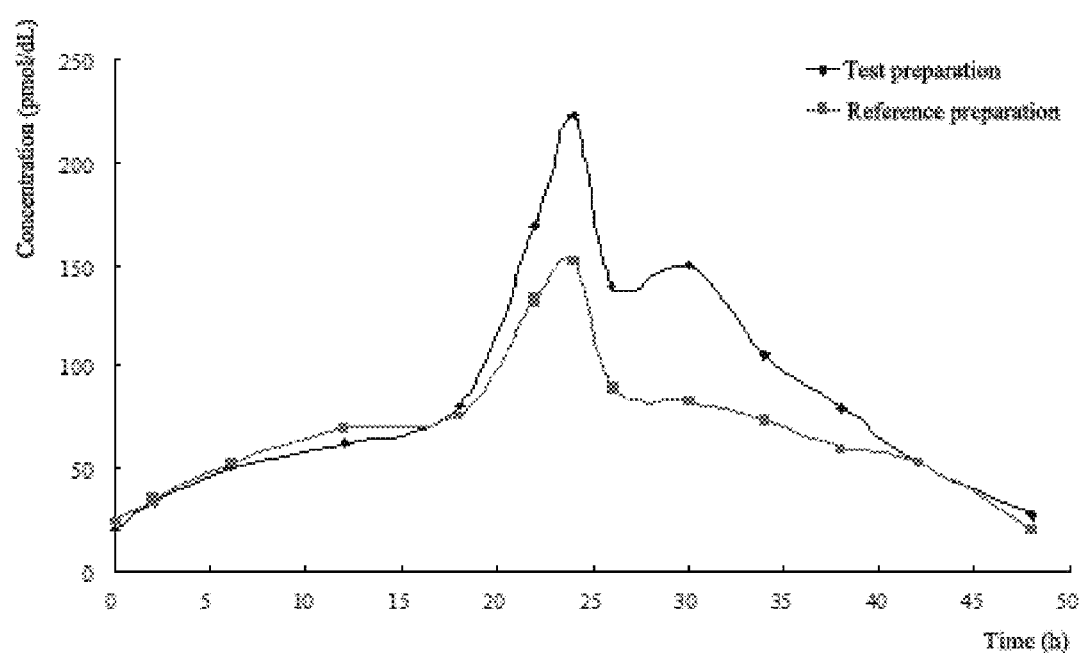
FIG. 16 shows the blood enzyme mean concentration-time curve after subcutaneous injection to 18 subjects with 9 μg rSIFN-co (SEQ ID NO: 1) and 9 μg INFERGEN® (SEQ ID NO: 1).

According to the measured serum 2',5'-OAS concentration, the mean enzyme concentration-time curve was drawn, see FIG. 16. As is shown in FIG. 16, the enzyme concentration-time curves had similar shape in both cases, but after subcutaneous injection of rSIFN-co (SEQ ID NO: 1), enzyme concentration-time curve peak concentration in blood was significantly higher than that of INFERGEN (SEQ ID NO: 1). The relative bioavailability (F) of Test preparation (rSIFN-co (SEQ ID NO: 1)) compared to reference preparation (INFERGEN (SEQ ID NO: 1)) can be calculated by the following formula:

$$F=[\text{AUC}_{test\ preparation}/\text{AUC}_{reference\ preparation}]\times[\text{reference preparations dose/test preparation dose}]\times 100\%$$

The results show that rSIFN-co (SEQ ID NO: 1) relative bioavailability (F0-48) was 125.4%. The $T_{max}$ difference between test preparation and reference preparation had no statistically significance (t=1.458, P=0.163). The difference between $AUC_{0-48}$ and $C_{max}$ had statistical significance (t=2.730, P=0.014; t=2.347, P=0.031), and the test preparation was higher than the reference preparation. In addition, adverse reactions were compared. The adverse reactions of the INFERGEN (SEQ ID NO: 1) group are higher than rSIFN-co (SEQ ID NO: 1) group in the incidence, extent and duration of the three aspects.

Conclusion (1) After subcutaneous injection respectively, both rSIFN-co (SEQ ID NO: 1) and INFERGEN (SEQ ID NO: 1) can induce 2',5'-OAS. The pharmacokinetics curves of the two drugs were of the same trend, and the main pharmacokinetics parameters showed no significant difference.

(2) The $C_{max}$ and $AUC_{0-48}$ of 2',5'-OAS induced by rSIFN-co (SEQ ID NO: 1) were larger than those of INFERGEN (SEQ ID NO: 1), indicating that rSIFN-co (SEQ ID NO: 1), at the same dose, whose efficacy may be better than INFERGEN (SEQ ID NO: 1).

(3) The adverse reactions of the INFERGEN (SEQ ID NO: 1) group are higher than rSIFN-co (SEQ ID NO: 1) group in the incidence, extent and duration of the three aspects.

(4) According to the serum 2',5' oligoadenylate synthase (2',5'-OAS) content measured at different times, the mean enzyme concentration-time curve was drawn. As shown in the curve, the 2',5'-OAS concentration induced by injection of rSIFN-co (SEQ ID NO: 1) generally appeared in double peaks and the area under the curve was significantly greater than that obtained by injection of INFERGEN (SEQ ID NO: 1) under the same conditions. The area under the curve did not increase the incidence of adverse reactions and/or the occurrence degree.

Example 4

Crystallization of Recombinant Interferon

The preparation of high-quality rSIFN-co (SEQ ID NO: 1) protein monocrystal was a prerequisite for determining its crystal structure. The present invention rSIFN-co (SEQ ID NO: 1) was used for crystal growth. The preparation method of the rSIFN-co monocrystal (SEQ ID NO: 1), the technical process, crystallization conditions and crystallographic parameters were as follow:

The present invention rSIFN-co (SEQ ID NO: 1), whose initial protein concentration was 0.42 mg/ml, was preserved at low temperature (−20° C.) in purified water. For initial crystallization trials, rSIFN-co (SEQ ID NO: 1) samples were concentrated to 3-3.5 mg/ml. Then, the samples were used for crystal growth experiment. Crystallization was completed by the hanging drop vapor diffusion method at room temperature (293K).

Figure 1:
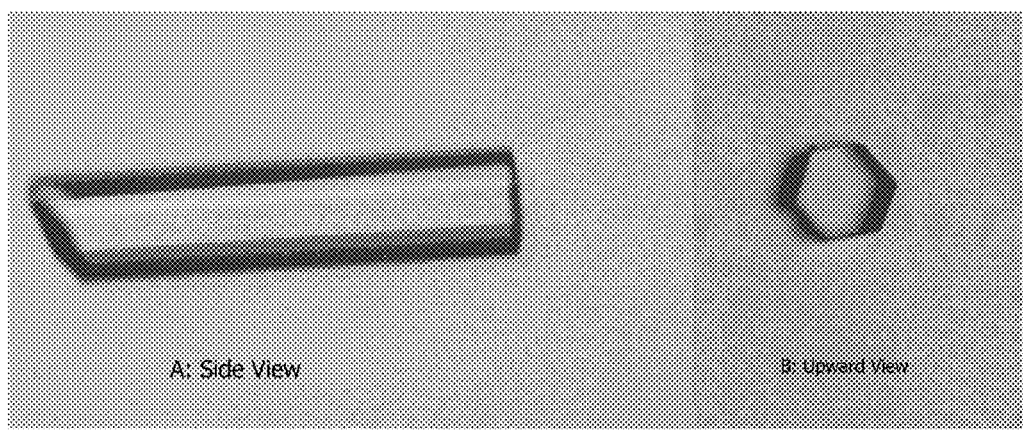
FIG. 1 shows a monocrystal of the recombinant interferon (rSIFN-co (SEQ ID NO: 1)) of the present invention for crystal structure analysis.

In the initial crystallization studies, microcrystalline rSIFN-co (SEQ ID NO: 1) could appear in multiple series, but it was difficult to obtain high-quality monocrystals that could be used for X-ray diffraction analysis and obtain sufficient resolution. After optimization of a large number of crystallization conditions, it was found that the crystallization condition of the best quality crystal obtained was 1.2M $LiSO_4$, 0.1M CAPS (3-(CYCLOHEXYLAMINO)-1-PROPANE-SULFONIC ACID), pH 11.1, 0.02M $MgCl_2$. A good monocrystal of rSIFN-co (SEQ ID NO: 1) protein was obtained after the prepared crystallization solution was left standing 3 days to 1 week. The monocrystal was tripartite crystal type, and its size was 0.42×0.08×0.08 mm. The rSIFN-co (SEQ ID NO: 1) protein crystal that was used for X-ray diffraction crystal structure analysis was shown in FIG. 1.

Example 5

Analysis of Crystal X-Ray Diffraction

Crystal Diffraction Data Collection:

Data collection was completed under low temperature conditions (100K) at synchrotron radiation BL5A line station of photon factory in Tsukuba, Japan. The crystal diffraction data was collected through the following steps:

(1) Under the microscope, a crystal placement tool was carefully used to gain crystals from mother liquor at the top loop of the tool.

(2) The loop containing the crystals was quickly soaked in antifreeze reagent paraffin oil (bought from Hampton Research Company) using quick-freezing technique (Flash-Cooling). Several seconds later, the crystal placement tool was quickly put on the goniometer head of the diffraction apparatus. At this time, crystal was placed in the low-temperature nitrogen stream (100K), which made the data collection under 100K low temperature.

(3) Data collection started after setting parameters, light source wavelength was 1.0 Å, detector was ADSC Quantum315CCD (charge-couple device detector), the crystal-to-detector distance was 310 mm. Datum were collected using oscillation method, oscillation angle of every picture used was 1°, exposure time was 12 seconds, and 110 pictures were collected in all (FIG. 2).

Figure 2:
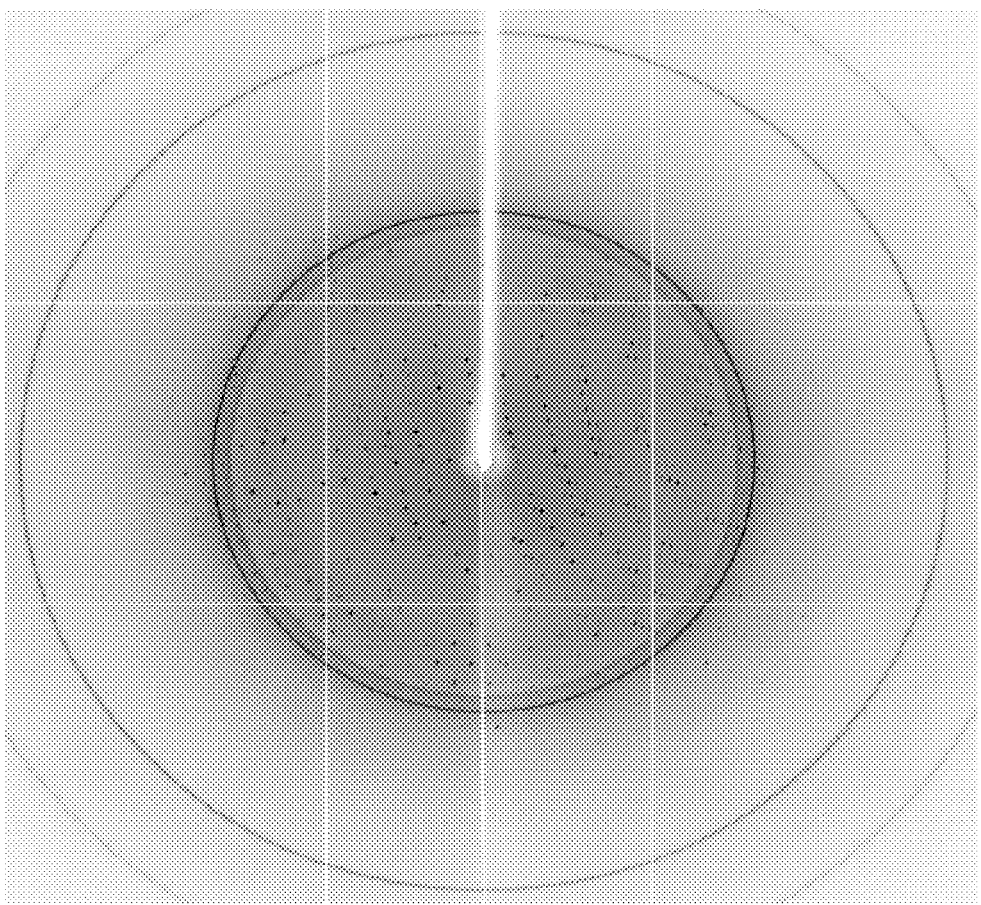
FIG. 2 shows an X-ray diffractogram of rSIFN-co crystal (SEQ ID NO: 1) (2.6 Å resolution).

Diffraction Data Processing and Analysis:

Firstly, the diffraction test collection obtained a set of intuitional diffraction images (FIG. 2). These images could be processed and analyzed using CCP4 through complete set of diffraction data collected, so that they could be used for diffraction data quality assessment and structural analysis. This process included: 1) indexing: transforming the diffraction data to crystallography index (h, k, l), and calculating unit cell parameter and space group; 2) parameter modification: Refining the distance and angle among cell parameters, crystals and detector and mosaic degrees and so on; 3) integration: Get intensity information from diffraction spot; 4) Data merge: Merged all symmetry related and reduplicate diffraction spots, generated a set of complete data constructed by independent diffraction spots; 5) Transformation of intensity data to structure amplitude. Results of rSIFN-co (SEQ ID NO: 1) crystal data collection and analysis are seen in Table 1.

TABLE 1

Results of rSIFN-co (SEQ ID NO: 1) crystal data collection and analysis

| | rSIFN-co |
|---|---|
| Data acquisition conditions | |
| X-ray source | PF, BL-5A |
| Wavelength (Å) | 1.0 |
| Detector | ADSC Quantum 315 CCD |
| Distance (mm) | 310 |
| Temperature (K) | 100 |

TABLE 1-continued

Results of rSIFN-co (SEQ ID NO: 1) crystal data collection and analysis

| | rSIFN-co |
|---|---|
| Data acquisition statistics | |
| Space group (number of molecules/asymmetric unit) | P3₁21(2) |
| Cell parameters | |
| a = b (Å) | 77.920 |
| c (Å) | 125.935 |
| α = β = 90°, γ = 120° | |
| Solvent content (%) | 56.7 |
| Resolution coverage (Å) | 67.58-2.60 |
| Diffraction spots (I/σ (I) > 0) | 86556 |
| Unique diffraction spot (I/σ (I) > 0) | 14052 |
| Outermost shell | 2.74-2.60 |
| Symmetry related diffraction spot quality factor R (%): | |
| Overall, (Outermost shell) | 7.1 (25.8) |
| Signal to noise ratio | 21.2 (4.5) |
| Intigrity (%): overall, (Outermost shell) | 99.5 (100.0) |
| Redundancy: overall, (Outermost shell) | 6.2 (6.5) |

Example 6

Analysis of Crystal Structure

Crystal Diffraction Phase Determination and the Construction of rsIFN-Co (SEQ ID NO: 1) Molecular Initial Structural Model The phase resolve of rSIFN-co (SEQ ID NO: 1) crystal structure adopted the molecular replacement method, selecting the crystal structure (PDB number 1B5L) of sheep INF-τ (54% sequence homology to rSIFN-co (SEQ ID NO: 1)) as the homologous structure model. The software program PHASER was used for analysis of accounts of rotation Function and translation Function in order to presume the location and orientation of rSIFN-co (SEQ ID NO: 1) molecules in the unit cell. In accordance with the discipline of Laue Group and systematic absence, it was determined space group being P3₁21 and simultaneously modified the molecular model (viz. preserving 12-25, 37-69, 79-101, 114-151 residues in the 1B5L structure). Calculation result followed from this: Z-score is 15.71, I1-gain is 307.79, clash is 0. Molecules in unit cell heaped up reasonably, and IL-gain gradually rose during the process of molecular replacement, indicating that the exact solution and determined initial phase of each diffraction point were attained. In turn, the mtz accompanied with initial phase which generated by PHASER was used to build the electron density map. Because the molecular initial structural model attained was well-matched of the electron density map, it was confirmed that the exact phase solution of all diffraction points of rSIFN-co (SEQ ID NO: 1) were attained. Based on the result above, the rSIFN-co (SEQ ID NO: 1) molecular initial structural model was built.

Rectification of rSIFN-co (SEQ ID NO: 1) Structural Model

With the aim of attaining an accurate rSIFN-co (SEQ ID NO: 1) molecular structural model, the coordinate parameters and temperature factors of all the non-hydrogen atoms in the rSIFN-co (SEQ ID NO: 1) molecular initial structural model underwent iterative refinement by molecular modeling and computerized optimization program.

Program CNS1.1 was used for structure modification. The data was phaseless population data, 10% of which was randomly extracted as testing set, and the same testing set extracted randomly was kept throughout. All the atoms in the structural model participated in the modification, and each atom possessed 4 modified parameters, including coordinates (x, y, z) and isotropic temperature factor B. In the entire process of modification, computerized automatic structure model modification was interchanged with manual adjustment constructed using software O. Restrictive NCS was used at the beginning of modification, and was out of use as long as structural adjustment basically accomplished. When Rwork factor (beneath 0.30) and Rfree factors remained practically undescended, water and solvent molecules were beginning to be added to the structure. Structure rectification was finally done, with Rwork value being 0.250, Rfree value being 0.286 as the major rectification indexes. The final major indexes of rSIFN-co (SEQ ID NO: 1) structure rectification are listed in Tables 2. The resulting atomic coordinates of rSIFN-co (SEQ ID NO: 1) was shown in Table 5.

TABLE 2

Major parameter indexes and qualitative statistical results of rSIFN-co (SEQ ID NO: 1) molecular structure

| | |
|---|---|
| Resolution ratio range(outermost shell) (Å) | 20.0-2.6 |
| Cutoff point of signal-to-noise | 0.0 |
| Crystallographic incongruent indexes (outermost shell) (%) | 25.0 (36.3) |
| Free incongruent indexes[1] (outermost shell) (%) | 28.6 (40.5) |
| Component of asymmetric unit | |
| Number of all the residues | 293 |
| Number of A chain residues (unbuilt residues) | 146 (20) |
| Number of B chain residues (unbuilt residues) | 147 (19) |
| Molecular number of water and solvent | 123 |
| Root mean square deviation[2] | |
| Bond length (Å) | 0.007 |
| Bond angle (°) | 1.379 |
| Dihedral angle (°) | 19.234 |
| Unfit angle (°) | 0.844 |
| Wilson temperature factor (Å²) | 70.7 |
| Average temperature factor (Å²) | |
| Number of all the atoms (2403) | 61.76 |
| Atomic number of protein (2254) | 61.11 |
| A chain of protein (1120) | 58.39 |
| B chain of protein (1134) | 63.79 |
| water and solvent (149) | 68.21 |
| Statistics of Ramachandran plot (%)[3] | |
| Optimal regions | 90.6 |
| Additionally regions | 9.1 |
| common allowed regions | 0.4 |
| Disallowed regions | 0.0 |

[1]Free incongruent indexes were calculated using 10% of the total diffraction points unmodified;
[2]Root mean square deviation was calculated using relative standard bond length/bond angle;
[3]Statistics of Ramachandran plot used software PROCHECK.

Example 7

Quality Characterization of rSIFN-co (SEQ ID NO: 1) Molecular Structural Model

Figure 3:
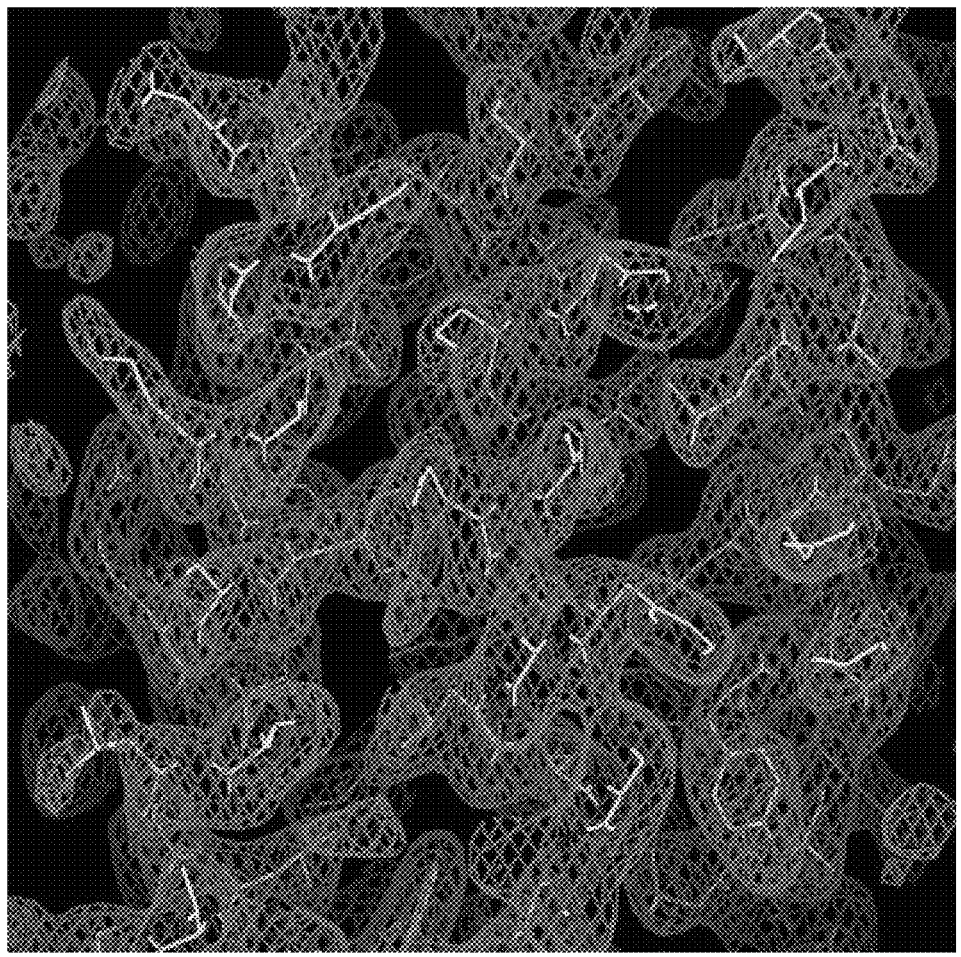
FIG. 3 shows a 1.0$\sigma$ electron-density map of 2Fo-Fc format within the crystal structure of rSIFN-co (SEQ ID NO: 1).

Quality Characterization of rSIFN-co (SEQ ID NO: 1) Molecular Structural Model (1) Electron density map of model: rSIFN-co (SEQ ID NO: 1) was displayed intuitively, clearly and accurately. FIG. 3 demonstrates views of a typical electron density map matched with the structure of amino acid residues in rSIFN-co (SEQ ID NO: 1) molecule, showing clearly the diverse spatial location and orientation of each amino acid residue.

(2) Distribution map of average temperature factor was along with the amino acid residues. (FIG. 4)

(3) Molecular stereochemical index—Ramachandran plot. Stereochemical rationality of rSIFN-co (SEQ ID NO: 1) molecule was represented by Ramachandran conformational plot (FIG. 5), showing 90.6% of the amino acid residues structure located in the optimal allowed regions, 9.1% in the allowed regions, 0.4% in the common allowed regions. This manifested that the rSIFN-co (SEQ ID NO: 1) molecular structural model was stereochemically rational.

Example 8

Crystal Structure Characteristics of rSIFN-co (SEQ ID NO: 1) Molecule

Stacking and Global Assignment of rSIFN-co (SEQ ID NO: 1) Molecule In Crystal

Figure 6:
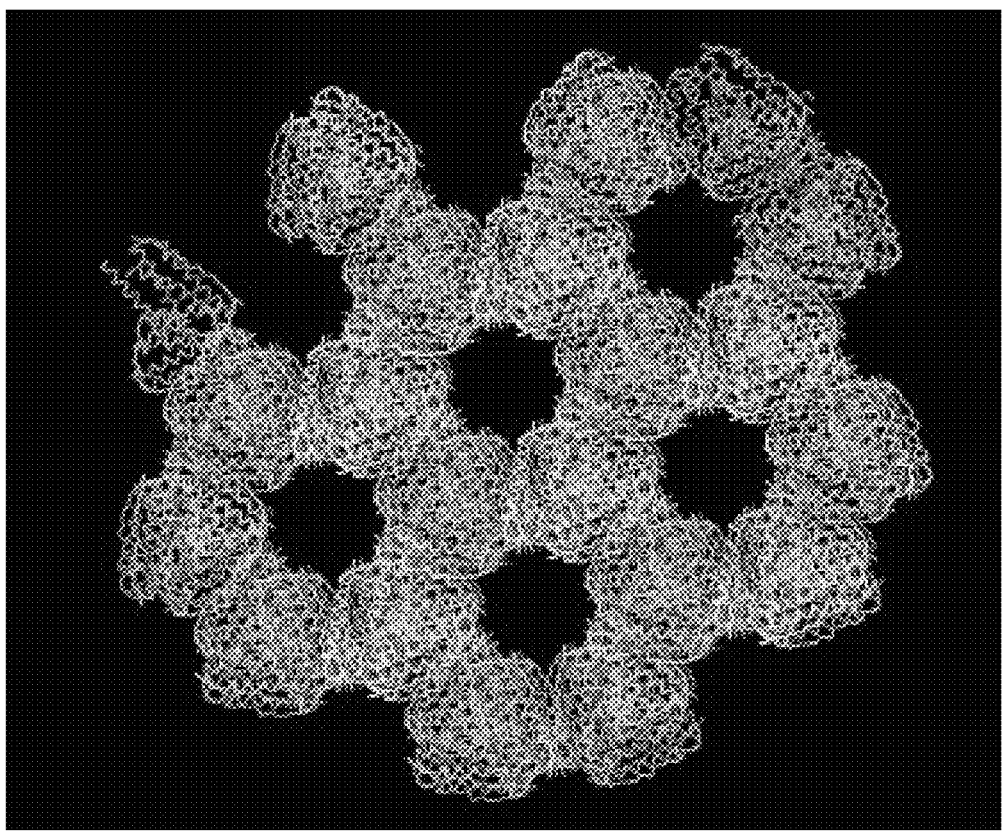
FIG. 6 shows a unit cell accumulation map of rSIFN-co (SEQ ID NO: 1).
Figure 7:
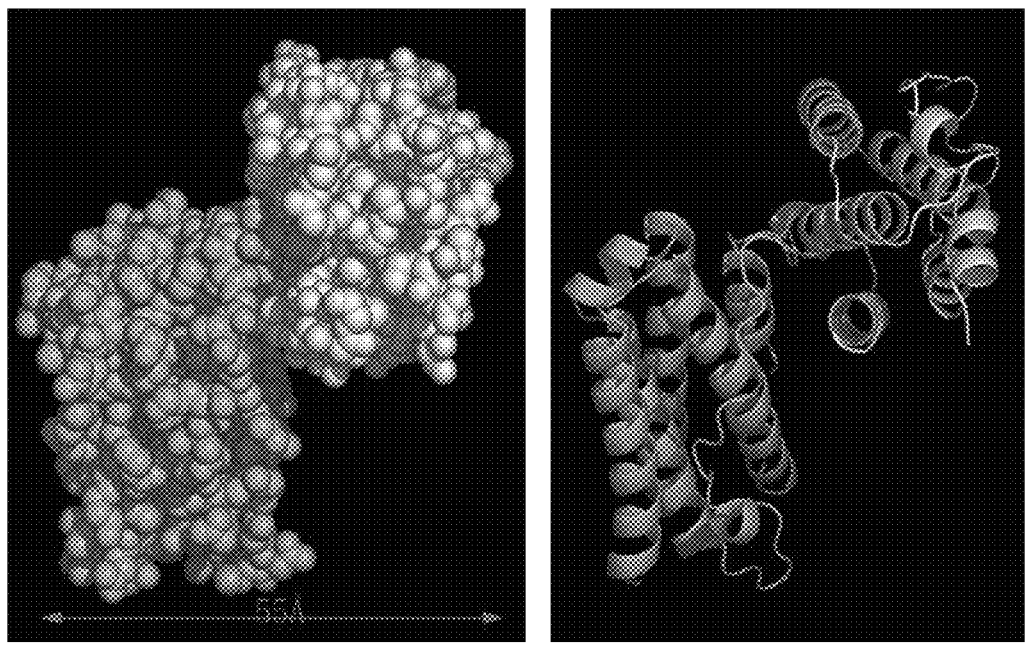
FIG. 7 shows a combination structure of rSIFN-co dimer (SEQ ID NO: 1).

FIG. 6 showed the stacking manner of the rSIFN-co (SEQ ID NO: 1) molecule in unit cell. An asymmetric unit in the rSIFN-co (SEQ ID NO: 1) crystal structure included two protein molecules (called crystallographic dimers) (FIG. 7). The embedding area among the dimer was 1033.3 Å$^2$ and each monomer contributed 516.6 Å$^2$ area that only accounted for 6.4% of the total area in the monomer. The A,B,F side of the A chain in the dimer corresponded to the C,D,E side of the B chain (see FIG. 9) Using software VADAR to calculate the monomer, the folding free energy of the dimer respectively was −126.9, −257.1, which meant the folding free energy of the dimer was quite close to the free energy of these two isolated monomers (−126.9×2). This manifested interaction between dimer was relatively weak. Meanwhile, there were only two weak hydrogen bonds among the dimer A12(ARG) NH$_2$ ... NH$_2$ B71(Arg), 3.05 Å; A145(Arg) NH$_1$ ... OH B90 (Tyr), 3.14 Å.

In the experiments regarding purification, the solution state of rSIFN-co (SEQ ID NO: 1) was proved to be monomer. Biochemistry function experiments have indicated that function unit of the kind of IFN-α is monomer. Therefore, this dimer may be formed from crystal packing.

Dimer Structure

Figure 8:
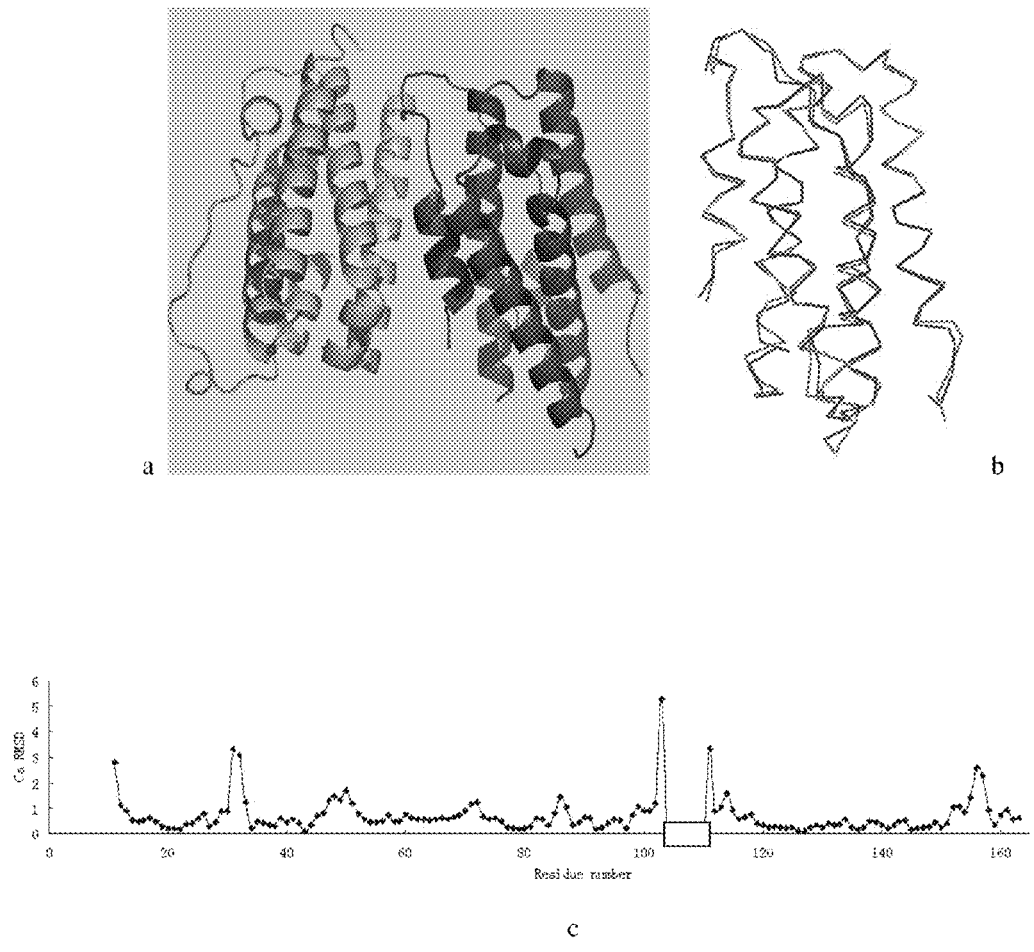
FIG. 8 shows the association of rSIFN-co dimer (SEQ ID NO: 1) (FIG. 8*a*, FIG. 8*b*) and the root-mean square deviation (RMSD) of $\alpha$ carbon atoms (the boxes represent missing residues) (FIG. 8*c*).

Two rSIFN-co (SEQ ID NO: 1) molecules in an asymmetric unit form a dimer. FIG. 8 shows the crystallographic dimeric organization of rSIFN-co (SEQ ID NO: 1). Chain A consists of residues 11-103 and 111-163 (residues 1-10, 104-110 and 164-166, which aren't exhibited in the electron density map, are not involved in building the crystal); chain B consists of residues 11-103 and 110-163 (1-10, 104-109, and 164-166, which aren't exhibited in electron density map, are not involved in building crystal). In the crystal structure of the dimer, Cys29 and Cys139 form an intramolecular disulfide bond and the intramolecular disulfide bond from Cys1 and Cys99 is not exhibited because of Cys1. Besides, since the density of side chains aren't exhibited, residues 30-33, 47-49 of chain A and residues 30-33, 48-50 of chain B are mainly constructed as Ala or Gly. Structures of the two monomers, linked by non-crystallographic symmetry, were roughly the same (from B to A, polar angle Omega, phi, Kappa is 170.64, 94.56, 118.35, respectively; tx, ty, tz is −1.061, −0.225, 0.155 respectively.). Superimposition and comparison of the two monomers, apart from a few loops on the molecular surface of each, have comparatively large flexibility; most of residues can superimpose completely (the distribution of all Cα RMSD according to amino acid) (FIG. 8), of which 127 residues (13-30, 34-44, 53-101, 115-163), RMSD of all Cα is 0.64 Å. The difference in local structure may result from comparatively large flexibility and different environment of crystal packing.

Single Molecule Structure

Figure 9:
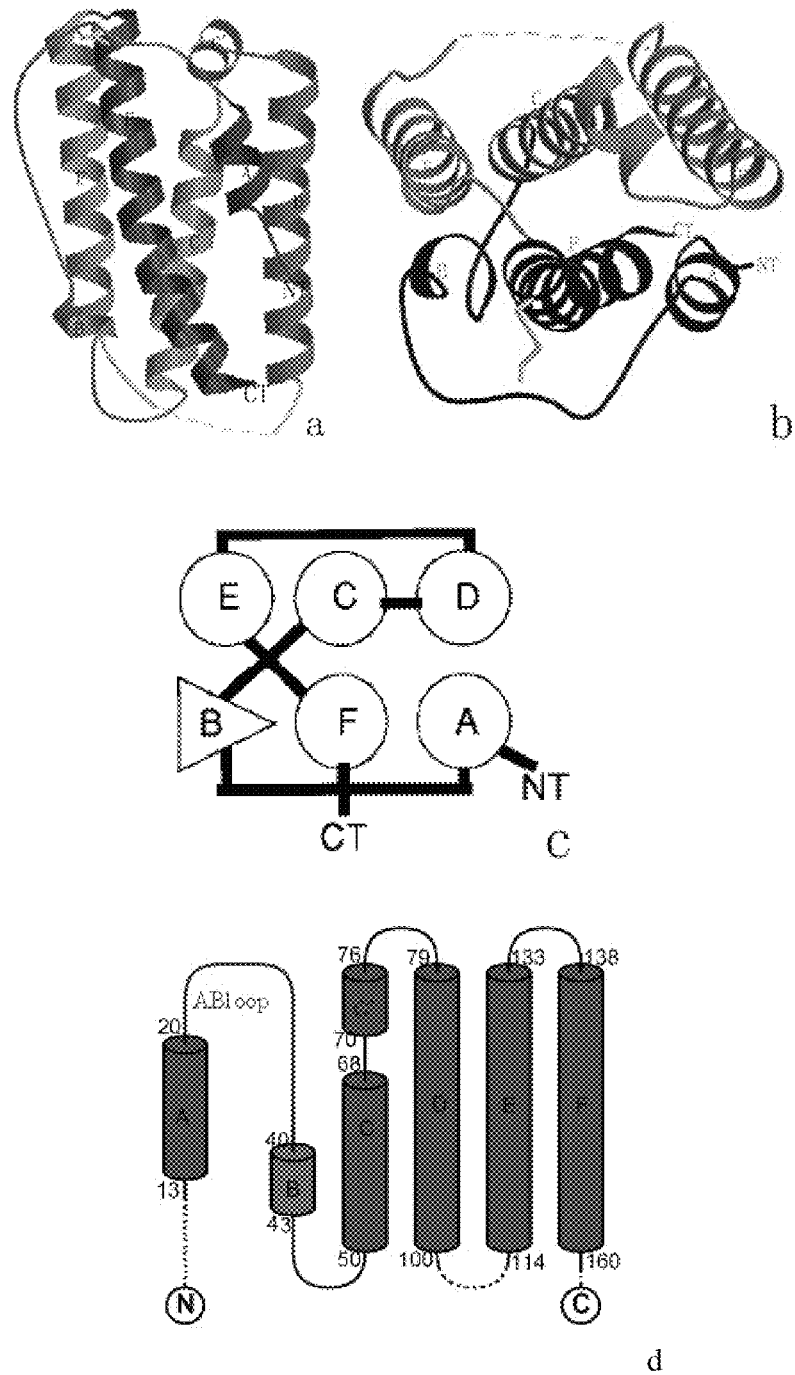
FIG. 9 shows the monomolecular structure of rSIFN-co (SEQ ID NO: 1) (main chain demonstrated only); (A) Side view; (B) Plan view; (C) Topology diagram; (D) Topology diagram of secondary structure.
Figure 10:
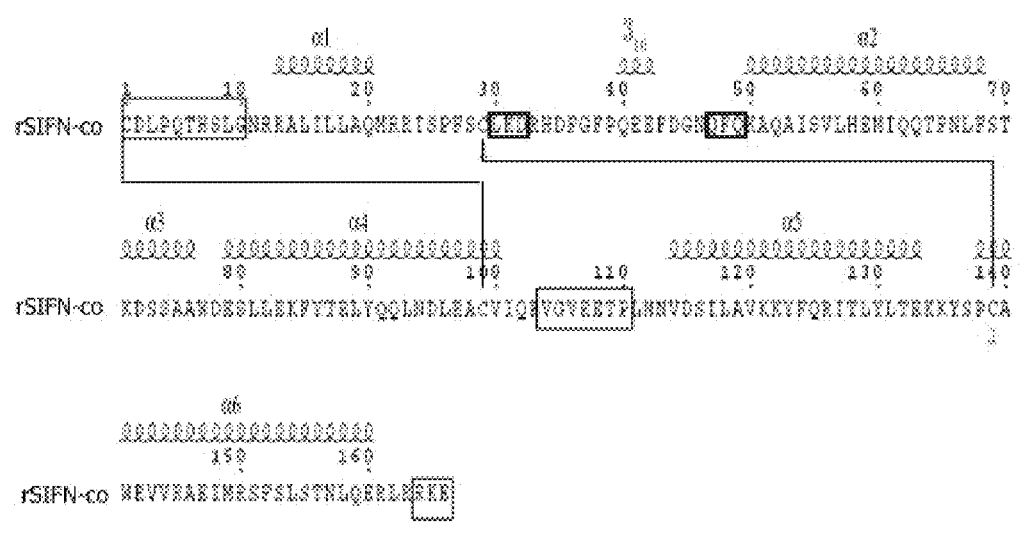

Each monomer is made up of six α-helices (A, C, C', D, E, F) and one 310 helix (B), connected to each other by loops. The overall monomer structure has been described as belonging to the helical cytokines (FIG. 9). The amino-acid residues which correspond to six α-helices (A, C, C', D, E, F) are 13-20, 50-68, 70-76, 79-100, 114-133, and 138-160, respectively. One 310 helix (B) involves residues 40-43. FIG. 9 has shown distinctly the distribution and organization of these secondary structures. FIG. 10 has demonstrated the Corresponding relationship between secondary structure and amino acid sequence.

Example 9

Three Dimensional Structure of rSIFN-co (SEQ ID NO: 1) and IFN-α2b

According to receptor, IFN can be divided into two types: type I and type II. Type I can also be separated into α, β, ω, etc. IFNα contains approximately fifteen different subtypes, typically exhibiting 80% sequence homology but diversity function. rSIFN-co (SEQ ID NO: 1) is considered to be an unnatural and artificially designed protein. To date, there are only six 3-D structures of type I IFNs (Table 3). The sequence alignment of the amino acid sequence of type I IFNs was shown in FIG. 11.

Figure 11:
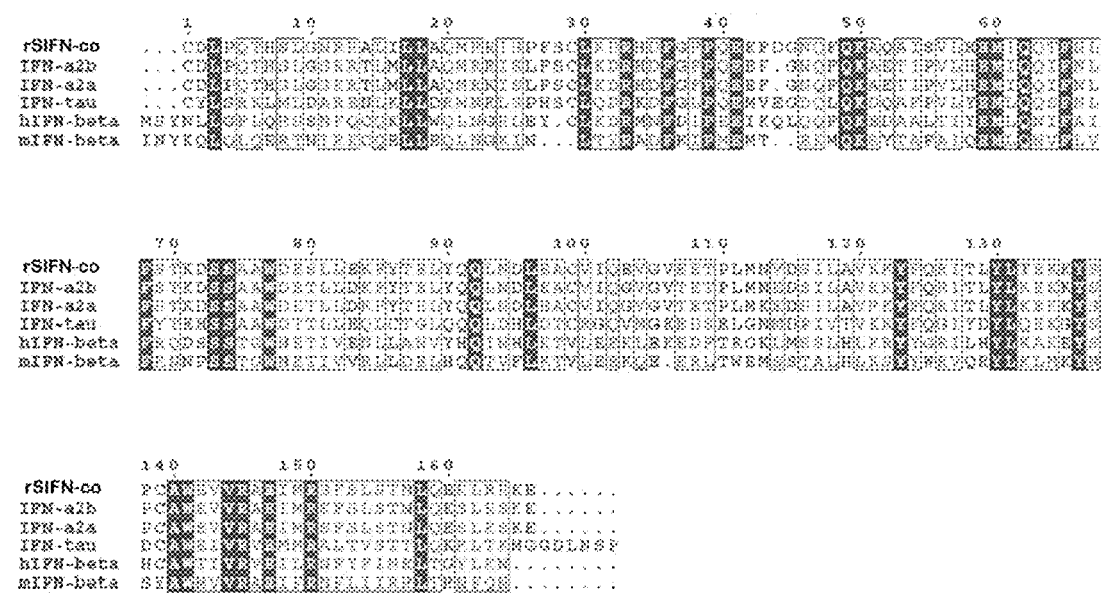
Figure 13:
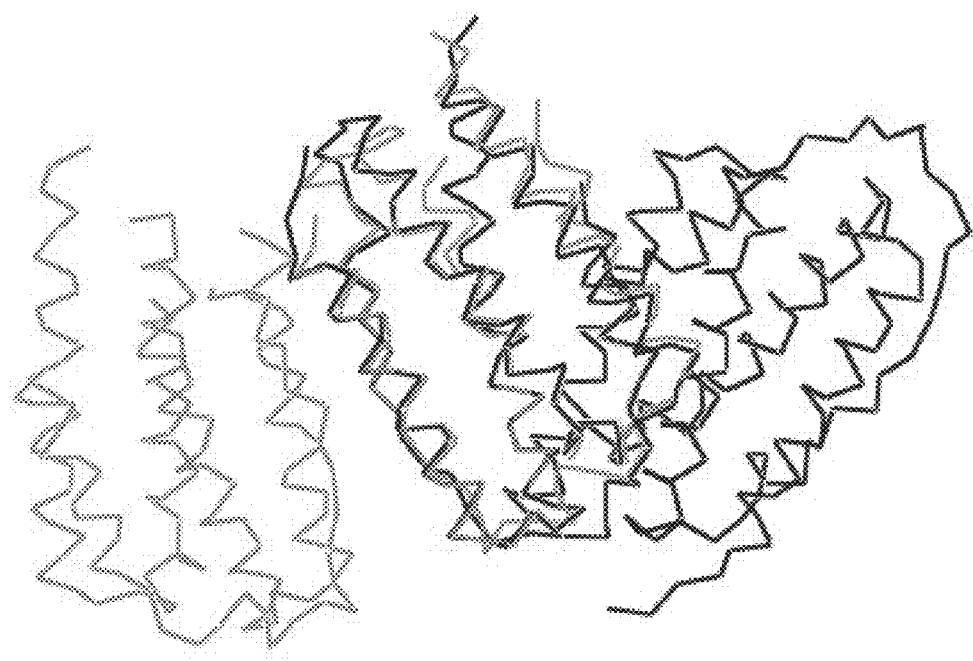
FIG. 13 shows a dimeric arrangement map of rSIFN-co (SEQ ID NO: 1) (right) and IFN-$\alpha$2b (left).

According to Table 3 and FIG. 11, the most similar crystal structure to rSIFN-co (SEQ ID NO: 1) was IFN-α2b (FIG. 12), with one more Asp than IFN-α2b at residue 45 and remarkably three dimension structure difference of the AB loop (residues 25-33) and BC loop (residues 44-52). The crystal structure of IFN-α2b has been determined at 2.9 Å, but only the coordinates of α-carbon atoms was collected in Protein Data Bank (PDB code: 1RH2). Therefore, the structure comparison between rSIFN-co (SEQ ID NO: 1) and IFN-α2b would be carried out at the α-carbon atom level. The RMSD between the α-carbon atoms was 1.577 Å, while the RMSD of AB loop and BC loop was 3.6 Å and 2.9 Å, respectively. Besides, the asymmetric unit of rSIFN-co (SEQ ID NO: 1) crystal structure consists of two moleculars while IFN-α2b is 6, which formed three dimers. These results demonstrate clear differences between the dimeric organization of rSIFN-co (SEQ ID NO: 1) and IFN-α2b (FIG. 13).

TABLE 3

The determined structure of IFNs

| Protein name | Organism | Method | Resolution (Å) | PDB code | Identify of rSIFN-co |
|---|---|---|---|---|---|
| rSIFN-co | Synthesis | X-ray | 2.6 | This invention | |
| IFN-α 2b | Human | X-ray | 2.9 | 1RH2 (Only Cα) | 89% |
| IFN-α 2a | Human | NMR | | 1ITF | 88% |
| IFN-τ | Human | X-ray | 2.1 | 1B5L | 54% |
| IFN-β | Human | X-ray | 2.2 | 1AU1 | 30% |
| IFN-β | Mouse | X-ray | 2.2 | 1RMI | 23% |

Figure 15:
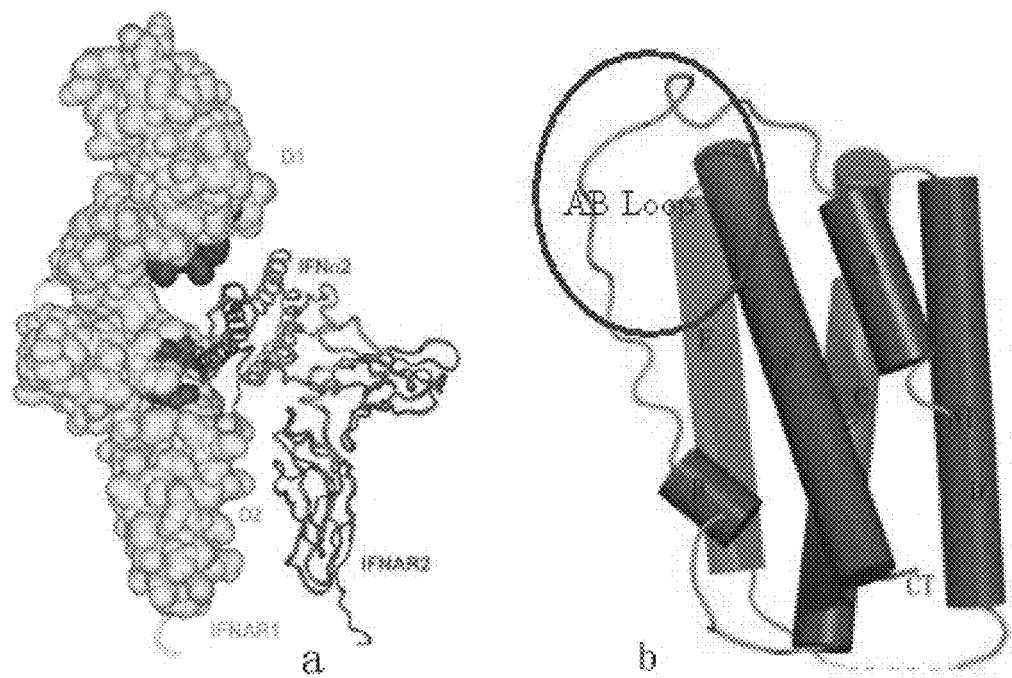
FIG. 15 shows (a) the combination model of protein IFN-α and its receptor; (b) the functional domain diagram of protein IFN-α(the important functional domain is illustrated by circle).

It is well known that IFN, a cytokine, firstly binds to the specific receptors on the cell membrane, subsequently activating many signal transduction pathways and exhibiting anti-viral, anti-tumor activities. The membrane receptors of rSIFN-co (SEQ ID NO: 1), which belongs to α-IFNs, consists of IFNAR1 and IFNAR2. And the 3-D structure model of receptors in complex with IFN-α was constructed (FIG. 15a). Based upon these finds, a series of molecular biology experiments illustrated that IFN-α interacted with IFNAR1 and IFNAR2 in a sandwich structure (FIG. 15a), in which the A, B and F side of IFN-α interacting with IFNAR2 while C, D and E side with INFAR2. Meanwhile, further site directed mutagenesis revealed the key function region of IFN-α, in which the AB loops, interacting with IFNAR2, was the primary region (FIG. 15). The structure comparison (FIG. 12 and Table 4) revealed the clear difference between the key region of rSIFN-co (SEQ ID NO: 1) and IFN-α2b. Subsequently, the difference may influence the changes of the receptor binding specificity characters, triggering different physiological or pharmacological effects.

It is clear that although the molecular skeleton of rSIFN-co (SEQ ID NO: 1) is similar with that of IFN-α2b, the key functional region bears a markedly different structure. Therefore, according to the local molecular structure associated pharmacological activities, the rSIFN-co (SEQ ID NO: 1) is a novel type of IFN. The distinction between rSIFN-co (SEQ ID NO: 1) and IFN-α2b leads to the remarkably diverse biological and pharmacological characteristics. Subsequently, on the basis of the specific key region of three dimension structure, rSIFN-co (SEQ ID NO: 1) could create the specific physiological and pharmacological effects.

TABLE 4

Root-Mean-Square Deviation (RMSD) of Cα between AB Loop and BC Loop of rSIFN-co (SEQ ID NO: 1) and IFN-α2b (unit: Å)

| Residue number of AB Loop | RMSD (Å) | Residue number of BC Loop | RMSD (Å) |
| --- | --- | --- | --- |
| 25 | 3.291 | 44 | 1.164 |
| 26 | 4.779 | 45 | 1.383 |
| 27 | 5.090 | 46 | 2.735 |
| 28 | 3.588 | 47 | 2.709 |
| 29 | 2.567 | 48 | 5.018 |
| 30 | 2.437 | 49 | 4.140 |
| 31 | 3.526 | 50 | 3.809 |
| 32 | 4.820 | 51 | 2.970 |
| 33 | 2.756 | 52 | 0.881 |
| Average RMSD of AB Loop | 3.63 | Average RMSD of BC Loop | 2.90 |
| RMSD of all Cα atoms | | | 1.60 |

TABLE 5

Atomic coordinates of rSIFN-co (SEQ ID NO: 1)

| CRYST1 | | 77.920 | | 77.920 | 125.935 | 90.00 | 90.00 | 120.00 | P 31 2 1 | |
| --- | --- | --- | --- | --- | --- | --- | --- | --- | --- | --- |
| ATOM | 1 | CB | ASN | A | 11 | −36.673 | 14.399 | −31.951 | 1.00 | 79.36 A |
| ATOM | 2 | CG | ASN | A | 11 | −37.660 | 14.647 | −33.090 | 1.00 | 81.91 A |
| ATOM | 3 | OD1 | ASN | A | 11 | −37.274 | 14.829 | −34.245 | 1.00 | 85.24 A |
| ATOM | 4 | ND2 | ASN | A | 11 | −38.947 | 14.622 | −32.764 | 1.00 | 82.54 A |
| ATOM | 5 | C | ASN | A | 11 | −34.980 | 16.273 | −31.802 | 1.00 | 76.68 A |
| ATOM | 6 | O | ASN | A | 11 | −34.061 | 16.507 | −31.007 | 1.00 | 76.57 A |
| ATOM | 7 | N | ASN | A | 11 | −34.283 | 13.985 | −31.533 | 1.00 | 78.32 A |
| ATOM | 8 | CA | ASN | A | 11 | −35.239 | 14.843 | −32.283 | 1.00 | 77.86 A |
| ATOM | 9 | N | ARG | A | 12 | −35.760 | 17.226 | −32.307 | 1.00 | 74.41 A |
| ATOM | 10 | CA | ARG | A | 12 | −35.635 | 18.622 | −31.899 | 1.00 | 69.90 A |
| ATOM | 11 | CB | ARG | A | 12 | −35.404 | 19.525 | −33.115 | 1.00 | 72.01 A |
| ATOM | 12 | CG | ARG | A | 12 | −34.052 | 19.300 | −33.792 | 1.00 | 77.29 A |
| ATOM | 13 | CD | ARG | A | 12 | −33.757 | 20.318 | −34.894 | 1.00 | 79.77 A |
| ATOM | 14 | NE | ARG | A | 12 | −32.967 | 21.461 | −34.430 | 1.00 | 83.05 A |
| ATOM | 15 | CZ | ARG | A | 12 | −31.669 | 21.635 | −34.679 | 1.00 | 84.53 A |
| ATOM | 16 | NH1 | ARG | A | 12 | −30.994 | 20.740 | −35.390 | 1.00 | 85.41 A |
| ATOM | 17 | NH2 | ARG | A | 12 | −31.049 | 22.721 | −34.235 | 1.00 | 84.48 A |
| ATOM | 18 | C | ARG | A | 12 | −36.917 | 19.021 | −31.174 | 1.00 | 65.99 A |
| ATOM | 19 | O | ARG | A | 12 | −37.334 | 20.177 | −31.210 | 1.00 | 65.41 A |
| ATOM | 20 | N | ARG | A | 13 | −37.530 | 18.037 | −30.521 | 1.00 | 61.78 A |
| ATOM | 21 | CA | ARG | A | 13 | −38.757 | 18.209 | −29.750 | 1.00 | 58.49 A |
| ATOM | 22 | CB | ARG | A | 13 | −39.049 | 16.937 | −28.963 | 1.00 | 61.57 A |
| ATOM | 23 | CG | ARG | A | 13 | −40.120 | 16.061 | −29.535 | 1.00 | 66.89 A |
| ATOM | 24 | CD | ARG | A | 13 | −40.996 | 15.577 | −28.414 | 1.00 | 69.61 A |
| ATOM | 25 | NE | ARG | A | 13 | −42.336 | 16.134 | −28.518 | 1.00 | 72.80 A |
| ATOM | 26 | CZ | ARG | A | 13 | −43.253 | 16.035 | −27.562 | 1.00 | 75.39 A |
| ATOM | 27 | NH1 | ARG | A | 13 | −42.964 | 15.403 | −26.425 | 1.00 | 74.38 A |
| ATOM | 28 | NH2 | ARG | A | 13 | −44.462 | 16.555 | −27.748 | 1.00 | 76.67 A |
| ATOM | 29 | C | ARG | A | 13 | −38.720 | 19.378 | −28.767 | 1.00 | 54.28 A |
| ATOM | 30 | O | ARG | A | 13 | −39.709 | 20.098 | −28.625 | 1.00 | 54.11 A |
| ATOM | 31 | N | ALA | A | 14 | −37.597 | 19.555 | −28.075 | 1.00 | 48.77 A |
| ATOM | 32 | CA | ALA | A | 14 | −37.481 | 20.645 | −27.116 | 1.00 | 45.39 A |
| ATOM | 33 | CB | ALA | A | 14 | −36.082 | 20.689 | −26.526 | 1.00 | 44.44 A |
| ATOM | 34 | C | ALA | A | 14 | −37.816 | 21.984 | −27.762 | 1.00 | 43.36 A |
| ATOM | 35 | O | ALA | A | 14 | −38.656 | 22.723 | −27.262 | 1.00 | 42.76 A |
| ATOM | 36 | N | LEU | A | 15 | −37.169 | 22.287 | −28.879 | 1.00 | 40.93 A |
| ATOM | 37 | CA | LEU | A | 15 | −37.402 | 23.542 | −29.568 | 1.00 | 39.71 A |
| ATOM | 38 | CB | LEU | A | 15 | −36.364 | 23.730 | −30.669 | 1.00 | 39.82 A |
| ATOM | 39 | CG | LEU | A | 15 | −34.952 | 23.714 | −30.072 | 1.00 | 40.23 A |
| ATOM | 40 | CD1 | LEU | A | 15 | −33.913 | 23.928 | −31.151 | 1.00 | 39.64 A |
| ATOM | 41 | CD2 | LEU | A | 15 | −34.850 | 24.800 | −29.005 | 1.00 | 40.94 A |
| ATOM | 42 | C | LEU | A | 15 | −38.802 | 23.667 | −30.130 | 1.00 | 40.00 A |
| ATOM | 43 | O | LEU | A | 15 | −39.372 | 24.751 | −30.100 | 1.00 | 39.95 A |
| ATOM | 44 | N | ILE | A | 16 | −39.364 | 22.572 | −30.638 | 1.00 | 40.32 A |
| ATOM | 45 | CA | ILE | A | 16 | −40.730 | 22.601 | −31.179 | 1.00 | 40.64 A |
| ATOM | 46 | CB | ILE | A | 16 | −41.213 | 21.189 | −31.637 | 1.00 | 43.33 A |
| ATOM | 47 | CG2 | ILE | A | 16 | −42.605 | 21.283 | −32.231 | 1.00 | 41.37 A |
| ATOM | 48 | CG1 | ILE | A | 16 | −40.257 | 20.590 | −32.673 | 1.00 | 44.72 A |
| ATOM | 49 | CD1 | ILE | A | 16 | −40.190 | 21.342 | −33.941 | 1.00 | 46.03 A |
| ATOM | 50 | C | ILE | A | 16 | −41.682 | 23.087 | −30.080 | 1.00 | 41.12 A |

TABLE 5-continued

Atomic coordinates of rSIFN-co (SEQ ID NO: 1)

| ATOM | 51 | O | ILE | A | 16 | −42.425 | 24.051 | −30.271 | 1.00 | 41.43 | A |
|---|---|---|---|---|---|---|---|---|---|---|---|
| ATOM | 52 | N | LEU | A | 17 | −41.662 | 22.411 | −28.930 | 1.00 | 40.37 | A |
| ATOM | 53 | CA | LEU | A | 17 | −42.516 | 22.794 | −27.812 | 1.00 | 41.00 | A |
| ATOM | 54 | CB | LEU | A | 17 | −42.303 | 21.837 | −26.640 | 1.00 | 42.66 | A |
| ATOM | 55 | CG | LEU | A | 17 | −42.835 | 20.411 | −26.850 | 1.00 | 43.03 | A |
| ATOM | 56 | CD1 | LEU | A | 17 | −42.045 | 19.434 | −25.983 | 1.00 | 39.82 | A |
| ATOM | 57 | CD2 | LEU | A | 17 | −44.328 | 20.368 | −26.526 | 1.00 | 40.26 | A |
| ATOM | 58 | C | LEU | A | 17 | −42.257 | 24.233 | −27.359 | 1.00 | 40.48 | A |
| ATOM | 59 | O | LEU | A | 17 | −43.187 | 25.022 | −27.212 | 1.00 | 39.35 | A |
| ATOM | 60 | N | LEU | A | 18 | −40.986 | 24.574 | −27.161 | 1.00 | 40.86 | A |
| ATOM | 61 | CA | LEU | A | 18 | −40.594 | 25.909 | −26.718 | 1.00 | 40.17 | A |
| ATOM | 62 | CB | LEU | A | 18 | −39.073 | 25.973 | −26.597 | 1.00 | 40.05 | A |
| ATOM | 63 | CG | LEU | A | 18 | −38.378 | 26.953 | −25.641 | 1.00 | 42.40 | A |
| ATOM | 64 | CD1 | LEU | A | 18 | −37.548 | 27.948 | −26.430 | 1.00 | 42.15 | A |
| ATOM | 65 | CD2 | LEU | A | 18 | −39.393 | 27.657 | −24.767 | 1.00 | 43.03 | A |
| ATOM | 66 | C | LEU | A | 18 | −41.094 | 26.966 | −27.698 | 1.00 | 40.88 | A |
| ATOM | 67 | O | LEU | A | 18 | −41.230 | 28.137 | −27.345 | 1.00 | 39.41 | A |
| ATOM | 68 | N | ALA | A | 19 | −41.373 | 26.539 | −28.929 | 1.00 | 41.87 | A |
| ATOM | 69 | CA | ALA | A | 19 | −41.861 | 27.432 | −29.975 | 1.00 | 44.08 | A |
| ATOM | 70 | CB | ALA | A | 19 | −41.536 | 26.866 | −31.358 | 1.00 | 42.64 | A |
| ATOM | 71 | C | ALA | A | 19 | −43.359 | 27.594 | −29.830 | 1.00 | 46.35 | A |
| ATOM | 72 | O | ALA | A | 19 | −43.905 | 28.665 | −30.090 | 1.00 | 47.47 | A |
| ATOM | 73 | N | GLN | A | 20 | −44.017 | 26.517 | −29.417 | 1.00 | 48.12 | A |
| ATOM | 74 | CA | GLN | A | 20 | −45.462 | 26.519 | −29.224 | 1.00 | 50.49 | A |
| ATOM | 75 | CB | GLN | A | 20 | −45.986 | 25.075 | −29.111 | 1.00 | 51.83 | A |
| ATOM | 76 | CG | GLN | A | 20 | −45.540 | 24.097 | −30.195 | 1.00 | 53.52 | A |
| ATOM | 77 | CD | GLN | A | 20 | −46.151 | 22.712 | −29.999 | 1.00 | 55.01 | A |
| ATOM | 78 | OE1 | GLN | A | 20 | −45.806 | 21.745 | −30.693 | 1.00 | 52.54 | A |
| ATOM | 79 | NE2 | GLN | A | 20 | −47.069 | 22.614 | −29.046 | 1.00 | 56.71 | A |
| ATOM | 80 | C | GLN | A | 20 | −45.855 | 27.284 | −27.941 | 1.00 | 51.19 | A |
| ATOM | 81 | O | GLN | A | 20 | −47.024 | 27.634 | −27.745 | 1.00 | 51.17 | A |
| ATOM | 82 | N | MET | A | 21 | −44.874 | 27.541 | −27.080 | 1.00 | 49.97 | A |
| ATOM | 83 | CA | MET | A | 21 | −45.110 | 28.204 | −25.802 | 1.00 | 48.63 | A |
| ATOM | 84 | CB | MET | A | 21 | −44.002 | 27.808 | −24.822 | 1.00 | 46.02 | A |
| ATOM | 85 | CG | MET | A | 21 | −44.097 | 26.374 | −24.330 | 1.00 | 43.96 | A |
| ATOM | 86 | SD | MET | A | 21 | −42.595 | 25.764 | −23.516 | 1.00 | 47.28 | A |
| ATOM | 87 | CE | MET | A | 21 | −42.353 | 27.001 | −22.206 | 1.00 | 42.84 | A |
| ATOM | 88 | C | MET | A | 21 | −45.272 | 29.723 | −25.809 | 1.00 | 49.74 | A |
| ATOM | 89 | O | MET | A | 21 | −45.696 | 30.303 | −24.807 | 1.00 | 49.63 | A |
| ATOM | 90 | N | ALA | A | 22 | −44.950 | 30.375 | −26.922 | 1.00 | 51.41 | A |
| ATOM | 91 | CA | ALA | A | 22 | −45.075 | 31.828 | −26.978 | 1.00 | 53.11 | A |
| ATOM | 92 | CB | ALA | A | 22 | −44.641 | 32.362 | −28.341 | 1.00 | 52.27 | A |
| ATOM | 93 | C | ALA | A | 22 | −46.517 | 32.196 | −26.716 | 1.00 | 53.84 | A |
| ATOM | 94 | O | ALA | A | 22 | −47.428 | 31.552 | −27.227 | 1.00 | 52.97 | A |
| ATOM | 95 | N | ARG | A | 23 | −46.719 | 33.225 | −25.904 | 1.00 | 56.56 | A |
| ATOM | 96 | CA | ARG | A | 23 | −48.064 | 33.683 | −25.581 | 1.00 | 59.73 | A |
| ATOM | 97 | CB | ARG | A | 23 | −48.367 | 33.484 | −24.094 | 1.00 | 60.59 | A |
| ATOM | 98 | CG | ARG | A | 23 | −48.309 | 32.059 | −23.604 | 1.00 | 62.22 | A |
| ATOM | 99 | CD | ARG | A | 23 | −48.845 | 31.998 | −22.183 | 1.00 | 66.26 | A |
| ATOM | 100 | NE | ARG | A | 23 | −50.250 | 32.397 | −22.143 | 1.00 | 70.17 | A |
| ATOM | 101 | CZ | ARG | A | 23 | −50.744 | 33.339 | −21.345 | 1.00 | 71.62 | A |
| ATOM | 102 | NH1 | ARG | A | 23 | −49.946 | 33.985 | −20.504 | 1.00 | 71.69 | A |
| ATOM | 103 | NH2 | ARG | A | 23 | −52.035 | 33.652 | −21.405 | 1.00 | 72.49 | A |
| ATOM | 104 | C | ARG | A | 23 | −48.242 | 35.158 | −25.921 | 1.00 | 61.02 | A |
| ATOM | 105 | O | ARG | A | 23 | −49.334 | 35.584 | −26.284 | 1.00 | 62.43 | A |
| ATOM | 106 | N | ALA | A | 24 | −47.171 | 35.937 | −25.799 | 1.00 | 61.98 | A |
| ATOM | 107 | CA | ALA | A | 24 | −47.236 | 37.366 | −26.080 | 1.00 | 63.61 | A |
| ATOM | 108 | CB | ALA | A | 24 | −46.139 | 38.093 | −25.319 | 1.00 | 62.75 | A |
| ATOM | 109 | C | ALA | A | 24 | −47.139 | 37.676 | −27.570 | 1.00 | 65.56 | A |
| ATOM | 110 | O | ALA | A | 24 | −46.450 | 36.983 | −28.322 | 1.00 | 65.76 | A |
| ATOM | 111 | N | SER | A | 25 | −47.848 | 38.724 | −27.984 | 1.00 | 67.91 | A |
| ATOM | 112 | CA | SER | A | 25 | −47.865 | 39.157 | −29.373 | 1.00 | 69.93 | A |
| ATOM | 113 | CB | SER | A | 25 | −49.175 | 39.887 | −29.698 | 1.00 | 71.12 | A |
| ATOM | 114 | OG | SER | A | 25 | −50.227 | 38.952 | −29.909 | 1.00 | 72.49 | A |
| ATOM | 115 | C | SER | A | 25 | −46.663 | 40.064 | −29.610 | 1.00 | 71.13 | A |
| ATOM | 116 | O | SER | A | 25 | −46.236 | 40.806 | −28.726 | 1.00 | 71.22 | A |
| ATOM | 117 | N | PRO | A | 26 | −46.109 | 40.027 | −30.825 | 1.00 | 71.97 | A |
| ATOM | 118 | CD | PRO | A | 26 | −46.787 | 39.560 | −32.046 | 1.00 | 72.50 | A |
| ATOM | 119 | CA | PRO | A | 26 | −44.938 | 40.842 | −31.165 | 1.00 | 73.26 | A |
| ATOM | 120 | CB | PRO | A | 26 | −44.887 | 40.767 | −32.702 | 1.00 | 73.01 | A |
| ATOM | 121 | CG | PRO | A | 26 | −45.664 | 39.526 | −33.023 | 1.00 | 72.89 | A |
| ATOM | 122 | C | PRO | A | 26 | −45.008 | 42.284 | −30.673 | 1.00 | 74.39 | A |
| ATOM | 123 | O | PRO | A | 26 | −43.979 | 42.872 | −30.322 | 1.00 | 74.28 | A |
| ATOM | 124 | N | PHE | A | 27 | −46.212 | 42.856 | −30.653 | 1.00 | 75.25 | A |
| ATOM | 125 | CA | PHE | A | 27 | −46.375 | 44.245 | −30.222 | 1.00 | 75.22 | A |
| ATOM | 126 | CB | PHE | A | 27 | −47.502 | 44.910 | −30.995 | 1.00 | 75.78 | A |
| ATOM | 127 | CG | PHE | A | 27 | −47.305 | 44.909 | −32.463 | 1.00 | 77.48 | A |
| ATOM | 128 | CD1 | PHE | A | 27 | −47.573 | 43.765 | −33.204 | 1.00 | 79.44 | A |

TABLE 5-continued

Atomic coordinates of rSIFN-co (SEQ ID NO: 1)

| ATOM | 129 | CD2 | PHE | A | 27 | −46.788 | 46.029 | −33.106 | 1.00 | 77.96 | A |
| ATOM | 130 | CE1 | PHE | A | 27 | −47.347 | 43.738 | −34.579 | 1.00 | 80.53 | A |
| ATOM | 131 | CE2 | PHE | A | 27 | −46.557 | 46.022 | −34.472 | 1.00 | 79.57 | A |
| ATOM | 132 | CZ | PHE | A | 27 | −46.826 | 44.870 | −35.215 | 1.00 | 80.89 | A |
| ATOM | 133 | C | PHE | A | 27 | −46.635 | 44.449 | −28.737 | 1.00 | 74.52 | A |
| ATOM | 134 | O | PHE | A | 27 | −46.415 | 45.540 | −28.218 | 1.00 | 74.03 | A |
| ATOM | 135 | N | ALA | A | 28 | −47.097 | 43.411 | −28.052 | 1.00 | 74.01 | A |
| ATOM | 136 | CA | ALA | A | 28 | −47.394 | 43.532 | −26.637 | 1.00 | 73.15 | A |
| ATOM | 137 | CB | ALA | A | 28 | −47.812 | 42.175 | −26.080 | 1.00 | 73.48 | A |
| ATOM | 138 | C | ALA | A | 28 | −46.241 | 44.112 | −25.822 | 1.00 | 73.09 | A |
| ATOM | 139 | O | ALA | A | 28 | −46.460 | 44.586 | −24.707 | 1.00 | 74.58 | A |
| ATOM | 140 | N | CYS | A | 29 | −45.030 | 44.090 | −26.383 | 1.00 | 72.82 | A |
| ATOM | 141 | CA | CYS | A | 29 | −43.820 | 44.598 | −25.713 | 1.00 | 73.33 | A |
| ATOM | 142 | C | CYS | A | 29 | −42.968 | 45.450 | −26.659 | 1.00 | 74.96 | A |
| ATOM | 143 | O | CYS | A | 29 | −43.340 | 45.648 | −27.812 | 1.00 | 75.82 | A |
| ATOM | 144 | CB | CYS | A | 29 | −42.967 | 43.432 | −25.217 | 1.00 | 71.43 | A |
| ATOM | 145 | SG | CYS | A | 29 | −43.896 | 42.126 | −24.366 | 1.00 | 69.57 | A |
| ATOM | 146 | N | GLY | A | 30 | −41.814 | 45.931 | −26.192 | 1.00 | 76.71 | A |
| ATOM | 147 | CA | GLY | A | 30 | −40.990 | 46.756 | −27.065 | 1.00 | 79.56 | A |
| ATOM | 148 | C | GLY | A | 30 | −39.496 | 46.977 | −26.848 | 1.00 | 81.04 | A |
| ATOM | 149 | O | GLY | A | 30 | −38.987 | 47.036 | −25.725 | 1.00 | 80.04 | A |
| ATOM | 150 | N | GLY | A | 31 | −38.800 | 47.111 | −27.976 | 1.00 | 83.09 | A |
| ATOM | 151 | CA | GLY | A | 31 | −37.365 | 47.369 | −27.994 | 1.00 | 86.03 | A |
| ATOM | 152 | C | GLY | A | 31 | −36.448 | 46.384 | −27.283 | 1.00 | 86.91 | A |
| ATOM | 153 | O | GLY | A | 31 | −36.097 | 45.330 | −27.822 | 1.00 | 87.85 | A |
| ATOM | 154 | N | GLY | A | 32 | −36.030 | 46.767 | −26.078 | 1.00 | 86.34 | A |
| ATOM | 155 | CA | GLY | A | 32 | −35.161 | 45.949 | −25.244 | 1.00 | 85.69 | A |
| ATOM | 156 | C | GLY | A | 32 | −34.216 | 44.887 | −25.810 | 1.00 | 84.42 | A |
| ATOM | 157 | O | GLY | A | 32 | −34.386 | 43.694 | −25.541 | 1.00 | 84.88 | A |
| ATOM | 158 | N | GLY | A | 33 | −33.200 | 45.298 | −26.562 | 1.00 | 82.49 | A |
| ATOM | 159 | CA | GLY | A | 33 | −32.247 | 44.327 | −27.076 | 1.00 | 81.23 | A |
| ATOM | 160 | C | GLY | A | 33 | −31.315 | 43.958 | −25.929 | 1.00 | 80.18 | A |
| ATOM | 161 | O | GLY | A | 33 | −30.199 | 44.473 | −25.846 | 1.00 | 79.67 | A |
| ATOM | 162 | N | HIS | A | 34 | −31.768 | 43.066 | −25.048 | 1.00 | 79.01 | A |
| ATOM | 163 | CA | HIS | A | 34 | −30.984 | 42.654 | −23.881 | 1.00 | 76.91 | A |
| ATOM | 164 | CB | HIS | A | 34 | −31.932 | 42.245 | −22.742 | 1.00 | 76.85 | A |
| ATOM | 165 | CG | HIS | A | 34 | −31.313 | 42.323 | −21.381 | 1.00 | 76.31 | A |
| ATOM | 166 | CD2 | HIS | A | 34 | −31.596 | 43.113 | −20.319 | 1.00 | 76.73 | A |
| ATOM | 167 | ND1 | HIS | A | 34 | −30.249 | 41.534 | −20.995 | 1.00 | 76.92 | A |
| ATOM | 168 | CE1 | HIS | A | 34 | −29.905 | 41.835 | −19.756 | 1.00 | 76.89 | A |
| ATOM | 169 | NE2 | HIS | A | 34 | −30.707 | 42.791 | −19.322 | 1.00 | 77.36 | A |
| ATOM | 170 | C | HIS | A | 34 | −29.992 | 41.525 | −24.168 | 1.00 | 74.89 | A |
| ATOM | 171 | O | HIS | A | 34 | −30.383 | 40.450 | −24.635 | 1.00 | 75.01 | A |
| ATOM | 172 | N | ASP | A | 35 | −28.716 | 41.783 | −23.869 | 1.00 | 71.97 | A |
| ATOM | 173 | CA | ASP | A | 35 | −27.631 | 40.823 | −24.089 | 1.00 | 69.11 | A |
| ATOM | 174 | CB | ASP | A | 35 | −26.366 | 41.561 | −24.542 | 1.00 | 71.02 | A |
| ATOM | 175 | CG | ASP | A | 35 | −25.270 | 40.617 | −25.018 | 1.00 | 73.48 | A |
| ATOM | 176 | OD1 | ASP | A | 35 | −25.490 | 39.904 | −26.022 | 1.00 | 76.44 | A |
| ATOM | 177 | OD2 | ASP | A | 35 | −24.183 | 40.591 | −24.398 | 1.00 | 74.76 | A |
| ATOM | 178 | C | ASP | A | 35 | −27.318 | 40.010 | −22.837 | 1.00 | 66.06 | A |
| ATOM | 179 | O | ASP | A | 35 | −26.862 | 40.554 | −21.830 | 1.00 | 66.03 | A |
| ATOM | 180 | N | PHE | A | 36 | −27.558 | 38.705 | −22.900 | 1.00 | 61.83 | A |
| ATOM | 181 | CA | PHE | A | 36 | −27.282 | 37.853 | −21.757 | 1.00 | 57.75 | A |
| ATOM | 182 | CB | PHE | A | 36 | −28.283 | 36.698 | −21.674 | 1.00 | 57.18 | A |
| ATOM | 183 | CG | PHE | A | 36 | −29.696 | 37.146 | −21.442 | 1.00 | 56.02 | A |
| ATOM | 184 | CD1 | PHE | A | 36 | −30.556 | 37.357 | −22.505 | 1.00 | 55.11 | A |
| ATOM | 185 | CD2 | PHE | A | 36 | −30.148 | 37.415 | −20.159 | 1.00 | 56.96 | A |
| ATOM | 186 | CE1 | PHE | A | 36 | −31.847 | 37.827 | −22.296 | 1.00 | 56.30 | A |
| ATOM | 187 | CE2 | PHE | A | 36 | −31.441 | 37.889 | −19.939 | 1.00 | 56.70 | A |
| ATOM | 188 | CZ | PHE | A | 36 | −32.289 | 38.097 | −21.010 | 1.00 | 56.38 | A |
| ATOM | 189 | C | PHE | A | 36 | −25.870 | 37.326 | −21.835 | 1.00 | 55.62 | A |
| ATOM | 190 | O | PHE | A | 36 | −25.367 | 36.747 | −20.882 | 1.00 | 55.22 | A |
| ATOM | 191 | N | GLY | A | 37 | −25.233 | 37.534 | −22.982 | 1.00 | 53.97 | A |
| ATOM | 192 | CA | GLY | A | 37 | −23.859 | 37.103 | −23.163 | 1.00 | 52.66 | A |
| ATOM | 193 | C | GLY | A | 37 | −23.589 | 35.614 | −23.171 | 1.00 | 52.31 | A |
| ATOM | 194 | O | GLY | A | 37 | −22.627 | 35.140 | −22.572 | 1.00 | 52.88 | A |
| ATOM | 195 | N | PHE | A | 38 | −24.439 | 34.868 | −23.856 | 1.00 | 52.34 | A |
| ATOM | 196 | CA | PHE | A | 38 | −24.272 | 33.428 | −23.960 | 1.00 | 53.26 | A |
| ATOM | 197 | CB | PHE | A | 38 | −25.329 | 32.873 | −24.925 | 1.00 | 50.67 | A |
| ATOM | 198 | CG | PHE | A | 38 | −25.161 | 31.424 | −25.244 | 1.00 | 48.53 | A |
| ATOM | 199 | CD1 | PHE | A | 38 | −25.352 | 30.457 | −24.264 | 1.00 | 47.04 | A |
| ATOM | 200 | CD2 | PHE | A | 38 | −24.793 | 31.023 | −26.529 | 1.00 | 47.77 | A |
| ATOM | 201 | CE1 | PHE | A | 38 | −25.177 | 29.110 | −24.559 | 1.00 | 47.91 | A |
| ATOM | 202 | CE2 | PHE | A | 38 | −24.615 | 29.676 | −26.834 | 1.00 | 46.88 | A |
| ATOM | 203 | CZ | PHE | A | 38 | −24.806 | 28.719 | −25.850 | 1.00 | 48.21 | A |
| ATOM | 204 | C | PHE | A | 38 | −22.863 | 33.114 | −24.478 | 1.00 | 54.82 | A |
| ATOM | 205 | O | PHE | A | 38 | −22.481 | 33.579 | −25.547 | 1.00 | 55.48 | A |
| ATOM | 206 | N | PRO | A | 39 | −22.071 | 32.327 | −23.724 | 1.00 | 56.41 | A |

TABLE 5-continued

Atomic coordinates of rSIFN-co (SEQ ID NO: 1)

| ATOM | 207 | CD | PRO | A | 39 | −22.373 | 31.704 | −22.422 | 1.00 | 56.33 | A |
|---|---|---|---|---|---|---|---|---|---|---|---|
| ATOM | 208 | CA | PRO | A | 39 | −20.711 | 31.982 | −24.158 | 1.00 | 57.36 | A |
| ATOM | 209 | CB | PRO | A | 39 | −20.084 | 31.414 | −22.889 | 1.00 | 55.84 | A |
| ATOM | 210 | CG | PRO | A | 39 | −21.234 | 30.702 | −22.266 | 1.00 | 56.06 | A |
| ATOM | 211 | C | PRO | A | 39 | −20.705 | 30.974 | −25.318 | 1.00 | 59.32 | A |
| ATOM | 212 | O | PRO | A | 39 | −20.292 | 29.824 | −25.153 | 1.00 | 59.38 | A |
| ATOM | 213 | N | GLN | A | 40 | −21.159 | 31.428 | −26.487 | 1.00 | 61.42 | A |
| ATOM | 214 | CA | GLN | A | 40 | −21.235 | 30.616 | −27.710 | 1.00 | 63.86 | A |
| ATOM | 215 | CB | GLN | A | 40 | −21.539 | 31.520 | −28.911 | 1.00 | 65.01 | A |
| ATOM | 216 | CG | GLN | A | 40 | −21.996 | 30.776 | −30.148 | 1.00 | 67.78 | A |
| ATOM | 217 | CD | GLN | A | 40 | −22.372 | 31.713 | −31.297 | 1.00 | 70.50 | A |
| ATOM | 218 | OE1 | GLN | A | 40 | −22.885 | 32.818 | −31.079 | 1.00 | 70.05 | A |
| ATOM | 219 | NE2 | GLN | A | 40 | −22.135 | 31.262 | −32.528 | 1.00 | 69.96 | A |
| ATOM | 220 | C | GLN | A | 40 | −19.979 | 29.797 | −28.011 | 1.00 | 64.05 | A |
| ATOM | 221 | O | GLN | A | 40 | −20.064 | 28.709 | −28.577 | 1.00 | 62.19 | A |
| ATOM | 222 | N | GLU | A | 41 | −18.821 | 30.329 | −27.630 | 1.00 | 66.08 | A |
| ATOM | 223 | CA | GLU | A | 41 | −17.537 | 29.667 | −27.854 | 1.00 | 68.16 | A |
| ATOM | 224 | CB | GLU | A | 41 | −16.405 | 30.478 | −27.216 | 1.00 | 68.78 | A |
| ATOM | 225 | CG | GLU | A | 41 | −16.575 | 31.993 | −27.302 | 1.00 | 71.65 | A |
| ATOM | 226 | CD | GLU | A | 41 | −17.599 | 32.538 | −26.309 | 1.00 | 71.91 | A |
| ATOM | 227 | OE1 | GLU | A | 41 | −17.436 | 32.289 | −25.095 | 1.00 | 70.55 | A |
| ATOM | 228 | OE2 | GLU | A | 41 | −18.558 | 33.220 | −26.742 | 1.00 | 72.43 | A |
| ATOM | 229 | C | GLU | A | 41 | −17.514 | 28.249 | −27.276 | 1.00 | 69.40 | A |
| ATOM | 230 | O | GLU | A | 41 | −16.971 | 27.327 | −27.884 | 1.00 | 70.02 | A |
| ATOM | 231 | N | GLU | A | 42 | −18.107 | 28.081 | −26.098 | 1.00 | 70.37 | A |
| ATOM | 232 | CA | GLU | A | 42 | −18.134 | 26.784 | −25.437 | 1.00 | 70.92 | A |
| ATOM | 233 | CB | GLU | A | 42 | −18.816 | 26.907 | −24.073 | 1.00 | 70.33 | A |
| ATOM | 234 | CG | GLU | A | 42 | −18.096 | 27.839 | −23.108 | 1.00 | 70.66 | A |
| ATOM | 235 | CD | GLU | A | 42 | −16.674 | 27.387 | −22.810 | 1.00 | 71.66 | A |
| ATOM | 236 | OE1 | GLU | A | 42 | −15.901 | 28.192 | −22.245 | 1.00 | 71.99 | A |
| ATOM | 237 | OE2 | GLU | A | 42 | −16.329 | 26.228 | −23.134 | 1.00 | 70.35 | A |
| ATOM | 238 | C | GLU | A | 42 | −18.817 | 25.703 | −26.263 | 1.00 | 72.31 | A |
| ATOM | 239 | O | GLU | A | 42 | −18.658 | 24.515 | −25.982 | 1.00 | 71.27 | A |
| ATOM | 240 | N | PHE | A | 43 | −19.565 | 26.115 | −27.285 | 1.00 | 74.43 | A |
| ATOM | 241 | CA | PHE | A | 43 | −20.279 | 25.169 | −28.142 | 1.00 | 77.01 | A |
| ATOM | 242 | CB | PHE | A | 43 | −21.801 | 25.343 | −27.982 | 1.00 | 73.77 | A |
| ATOM | 243 | CG | PHE | A | 43 | −22.266 | 25.393 | −26.551 | 1.00 | 70.14 | A |
| ATOM | 244 | CD1 | PHE | A | 43 | −22.212 | 26.580 | −25.829 | 1.00 | 69.12 | A |
| ATOM | 245 | CD2 | PHE | A | 43 | −22.728 | 24.249 | −25.916 | 1.00 | 69.47 | A |
| ATOM | 246 | CE1 | PHE | A | 43 | −22.608 | 26.627 | −24.498 | 1.00 | 66.90 | A |
| ATOM | 247 | CE2 | PHE | A | 43 | −23.126 | 24.287 | −24.579 | 1.00 | 68.62 | A |
| ATOM | 248 | CZ | PHE | A | 43 | −23.065 | 25.480 | −23.873 | 1.00 | 67.55 | A |
| ATOM | 249 | C | PHE | A | 43 | −19.904 | 25.329 | −29.620 | 1.00 | 80.52 | A |
| ATOM | 250 | O | PHE | A | 43 | −19.615 | 24.350 | −30.312 | 1.00 | 80.71 | A |
| ATOM | 251 | N | GLY | A | 44 | −19.917 | 26.571 | −30.093 | 1.00 | 84.43 | A |
| ATOM | 252 | CA | GLY | A | 44 | −19.594 | 26.849 | −31.483 | 1.00 | 87.53 | A |
| ATOM | 253 | C | GLY | A | 44 | −18.109 | 26.912 | −31.796 | 1.00 | 89.96 | A |
| ATOM | 254 | O | GLY | A | 44 | −17.397 | 27.829 | −31.367 | 1.00 | 89.88 | A |
| ATOM | 255 | N | GLY | A | 45 | −17.642 | 25.933 | −32.564 | 1.00 | 91.49 | A |
| ATOM | 256 | CA | GLY | A | 45 | −16.243 | 25.889 | −32.936 | 1.00 | 93.11 | A |
| ATOM | 257 | C | GLY | A | 45 | −15.734 | 24.468 | −33.038 | 1.00 | 94.05 | A |
| ATOM | 258 | O | GLY | A | 45 | −16.213 | 23.577 | −32.333 | 1.00 | 93.98 | A |
| ATOM | 259 | N | GLY | A | 46 | −14.767 | 24.255 | −33.925 | 1.00 | 94.77 | A |
| ATOM | 260 | CA | GLY | A | 46 | −14.195 | 22.935 | −34.098 | 1.00 | 95.42 | A |
| ATOM | 261 | C | GLY | A | 46 | −13.231 | 22.606 | −32.972 | 1.00 | 95.90 | A |
| ATOM | 262 | O | GLY | A | 46 | −12.194 | 21.976 | −33.199 | 1.00 | 96.10 | A |
| ATOM | 263 | N | GLY | A | 47 | −13.570 | 23.040 | −31.759 | 1.00 | 95.61 | A |
| ATOM | 264 | CA | GLY | A | 47 | −12.726 | 22.778 | −30.606 | 1.00 | 95.48 | A |
| ATOM | 265 | C | GLY | A | 47 | −12.428 | 21.298 | −30.455 | 1.00 | 95.42 | A |
| ATOM | 266 | O | GLY | A | 47 | −11.319 | 20.921 | −30.073 | 1.00 | 95.45 | A |
| ATOM | 267 | N | GLY | A | 48 | −13.425 | 20.466 | −30.760 | 1.00 | 94.95 | A |
| ATOM | 268 | CA | GLY | A | 48 | −13.272 | 19.023 | −30.674 | 1.00 | 93.55 | A |
| ATOM | 269 | C | GLY | A | 48 | −12.943 | 18.541 | −29.279 | 1.00 | 93.16 | A |
| ATOM | 270 | O | GLY | A | 48 | −12.016 | 19.041 | −28.649 | 1.00 | 94.44 | A |
| ATOM | 271 | N | ALA | A | 49 | −13.705 | 17.566 | −28.796 | 1.00 | 91.77 | A |
| ATOM | 272 | CA | ALA | A | 49 | −13.507 | 17.000 | −27.463 | 1.00 | 90.57 | A |
| ATOM | 273 | CB | ALA | A | 49 | −13.219 | 18.103 | −26.449 | 1.00 | 90.50 | A |
| ATOM | 274 | C | ALA | A | 49 | −14.771 | 16.245 | −27.069 | 1.00 | 89.91 | A |
| ATOM | 275 | O | ALA | A | 49 | −15.801 | 16.855 | −26.774 | 1.00 | 90.84 | A |
| ATOM | 276 | N | GLY | A | 50 | −14.690 | 14.919 | −27.068 | 1.00 | 88.13 | A |
| ATOM | 277 | CA | GLY | A | 50 | −15.844 | 14.113 | −26.727 | 1.00 | 86.16 | A |
| ATOM | 278 | C | GLY | A | 50 | −16.495 | 14.504 | −25.416 | 1.00 | 85.07 | A |
| ATOM | 279 | O | GLY | A | 50 | −17.671 | 14.870 | −25.387 | 1.00 | 84.82 | A |
| ATOM | 280 | N | ALA | A | 51 | −15.721 | 14.442 | −24.335 | 1.00 | 83.62 | A |
| ATOM | 281 | CA | ALA | A | 51 | −16.211 | 14.753 | −22.992 | 1.00 | 81.83 | A |
| ATOM | 282 | CB | ALA | A | 51 | −15.276 | 14.138 | −21.955 | 1.00 | 82.10 | A |
| ATOM | 283 | C | ALA | A | 51 | −16.424 | 16.235 | −22.685 | 1.00 | 79.92 | A |
| ATOM | 284 | O | ALA | A | 51 | −17.409 | 16.602 | −22.049 | 1.00 | 79.80 | A |

TABLE 5-continued

Atomic coordinates of rSIFN-co (SEQ ID NO: 1)

| ATOM | 285 | N | ALA | A | 52 | −15.504 | 17.088 | −23.115 | 1.00 | 77.79 | A |
|---|---|---|---|---|---|---|---|---|---|---|---|
| ATOM | 286 | CA | ALA | A | 52 | −15.655 | 18.511 | −22.852 | 1.00 | 76.55 | A |
| ATOM | 287 | CB | ALA | A | 52 | −14.469 | 19.286 | −23.424 | 1.00 | 76.24 | A |
| ATOM | 288 | C | ALA | A | 52 | −16.965 | 19.027 | −23.450 | 1.00 | 75.56 | A |
| ATOM | 289 | O | ALA | A | 52 | −17.473 | 20.072 | −23.037 | 1.00 | 76.89 | A |
| ATOM | 290 | N | ALA | A | 53 | −17.510 | 18.288 | −24.416 | 1.00 | 72.47 | A |
| ATOM | 291 | CA | ALA | A | 53 | −18.756 | 18.677 | −25.080 | 1.00 | 68.45 | A |
| ATOM | 292 | CB | ALA | A | 53 | −18.737 | 18.220 | −26.532 | 1.00 | 69.53 | A |
| ATOM | 293 | C | ALA | A | 53 | −19.980 | 18.108 | −24.374 | 1.00 | 64.99 | A |
| ATOM | 294 | O | ALA | A | 53 | −21.033 | 18.738 | −24.329 | 1.00 | 63.06 | A |
| ATOM | 295 | N | ILE | A | 54 | −19.838 | 16.903 | −23.841 | 1.00 | 62.13 | A |
| ATOM | 296 | CA | ILE | A | 54 | −20.926 | 16.269 | −23.119 | 1.00 | 59.68 | A |
| ATOM | 297 | CB | ILE | A | 54 | −20.601 | 14.793 | −22.815 | 1.00 | 59.54 | A |
| ATOM | 298 | CG2 | ILE | A | 54 | −21.606 | 14.224 | −21.820 | 1.00 | 60.50 | A |
| ATOM | 299 | CG1 | ILE | A | 54 | −20.611 | 13.993 | −24.117 | 1.00 | 59.64 | A |
| ATOM | 300 | CD1 | ILE | A | 54 | −20.368 | 12.518 | −23.930 | 1.00 | 59.00 | A |
| ATOM | 301 | C | ILE | A | 54 | −21.164 | 17.028 | −21.813 | 1.00 | 57.90 | A |
| ATOM | 302 | O | ILE | A | 54 | −22.290 | 17.095 | −21.327 | 1.00 | 57.31 | A |
| ATOM | 303 | N | SER | A | 55 | −20.097 | 17.601 | −21.259 | 1.00 | 55.70 | A |
| ATOM | 304 | CA | SER | A | 55 | −20.184 | 18.370 | −20.023 | 1.00 | 54.92 | A |
| ATOM | 305 | CB | SER | A | 55 | −18.793 | 18.751 | −19.519 | 1.00 | 55.15 | A |
| ATOM | 306 | OG | SER | A | 55 | −18.065 | 17.604 | −19.145 | 1.00 | 57.20 | A |
| ATOM | 307 | C | SER | A | 55 | −20.984 | 19.640 | −20.247 | 1.00 | 53.44 | A |
| ATOM | 308 | O | SER | A | 55 | −22.026 | 19.837 | −19.627 | 1.00 | 55.68 | A |
| ATOM | 309 | N | VAL | A | 56 | −20.494 | 20.502 | −21.127 | 1.00 | 50.22 | A |
| ATOM | 310 | CA | VAL | A | 56 | −21.178 | 21.752 | −21.415 | 1.00 | 50.34 | A |
| ATOM | 311 | CB | VAL | A | 56 | −20.418 | 22.574 | −22.478 | 1.00 | 50.53 | A |
| ATOM | 312 | CG1 | VAL | A | 56 | −19.161 | 23.152 | −21.878 | 1.00 | 50.53 | A |
| ATOM | 313 | CG2 | VAL | A | 56 | −20.078 | 21.697 | −23.668 | 1.00 | 51.00 | A |
| ATOM | 314 | C | VAL | A | 56 | −22.610 | 21.528 | −21.894 | 1.00 | 49.62 | A |
| ATOM | 315 | O | VAL | A | 56 | −23.516 | 22.293 | −21.567 | 1.00 | 49.30 | A |
| ATOM | 316 | N | LEU | A | 57 | −22.812 | 20.475 | −22.673 | 1.00 | 49.64 | A |
| ATOM | 317 | CA | LEU | A | 57 | −24.136 | 20.154 | −23.190 | 1.00 | 49.65 | A |
| ATOM | 318 | CB | LEU | A | 57 | −24.032 | 18.974 | −24.152 | 1.00 | 51.00 | A |
| ATOM | 319 | CG | LEU | A | 57 | −25.034 | 18.931 | −25.301 | 1.00 | 52.21 | A |
| ATOM | 320 | CD1 | LEU | A | 57 | −25.250 | 20.322 | −25.881 | 1.00 | 52.24 | A |
| ATOM | 321 | CD2 | LEU | A | 57 | −24.488 | 17.992 | −26.361 | 1.00 | 54.20 | A |
| ATOM | 322 | C | LEU | A | 57 | −25.054 | 19.800 | −22.027 | 1.00 | 47.55 | A |
| ATOM | 323 | O | LEU | A | 57 | −26.140 | 20.356 | −21.870 | 1.00 | 46.60 | A |
| ATOM | 324 | N | HIS | A | 58 | −24.592 | 18.862 | −21.216 | 1.00 | 46.31 | A |
| ATOM | 325 | CA | HIS | A | 58 | −25.319 | 18.415 | −20.043 | 1.00 | 45.33 | A |
| ATOM | 326 | CB | HIS | A | 58 | −24.482 | 17.375 | −19.301 | 1.00 | 46.40 | A |
| ATOM | 327 | CG | HIS | A | 58 | −25.242 | 16.619 | −18.263 | 1.00 | 46.64 | A |
| ATOM | 328 | CD2 | HIS | A | 58 | −25.757 | 15.368 | −18.275 | 1.00 | 46.79 | A |
| ATOM | 329 | ND1 | HIS | A | 58 | −25.582 | 17.164 | −17.044 | 1.00 | 46.24 | A |
| ATOM | 330 | CE1 | HIS | A | 58 | −26.275 | 16.280 | −16.352 | 1.00 | 48.22 | A |
| ATOM | 331 | NE2 | HIS | A | 58 | −26.397 | 15.180 | −17.076 | 1.00 | 46.23 | A |
| ATOM | 332 | C | HIS | A | 58 | −25.649 | 19.590 | −19.118 | 1.00 | 43.94 | A |
| ATOM | 333 | O | HIS | A | 58 | −26.783 | 19.724 | −18.663 | 1.00 | 42.85 | A |
| ATOM | 334 | N | GLU | A | 59 | −24.664 | 20.442 | −18.847 | 1.00 | 41.52 | A |
| ATOM | 335 | CA | GLU | A | 59 | −24.896 | 21.585 | −17.979 | 1.00 | 41.77 | A |
| ATOM | 336 | CB | GLU | A | 59 | −23.600 | 22.326 | −17.702 | 1.00 | 43.24 | A |
| ATOM | 337 | CG | GLU | A | 59 | −23.694 | 23.232 | −16.489 | 1.00 | 47.79 | A |
| ATOM | 338 | CD | GLU | A | 59 | −24.197 | 22.493 | −15.249 | 1.00 | 49.54 | A |
| ATOM | 339 | OE1 | GLU | A | 59 | −23.853 | 21.304 | −15.074 | 1.00 | 49.34 | A |
| ATOM | 340 | OE2 | GLU | A | 59 | −24.928 | 23.107 | −14.442 | 1.00 | 52.72 | A |
| ATOM | 341 | C | GLU | A | 59 | −25.882 | 22.536 | −18.619 | 1.00 | 41.87 | A |
| ATOM | 342 | O | GLU | A | 59 | −26.719 | 23.135 | −17.942 | 1.00 | 41.28 | A |
| ATOM | 343 | N | MET | A | 60 | −25.770 | 22.677 | −19.935 | 1.00 | 42.94 | A |
| ATOM | 344 | CA | MET | A | 60 | −26.662 | 23.542 | −20.692 | 1.00 | 42.22 | A |
| ATOM | 345 | CB | MET | A | 60 | −26.290 | 23.512 | −22.165 | 1.00 | 43.31 | A |
| ATOM | 346 | CG | MET | A | 60 | −27.230 | 24.305 | −23.017 | 1.00 | 45.06 | A |
| ATOM | 347 | SD | MET | A | 60 | −27.202 | 26.008 | −22.511 | 1.00 | 51.70 | A |
| ATOM | 348 | CE | MET | A | 60 | −27.674 | 26.784 | −24.033 | 1.00 | 51.65 | A |
| ATOM | 349 | C | MET | A | 60 | −28.096 | 23.052 | −20.545 | 1.00 | 42.26 | A |
| ATOM | 350 | O | MET | A | 60 | −29.039 | 23.839 | −20.450 | 1.00 | 40.80 | A |
| ATOM | 351 | N | ILE | A | 61 | −28.245 | 21.733 | −20.534 | 1.00 | 40.98 | A |
| ATOM | 352 | CA | ILE | A | 61 | −29.548 | 21.123 | −20.418 | 1.00 | 40.78 | A |
| ATOM | 353 | CB | ILE | A | 61 | −29.504 | 19.681 | −20.995 | 1.00 | 42.85 | A |
| ATOM | 354 | CG2 | ILE | A | 61 | −30.790 | 18.936 | −20.694 | 1.00 | 41.14 | A |
| ATOM | 355 | CG1 | ILE | A | 61 | −29.312 | 19.763 | −22.518 | 1.00 | 42.64 | A |
| ATOM | 356 | CD1 | ILE | A | 61 | −29.143 | 18.421 | −23.214 | 1.00 | 43.13 | A |
| ATOM | 357 | C | ILE | A | 61 | −30.060 | 21.159 | −18.984 | 1.00 | 39.56 | A |
| ATOM | 358 | O | ILE | A | 61 | −31.195 | 21.558 | −18.744 | 1.00 | 39.81 | A |
| ATOM | 359 | N | GLN | A | 62 | −29.224 | 20.781 | −18.026 | 1.00 | 39.29 | A |
| ATOM | 360 | CA | GLN | A | 62 | −29.639 | 20.793 | −16.627 | 1.00 | 38.51 | A |
| ATOM | 361 | CB | GLN | A | 62 | −28.488 | 20.338 | −15.726 | 1.00 | 39.26 | A |
| ATOM | 362 | CG | GLN | A | 62 | −28.827 | 20.246 | −14.242 | 1.00 | 39.53 | A |

TABLE 5-continued

Atomic coordinates of rSIFN-co (SEQ ID NO: 1)

| ATOM | 363 | CD   | GLN | A | 62 | −30.002 | 19.321 | −13.941 | 1.00 | 40.52 | A |
|------|-----|------|-----|---|----|---------|--------|---------|------|-------|---|
| ATOM | 364 | OE1  | GLN | A | 62 | −31.042 | 19.758 | −13.438 | 1.00 | 39.54 | A |
| ATOM | 365 | NE2  | GLN | A | 62 | −29.840 | 18.040 | −14.248 | 1.00 | 39.51 | A |
| ATOM | 366 | C    | GLN | A | 62 | −30.102 | 22.189 | −16.221 | 1.00 | 38.93 | A |
| ATOM | 367 | O    | GLN | A | 62 | −31.106 | 22.348 | −15.522 | 1.00 | 37.04 | A |
| ATOM | 368 | N    | GLN | A | 63 | −29.383 | 23.204 | −16.683 | 1.00 | 39.52 | A |
| ATOM | 369 | CA   | GLN | A | 63 | −29.741 | 24.578 | −16.353 | 1.00 | 40.38 | A |
| ATOM | 370 | CB   | GLN | A | 63 | −28.644 | 25.543 | −16.797 | 1.00 | 41.37 | A |
| ATOM | 371 | CG   | GLN | A | 63 | −27.350 | 25.361 | −16.049 | 1.00 | 42.32 | A |
| ATOM | 372 | CD   | GLN | A | 63 | −27.523 | 25.576 | −14.563 | 1.00 | 46.04 | A |
| ATOM | 373 | OE1  | GLN | A | 63 | −26.881 | 24.907 | −13.753 | 1.00 | 47.35 | A |
| ATOM | 374 | NE2  | GLN | A | 63 | −28.386 | 26.526 | −14.192 | 1.00 | 46.16 | A |
| ATOM | 375 | C    | GLN | A | 63 | −31.062 | 25.006 | −16.957 | 1.00 | 40.51 | A |
| ATOM | 376 | O    | GLN | A | 63 | −31.837 | 25.685 | −16.286 | 1.00 | 43.32 | A |
| ATOM | 377 | N    | THR | A | 64 | −31.313 | 24.625 | −18.215 | 1.00 | 39.04 | A |
| ATOM | 378 | CA   | THR | A | 64 | −32.564 | 24.972 | −18.904 | 1.00 | 37.15 | A |
| ATOM | 379 | CB   | THR | A | 64 | −32.539 | 24.536 | −20.398 | 1.00 | 36.84 | A |
| ATOM | 380 | OG1  | THR | A | 64 | −31.493 | 25.233 | −21.084 | 1.00 | 35.39 | A |
| ATOM | 381 | CG2  | THR | A | 64 | −33.872 | 24.834 | −21.077 | 1.00 | 32.91 | A |
| ATOM | 382 | C    | THR | A | 64 | −33.714 | 24.265 | −18.181 | 1.00 | 37.88 | A |
| ATOM | 383 | O    | THR | A | 64 | −34.827 | 24.791 | −18.061 | 1.00 | 37.95 | A |
| ATOM | 384 | N    | PHE | A | 65 | −33.438 | 23.061 | −17.700 | 1.00 | 37.24 | A |
| ATOM | 385 | CA   | PHE | A | 65 | −34.435 | 22.326 | −16.951 | 1.00 | 37.39 | A |
| ATOM | 386 | CB   | PHE | A | 65 | −33.934 | 20.930 | −16.625 | 1.00 | 37.39 | A |
| ATOM | 387 | CG   | PHE | A | 65 | −34.874 | 20.159 | −15.749 | 1.00 | 40.42 | A |
| ATOM | 388 | CD1  | PHE | A | 65 | −35.967 | 19.503 | −16.292 | 1.00 | 39.82 | A |
| ATOM | 389 | CD2  | PHE | A | 65 | −34.706 | 20.155 | −14.370 | 1.00 | 40.52 | A |
| ATOM | 390 | CE1  | PHE | A | 65 | −36.871 | 18.861 | −15.485 | 1.00 | 40.75 | A |
| ATOM | 391 | CE2  | PHE | A | 65 | −35.611 | 19.511 | −13.556 | 1.00 | 40.34 | A |
| ATOM | 392 | CZ   | PHE | A | 65 | −36.697 | 18.867 | −14.115 | 1.00 | 40.24 | A |
| ATOM | 393 | C    | PHE | A | 65 | −34.756 | 23.070 | −15.639 | 1.00 | 36.83 | A |
| ATOM | 394 | O    | PHE | A | 65 | −35.918 | 23.289 | −15.317 | 1.00 | 37.76 | A |
| ATOM | 395 | N    | ASN | A | 66 | −33.730 | 23.450 | −14.880 | 1.00 | 35.91 | A |
| ATOM | 396 | CA   | ASN | A | 66 | −33.950 | 24.177 | −13.633 | 1.00 | 34.39 | A |
| ATOM | 397 | CB   | ASN | A | 66 | −32.631 | 24.485 | −12.935 | 1.00 | 32.13 | A |
| ATOM | 398 | CG   | ASN | A | 66 | −31.851 | 23.238 | −12.606 | 1.00 | 34.28 | A |
| ATOM | 399 | OD1  | ASN | A | 66 | −32.418 | 22.153 | −12.512 | 1.00 | 37.35 | A |
| ATOM | 400 | ND2  | ASN | A | 66 | −30.545 | 23.380 | −12.424 | 1.00 | 33.10 | A |
| ATOM | 401 | C    | ASN | A | 66 | −34.678 | 25.481 | −13.900 | 1.00 | 34.39 | A |
| ATOM | 402 | O    | ASN | A | 66 | −35.582 | 25.851 | −13.163 | 1.00 | 35.59 | A |
| ATOM | 403 | N    | LEU | A | 67 | −34.299 | 26.172 | −14.963 | 1.00 | 34.07 | A |
| ATOM | 404 | CA   | LEU | A | 67 | −34.937 | 27.440 | −15.292 | 1.00 | 34.52 | A |
| ATOM | 405 | CB   | LEU | A | 67 | −34.189 | 28.135 | −16.434 | 1.00 | 31.74 | A |
| ATOM | 406 | CG   | LEU | A | 67 | −34.902 | 29.382 | −16.972 | 1.00 | 32.77 | A |
| ATOM | 407 | CD1  | LEU | A | 67 | −34.922 | 30.487 | −15.907 | 1.00 | 29.39 | A |
| ATOM | 408 | CD2  | LEU | A | 67 | −34.216 | 29.848 | −18.259 | 1.00 | 31.96 | A |
| ATOM | 409 | C    | LEU | A | 67 | −36.417 | 27.335 | −15.655 | 1.00 | 34.13 | A |
| ATOM | 410 | O    | LEU | A | 67 | −37.185 | 28.238 | −15.362 | 1.00 | 35.27 | A |
| ATOM | 411 | N    | PHE | A | 68 | −36.824 | 26.236 | −16.280 | 1.00 | 36.35 | A |
| ATOM | 412 | CA   | PHE | A | 68 | −38.218 | 26.081 | −16.690 | 1.00 | 37.11 | A |
| ATOM | 413 | CB   | PHE | A | 68 | −38.284 | 25.620 | −18.150 | 1.00 | 33.91 | A |
| ATOM | 414 | CG   | PHE | A | 68 | −38.023 | 26.708 | −19.133 | 1.00 | 31.92 | A |
| ATOM | 415 | CD1  | PHE | A | 68 | −36.724 | 26.985 | −19.563 | 1.00 | 33.37 | A |
| ATOM | 416 | CD2  | PHE | A | 68 | −39.071 | 27.494 | −19.607 | 1.00 | 30.01 | A |
| ATOM | 417 | CE1  | PHE | A | 68 | −36.469 | 28.045 | −20.466 | 1.00 | 31.57 | A |
| ATOM | 418 | CE2  | PHE | A | 68 | −38.835 | 28.553 | −20.504 | 1.00 | 30.12 | A |
| ATOM | 419 | CZ   | PHE | A | 68 | −37.534 | 28.830 | −20.932 | 1.00 | 28.79 | A |
| ATOM | 420 | C    | PHE | A | 68 | −39.128 | 25.186 | −15.845 | 1.00 | 39.17 | A |
| ATOM | 421 | O    | PHE | A | 68 | −40.318 | 25.067 | −16.131 | 1.00 | 39.72 | A |
| ATOM | 422 | N    | SER | A | 69 | −38.592 | 24.558 | −14.806 | 1.00 | 41.24 | A |
| ATOM | 423 | CA   | SER | A | 69 | −39.424 | 23.709 | −13.969 | 1.00 | 41.35 | A |
| ATOM | 424 | CB   | SER | A | 69 | −38.721 | 22.398 | −13.704 | 1.00 | 39.74 | A |
| ATOM | 425 | OG   | SER | A | 69 | −37.509 | 22.664 | −13.042 | 1.00 | 40.54 | A |
| ATOM | 426 | C    | SER | A | 69 | −39.790 | 24.355 | −12.635 | 1.00 | 42.76 | A |
| ATOM | 427 | O    | SER | A | 69 | −40.328 | 23.687 | −11.772 | 1.00 | 45.46 | A |
| ATOM | 428 | N    | THR | A | 70 | −39.508 | 25.642 | −12.459 | 1.00 | 44.33 | A |
| ATOM | 429 | CA   | THR | A | 70 | −39.839 | 26.316 | −11.201 | 1.00 | 47.21 | A |
| ATOM | 430 | CB   | THR | A | 70 | −39.038 | 27.630 | −10.990 | 1.00 | 47.32 | A |
| ATOM | 431 | OG1  | THR | A | 70 | −39.366 | 28.565 | −12.031 | 1.00 | 49.98 | A |
| ATOM | 432 | CG2  | THR | A | 70 | −37.547 | 27.364 | −10.977 | 1.00 | 45.16 | A |
| ATOM | 433 | C    | THR | A | 70 | −41.307 | 26.709 | −11.179 | 1.00 | 50.70 | A |
| ATOM | 434 | O    | THR | A | 70 | −42.001 | 26.617 | −12.195 | 1.00 | 50.43 | A |
| ATOM | 435 | N    | ARG | A | 71 | −41.777 | 27.164 | −10.018 | 1.00 | 53.44 | A |
| ATOM | 436 | CA   | ARG | A | 71 | −43.164 | 27.594 | −9.908  | 1.00 | 55.27 | A |
| ATOM | 437 | CB   | ARG | A | 71 | −43.576 | 27.847 | −8.449  | 1.00 | 57.92 | A |
| ATOM | 438 | CG   | ARG | A | 71 | −43.186 | 26.760 | −7.454  | 1.00 | 61.59 | A |
| ATOM | 439 | CD   | ARG | A | 71 | −41.834 | 27.104 | −6.805  | 1.00 | 64.19 | A |
| ATOM | 440 | NE   | ARG | A | 71 | −40.663 | 26.474 | −7.420  | 1.00 | 58.72 | A |

TABLE 5-continued

Atomic coordinates of rSIFN-co (SEQ ID NO: 1)

| ATOM | 441 | CZ | ARG | A | 71 | −39.469 | 27.046 | −7.453 | 1.00 | 55.24 | A |
|---|---|---|---|---|---|---|---|---|---|---|---|
| ATOM | 442 | NH1 | ARG | A | 71 | −39.304 | 28.250 | −6.929 | 1.00 | 52.89 | A |
| ATOM | 443 | NH2 | ARG | A | 71 | −38.435 | 26.399 | −7.964 | 1.00 | 55.93 | A |
| ATOM | 444 | C | ARG | A | 71 | −43.298 | 28.891 | −10.697 | 1.00 | 53.94 | A |
| ATOM | 445 | O | ARG | A | 71 | −44.382 | 29.232 | −11.171 | 1.00 | 53.96 | A |
| ATOM | 446 | N | ASP | A | 72 | −42.196 | 29.619 | −10.832 | 1.00 | 52.47 | A |
| ATOM | 447 | CA | ASP | A | 72 | −42.232 | 30.857 | −11.588 | 1.00 | 53.16 | A |
| ATOM | 448 | CB | ASP | A | 72 | −40.896 | 31.592 | −11.491 | 1.00 | 55.60 | A |
| ATOM | 449 | CG | ASP | A | 72 | −40.517 | 31.929 | −10.069 | 1.00 | 56.39 | A |
| ATOM | 450 | OD1 | ASP | A | 72 | −39.627 | 31.244 | −9.517 | 1.00 | 57.77 | A |
| ATOM | 451 | OD2 | ASP | A | 72 | −41.114 | 32.874 | −9.510 | 1.00 | 56.32 | A |
| ATOM | 452 | C | ASP | A | 72 | −42.524 | 30.523 | −13.050 | 1.00 | 52.84 | A |
| ATOM | 453 | O | ASP | A | 72 | −43.402 | 31.114 | −13.672 | 1.00 | 51.84 | A |
| ATOM | 454 | N | SER | A | 73 | −41.780 | 29.569 | −13.592 | 1.00 | 51.97 | A |
| ATOM | 455 | CA | SER | A | 73 | −41.980 | 29.169 | −14.971 | 1.00 | 52.26 | A |
| ATOM | 456 | CB | SER | A | 73 | −40.981 | 28.062 | −15.347 | 1.00 | 51.52 | A |
| ATOM | 457 | OG | SER | A | 73 | −41.246 | 27.525 | −16.629 | 1.00 | 48.35 | A |
| ATOM | 458 | C | SER | A | 73 | −43.416 | 28.674 | −15.134 | 1.00 | 53.10 | A |
| ATOM | 459 | O | SER | A | 73 | −44.097 | 29.008 | −16.107 | 1.00 | 54.40 | A |
| ATOM | 460 | N | SER | A | 74 | −43.882 | 27.893 | −14.165 | 1.00 | 53.63 | A |
| ATOM | 461 | CA | SER | A | 74 | −45.231 | 27.342 | −14.222 | 1.00 | 53.33 | A |
| ATOM | 462 | CB | SER | A | 74 | −45.484 | 26.414 | −13.041 | 1.00 | 51.87 | A |
| ATOM | 463 | OG | SER | A | 74 | −45.620 | 25.076 | −13.494 | 1.00 | 53.40 | A |
| ATOM | 464 | C | SER | A | 74 | −46.320 | 28.389 | −14.274 | 1.00 | 52.78 | A |
| ATOM | 465 | O | SER | A | 74 | −47.411 | 28.125 | −14.771 | 1.00 | 54.19 | A |
| ATOM | 466 | N | ALA | A | 75 | −46.021 | 29.579 | −13.770 | 1.00 | 51.42 | A |
| ATOM | 467 | CA | ALA | A | 75 | −46.990 | 30.662 | −13.755 | 1.00 | 50.95 | A |
| ATOM | 468 | CB | ALA | A | 75 | −46.727 | 31.573 | −12.556 | 1.00 | 48.85 | A |
| ATOM | 469 | C | ALA | A | 75 | −46.927 | 31.473 | −15.041 | 1.00 | 50.90 | A |
| ATOM | 470 | O | ALA | A | 75 | −47.774 | 32.319 | −15.292 | 1.00 | 52.54 | A |
| ATOM | 471 | N | ALA | A | 76 | −45.923 | 31.213 | −15.860 | 1.00 | 49.86 | A |
| ATOM | 472 | CA | ALA | A | 76 | −45.769 | 31.969 | −17.080 | 1.00 | 49.41 | A |
| ATOM | 473 | CB | ALA | A | 76 | −44.334 | 32.491 | −17.168 | 1.00 | 50.92 | A |
| ATOM | 474 | C | ALA | A | 76 | −46.122 | 31.192 | −18.341 | 1.00 | 49.59 | A |
| ATOM | 475 | O | ALA | A | 76 | −46.417 | 31.794 | −19.378 | 1.00 | 50.18 | A |
| ATOM | 476 | N | TRP | A | 77 | −46.111 | 29.866 | −18.259 | 1.00 | 47.56 | A |
| ATOM | 477 | CA | TRP | A | 77 | −46.387 | 29.063 | −19.438 | 1.00 | 46.48 | A |
| ATOM | 478 | CB | TRP | A | 77 | −45.110 | 28.355 | −19.877 | 1.00 | 44.34 | A |
| ATOM | 479 | CG | TRP | A | 77 | −43.913 | 29.259 | −19.895 | 1.00 | 42.62 | A |
| ATOM | 480 | CD2 | TRP | A | 77 | −43.655 | 30.325 | −20.813 | 1.00 | 40.67 | A |
| ATOM | 481 | CE2 | TRP | A | 77 | −42.422 | 30.902 | −20.448 | 1.00 | 40.13 | A |
| ATOM | 482 | CE3 | TRP | A | 77 | −44.344 | 30.847 | −21.914 | 1.00 | 42.24 | A |
| ATOM | 483 | CD1 | TRP | A | 77 | −42.860 | 29.232 | −19.036 | 1.00 | 40.98 | A |
| ATOM | 484 | NE1 | TRP | A | 77 | −41.958 | 30.213 | −19.360 | 1.00 | 41.31 | A |
| ATOM | 485 | CZ2 | TRP | A | 77 | −41.857 | 31.981 | −21.140 | 1.00 | 41.93 | A |
| ATOM | 486 | CZ3 | TRP | A | 77 | −43.780 | 31.927 | −22.612 | 1.00 | 42.72 | A |
| ATOM | 487 | CH2 | TRP | A | 77 | −42.548 | 32.479 | −22.218 | 1.00 | 40.65 | A |
| ATOM | 488 | C | TRP | A | 77 | −47.499 | 28.044 | −19.317 | 1.00 | 47.54 | A |
| ATOM | 489 | O | TRP | A | 77 | −47.927 | 27.687 | −18.228 | 1.00 | 47.95 | A |
| ATOM | 490 | N | ASP | A | 78 | −47.964 | 27.578 | −20.467 | 1.00 | 50.28 | A |
| ATOM | 491 | CA | ASP | A | 78 | −49.024 | 26.590 | −20.526 | 1.00 | 52.24 | A |
| ATOM | 492 | CB | ASP | A | 78 | −49.376 | 26.310 | −21.986 | 1.00 | 53.78 | A |
| ATOM | 493 | CG | ASP | A | 78 | −50.539 | 25.368 | −22.128 | 1.00 | 55.91 | A |
| ATOM | 494 | OD1 | ASP | A | 78 | −50.307 | 24.144 | −22.238 | 1.00 | 57.57 | A |
| ATOM | 495 | OD2 | ASP | A | 78 | −51.689 | 25.857 | −22.115 | 1.00 | 57.70 | A |
| ATOM | 496 | C | ASP | A | 78 | −48.591 | 25.309 | −19.815 | 1.00 | 53.52 | A |
| ATOM | 497 | O | ASP | A | 78 | −47.633 | 24.638 | −20.217 | 1.00 | 53.27 | A |
| ATOM | 498 | N | ALA | A | 79 | −49.304 | 24.978 | −18.746 | 1.00 | 54.38 | A |
| ATOM | 499 | CA | ALA | A | 79 | −48.983 | 23.797 | −17.961 | 1.00 | 54.80 | A |
| ATOM | 500 | CB | ALA | A | 79 | −50.123 | 23.488 | −16.991 | 1.00 | 54.45 | A |
| ATOM | 501 | C | ALA | A | 79 | −48.692 | 22.594 | −18.843 | 1.00 | 54.31 | A |
| ATOM | 502 | O | ALA | A | 79 | −47.633 | 21.994 | −18.747 | 1.00 | 55.97 | A |
| ATOM | 503 | N | SER | A | 80 | −49.619 | 22.255 | −19.722 | 1.00 | 54.29 | A |
| ATOM | 504 | CA | SER | A | 80 | −49.438 | 21.096 | −20.588 | 1.00 | 54.78 | A |
| ATOM | 505 | CB | SER | A | 80 | −50.677 | 20.900 | −21.471 | 1.00 | 56.80 | A |
| ATOM | 506 | OG | SER | A | 80 | −50.573 | 19.708 | −22.235 | 1.00 | 60.99 | A |
| ATOM | 507 | C | SER | A | 80 | −48.184 | 21.198 | −21.453 | 1.00 | 53.08 | A |
| ATOM | 508 | O | SER | A | 80 | −47.441 | 20.225 | −21.602 | 1.00 | 52.66 | A |
| ATOM | 509 | N | LEU | A | 81 | −47.956 | 22.372 | −22.030 | 1.00 | 51.48 | A |
| ATOM | 510 | CA | LEU | A | 81 | −46.781 | 22.579 | −22.858 | 1.00 | 50.28 | A |
| ATOM | 511 | CB | LEU | A | 81 | −46.848 | 23.939 | −23.567 | 1.00 | 50.13 | A |
| ATOM | 512 | CG | LEU | A | 81 | −47.794 | 24.078 | −24.770 | 1.00 | 52.07 | A |
| ATOM | 513 | CD1 | LEU | A | 81 | −47.823 | 25.523 | −25.274 | 1.00 | 50.96 | A |
| ATOM | 514 | CD2 | LEU | A | 81 | −47.338 | 23.143 | −25.881 | 1.00 | 51.96 | A |
| ATOM | 515 | C | LEU | A | 81 | −45.533 | 22.495 | −21.981 | 1.00 | 49.31 | A |
| ATOM | 516 | O | LEU | A | 81 | −44.655 | 21.673 | −22.231 | 1.00 | 49.33 | A |
| ATOM | 517 | N | LEU | A | 82 | −45.473 | 23.319 | −20.936 | 1.00 | 47.57 | A |
| ATOM | 518 | CA | LEU | A | 82 | −44.323 | 23.330 | −20.033 | 1.00 | 45.33 | A |

TABLE 5-continued

Atomic coordinates of rSIFN-co (SEQ ID NO: 1)

| ATOM | 519 | CB | LEU | A | 82 | −44.636 | 24.117 | −18.770 | 1.00 | 46.40 | A |
|---|---|---|---|---|---|---|---|---|---|---|---|
| ATOM | 520 | CG | LEU | A | 82 | −43.611 | 25.158 | −18.335 | 1.00 | 45.80 | A |
| ATOM | 521 | CD1 | LEU | A | 82 | −43.773 | 25.372 | −16.834 | 1.00 | 43.68 | A |
| ATOM | 522 | CD2 | LEU | A | 82 | −42.207 | 24.705 | −18.670 | 1.00 | 43.36 | A |
| ATOM | 523 | C | LEU | A | 82 | −43.864 | 21.945 | −19.618 | 1.00 | 43.50 | A |
| ATOM | 524 | O | LEU | A | 82 | −42.689 | 21.626 | −19.728 | 1.00 | 43.15 | A |
| ATOM | 525 | N | ALA | A | 83 | −44.785 | 21.114 | −19.146 | 1.00 | 43.10 | A |
| ATOM | 526 | CA | ALA | A | 83 | −44.405 | 19.775 | −18.706 | 1.00 | 43.00 | A |
| ATOM | 527 | CB | ALA | A | 83 | −45.606 | 19.052 | −18.090 | 1.00 | 43.77 | A |
| ATOM | 528 | C | ALA | A | 83 | −43.791 | 18.937 | −19.826 | 1.00 | 42.10 | A |
| ATOM | 529 | O | ALA | A | 83 | −42.857 | 18.179 | −19.591 | 1.00 | 41.05 | A |
| ATOM | 530 | N | LYS | A | 84 | −44.295 | 19.052 | −21.049 | 1.00 | 42.19 | A |
| ATOM | 531 | CA | LYS | A | 84 | −43.688 | 18.251 | −22.101 | 1.00 | 42.91 | A |
| ATOM | 532 | CB | LYS | A | 84 | −44.509 | 18.300 | −23.373 | 1.00 | 44.87 | A |
| ATOM | 533 | CG | LYS | A | 84 | −45.866 | 17.660 | −23.231 | 1.00 | 48.00 | A |
| ATOM | 534 | CD | LYS | A | 84 | −46.263 | 16.952 | −24.500 | 1.00 | 49.01 | A |
| ATOM | 535 | CE | LYS | A | 84 | −47.734 | 17.105 | −24.720 | 1.00 | 51.13 | A |
| ATOM | 536 | NZ | LYS | A | 84 | −48.023 | 18.541 | −24.942 | 1.00 | 52.74 | A |
| ATOM | 537 | C | LYS | A | 84 | −42.285 | 18.763 | −22.359 | 1.00 | 43.12 | A |
| ATOM | 538 | O | LYS | A | 84 | −41.347 | 17.987 | −22.527 | 1.00 | 44.29 | A |
| ATOM | 539 | N | PHE | A | 85 | −42.144 | 20.081 | −22.363 | 1.00 | 42.32 | A |
| ATOM | 540 | CA | PHE | A | 85 | −40.852 | 20.704 | −22.571 | 1.00 | 42.58 | A |
| ATOM | 541 | CB | PHE | A | 85 | −40.964 | 22.222 | −22.450 | 1.00 | 43.25 | A |
| ATOM | 542 | CG | PHE | A | 85 | −39.681 | 22.944 | −22.734 | 1.00 | 42.84 | A |
| ATOM | 543 | CD1 | PHE | A | 85 | −39.076 | 22.847 | −23.982 | 1.00 | 43.39 | A |
| ATOM | 544 | CD2 | PHE | A | 85 | −39.084 | 23.734 | −21.768 | 1.00 | 42.83 | A |
| ATOM | 545 | CE1 | PHE | A | 85 | −37.897 | 23.528 | −24.265 | 1.00 | 42.40 | A |
| ATOM | 546 | CE2 | PHE | A | 85 | −37.904 | 24.417 | −22.043 | 1.00 | 43.37 | A |
| ATOM | 547 | CZ | PHE | A | 85 | −37.312 | 24.313 | −23.295 | 1.00 | 42.70 | A |
| ATOM | 548 | C | PHE | A | 85 | −39.813 | 20.206 | −21.572 | 1.00 | 44.30 | A |
| ATOM | 549 | O | PHE | A | 85 | −38.835 | 19.562 | −21.964 | 1.00 | 45.07 | A |
| ATOM | 550 | N | TYR | A | 86 | −40.014 | 20.482 | −20.282 | 1.00 | 43.21 | A |
| ATOM | 551 | CA | TYR | A | 86 | −39.018 | 20.055 | −19.319 | 1.00 | 44.18 | A |
| ATOM | 552 | CB | TYR | A | 86 | −39.208 | 20.748 | −17.948 | 1.00 | 45.30 | A |
| ATOM | 553 | CG | TYR | A | 86 | −40.455 | 20.448 | −17.144 | 1.00 | 44.10 | A |
| ATOM | 554 | CD1 | TYR | A | 86 | −41.328 | 21.474 | −16.797 | 1.00 | 43.43 | A |
| ATOM | 555 | CE1 | TYR | A | 86 | −42.432 | 21.239 | −15.988 | 1.00 | 45.72 | A |
| ATOM | 556 | CD2 | TYR | A | 86 | −40.720 | 19.163 | −16.662 | 1.00 | 43.84 | A |
| ATOM | 557 | CE2 | TYR | A | 86 | −41.828 | 18.915 | −15.846 | 1.00 | 46.21 | A |
| ATOM | 558 | CZ | TYR | A | 86 | −42.678 | 19.963 | −15.513 | 1.00 | 47.37 | A |
| ATOM | 559 | OH | TYR | A | 86 | −43.764 | 19.756 | −14.691 | 1.00 | 49.38 | A |
| ATOM | 560 | C | TYR | A | 86 | −38.862 | 18.549 | −19.164 | 1.00 | 44.37 | A |
| ATOM | 561 | O | TYR | A | 86 | −37.848 | 18.080 | −18.656 | 1.00 | 44.46 | A |
| ATOM | 562 | N | THR | A | 87 | −39.846 | 17.785 | −19.621 | 1.00 | 44.44 | A |
| ATOM | 563 | CA | THR | A | 87 | −39.752 | 16.330 | −19.537 | 1.00 | 43.78 | A |
| ATOM | 564 | CB | THR | A | 87 | −41.129 | 15.644 | −19.751 | 1.00 | 43.93 | A |
| ATOM | 565 | OG1 | THR | A | 87 | −42.035 | 16.055 | −18.722 | 1.00 | 42.91 | A |
| ATOM | 566 | CG2 | THR | A | 87 | −40.986 | 14.130 | −19.712 | 1.00 | 40.48 | A |
| ATOM | 567 | C | THR | A | 87 | −38.813 | 15.905 | −20.654 | 1.00 | 43.41 | A |
| ATOM | 568 | O | THR | A | 87 | −38.040 | 14.962 | −20.509 | 1.00 | 42.95 | A |
| ATOM | 569 | N | GLU | A | 88 | −38.898 | 16.620 | −21.774 | 1.00 | 43.70 | A |
| ATOM | 570 | CA | GLU | A | 88 | −38.057 | 16.359 | −22.932 | 1.00 | 42.33 | A |
| ATOM | 571 | CB | GLU | A | 88 | −38.503 | 17.245 | −24.098 | 1.00 | 43.68 | A |
| ATOM | 572 | CG | GLU | A | 88 | −37.754 | 17.014 | −25.394 | 1.00 | 48.37 | A |
| ATOM | 573 | CD | GLU | A | 88 | −37.718 | 15.546 | −25.822 | 1.00 | 51.49 | A |
| ATOM | 574 | OE1 | GLU | A | 88 | −38.767 | 14.864 | −25.751 | 1.00 | 51.50 | A |
| ATOM | 575 | OE2 | GLU | A | 88 | −36.634 | 15.083 | −26.242 | 1.00 | 52.60 | A |
| ATOM | 576 | C | GLU | A | 88 | −36.616 | 16.664 | −22.541 | 1.00 | 40.76 | A |
| ATOM | 577 | O | GLU | A | 88 | −35.695 | 15.921 | −22.878 | 1.00 | 40.05 | A |
| ATOM | 578 | N | LEU | A | 89 | −36.428 | 17.756 | −21.809 | 1.00 | 39.65 | A |
| ATOM | 579 | CA | LEU | A | 89 | −35.096 | 18.127 | −21.373 | 1.00 | 40.05 | A |
| ATOM | 580 | CB | LEU | A | 89 | −35.128 | 19.464 | −20.619 | 1.00 | 39.26 | A |
| ATOM | 581 | CG | LEU | A | 89 | −35.580 | 20.688 | −21.432 | 1.00 | 39.90 | A |
| ATOM | 582 | CD1 | LEU | A | 89 | −35.594 | 21.916 | −20.546 | 1.00 | 41.45 | A |
| ATOM | 583 | CD2 | LEU | A | 89 | −34.647 | 20.917 | −22.599 | 1.00 | 37.56 | A |
| ATOM | 584 | C | LEU | A | 89 | −34.555 | 17.030 | −20.481 | 1.00 | 40.50 | A |
| ATOM | 585 | O | LEU | A | 89 | −33.394 | 16.638 | −20.598 | 1.00 | 39.83 | A |
| ATOM | 586 | N | TYR | A | 90 | −35.412 | 16.520 | −19.598 | 1.00 | 42.46 | A |
| ATOM | 587 | CA | TYR | A | 90 | −35.020 | 15.465 | −18.674 | 1.00 | 43.11 | A |
| ATOM | 588 | CB | TYR | A | 90 | −36.154 | 15.134 | −17.711 | 1.00 | 45.71 | A |
| ATOM | 589 | CG | TYR | A | 90 | −35.682 | 14.361 | −16.502 | 1.00 | 49.69 | A |
| ATOM | 590 | CD1 | TYR | A | 90 | −35.034 | 15.013 | −15.447 | 1.00 | 50.12 | A |
| ATOM | 591 | CE1 | TYR | A | 90 | −34.535 | 14.307 | −14.365 | 1.00 | 52.01 | A |
| ATOM | 592 | CD2 | TYR | A | 90 | −35.820 | 12.974 | −16.435 | 1.00 | 50.69 | A |
| ATOM | 593 | CE2 | TYR | A | 90 | −35.326 | 12.256 | −15.349 | 1.00 | 53.04 | A |
| ATOM | 594 | CZ | TYR | A | 90 | −34.680 | 12.929 | −14.321 | 1.00 | 53.92 | A |
| ATOM | 595 | OH | TYR | A | 90 | −34.161 | 12.227 | −13.256 | 1.00 | 56.71 | A |
| ATOM | 596 | C | TYR | A | 90 | −34.643 | 14.217 | −19.446 | 1.00 | 43.97 | A |

TABLE 5-continued

Atomic coordinates of rSIFN-co (SEQ ID NO: 1)

| ATOM | 597 | O | TYR | A | 90 | −33.682 | 13.534 | −19.106 | 1.00 | 44.98 | A |
| --- | --- | --- | --- | --- | --- | --- | --- | --- | --- | --- | --- |
| ATOM | 598 | N | GLN | A | 91 | −35.406 | 13.915 | −20.489 | 1.00 | 45.76 | A |
| ATOM | 599 | CA | GLN | A | 91 | −35.116 | 12.748 | −21.300 | 1.00 | 48.45 | A |
| ATOM | 600 | CB | GLN | A | 91 | −36.126 | 12.616 | −22.440 | 1.00 | 51.91 | A |
| ATOM | 601 | CG | GLN | A | 91 | −36.964 | 11.363 | −22.371 | 1.00 | 56.69 | A |
| ATOM | 602 | CD | GLN | A | 91 | −36.141 | 10.178 | −21.917 | 1.00 | 61.59 | A |
| ATOM | 603 | OE1 | GLN | A | 91 | −36.223 | 9.756 | −20.760 | 1.00 | 63.01 | A |
| ATOM | 604 | NE2 | GLN | A | 91 | −35.322 | 9.648 | −22.816 | 1.00 | 61.97 | A |
| ATOM | 605 | C | GLN | A | 91 | −33.719 | 12.909 | −21.880 | 1.00 | 48.95 | A |
| ATOM | 606 | O | GLN | A | 91 | −32.906 | 11.984 | −21.826 | 1.00 | 48.74 | A |
| ATOM | 607 | N | GLN | A | 92 | −33.451 | 14.098 | −22.419 | 1.00 | 48.30 | A |
| ATOM | 608 | CA | GLN | A | 92 | −32.166 | 14.403 | −23.030 | 1.00 | 49.20 | A |
| ATOM | 609 | CB | GLN | A | 92 | −32.204 | 15.800 | −23.666 | 1.00 | 49.21 | A |
| ATOM | 610 | CG | GLN | A | 92 | −32.906 | 15.825 | −25.020 | 1.00 | 50.13 | A |
| ATOM | 611 | CD | GLN | A | 92 | −33.021 | 17.215 | −25.621 | 1.00 | 51.05 | A |
| ATOM | 612 | OE1 | GLN | A | 92 | −32.087 | 18.010 | −25.566 | 1.00 | 53.57 | A |
| ATOM | 613 | NE2 | GLN | A | 92 | −34.166 | 17.505 | −26.214 | 1.00 | 52.77 | A |
| ATOM | 614 | C | GLN | A | 92 | −30.998 | 14.279 | −22.061 | 1.00 | 49.71 | A |
| ATOM | 615 | O | GLN | A | 92 | −29.895 | 13.902 | −22.462 | 1.00 | 50.06 | A |
| ATOM | 616 | N | LEU | A | 93 | −31.223 | 14.602 | −20.790 | 1.00 | 48.85 | A |
| ATOM | 617 | CA | LEU | A | 93 | −30.148 | 14.463 | −19.820 | 1.00 | 49.45 | A |
| ATOM | 618 | CB | LEU | A | 93 | −30.545 | 15.025 | −18.454 | 1.00 | 47.86 | A |
| ATOM | 619 | CG | LEU | A | 93 | −30.469 | 16.530 | −18.237 | 1.00 | 45.97 | A |
| ATOM | 620 | CD1 | LEU | A | 93 | −30.980 | 16.854 | −16.851 | 1.00 | 45.24 | A |
| ATOM | 621 | CD2 | LEU | A | 93 | −29.042 | 16.997 | −18.410 | 1.00 | 45.80 | A |
| ATOM | 622 | C | LEU | A | 93 | −29.883 | 12.974 | −19.679 | 1.00 | 51.53 | A |
| ATOM | 623 | O | LEU | A | 93 | −28.730 | 12.531 | −19.661 | 1.00 | 49.61 | A |
| ATOM | 624 | N | ALA | A | 94 | −30.974 | 12.212 | −19.585 | 1.00 | 54.03 | A |
| ATOM | 625 | CA | ALA | A | 94 | −30.902 | 10.766 | −19.439 | 1.00 | 56.50 | A |
| ATOM | 626 | CB | ALA | A | 94 | −32.306 | 10.177 | −19.305 | 1.00 | 55.64 | A |
| ATOM | 627 | C | ALA | A | 94 | −30.161 | 10.139 | −20.618 | 1.00 | 58.27 | A |
| ATOM | 628 | O | ALA | A | 94 | −29.383 | 9.208 | −20.431 | 1.00 | 60.16 | A |
| ATOM | 629 | N | ASP | A | 95 | −30.382 | 10.654 | −21.826 | 1.00 | 59.89 | A |
| ATOM | 630 | CA | ASP | A | 95 | −29.696 | 10.115 | −22.998 | 1.00 | 60.86 | A |
| ATOM | 631 | CB | ASP | A | 95 | −30.293 | 10.665 | −24.295 | 1.00 | 61.06 | A |
| ATOM | 632 | CG | ASP | A | 95 | −31.745 | 10.259 | −24.489 | 1.00 | 64.37 | A |
| ATOM | 633 | OD1 | ASP | A | 95 | −32.123 | 9.156 | −24.038 | 1.00 | 65.54 | A |
| ATOM | 634 | OD2 | ASP | A | 95 | −32.513 | 11.034 | −25.101 | 1.00 | 65.80 | A |
| ATOM | 635 | C | ASP | A | 95 | −28.208 | 10.424 | −22.960 | 1.00 | 62.01 | A |
| ATOM | 636 | O | ASP | A | 95 | −27.396 | 9.594 | −23.349 | 1.00 | 62.85 | A |
| ATOM | 637 | N | LEU | A | 96 | −27.840 | 11.612 | −22.492 | 1.00 | 63.44 | A |
| ATOM | 638 | CA | LEU | A | 96 | −26.429 | 11.968 | −22.434 | 1.00 | 65.26 | A |
| ATOM | 639 | CB | LEU | A | 96 | −26.250 | 13.437 | −22.063 | 1.00 | 64.67 | A |
| ATOM | 640 | CG | LEU | A | 96 | −26.228 | 14.431 | −23.223 | 1.00 | 64.38 | A |
| ATOM | 641 | CD1 | LEU | A | 96 | −25.876 | 15.815 | −22.699 | 1.00 | 63.39 | A |
| ATOM | 642 | CD2 | LEU | A | 96 | −25.213 | 13.978 | −24.256 | 1.00 | 62.74 | A |
| ATOM | 643 | C | LEU | A | 96 | −25.665 | 11.115 | −21.444 | 1.00 | 67.97 | A |
| ATOM | 644 | O | LEU | A | 96 | −24.520 | 10.735 | −21.693 | 1.00 | 68.62 | A |
| ATOM | 645 | N | GLU | A | 97 | −26.300 | 10.811 | −20.321 | 1.00 | 70.13 | A |
| ATOM | 646 | CA | GLU | A | 97 | −25.657 | 10.017 | −19.291 | 1.00 | 72.55 | A |
| ATOM | 647 | CB | GLU | A | 97 | −26.488 | 10.075 | −18.019 | 1.00 | 71.72 | A |
| ATOM | 648 | CG | GLU | A | 97 | −26.985 | 11.485 | −17.769 | 1.00 | 74.81 | A |
| ATOM | 649 | CD | GLU | A | 97 | −27.241 | 11.799 | −16.314 | 1.00 | 75.51 | A |
| ATOM | 650 | OE1 | GLU | A | 97 | −27.747 | 12.905 | −16.036 | 1.00 | 74.77 | A |
| ATOM | 651 | OE2 | GLU | A | 97 | −26.931 | 10.953 | −15.451 | 1.00 | 77.73 | A |
| ATOM | 652 | C | GLU | A | 97 | −25.450 | 8.588 | −19.762 | 1.00 | 74.96 | A |
| ATOM | 653 | O | GLU | A | 97 | −24.468 | 7.943 | −19.390 | 1.00 | 76.46 | A |
| ATOM | 654 | N | ALA | A | 98 | −26.366 | 8.089 | −20.586 | 1.00 | 76.86 | A |
| ATOM | 655 | CA | ALA | A | 98 | −26.223 | 6.737 | −21.115 | 1.00 | 78.82 | A |
| ATOM | 656 | CB | ALA | A | 98 | −27.433 | 6.366 | −21.954 | 1.00 | 77.13 | A |
| ATOM | 657 | C | ALA | A | 98 | −24.965 | 6.775 | −21.980 | 1.00 | 81.25 | A |
| ATOM | 658 | O | ALA | A | 98 | −24.070 | 5.941 | −21.838 | 1.00 | 81.55 | A |
| ATOM | 659 | N | CYS | A | 99 | −24.907 | 7.778 | −22.854 | 1.00 | 83.47 | A |
| ATOM | 660 | CA | CYS | A | 99 | −23.786 | 7.987 | −23.759 | 1.00 | 85.46 | A |
| ATOM | 661 | CB | CYS | A | 99 | −23.981 | 9.310 | −24.517 | 1.00 | 86.41 | A |
| ATOM | 662 | SG | CYS | A | 99 | −22.959 | 9.545 | −26.007 | 1.00 | 89.76 | A |
| ATOM | 663 | C | CYS | A | 99 | −22.462 | 8.000 | −22.988 | 1.00 | 86.47 | A |
| ATOM | 664 | O | CYS | A | 99 | −21.478 | 7.415 | −23.436 | 1.00 | 87.19 | A |
| ATOM | 665 | N | VAL | A | 100 | −22.438 | 8.659 | −21.832 | 1.00 | 87.06 | A |
| ATOM | 666 | CA | VAL | A | 100 | −21.221 | 8.718 | −21.018 | 1.00 | 88.28 | A |
| ATOM | 667 | CB | VAL | A | 100 | −21.364 | 9.721 | −19.840 | 1.00 | 87.74 | A |
| ATOM | 668 | CG1 | VAL | A | 100 | −20.109 | 9.704 | −18.980 | 1.00 | 87.01 | A |
| ATOM | 669 | CG2 | VAL | A | 100 | −21.603 | 11.118 | −20.371 | 1.00 | 87.68 | A |
| ATOM | 670 | C | VAL | A | 100 | −20.878 | 7.339 | −20.442 | 1.00 | 89.50 | A |
| ATOM | 671 | O | VAL | A | 100 | −19.728 | 6.899 | −20.506 | 1.00 | 89.46 | A |
| ATOM | 672 | N | ALA | A | 101 | −21.881 | 6.666 | −19.880 | 1.00 | 90.52 | A |
| ATOM | 673 | CA | ALA | A | 101 | −21.696 | 5.340 | −19.294 | 1.00 | 91.37 | A |
| ATOM | 674 | CB | ALA | A | 101 | −22.924 | 4.958 | −18.477 | 1.00 | 90.68 | A |

TABLE 5-continued

Atomic coordinates of rSIFN-co (SEQ ID NO: 1)

| ATOM | 675 | C   | ALA | A | 101 | −21.448 | 4.305  | −20.390 | 1.00 | 92.11 | A |
|------|-----|-----|-----|---|-----|---------|--------|---------|------|-------|---|
| ATOM | 676 | O   | ALA | A | 101 | −22.144 | 3.290  | −20.483 | 1.00 | 92.02 | A |
| ATOM | 677 | N   | GLY | A | 102 | −20.445 | 4.572  | −21.218 | 1.00 | 92.66 | A |
| ATOM | 678 | CA  | GLY | A | 102 | −20.117 | 3.672  | −22.303 | 1.00 | 93.77 | A |
| ATOM | 679 | C   | GLY | A | 102 | −19.599 | 4.456  | −23.490 | 1.00 | 94.37 | A |
| ATOM | 680 | O   | GLY | A | 102 | −20.320 | 4.666  | −24.467 | 1.00 | 94.30 | A |
| ATOM | 681 | N   | GLY | A | 103 | −18.345 | 4.893  | −23.399 | 1.00 | 94.78 | A |
| ATOM | 682 | CA  | GLY | A | 103 | −17.741 | 5.662  | −24.472 | 1.00 | 94.59 | A |
| ATOM | 683 | C   | GLY | A | 103 | −17.097 | 6.930  | −23.948 | 1.00 | 94.45 | A |
| ATOM | 684 | O   | GLY | A | 103 | −17.324 | 7.326  | −22.804 | 1.00 | 94.32 | A |
| ATOM | 685 | N   | ALA | A | 111 | −11.108 | 13.549 | −17.360 | 1.00 | 90.11 | A |
| ATOM | 686 | CA  | ALA | A | 111 | −11.032 | 14.851 | −16.699 | 1.00 | 90.12 | A |
| ATOM | 687 | CB  | ALA | A | 111 | −9.569  | 15.220 | −16.438 | 1.00 | 89.81 | A |
| ATOM | 688 | C   | ALA | A | 111 | −11.713 | 15.942 | −17.530 | 1.00 | 89.66 | A |
| ATOM | 689 | O   | ALA | A | 111 | −12.411 | 15.650 | −18.506 | 1.00 | 90.16 | A |
| ATOM | 690 | N   | GLY | A | 112 | −11.509 | 17.197 | −17.136 | 1.00 | 88.41 | A |
| ATOM | 691 | CA  | GLY | A | 112 | −12.108 | 18.312 | −17.853 | 1.00 | 86.60 | A |
| ATOM | 692 | C   | GLY | A | 112 | −11.712 | 19.656 | −17.267 | 1.00 | 85.50 | A |
| ATOM | 693 | O   | GLY | A | 112 | −10.617 | 19.797 | −16.709 | 1.00 | 86.67 | A |
| ATOM | 694 | N   | ASN | A | 113 | −12.590 | 20.650 | −17.400 | 1.00 | 82.82 | A |
| ATOM | 695 | CA  | ASN | A | 113 | −12.309 | 21.975 | −16.860 | 1.00 | 79.24 | A |
| ATOM | 696 | CB  | ASN | A | 113 | −11.567 | 22.843 | −17.893 | 1.00 | 81.82 | A |
| ATOM | 697 | CG  | ASN | A | 113 | −12.359 | 23.059 | −19.177 | 1.00 | 83.86 | A |
| ATOM | 698 | OD1 | ASN | A | 113 | −12.808 | 22.103 | −19.818 | 1.00 | 85.28 | A |
| ATOM | 699 | ND2 | ASN | A | 113 | −12.518 | 24.324 | −19.569 | 1.00 | 83.13 | A |
| ATOM | 700 | C   | ASN | A | 113 | −13.551 | 22.693 | −16.339 | 1.00 | 75.65 | A |
| ATOM | 701 | O   | ASN | A | 113 | −14.603 | 22.722 | −16.985 | 1.00 | 74.61 | A |
| ATOM | 702 | N   | ALA | A | 114 | −13.397 | 23.272 | −15.152 | 1.00 | 71.33 | A |
| ATOM | 703 | CA  | ALA | A | 114 | −14.456 | 23.986 | −14.447 | 1.00 | 66.25 | A |
| ATOM | 704 | CB  | ALA | A | 114 | −14.016 | 24.237 | −13.002 | 1.00 | 65.33 | A |
| ATOM | 705 | C   | ALA | A | 114 | −14.901 | 25.299 | −15.078 | 1.00 | 61.91 | A |
| ATOM | 706 | O   | ALA | A | 114 | −16.020 | 25.746 | −14.859 | 1.00 | 60.64 | A |
| ATOM | 707 | N   | ASP | A | 115 | −14.037 | 25.924 | −15.858 | 1.00 | 58.78 | A |
| ATOM | 708 | CA  | ASP | A | 115 | −14.404 | 27.197 | −16.444 | 1.00 | 57.63 | A |
| ATOM | 709 | CB  | ASP | A | 115 | −13.170 | 27.864 | −17.050 | 1.00 | 58.76 | A |
| ATOM | 710 | CG  | ASP | A | 115 | −12.240 | 28.440 | −15.977 | 1.00 | 60.80 | A |
| ATOM | 711 | OD1 | ASP | A | 115 | −12.644 | 29.410 | −15.283 | 1.00 | 58.59 | A |
| ATOM | 712 | OD2 | ASP | A | 115 | −11.114 | 27.911 | −15.822 | 1.00 | 60.92 | A |
| ATOM | 713 | C   | ASP | A | 115 | −15.553 | 27.143 | −17.441 | 1.00 | 56.69 | A |
| ATOM | 714 | O   | ASP | A | 115 | −16.446 | 27.994 | −17.395 | 1.00 | 55.98 | A |
| ATOM | 715 | N   | SER | A | 116 | −15.547 | 26.154 | −18.332 | 1.00 | 54.36 | A |
| ATOM | 716 | CA  | SER | A | 116 | −16.629 | 26.025 | −19.305 | 1.00 | 51.56 | A |
| ATOM | 717 | CB  | SER | A | 116 | −16.464 | 24.749 | −20.132 | 1.00 | 51.85 | A |
| ATOM | 718 | OG  | SER | A | 116 | −15.262 | 24.765 | −20.875 | 1.00 | 52.43 | A |
| ATOM | 719 | C   | SER | A | 116 | −17.957 | 25.964 | −18.549 | 1.00 | 50.12 | A |
| ATOM | 720 | O   | SER | A | 116 | −18.876 | 26.747 | −18.798 | 1.00 | 48.52 | A |
| ATOM | 721 | N   | ILE | A | 117 | −18.035 | 25.028 | −17.612 | 1.00 | 48.20 | A |
| ATOM | 722 | CA  | ILE | A | 117 | −19.234 | 24.839 | −16.809 | 1.00 | 47.04 | A |
| ATOM | 723 | CB  | ILE | A | 117 | −19.056 | 23.654 | −15.843 | 1.00 | 45.89 | A |
| ATOM | 724 | CG2 | ILE | A | 117 | −20.128 | 23.680 | −14.771 | 1.00 | 41.04 | A |
| ATOM | 725 | CG1 | ILE | A | 117 | −19.086 | 22.351 | −16.645 | 1.00 | 44.74 | A |
| ATOM | 726 | CD1 | ILE | A | 117 | −18.727 | 21.139 | −15.847 | 1.00 | 47.83 | A |
| ATOM | 727 | C   | ILE | A | 117 | −19.577 | 26.093 | −16.029 | 1.00 | 47.34 | A |
| ATOM | 728 | O   | ILE | A | 117 | −20.747 | 26.363 | −15.755 | 1.00 | 47.25 | A |
| ATOM | 729 | N   | LEU | A | 118 | −18.549 | 26.857 | −15.676 | 1.00 | 47.11 | A |
| ATOM | 730 | CA  | LEU | A | 118 | −18.743 | 28.095 | −14.941 | 1.00 | 46.33 | A |
| ATOM | 731 | CB  | LEU | A | 118 | −17.391 | 28.640 | −14.481 | 1.00 | 46.21 | A |
| ATOM | 732 | CG  | LEU | A | 118 | −17.207 | 29.082 | −13.023 | 1.00 | 47.56 | A |
| ATOM | 733 | CD1 | LEU | A | 118 | −17.864 | 28.110 | −12.045 | 1.00 | 45.29 | A |
| ATOM | 734 | CD2 | LEU | A | 118 | −15.717 | 29.169 | −12.742 | 1.00 | 46.63 | A |
| ATOM | 735 | C   | LEU | A | 118 | −19.419 | 29.071 | −15.894 | 1.00 | 45.37 | A |
| ATOM | 736 | O   | LEU | A | 118 | −20.361 | 29.770 | −15.522 | 1.00 | 45.75 | A |
| ATOM | 737 | N   | ALA | A | 119 | −18.947 | 29.095 | −17.135 | 1.00 | 43.53 | A |
| ATOM | 738 | CA  | ALA | A | 119 | −19.515 | 29.980 | −18.145 | 1.00 | 44.02 | A |
| ATOM | 739 | CB  | ALA | A | 119 | −18.835 | 29.746 | −19.483 | 1.00 | 43.57 | A |
| ATOM | 740 | C   | ALA | A | 119 | −21.022 | 29.760 | −18.282 | 1.00 | 44.16 | A |
| ATOM | 741 | O   | ALA | A | 119 | −21.802 | 30.707 | −18.185 | 1.00 | 43.43 | A |
| ATOM | 742 | N   | VAL | A | 120 | −21.420 | 28.506 | −18.504 | 1.00 | 43.64 | A |
| ATOM | 743 | CA  | VAL | A | 120 | −22.826 | 28.157 | −18.653 | 1.00 | 41.82 | A |
| ATOM | 744 | CB  | VAL | A | 120 | −23.023 | 26.629 | −18.940 | 1.00 | 41.05 | A |
| ATOM | 745 | CG1 | VAL | A | 120 | −24.488 | 26.335 | −19.229 | 1.00 | 38.92 | A |
| ATOM | 746 | CG2 | VAL | A | 120 | −22.176 | 26.185 | −20.109 | 1.00 | 35.59 | A |
| ATOM | 747 | C   | VAL | A | 120 | −23.582 | 28.530 | −17.378 | 1.00 | 42.89 | A |
| ATOM | 748 | O   | VAL | A | 120 | −24.632 | 29.168 | −17.443 | 1.00 | 43.59 | A |
| ATOM | 749 | N   | LYS | A | 121 | −23.050 | 28.148 | −16.218 | 1.00 | 43.62 | A |
| ATOM | 750 | CA  | LYS | A | 121 | −23.713 | 28.470 | −14.950 | 1.00 | 43.47 | A |
| ATOM | 751 | CB  | LYS | A | 121 | −22.938 | 27.909 | −13.757 | 1.00 | 42.82 | A |
| ATOM | 752 | CG  | LYS | A | 121 | −23.098 | 26.405 | −13.565 | 1.00 | 42.66 | A |

TABLE 5-continued

Atomic coordinates of rSIFN-co (SEQ ID NO: 1)

| ATOM | 753 | CD | LYS | A | 121 | −22.183 | 25.886 | −12.463 | 1.00 | 44.00 | A |
|---|---|---|---|---|---|---|---|---|---|---|---|
| ATOM | 754 | CE | LYS | A | 121 | −22.464 | 24.418 | −12.136 | 1.00 | 45.31 | A |
| ATOM | 755 | NZ | LYS | A | 121 | −23.826 | 24.200 | −11.551 | 1.00 | 43.66 | A |
| ATOM | 756 | C | LYS | A | 121 | −23.892 | 29.963 | −14.773 | 1.00 | 43.91 | A |
| ATOM | 757 | O | LYS | A | 121 | −24.932 | 30.404 | −14.305 | 1.00 | 45.66 | A |
| ATOM | 758 | N | LYS | A | 122 | −22.889 | 30.746 | −15.156 | 1.00 | 45.29 | A |
| ATOM | 759 | CA | LYS | A | 122 | −22.979 | 32.200 | −15.028 | 1.00 | 45.49 | A |
| ATOM | 760 | CB | LYS | A | 122 | −21.584 | 32.824 | −15.117 | 1.00 | 46.13 | A |
| ATOM | 761 | CG | LYS | A | 122 | −20.822 | 32.741 | −13.784 | 1.00 | 49.15 | A |
| ATOM | 762 | CD | LYS | A | 122 | −19.309 | 32.760 | −13.945 | 1.00 | 52.08 | A |
| ATOM | 763 | CE | LYS | A | 122 | −18.822 | 33.994 | −14.692 | 1.00 | 54.97 | A |
| ATOM | 764 | NZ | LYS | A | 122 | −17.332 | 33.997 | −14.825 | 1.00 | 58.31 | A |
| ATOM | 765 | C | LYS | A | 122 | −23.930 | 32.815 | −16.051 | 1.00 | 44.74 | A |
| ATOM | 766 | O | LYS | A | 122 | −24.576 | 33.819 | −15.774 | 1.00 | 44.79 | A |
| ATOM | 767 | N | TYR | A | 123 | −24.035 | 32.201 | −17.226 | 1.00 | 43.85 | A |
| ATOM | 768 | CA | TYR | A | 123 | −24.959 | 32.687 | −18.249 | 1.00 | 41.73 | A |
| ATOM | 769 | CB | TYR | A | 123 | −24.823 | 31.864 | −19.534 | 1.00 | 43.00 | A |
| ATOM | 770 | CG | TYR | A | 123 | −26.012 | 31.914 | −20.483 | 1.00 | 43.26 | A |
| ATOM | 771 | CD1 | TYR | A | 123 | −26.334 | 33.079 | −21.181 | 1.00 | 42.96 | A |
| ATOM | 772 | CE1 | TYR | A | 123 | −27.375 | 33.096 | −22.120 | 1.00 | 43.17 | A |
| ATOM | 773 | CD2 | TYR | A | 123 | −26.768 | 30.761 | −20.739 | 1.00 | 44.34 | A |
| ATOM | 774 | CE2 | TYR | A | 123 | −27.808 | 30.764 | −21.676 | 1.00 | 43.97 | A |
| ATOM | 775 | CZ | TYR | A | 123 | −28.100 | 31.934 | −22.361 | 1.00 | 43.84 | A |
| ATOM | 776 | OH | TYR | A | 123 | −29.106 | 31.942 | −23.289 | 1.00 | 43.65 | A |
| ATOM | 777 | C | TYR | A | 123 | −26.374 | 32.558 | −17.718 | 1.00 | 40.54 | A |
| ATOM | 778 | O | TYR | A | 123 | −27.180 | 33.464 | −17.886 | 1.00 | 40.80 | A |
| ATOM | 779 | N | PHE | A | 124 | −26.667 | 31.429 | −17.076 | 1.00 | 40.17 | A |
| ATOM | 780 | CA | PHE | A | 124 | −27.993 | 31.187 | −16.520 | 1.00 | 42.42 | A |
| ATOM | 781 | CB | PHE | A | 124 | −28.188 | 29.688 | −16.247 | 1.00 | 41.69 | A |
| ATOM | 782 | CG | PHE | A | 124 | −28.617 | 28.909 | −17.462 | 1.00 | 42.10 | A |
| ATOM | 783 | CD1 | PHE | A | 124 | −29.922 | 29.007 | −17.939 | 1.00 | 42.51 | A |
| ATOM | 784 | CD2 | PHE | A | 124 | −27.708 | 28.120 | −18.165 | 1.00 | 40.74 | A |
| ATOM | 785 | CE1 | PHE | A | 124 | −30.317 | 28.332 | −19.106 | 1.00 | 41.41 | A |
| ATOM | 786 | CE2 | PHE | A | 124 | −28.095 | 27.445 | −19.329 | 1.00 | 41.37 | A |
| ATOM | 787 | CZ | PHE | A | 124 | −29.400 | 27.554 | −19.797 | 1.00 | 39.97 | A |
| ATOM | 788 | C | PHE | A | 124 | −28.242 | 32.023 | −15.264 | 1.00 | 43.39 | A |
| ATOM | 789 | O | PHE | A | 124 | −29.378 | 32.322 | −14.922 | 1.00 | 42.59 | A |
| ATOM | 790 | N | GLN | A | 125 | −27.179 | 32.421 | −14.587 | 1.00 | 45.23 | A |
| ATOM | 791 | CA | GLN | A | 125 | −27.343 | 33.251 | −13.415 | 1.00 | 48.87 | A |
| ATOM | 792 | CB | GLN | A | 125 | −25.980 | 33.479 | −12.749 | 1.00 | 52.70 | A |
| ATOM | 793 | CG | GLN | A | 125 | −26.006 | 34.131 | −11.371 | 1.00 | 53.89 | A |
| ATOM | 794 | CD | GLN | A | 125 | −26.959 | 33.442 | −10.402 | 1.00 | 58.25 | A |
| ATOM | 795 | OE1 | GLN | A | 125 | −27.117 | 32.216 | −10.422 | 1.00 | 58.23 | A |
| ATOM | 796 | NE2 | GLN | A | 125 | −27.590 | 34.233 | −9.534 | 1.00 | 58.44 | A |
| ATOM | 797 | C | GLN | A | 125 | −27.942 | 34.565 | −13.920 | 1.00 | 49.60 | A |
| ATOM | 798 | O | GLN | A | 125 | −28.921 | 35.070 | −13.366 | 1.00 | 50.24 | A |
| ATOM | 799 | N | ARG | A | 126 | −27.361 | 35.119 | −14.979 | 1.00 | 50.02 | A |
| ATOM | 800 | CA | ARG | A | 126 | −27.883 | 36.362 | −15.537 | 1.00 | 51.12 | A |
| ATOM | 801 | CB | ARG | A | 126 | −27.070 | 36.766 | −16.753 | 1.00 | 50.74 | A |
| ATOM | 802 | CG | ARG | A | 126 | −25.703 | 37.248 | −16.397 | 1.00 | 51.91 | A |
| ATOM | 803 | CD | ARG | A | 126 | −24.873 | 37.578 | −17.655 | 1.00 | 53.15 | A |
| ATOM | 804 | NE | ARG | A | 126 | −23.567 | 36.942 | −17.591 | 1.00 | 56.26 | A |
| ATOM | 805 | CZ | ARG | A | 126 | −23.143 | 36.070 | −18.500 | 1.00 | 56.88 | A |
| ATOM | 806 | NH1 | ARG | A | 126 | −21.926 | 35.525 | −18.418 | 1.00 | 61.63 | A |
| ATOM | 807 | NH2 | ARG | A | 126 | −23.950 | 35.718 | −19.488 | 1.00 | 57.30 | A |
| ATOM | 808 | C | ARG | A | 126 | −29.365 | 36.270 | −15.891 | 1.00 | 51.99 | A |
| ATOM | 809 | O | ARG | A | 126 | −30.141 | 37.168 | −15.542 | 1.00 | 53.15 | A |
| ATOM | 810 | N | ILE | A | 127 | −29.758 | 35.181 | −16.554 | 1.00 | 51.87 | A |
| ATOM | 811 | CA | ILE | A | 127 | −31.152 | 34.972 | −16.914 | 1.00 | 50.67 | A |
| ATOM | 812 | CB | ILE | A | 127 | −31.403 | 33.556 | −17.498 | 1.00 | 49.15 | A |
| ATOM | 813 | CG2 | ILE | A | 127 | −32.888 | 33.373 | −17.759 | 1.00 | 45.24 | A |
| ATOM | 814 | CG1 | ILE | A | 127 | −30.611 | 33.343 | −18.790 | 1.00 | 49.62 | A |
| ATOM | 815 | CD1 | ILE | A | 127 | −31.121 | 34.119 | −19.945 | 1.00 | 50.32 | A |
| ATOM | 816 | C | ILE | A | 127 | −31.992 | 35.089 | −15.644 | 1.00 | 51.30 | A |
| ATOM | 817 | O | ILE | A | 127 | −32.917 | 35.891 | −15.579 | 1.00 | 50.89 | A |
| ATOM | 818 | N | THR | A | 128 | −31.669 | 34.274 | −14.644 | 1.00 | 52.07 | A |
| ATOM | 819 | CA | THR | A | 128 | −32.412 | 34.277 | −13.391 | 1.00 | 55.06 | A |
| ATOM | 820 | CB | THR | A | 128 | −31.762 | 33.325 | −12.358 | 1.00 | 54.18 | A |
| ATOM | 821 | OG1 | THR | A | 128 | −32.194 | 31.987 | −12.618 | 1.00 | 55.56 | A |
| ATOM | 822 | CG2 | THR | A | 128 | −32.163 | 33.691 | −10.943 | 1.00 | 56.16 | A |
| ATOM | 823 | C | THR | A | 128 | −32.517 | 35.679 | −12.811 | 1.00 | 56.81 | A |
| ATOM | 824 | O | THR | A | 128 | −33.602 | 36.128 | −12.445 | 1.00 | 56.02 | A |
| ATOM | 825 | N | LEU | A | 129 | −31.383 | 36.370 | −12.754 | 1.00 | 59.30 | A |
| ATOM | 826 | CA | LEU | A | 129 | −31.321 | 37.718 | −12.212 | 1.00 | 60.85 | A |
| ATOM | 827 | CB | LEU | A | 129 | −29.863 | 38.176 | −12.166 | 1.00 | 63.37 | A |
| ATOM | 828 | CG | LEU | A | 129 | −29.428 | 39.036 | −10.972 | 1.00 | 67.01 | A |
| ATOM | 829 | CD1 | LEU | A | 129 | −27.937 | 38.819 | −10.757 | 1.00 | 67.40 | A |
| ATOM | 830 | CD2 | LEU | A | 129 | −29.758 | 40.522 | −11.184 | 1.00 | 65.11 | A |

TABLE 5-continued

Atomic coordinates of rSIFN-co (SEQ ID NO: 1)

| ATOM | 831 | C   | LEU | A | 129 | −32.158 | 38.693 | −13.037 | 1.00 | 61.24 | A |
|------|-----|-----|-----|---|-----|---------|--------|---------|------|-------|---|
| ATOM | 832 | O   | LEU | A | 129 | −32.768 | 39.610 | −12.491 | 1.00 | 62.01 | A |
| ATOM | 833 | N   | TYR | A | 130 | −32.181 | 38.497 | −14.351 | 1.00 | 60.00 | A |
| ATOM | 834 | CA  | TYR | A | 130 | −32.953 | 39.357 | −15.243 | 1.00 | 58.99 | A |
| ATOM | 835 | CB  | TYR | A | 130 | −32.663 | 38.993 | −16.701 | 1.00 | 58.50 | A |
| ATOM | 836 | CG  | TYR | A | 130 | −33.584 | 39.637 | −17.715 | 1.00 | 57.74 | A |
| ATOM | 837 | CD1 | TYR | A | 130 | −33.439 | 40.974 | −18.074 | 1.00 | 58.05 | A |
| ATOM | 838 | CE1 | TYR | A | 130 | −34.279 | 41.560 | −19.020 | 1.00 | 58.22 | A |
| ATOM | 839 | CD2 | TYR | A | 130 | −34.594 | 38.901 | −18.327 | 1.00 | 58.06 | A |
| ATOM | 840 | CE2 | TYR | A | 130 | −35.437 | 39.478 | −19.272 | 1.00 | 57.76 | A |
| ATOM | 841 | CZ  | TYR | A | 130 | −35.274 | 40.805 | −19.613 | 1.00 | 58.23 | A |
| ATOM | 842 | OH  | TYR | A | 130 | −36.113 | 41.378 | −20.540 | 1.00 | 58.83 | A |
| ATOM | 843 | C   | TYR | A | 130 | −34.434 | 39.166 | −14.957 | 1.00 | 59.31 | A |
| ATOM | 844 | O   | TYR | A | 130 | −35.183 | 40.134 | −14.814 | 1.00 | 59.29 | A |
| ATOM | 845 | N   | LEU | A | 131 | −34.844 | 37.904 | −14.875 | 1.00 | 58.83 | A |
| ATOM | 846 | CA  | LEU | A | 131 | −36.233 | 37.558 | −14.617 | 1.00 | 58.58 | A |
| ATOM | 847 | CB  | LEU | A | 131 | −36.390 | 36.037 | −14.555 | 1.00 | 55.68 | A |
| ATOM | 848 | CG  | LEU | A | 131 | −36.422 | 35.361 | −15.922 | 1.00 | 53.74 | A |
| ATOM | 849 | CD1 | LEU | A | 131 | −36.318 | 33.863 | −15.755 | 1.00 | 54.07 | A |
| ATOM | 850 | CD2 | LEU | A | 131 | −37.699 | 35.742 | −16.649 | 1.00 | 52.53 | A |
| ATOM | 851 | C   | LEU | A | 131 | −36.740 | 38.193 | −13.330 | 1.00 | 59.15 | A |
| ATOM | 852 | O   | LEU | A | 131 | −37.811 | 38.807 | −13.304 | 1.00 | 57.39 | A |
| ATOM | 853 | N   | THR | A | 132 | −35.966 | 38.041 | −12.262 | 1.00 | 60.31 | A |
| ATOM | 854 | CA  | THR | A | 132 | −36.342 | 38.608 | −10.982 | 1.00 | 61.04 | A |
| ATOM | 855 | CB  | THR | A | 132 | −35.474 | 38.034 | −9.826  | 1.00 | 61.40 | A |
| ATOM | 856 | OG1 | THR | A | 132 | −35.587 | 38.887 | −8.680  | 1.00 | 64.65 | A |
| ATOM | 857 | CG2 | THR | A | 132 | −34.026 | 37.929 | −10.227 | 1.00 | 59.77 | A |
| ATOM | 858 | C   | THR | A | 132 | −36.212 | 40.125 | −11.044 | 1.00 | 61.41 | A |
| ATOM | 859 | O   | THR | A | 132 | −37.112 | 40.853 | −10.624 | 1.00 | 61.07 | A |
| ATOM | 860 | N   | GLY | A | 133 | −35.102 | 40.598 | −11.597 | 1.00 | 62.03 | A |
| ATOM | 861 | CA  | GLY | A | 133 | −34.891 | 42.029 | −11.705 | 1.00 | 62.46 | A |
| ATOM | 862 | C   | GLY | A | 133 | −35.929 | 42.684 | −12.592 | 1.00 | 62.83 | A |
| ATOM | 863 | O   | GLY | A | 133 | −36.032 | 43.905 | −12.634 | 1.00 | 63.96 | A |
| ATOM | 864 | N   | LYS | A | 134 | −36.708 | 41.869 | −13.295 | 1.00 | 62.98 | A |
| ATOM | 865 | CA  | LYS | A | 134 | −37.729 | 42.375 | −14.205 | 1.00 | 62.76 | A |
| ATOM | 866 | CB  | LYS | A | 134 | −37.523 | 41.775 | −15.595 | 1.00 | 63.31 | A |
| ATOM | 867 | CG  | LYS | A | 134 | −37.830 | 42.712 | −16.742 | 1.00 | 63.91 | A |
| ATOM | 868 | CD  | LYS | A | 134 | −36.734 | 43.744 | −16.932 | 1.00 | 64.03 | A |
| ATOM | 869 | CE  | LYS | A | 134 | −37.008 | 44.589 | −18.172 | 1.00 | 65.71 | A |
| ATOM | 870 | NZ  | LYS | A | 134 | −35.986 | 45.656 | −18.394 | 1.00 | 66.60 | A |
| ATOM | 871 | C   | LYS | A | 134 | −39.122 | 42.026 | −13.694 | 1.00 | 62.52 | A |
| ATOM | 872 | O   | LYS | A | 134 | −40.118 | 42.159 | −14.408 | 1.00 | 61.64 | A |
| ATOM | 873 | N   | ALA | A | 135 | −39.175 | 41.558 | −12.454 | 1.00 | 62.91 | A |
| ATOM | 874 | CA  | ALA | A | 135 | −40.433 | 41.207 | −11.809 | 1.00 | 62.68 | A |
| ATOM | 875 | CB  | ALA | A | 135 | −41.307 | 42.469 | −11.671 | 1.00 | 63.48 | A |
| ATOM | 876 | C   | ALA | A | 135 | −41.221 | 40.096 | −12.501 | 1.00 | 61.65 | A |
| ATOM | 877 | O   | ALA | A | 135 | −42.444 | 40.041 | −12.385 | 1.00 | 61.18 | A |
| ATOM | 878 | N   | TYR | A | 136 | −40.525 | 39.215 | −13.213 | 1.00 | 60.39 | A |
| ATOM | 879 | CA  | TYR | A | 136 | −41.166 | 38.091 | −13.908 | 1.00 | 60.51 | A |
| ATOM | 880 | CB  | TYR | A | 136 | −41.622 | 37.024 | −12.899 | 1.00 | 60.08 | A |
| ATOM | 881 | CG  | TYR | A | 136 | −40.547 | 36.596 | −11.924 | 1.00 | 62.10 | A |
| ATOM | 882 | CD1 | TYR | A | 136 | −40.241 | 37.378 | −10.807 | 1.00 | 62.66 | A |
| ATOM | 883 | CE1 | TYR | A | 136 | −39.227 | 37.007 | −9.919  | 1.00 | 63.23 | A |
| ATOM | 884 | CD2 | TYR | A | 136 | −39.811 | 35.424 | −12.131 | 1.00 | 62.49 | A |
| ATOM | 885 | CE2 | TYR | A | 136 | −38.792 | 35.044 | −11.249 | 1.00 | 64.05 | A |
| ATOM | 886 | CZ  | TYR | A | 136 | −38.507 | 35.844 | −10.146 | 1.00 | 63.71 | A |
| ATOM | 887 | OH  | TYR | A | 136 | −37.495 | 35.495 | −9.280  | 1.00 | 63.34 | A |
| ATOM | 888 | C   | TYR | A | 136 | −42.359 | 38.479 | −14.785 | 1.00 | 60.49 | A |
| ATOM | 889 | O   | TYR | A | 136 | −43.334 | 37.731 | −14.882 | 1.00 | 60.06 | A |
| ATOM | 890 | N   | SER | A | 137 | −42.289 | 39.641 | −15.425 | 1.00 | 61.06 | A |
| ATOM | 891 | CA  | SER | A | 137 | −43.383 | 40.088 | −16.284 | 1.00 | 61.14 | A |
| ATOM | 892 | CB  | SER | A | 137 | −43.205 | 41.557 | −16.650 | 1.00 | 60.90 | A |
| ATOM | 893 | OG  | SER | A | 137 | −42.133 | 41.713 | −17.559 | 1.00 | 63.48 | A |
| ATOM | 894 | C   | SER | A | 137 | −43.432 | 39.257 | −17.563 | 1.00 | 61.21 | A |
| ATOM | 895 | O   | SER | A | 137 | −42.414 | 38.718 | −18.004 | 1.00 | 59.84 | A |
| ATOM | 896 | N   | PRO | A | 138 | −44.624 | 39.150 | −18.178 | 1.00 | 61.71 | A |
| ATOM | 897 | CD  | PRO | A | 138 | −45.906 | 39.727 | −17.725 | 1.00 | 60.80 | A |
| ATOM | 898 | CA  | PRO | A | 138 | −44.819 | 38.384 | −19.414 | 1.00 | 60.13 | A |
| ATOM | 899 | CB  | PRO | A | 138 | −46.238 | 38.773 | −19.831 | 1.00 | 59.80 | A |
| ATOM | 900 | CG  | PRO | A | 138 | −46.929 | 38.932 | −18.523 | 1.00 | 58.23 | A |
| ATOM | 901 | C   | PRO | A | 138 | −43.783 | 38.661 | −20.506 | 1.00 | 59.03 | A |
| ATOM | 902 | O   | PRO | A | 138 | −43.361 | 37.737 | −21.199 | 1.00 | 59.70 | A |
| ATOM | 903 | N   | CYS | A | 139 | −43.382 | 39.922 | −20.659 | 1.00 | 57.95 | A |
| ATOM | 904 | CA  | CYS | A | 139 | −42.392 | 40.296 | −21.666 | 1.00 | 58.35 | A |
| ATOM | 905 | C   | CYS | A | 139 | −41.024 | 39.758 | −21.311 | 1.00 | 57.19 | A |
| ATOM | 906 | O   | CYS | A | 139 | −40.267 | 39.329 | −22.185 | 1.00 | 57.07 | A |
| ATOM | 907 | CB  | CYS | A | 139 | −42.280 | 41.813 | −21.798 | 1.00 | 60.88 | A |
| ATOM | 908 | SG  | CYS | A | 139 | −43.778 | 42.639 | −22.404 | 1.00 | 68.54 | A |

TABLE 5-continued

Atomic coordinates of rSIFN-co (SEQ ID NO: 1)

| ATOM | 909 | N | ALA | A | 140 | −40.701 | 39.807 | −20.022 | 1.00 | 55.95 | A |
|---|---|---|---|---|---|---|---|---|---|---|---|
| ATOM | 910 | CA | ALA | A | 140 | −39.420 | 39.318 | −19.537 | 1.00 | 53.50 | A |
| ATOM | 911 | CB | ALA | A | 140 | −39.307 | 39.547 | −18.039 | 1.00 | 51.95 | A |
| ATOM | 912 | C | ALA | A | 140 | −39.311 | 37.831 | −19.857 | 1.00 | 52.02 | A |
| ATOM | 913 | O | ALA | A | 140 | −38.249 | 37.350 | −20.237 | 1.00 | 52.56 | A |
| ATOM | 914 | N | TRP | A | 141 | −40.418 | 37.111 | −19.714 | 1.00 | 50.19 | A |
| ATOM | 915 | CA | TRP | A | 141 | −40.429 | 35.685 | −19.990 | 1.00 | 49.75 | A |
| ATOM | 916 | CB | TRP | A | 141 | −41.662 | 35.034 | −19.365 | 1.00 | 48.78 | A |
| ATOM | 917 | CG | TRP | A | 141 | −41.411 | 34.516 | −17.981 | 1.00 | 49.84 | A |
| ATOM | 918 | CD2 | TRP | A | 141 | −40.564 | 33.415 | −17.616 | 1.00 | 48.87 | A |
| ATOM | 919 | CE2 | TRP | A | 141 | −40.649 | 33.274 | −16.212 | 1.00 | 48.13 | A |
| ATOM | 920 | CE3 | TRP | A | 141 | −39.744 | 32.534 | −18.340 | 1.00 | 46.28 | A |
| ATOM | 921 | CD1 | TRP | A | 141 | −41.953 | 34.984 | −16.814 | 1.00 | 47.90 | A |
| ATOM | 922 | NE1 | TRP | A | 141 | −41.501 | 34.243 | −15.754 | 1.00 | 47.02 | A |
| ATOM | 923 | CZ2 | TRP | A | 141 | −39.944 | 32.281 | −15.514 | 1.00 | 46.41 | A |
| ATOM | 924 | CZ3 | TRP | A | 141 | −39.042 | 31.544 | −17.644 | 1.00 | 44.50 | A |
| ATOM | 925 | CH2 | TRP | A | 141 | −39.150 | 31.428 | −16.246 | 1.00 | 46.31 | A |
| ATOM | 926 | C | TRP | A | 141 | −40.373 | 35.394 | −21.487 | 1.00 | 49.99 | A |
| ATOM | 927 | O | TRP | A | 141 | −39.865 | 34.356 | −21.908 | 1.00 | 49.91 | A |
| ATOM | 928 | N | GLU | A | 142 | −40.902 | 36.314 | −22.285 | 1.00 | 49.68 | A |
| ATOM | 929 | CA | GLU | A | 142 | −40.885 | 36.176 | −23.734 | 1.00 | 49.54 | A |
| ATOM | 930 | CB | GLU | A | 142 | −41.879 | 37.161 | −24.359 | 1.00 | 51.93 | A |
| ATOM | 931 | CG | GLU | A | 142 | −42.054 | 37.014 | −25.862 | 1.00 | 55.37 | A |
| ATOM | 932 | CD | GLU | A | 142 | −42.079 | 35.566 | −26.315 | 1.00 | 58.44 | A |
| ATOM | 933 | OE1 | GLU | A | 142 | −42.804 | 34.747 | −25.698 | 1.00 | 59.65 | A |
| ATOM | 934 | OE2 | GLU | A | 142 | −41.371 | 35.252 | −27.296 | 1.00 | 58.89 | A |
| ATOM | 935 | C | GLU | A | 142 | −39.457 | 36.445 | −24.235 | 1.00 | 48.12 | A |
| ATOM | 936 | O | GLU | A | 142 | −38.990 | 35.830 | −25.195 | 1.00 | 46.88 | A |
| ATOM | 937 | N | VAL | A | 143 | −38.766 | 37.363 | −23.569 | 1.00 | 46.47 | A |
| ATOM | 938 | CA | VAL | A | 143 | −37.387 | 37.685 | −23.918 | 1.00 | 46.26 | A |
| ATOM | 939 | CB | VAL | A | 143 | −36.925 | 38.990 | −23.219 | 1.00 | 46.29 | A |
| ATOM | 940 | CG1 | VAL | A | 143 | −35.505 | 39.327 | −23.605 | 1.00 | 43.99 | A |
| ATOM | 941 | CG2 | VAL | A | 143 | −37.855 | 40.124 | −23.594 | 1.00 | 48.07 | A |
| ATOM | 942 | C | VAL | A | 143 | −36.471 | 36.532 | −23.490 | 1.00 | 45.08 | A |
| ATOM | 943 | O | VAL | A | 143 | −35.421 | 36.312 | −24.087 | 1.00 | 46.32 | A |
| ATOM | 944 | N | VAL | A | 144 | −36.861 | 35.800 | −22.451 | 1.00 | 42.03 | A |
| ATOM | 945 | CA | VAL | A | 144 | −36.051 | 34.680 | −22.010 | 1.00 | 40.59 | A |
| ATOM | 946 | CB | VAL | A | 144 | −36.331 | 34.343 | −20.517 | 1.00 | 39.36 | A |
| ATOM | 947 | CG1 | VAL | A | 144 | −35.716 | 32.999 | −20.144 | 1.00 | 38.27 | A |
| ATOM | 948 | CG2 | VAL | A | 144 | −35.722 | 35.421 | −19.626 | 1.00 | 37.69 | A |
| ATOM | 949 | C | VAL | A | 144 | −36.328 | 33.472 | −22.916 | 1.00 | 41.36 | A |
| ATOM | 950 | O | VAL | A | 144 | −35.419 | 32.715 | −23.262 | 1.00 | 39.87 | A |
| ATOM | 951 | N | ARG | A | 145 | −37.584 | 33.304 | −23.311 | 1.00 | 42.03 | A |
| ATOM | 952 | CA | ARG | A | 145 | −37.954 | 32.200 | −24.178 | 1.00 | 43.63 | A |
| ATOM | 953 | CB | ARG | A | 145 | −39.458 | 32.238 | −24.485 | 1.00 | 43.53 | A |
| ATOM | 954 | CG | ARG | A | 145 | −40.010 | 30.975 | −25.172 | 1.00 | 44.12 | A |
| ATOM | 955 | CD | ARG | A | 145 | −41.466 | 31.179 | −25.671 | 1.00 | 47.31 | A |
| ATOM | 956 | NE | ARG | A | 145 | −41.546 | 32.147 | −26.772 | 1.00 | 49.05 | A |
| ATOM | 957 | CZ | ARG | A | 145 | −41.087 | 31.924 | −28.005 | 1.00 | 47.86 | A |
| ATOM | 958 | NH1 | ARG | A | 145 | −40.526 | 30.765 | −28.323 | 1.00 | 47.20 | A |
| ATOM | 959 | NH2 | ARG | A | 145 | −41.141 | 32.882 | −28.910 | 1.00 | 48.43 | A |
| ATOM | 960 | C | ARG | A | 145 | −37.144 | 32.333 | −25.474 | 1.00 | 44.89 | A |
| ATOM | 961 | O | ARG | A | 145 | −36.551 | 31.367 | −25.952 | 1.00 | 44.68 | A |
| ATOM | 962 | N | ALA | A | 146 | −37.098 | 33.542 | −26.024 | 1.00 | 45.26 | A |
| ATOM | 963 | CA | ALA | A | 146 | −36.366 | 33.786 | −27.267 | 1.00 | 44.68 | A |
| ATOM | 964 | CB | ALA | A | 146 | −36.639 | 35.199 | −27.766 | 1.00 | 41.89 | A |
| ATOM | 965 | C | ALA | A | 146 | −34.865 | 33.564 | −27.115 | 1.00 | 44.62 | A |
| ATOM | 966 | O | ALA | A | 146 | −34.214 | 33.063 | −28.028 | 1.00 | 45.73 | A |
| ATOM | 967 | N | GLU | A | 147 | −34.319 | 33.940 | −25.963 | 1.00 | 43.92 | A |
| ATOM | 968 | CA | GLU | A | 147 | −32.894 | 33.772 | −25.697 | 1.00 | 42.58 | A |
| ATOM | 969 | CB | GLU | A | 147 | −32.512 | 34.500 | −24.403 | 1.00 | 40.40 | A |
| ATOM | 970 | CG | GLU | A | 147 | −31.124 | 34.186 | −23.878 | 1.00 | 40.78 | A |
| ATOM | 971 | CD | GLU | A | 147 | −30.021 | 34.667 | −24.802 | 1.00 | 44.78 | A |
| ATOM | 972 | OE1 | GLU | A | 147 | −30.039 | 35.853 | −25.201 | 1.00 | 46.12 | A |
| ATOM | 973 | OE2 | GLU | A | 147 | −29.125 | 33.862 | −25.128 | 1.00 | 46.08 | A |
| ATOM | 974 | C | GLU | A | 147 | −32.526 | 32.288 | −25.600 | 1.00 | 42.73 | A |
| ATOM | 975 | O | GLU | A | 147 | −31.490 | 31.871 | −26.130 | 1.00 | 41.47 | A |
| ATOM | 976 | N | ILE | A | 148 | −33.367 | 31.497 | −24.929 | 1.00 | 41.27 | A |
| ATOM | 977 | CA | ILE | A | 148 | −33.103 | 30.066 | −24.794 | 1.00 | 42.00 | A |
| ATOM | 978 | CB | ILE | A | 148 | −34.031 | 29.409 | −23.715 | 1.00 | 42.87 | A |
| ATOM | 979 | CG2 | ILE | A | 148 | −34.159 | 27.894 | −23.939 | 1.00 | 41.81 | A |
| ATOM | 980 | CG1 | ILE | A | 148 | −33.423 | 29.613 | −22.331 | 1.00 | 42.77 | A |
| ATOM | 981 | CD1 | ILE | A | 148 | −33.158 | 31.046 | −21.993 | 1.00 | 47.88 | A |
| ATOM | 982 | C | ILE | A | 148 | −33.284 | 29.382 | −26.148 | 1.00 | 42.52 | A |
| ATOM | 983 | O | ILE | A | 148 | −32.521 | 28.489 | −26.510 | 1.00 | 40.95 | A |
| ATOM | 984 | N | MET | A | 149 | −34.297 | 29.820 | −26.890 | 1.00 | 43.15 | A |
| ATOM | 985 | CA | MET | A | 149 | −34.594 | 29.288 | −28.210 | 1.00 | 43.66 | A |
| ATOM | 986 | CB | MET | A | 149 | −35.738 | 30.082 | −28.840 | 1.00 | 45.34 | A |

TABLE 5-continued

| | | | | Atomic coordinates of rSIFN-co (SEQ ID NO: 1) | | | | | |
|---|---|---|---|---|---|---|---|---|---|
| ATOM | 987 | CG | MET | A | 149 | −36.136 | 29.660 | −30.241 | 1.00 | 47.78 A |
| ATOM | 988 | SD | MET | A | 149 | −37.331 | 28.311 | −30.248 | 1.00 | 53.42 A |
| ATOM | 989 | CE | MET | A | 149 | −36.351 | 27.036 | −30.894 | 1.00 | 52.10 A |
| ATOM | 990 | C | MET | A | 149 | −33.342 | 29.456 | −29.052 | 1.00 | 45.41 A |
| ATOM | 991 | O | MET | A | 149 | −32.924 | 28.543 | −29.776 | 1.00 | 46.37 A |
| ATOM | 992 | N | ARG | A | 150 | −32.733 | 30.629 | −28.945 | 1.00 | 45.61 A |
| ATOM | 993 | CA | ARG | A | 150 | −31.540 | 30.895 | −29.709 | 1.00 | 47.17 A |
| ATOM | 994 | CB | ARG | A | 150 | −31.254 | 32.389 | −29.720 | 1.00 | 48.49 A |
| ATOM | 995 | CG | ARG | A | 150 | −30.191 | 32.777 | −30.712 | 1.00 | 53.95 A |
| ATOM | 996 | CD | ARG | A | 150 | −29.717 | 34.199 | −30.516 | 1.00 | 59.85 A |
| ATOM | 997 | NE | ARG | A | 150 | −28.745 | 34.560 | −31.546 | 1.00 | 66.19 A |
| ATOM | 998 | CZ | ARG | A | 150 | −27.975 | 35.644 | −31.513 | 1.00 | 69.41 A |
| ATOM | 999 | NH1 | ARG | A | 150 | −28.053 | 36.493 | −30.488 | 1.00 | 70.95 A |
| ATOM | 1000 | NH2 | ARG | A | 150 | −27.129 | 35.882 | −32.510 | 1.00 | 69.33 A |
| ATOM | 1001 | C | ARG | A | 150 | −30.334 | 30.126 | −29.161 | 1.00 | 48.23 A |
| ATOM | 1002 | O | ARG | A | 150 | −29.612 | 29.473 | −29.923 | 1.00 | 48.56 A |
| ATOM | 1003 | N | SER | A | 151 | −30.122 | 30.177 | −27.847 | 1.00 | 47.72 A |
| ATOM | 1004 | CA | SER | A | 151 | −28.973 | 29.492 | −27.258 | 1.00 | 48.57 A |
| ATOM | 1005 | CB | SER | A | 151 | −28.714 | 29.993 | −25.837 | 1.00 | 48.92 A |
| ATOM | 1006 | OG | SER | A | 151 | −29.880 | 29.900 | −25.045 | 1.00 | 54.27 A |
| ATOM | 1007 | C | SER | A | 151 | −29.090 | 27.979 | −27.253 | 1.00 | 48.50 A |
| ATOM | 1008 | O | SER | A | 151 | −28.113 | 27.278 | −27.517 | 1.00 | 46.55 A |
| ATOM | 1009 | N | PHE | A | 152 | −30.277 | 27.468 | −26.953 | 1.00 | 49.05 A |
| ATOM | 1010 | CA | PHE | A | 152 | −30.463 | 26.024 | −26.938 | 1.00 | 50.72 A |
| ATOM | 1011 | CB | PHE | A | 152 | −31.808 | 25.667 | −26.301 | 1.00 | 48.90 A |
| ATOM | 1012 | CG | PHE | A | 152 | −31.872 | 24.270 | −25.772 | 1.00 | 47.92 A |
| ATOM | 1013 | CD1 | PHE | A | 152 | −31.364 | 23.970 | −24.514 | 1.00 | 48.09 A |
| ATOM | 1014 | CD2 | PHE | A | 152 | −32.430 | 23.246 | −26.535 | 1.00 | 48.59 A |
| ATOM | 1015 | CE1 | PHE | A | 152 | −31.406 | 22.667 | −24.010 | 1.00 | 47.02 A |
| ATOM | 1016 | CE2 | PHE | A | 152 | −32.480 | 21.938 | −26.047 | 1.00 | 49.53 A |
| ATOM | 1017 | CZ | PHE | A | 152 | −31.964 | 21.649 | −24.775 | 1.00 | 48.38 A |
| ATOM | 1018 | C | PHE | A | 152 | −30.376 | 25.492 | −28.387 | 1.00 | 52.04 A |
| ATOM | 1019 | O | PHE | A | 152 | −30.086 | 24.319 | −28.612 | 1.00 | 51.28 A |
| ATOM | 1020 | N | ALA | A | 153 | −30.628 | 26.359 | −29.366 | 1.00 | 53.53 A |
| ATOM | 1021 | CA | ALA | A | 153 | −30.521 | 25.960 | −30.771 | 1.00 | 55.59 A |
| ATOM | 1022 | CB | ALA | A | 153 | −31.077 | 27.049 | −31.698 | 1.00 | 53.76 A |
| ATOM | 1023 | C | ALA | A | 153 | −29.040 | 25.729 | −31.060 | 1.00 | 55.66 A |
| ATOM | 1024 | O | ALA | A | 153 | −28.665 | 24.692 | −31.599 | 1.00 | 55.80 A |
| ATOM | 1025 | N | LEU | A | 154 | −28.205 | 26.699 | −30.696 | 1.00 | 57.44 A |
| ATOM | 1026 | CA | LEU | A | 154 | −26.756 | 26.584 | −30.891 | 1.00 | 60.09 A |
| ATOM | 1027 | CB | LEU | A | 154 | −26.045 | 27.854 | −30.407 | 1.00 | 57.36 A |
| ATOM | 1028 | CG | LEU | A | 154 | −26.306 | 29.106 | −31.239 | 1.00 | 56.81 A |
| ATOM | 1029 | CD1 | LEU | A | 154 | −25.681 | 30.305 | −30.566 | 1.00 | 54.66 A |
| ATOM | 1030 | CD2 | LEU | A | 154 | −25.746 | 28.915 | −32.642 | 1.00 | 54.86 A |
| ATOM | 1031 | C | LEU | A | 154 | −26.212 | 25.376 | −30.122 | 1.00 | 61.78 A |
| ATOM | 1032 | O | LEU | A | 154 | −25.251 | 24.730 | −30.550 | 1.00 | 62.63 A |
| ATOM | 1033 | N | SER | A | 155 | −26.840 | 25.084 | −28.986 | 1.00 | 62.76 A |
| ATOM | 1034 | CA | SER | A | 155 | −26.446 | 23.966 | −28.146 | 1.00 | 63.82 A |
| ATOM | 1035 | CB | SER | A | 155 | −27.144 | 24.065 | −26.797 | 1.00 | 63.60 A |
| ATOM | 1036 | OG | SER | A | 155 | −26.966 | 22.869 | −26.066 | 1.00 | 65.69 A |
| ATOM | 1037 | C | SER | A | 155 | −26.779 | 22.627 | −28.798 | 1.00 | 65.21 A |
| ATOM | 1038 | O | SER | A | 155 | −25.974 | 21.697 | −28.767 | 1.00 | 65.58 A |
| ATOM | 1039 | N | THR | A | 156 | −27.976 | 22.531 | −29.371 | 1.00 | 66.30 A |
| ATOM | 1040 | CA | THR | A | 156 | −28.422 | 21.319 | −30.050 | 1.00 | 67.72 A |
| ATOM | 1041 | CB | THR | A | 156 | −29.893 | 21.452 | −30.519 | 1.00 | 67.52 A |
| ATOM | 1042 | OG1 | THR | A | 156 | −30.765 | 21.393 | −29.386 | 1.00 | 69.40 A |
| ATOM | 1043 | CG2 | THR | A | 156 | −30.262 | 20.339 | −31.479 | 1.00 | 68.25 A |
| ATOM | 1044 | C | THR | A | 156 | −27.535 | 21.032 | −31.267 | 1.00 | 69.26 A |
| ATOM | 1045 | O | THR | A | 156 | −27.422 | 19.885 | −31.693 | 1.00 | 69.59 A |
| ATOM | 1046 | N | ASN | A | 157 | −26.915 | 22.076 | −31.822 | 1.00 | 70.20 A |
| ATOM | 1047 | CA | ASN | A | 157 | −26.031 | 21.928 | −32.979 | 1.00 | 70.93 A |
| ATOM | 1048 | CB | ASN | A | 157 | −25.561 | 23.295 | −33.490 | 1.00 | 71.29 A |
| ATOM | 1049 | CG | ASN | A | 157 | −26.661 | 24.082 | −34.186 | 1.00 | 71.77 A |
| ATOM | 1050 | OD1 | ASN | A | 157 | −27.846 | 23.776 | −34.054 | 1.00 | 71.35 A |
| ATOM | 1051 | ND2 | ASN | A | 157 | −26.268 | 25.116 | −34.924 | 1.00 | 72.68 A |
| ATOM | 1052 | C | ASN | A | 157 | −24.818 | 21.117 | −32.560 | 1.00 | 72.23 A |
| ATOM | 1053 | O | ASN | A | 157 | −24.347 | 20.254 | −33.302 | 1.00 | 73.06 A |
| ATOM | 1054 | N | LEU | A | 158 | −24.309 | 21.409 | −31.367 | 1.00 | 73.17 A |
| ATOM | 1055 | CA | LEU | A | 158 | −23.152 | 20.701 | −30.836 | 1.00 | 73.49 A |
| ATOM | 1056 | CB | LEU | A | 158 | −22.680 | 21.363 | −29.539 | 1.00 | 73.26 A |
| ATOM | 1057 | CG | LEU | A | 158 | −21.264 | 21.080 | −29.018 | 1.00 | 74.00 A |
| ATOM | 1058 | CD1 | LEU | A | 158 | −21.085 | 21.764 | −27.673 | 1.00 | 73.67 A |
| ATOM | 1059 | CD2 | LEU | A | 158 | −21.025 | 19.591 | −28.866 | 1.00 | 74.47 A |
| ATOM | 1060 | C | LEU | A | 158 | −23.601 | 19.270 | −30.561 | 1.00 | 73.89 A |
| ATOM | 1061 | O | LEU | A | 158 | −22.823 | 18.328 | −30.663 | 1.00 | 72.76 A |
| ATOM | 1062 | N | GLN | A | 159 | −24.875 | 19.120 | −30.220 | 1.00 | 75.65 A |
| ATOM | 1063 | CA | GLN | A | 159 | −25.439 | 17.811 | −29.926 | 1.00 | 78.32 A |
| ATOM | 1064 | CB | GLN | A | 159 | −26.861 | 17.972 | −29.374 | 1.00 | 79.21 A |

TABLE 5-continued

Atomic coordinates of rSIFN-co (SEQ ID NO: 1)

| ATOM | 1065 | CG | GLN | A | 159 | −27.392 | 16.753 | −28.635 | 1.00 | 80.98 | A |
|---|---|---|---|---|---|---|---|---|---|---|---|
| ATOM | 1066 | CD | GLN | A | 159 | −28.629 | 17.063 | −27.811 | 1.00 | 81.67 | A |
| ATOM | 1067 | OE1 | GLN | A | 159 | −29.666 | 17.463 | −28.347 | 1.00 | 82.31 | A |
| ATOM | 1068 | NE2 | GLN | A | 159 | −28.522 | 16.883 | −26.499 | 1.00 | 80.98 | A |
| ATOM | 1069 | C | GLN | A | 159 | −25.446 | 16.967 | −31.198 | 1.00 | 79.66 | A |
| ATOM | 1070 | O | GLN | A | 159 | −25.157 | 15.769 | −31.165 | 1.00 | 79.48 | A |
| ATOM | 1071 | N | GLY | A | 160 | −25.776 | 17.605 | −32.320 | 1.00 | 81.34 | A |
| ATOM | 1072 | CA | GLY | A | 160 | −25.793 | 16.909 | −33.592 | 1.00 | 81.32 | A |
| ATOM | 1073 | C | GLY | A | 160 | −24.383 | 16.471 | −33.944 | 1.00 | 82.28 | A |
| ATOM | 1074 | O | GLY | A | 160 | −24.160 | 15.338 | −34.363 | 1.00 | 82.91 | A |
| ATOM | 1075 | N | ALA | A | 161 | −23.420 | 17.369 | −33.756 | 1.00 | 82.27 | A |
| ATOM | 1076 | CA | ALA | A | 161 | −22.023 | 17.071 | −34.057 | 1.00 | 82.68 | A |
| ATOM | 1077 | CB | ALA | A | 161 | −21.197 | 18.371 | −34.048 | 1.00 | 82.24 | A |
| ATOM | 1078 | C | ALA | A | 161 | −21.435 | 16.061 | −33.067 | 1.00 | 82.41 | A |
| ATOM | 1079 | O | ALA | A | 161 | −20.248 | 15.738 | −33.117 | 1.00 | 82.19 | A |
| ATOM | 1080 | N | LEU | A | 162 | −22.274 | 15.560 | −32.171 | 1.00 | 82.59 | A |
| ATOM | 1081 | CA | LEU | A | 162 | −21.833 | 14.600 | −31.169 | 1.00 | 82.81 | A |
| ATOM | 1082 | CB | LEU | A | 162 | −22.266 | 15.075 | −29.776 | 1.00 | 81.71 | A |
| ATOM | 1083 | CG | LEU | A | 162 | −22.133 | 14.141 | −28.573 | 1.00 | 80.63 | A |
| ATOM | 1084 | CD1 | LEU | A | 162 | −21.690 | 14.939 | −27.359 | 1.00 | 80.31 | A |
| ATOM | 1085 | CD2 | LEU | A | 162 | −23.463 | 13.447 | −28.309 | 1.00 | 79.59 | A |
| ATOM | 1086 | C | LEU | A | 162 | −22.379 | 13.206 | −31.450 | 1.00 | 83.84 | A |
| ATOM | 1087 | O | LEU | A | 162 | −21.694 | 12.207 | −31.222 | 1.00 | 83.86 | A |
| ATOM | 1088 | N | GLY | A | 163 | −23.606 | 13.142 | −31.958 | 1.00 | 84.78 | A |
| ATOM | 1089 | CA | GLY | A | 163 | −24.212 | 11.855 | −32.255 | 1.00 | 85.12 | A |
| ATOM | 1090 | C | GLY | A | 163 | −23.963 | 11.378 | −33.671 | 1.00 | 85.32 | A |
| ATOM | 1091 | O | GLY | A | 163 | −24.939 | 10.958 | −34.330 | 1.00 | 85.87 | A |
| ATOM | 1092 | OXT | GLY | A | 163 | −22.795 | 11.408 | −34.121 | 1.00 | 84.75 | A |
| ATOM | 1093 | CB | ASN | B | 11 | −36.003 | 31.054 | −49.710 | 1.00 | 85.15 | B |
| ATOM | 1094 | CG | ASN | B | 11 | −35.553 | 29.922 | −50.640 | 1.00 | 85.60 | B |
| ATOM | 1095 | OD1 | ASN | B | 11 | −34.661 | 29.139 | −50.297 | 1.00 | 84.41 | B |
| ATOM | 1096 | ND2 | ASN | B | 11 | −36.172 | 29.834 | −51.818 | 1.00 | 84.86 | B |
| ATOM | 1097 | C | ASN | B | 11 | −38.419 | 31.748 | −49.975 | 1.00 | 83.40 | B |
| ATOM | 1098 | O | ASN | B | 11 | −38.848 | 32.106 | −48.869 | 1.00 | 83.24 | B |
| ATOM | 1099 | N | ASN | B | 11 | −36.612 | 33.443 | −50.017 | 1.00 | 85.25 | B |
| ATOM | 1100 | CA | ASN | B | 11 | −36.970 | 32.041 | −50.393 | 1.00 | 84.75 | B |
| ATOM | 1101 | N | ARG | B | 12 | −39.176 | 31.116 | −50.871 | 1.00 | 80.64 | B |
| ATOM | 1102 | CA | ARG | B | 12 | −40.566 | 30.781 | −50.583 | 1.00 | 75.89 | B |
| ATOM | 1103 | CB | ARG | B | 12 | −41.494 | 31.295 | −51.681 | 1.00 | 76.32 | B |
| ATOM | 1104 | CG | ARG | B | 12 | −42.957 | 31.189 | −51.303 | 1.00 | 77.28 | B |
| ATOM | 1105 | CD | ARG | B | 12 | −43.165 | 31.751 | −49.908 | 1.00 | 77.55 | B |
| ATOM | 1106 | NE | ARG | B | 12 | −44.512 | 32.270 | −49.718 | 1.00 | 78.19 | B |
| ATOM | 1107 | CZ | ARG | B | 12 | −44.864 | 33.064 | −48.715 | 1.00 | 77.18 | B |
| ATOM | 1108 | NH1 | ARG | B | 12 | −43.962 | 33.426 | −47.813 | 1.00 | 76.35 | B |
| ATOM | 1109 | NH2 | ARG | B | 12 | −46.113 | 33.503 | −48.622 | 1.00 | 76.77 | B |
| ATOM | 1110 | C | ARG | B | 12 | −40.747 | 29.286 | −50.453 | 1.00 | 72.00 | B |
| ATOM | 1111 | O | ARG | B | 12 | −41.679 | 28.718 | −51.024 | 1.00 | 69.87 | B |
| ATOM | 1112 | N | ARG | B | 13 | −39.860 | 28.652 | −49.694 | 1.00 | 68.53 | B |
| ATOM | 1113 | CA | ARG | B | 13 | −39.940 | 27.215 | −49.514 | 1.00 | 66.86 | B |
| ATOM | 1114 | CB | ARG | B | 13 | −38.635 | 26.669 | −48.944 | 1.00 | 69.00 | B |
| ATOM | 1115 | CG | ARG | B | 13 | −38.279 | 27.157 | −47.572 | 1.00 | 72.00 | B |
| ATOM | 1116 | CD | ARG | B | 13 | −37.016 | 26.456 | −47.145 | 1.00 | 75.81 | B |
| ATOM | 1117 | NE | ARG | B | 13 | −37.112 | 25.019 | −47.396 | 1.00 | 78.98 | B |
| ATOM | 1118 | CZ | ARG | B | 13 | −36.088 | 24.176 | −47.307 | 1.00 | 80.56 | B |
| ATOM | 1119 | NH1 | ARG | B | 13 | −34.886 | 24.632 | −46.971 | 1.00 | 82.00 | B |
| ATOM | 1120 | NH2 | ARG | B | 13 | −36.263 | 22.882 | −47.557 | 1.00 | 78.63 | B |
| ATOM | 1121 | C | ARG | B | 13 | −41.110 | 26.828 | −48.628 | 1.00 | 63.21 | B |
| ATOM | 1122 | O | ARG | B | 13 | −41.297 | 25.660 | −48.296 | 1.00 | 63.10 | B |
| ATOM | 1123 | N | ALA | B | 14 | −41.906 | 27.819 | −48.256 | 1.00 | 58.81 | B |
| ATOM | 1124 | CA | ALA | B | 14 | −43.068 | 27.565 | −47.439 | 1.00 | 56.19 | B |
| ATOM | 1125 | CB | ALA | B | 14 | −43.667 | 28.874 | −46.988 | 1.00 | 57.98 | B |
| ATOM | 1126 | C | ALA | B | 14 | −44.066 | 26.779 | −48.288 | 1.00 | 54.53 | B |
| ATOM | 1127 | O | ALA | B | 14 | −44.438 | 25.651 | −47.958 | 1.00 | 53.40 | B |
| ATOM | 1128 | N | LEU | B | 15 | −44.490 | 27.379 | −49.393 | 1.00 | 53.25 | B |
| ATOM | 1129 | CA | LEU | B | 15 | −45.437 | 26.730 | −50.287 | 1.00 | 51.60 | B |
| ATOM | 1130 | CB | LEU | B | 15 | −45.868 | 27.717 | −51.376 | 1.00 | 53.42 | B |
| ATOM | 1131 | CG | LEU | B | 15 | −46.780 | 28.860 | −50.918 | 1.00 | 54.05 | B |
| ATOM | 1132 | CD1 | LEU | B | 15 | −46.739 | 30.011 | −51.905 | 1.00 | 53.59 | B |
| ATOM | 1133 | CD2 | LEU | B | 15 | −48.192 | 28.335 | −50.780 | 1.00 | 55.07 | B |
| ATOM | 1134 | C | LEU | B | 15 | −44.836 | 25.465 | −50.911 | 1.00 | 49.98 | B |
| ATOM | 1135 | O | LEU | B | 15 | −45.538 | 24.473 | −51.136 | 1.00 | 49.36 | B |
| ATOM | 1136 | N | ILE | B | 16 | −43.535 | 25.491 | −51.178 | 1.00 | 46.77 | B |
| ATOM | 1137 | CA | ILE | B | 16 | −42.883 | 24.334 | −51.765 | 1.00 | 45.58 | B |
| ATOM | 1138 | CB | ILE | B | 16 | −41.435 | 24.679 | −52.164 | 1.00 | 45.17 | B |
| ATOM | 1139 | CG2 | ILE | B | 16 | −40.607 | 23.420 | −52.375 | 1.00 | 42.57 | B |
| ATOM | 1140 | CG1 | ILE | B | 16 | −41.466 | 25.512 | −53.448 | 1.00 | 44.62 | B |
| ATOM | 1141 | CD1 | ILE | B | 16 | −40.094 | 25.930 | −53.945 | 1.00 | 47.42 | B |
| ATOM | 1142 | C | ILE | B | 16 | −42.926 | 23.097 | −50.863 | 1.00 | 46.11 | B |

TABLE 5-continued

| | | | | | | | | | |
|---|---|---|---|---|---|---|---|---|---|
| colspan="10" | Atomic coordinates of rSIFN-co (SEQ ID NO: 1) |

| ATOM | 1143 | O | ILE | B | 16 | −43.308 | 22.013 | −51.309 | 1.00 | 45.20 | B |
|---|---|---|---|---|---|---|---|---|---|---|---|
| ATOM | 1144 | N | LEU | B | 17 | −42.548 | 23.246 | −49.596 | 1.00 | 46.19 | B |
| ATOM | 1145 | CA | LEU | B | 17 | −42.584 | 22.105 | −48.676 | 1.00 | 45.40 | B |
| ATOM | 1146 | CB | LEU | B | 17 | −42.067 | 22.519 | −47.303 | 1.00 | 43.77 | B |
| ATOM | 1147 | CG | LEU | B | 17 | −40.618 | 22.983 | −47.397 | 1.00 | 43.17 | B |
| ATOM | 1148 | CD1 | LEU | B | 17 | −40.256 | 23.847 | −46.210 | 1.00 | 42.11 | B |
| ATOM | 1149 | CD2 | LEU | B | 17 | −39.723 | 21.774 | −47.522 | 1.00 | 42.21 | B |
| ATOM | 1150 | C | LEU | B | 17 | −44.007 | 21.566 | −48.567 | 1.00 | 45.21 | B |
| ATOM | 1151 | O | LEU | B | 17 | −44.219 | 20.354 | −48.575 | 1.00 | 45.78 | B |
| ATOM | 1152 | N | LEU | B | 18 | −44.983 | 22.464 | −48.466 | 1.00 | 44.38 | B |
| ATOM | 1153 | CA | LEU | B | 18 | −46.373 | 22.046 | −48.391 | 1.00 | 44.44 | B |
| ATOM | 1154 | CB | LEU | B | 18 | −47.291 | 23.257 | −48.262 | 1.00 | 43.44 | B |
| ATOM | 1155 | CG | LEU | B | 18 | −47.574 | 23.721 | −46.831 | 1.00 | 43.94 | B |
| ATOM | 1156 | CD1 | LEU | B | 18 | −48.104 | 25.149 | −46.842 | 1.00 | 42.55 | B |
| ATOM | 1157 | CD2 | LEU | B | 18 | −48.565 | 22.761 | −46.172 | 1.00 | 40.40 | B |
| ATOM | 1158 | C | LEU | B | 18 | −46.713 | 21.278 | −49.654 | 1.00 | 46.61 | B |
| ATOM | 1159 | O | LEU | B | 18 | −47.504 | 20.332 | −49.628 | 1.00 | 47.62 | B |
| ATOM | 1160 | N | ALA | B | 19 | −46.107 | 21.692 | −50.764 | 1.00 | 47.27 | B |
| ATOM | 1161 | CA | ALA | B | 19 | −46.326 | 21.043 | −52.053 | 1.00 | 47.65 | B |
| ATOM | 1162 | CB | ALA | B | 19 | −45.762 | 21.912 | −53.174 | 1.00 | 47.43 | B |
| ATOM | 1163 | C | ALA | B | 19 | −45.679 | 19.659 | −52.087 | 1.00 | 48.06 | B |
| ATOM | 1164 | O | ALA | B | 19 | −46.257 | 18.715 | −52.620 | 1.00 | 47.48 | B |
| ATOM | 1165 | N | GLN | B | 20 | −44.474 | 19.553 | −51.526 | 1.00 | 49.52 | B |
| ATOM | 1166 | CA | GLN | B | 20 | −43.742 | 18.286 | −51.482 | 1.00 | 50.43 | B |
| ATOM | 1167 | CB | GLN | B | 20 | −42.266 | 18.521 | −51.141 | 1.00 | 50.28 | B |
| ATOM | 1168 | CG | GLN | B | 20 | −41.409 | 19.164 | −52.227 | 1.00 | 48.64 | B |
| ATOM | 1169 | CD | GLN | B | 20 | −40.000 | 19.484 | −51.738 | 1.00 | 49.87 | B |
| ATOM | 1170 | OE1 | GLN | B | 20 | −39.518 | 18.888 | −50.778 | 1.00 | 51.73 | B |
| ATOM | 1171 | NE2 | GLN | B | 20 | −39.333 | 20.418 | −52.403 | 1.00 | 49.40 | B |
| ATOM | 1172 | C | GLN | B | 20 | −44.352 | 17.371 | −50.428 | 1.00 | 51.95 | B |
| ATOM | 1173 | O | GLN | B | 20 | −44.020 | 16.199 | −50.350 | 1.00 | 52.62 | B |
| ATOM | 1174 | N | MET | B | 21 | −45.249 | 17.915 | −49.618 | 1.00 | 54.15 | B |
| ATOM | 1175 | CA | MET | B | 21 | −45.892 | 17.138 | −48.568 | 1.00 | 56.60 | B |
| ATOM | 1176 | CB | MET | B | 21 | −46.325 | 18.064 | −47.420 | 1.00 | 56.38 | B |
| ATOM | 1177 | CG | MET | B | 21 | −45.231 | 18.357 | −46.394 | 1.00 | 57.01 | B |
| ATOM | 1178 | SD | MET | B | 21 | −45.690 | 19.612 | −45.174 | 1.00 | 57.20 | B |
| ATOM | 1179 | CE | MET | B | 21 | −47.211 | 18.885 | −44.499 | 1.00 | 57.95 | B |
| ATOM | 1180 | C | MET | B | 21 | −47.090 | 16.327 | −49.056 | 1.00 | 58.24 | B |
| ATOM | 1181 | O | MET | B | 21 | −47.551 | 15.424 | −48.363 | 1.00 | 58.12 | B |
| ATOM | 1182 | N | ALA | B | 22 | −47.600 | 16.645 | −50.243 | 1.00 | 61.09 | B |
| ATOM | 1183 | CA | ALA | B | 22 | −48.754 | 15.922 | −50.773 | 1.00 | 62.96 | B |
| ATOM | 1184 | CB | ALA | B | 22 | −49.151 | 16.468 | −52.145 | 1.00 | 61.96 | B |
| ATOM | 1185 | C | ALA | B | 22 | −48.415 | 14.446 | −50.872 | 1.00 | 64.38 | B |
| ATOM | 1186 | O | ALA | B | 22 | −47.323 | 14.086 | −51.300 | 1.00 | 64.43 | B |
| ATOM | 1187 | N | ARG | B | 23 | −49.352 | 13.596 | −50.463 | 1.00 | 67.27 | B |
| ATOM | 1188 | CA | ARG | B | 23 | −49.132 | 12.158 | −50.508 | 1.00 | 70.44 | B |
| ATOM | 1189 | CB | ARG | B | 23 | −48.613 | 11.669 | −49.152 | 1.00 | 71.01 | B |
| ATOM | 1190 | CG | ARG | B | 23 | −49.450 | 12.102 | −47.968 | 1.00 | 72.18 | B |
| ATOM | 1191 | CD | ARG | B | 23 | −48.731 | 11.815 | −46.667 | 1.00 | 73.33 | B |
| ATOM | 1192 | NE | ARG | B | 23 | −48.552 | 10.385 | −46.450 | 1.00 | 76.38 | B |
| ATOM | 1193 | CZ | ARG | B | 23 | −47.854 | 9.860 | −45.445 | 1.00 | 78.19 | B |
| ATOM | 1194 | NH1 | ARG | B | 23 | −47.256 | 10.649 | −44.553 | 1.00 | 77.51 | B |
| ATOM | 1195 | NH2 | ARG | B | 23 | −47.760 | 8.538 | −45.329 | 1.00 | 77.90 | B |
| ATOM | 1196 | C | ARG | B | 23 | −50.362 | 11.354 | −50.923 | 1.00 | 72.04 | B |
| ATOM | 1197 | O | ARG | B | 23 | −50.280 | 10.139 | −51.102 | 1.00 | 73.43 | B |
| ATOM | 1198 | N | ALA | B | 24 | −51.500 | 12.023 | −51.077 | 1.00 | 73.32 | B |
| ATOM | 1199 | CA | ALA | B | 24 | −52.721 | 11.340 | −51.489 | 1.00 | 75.11 | B |
| ATOM | 1200 | CB | ALA | B | 24 | −53.947 | 12.016 | −50.872 | 1.00 | 72.05 | B |
| ATOM | 1201 | C | ALA | B | 24 | −52.817 | 11.370 | −53.011 | 1.00 | 77.82 | B |
| ATOM | 1202 | O | ALA | B | 24 | −52.334 | 12.309 | −53.653 | 1.00 | 78.81 | B |
| ATOM | 1203 | N | SER | B | 25 | −53.429 | 10.339 | −53.588 | 1.00 | 79.74 | B |
| ATOM | 1204 | CA | SER | B | 25 | −53.599 | 10.261 | −55.033 | 1.00 | 82.06 | B |
| ATOM | 1205 | CB | SER | B | 25 | −53.912 | 8.827 | −55.442 | 1.00 | 82.21 | B |
| ATOM | 1206 | OG | SER | B | 25 | −55.044 | 8.348 | −54.737 | 1.00 | 83.63 | B |
| ATOM | 1207 | C | SER | B | 25 | −54.746 | 11.178 | −55.459 | 1.00 | 84.39 | B |
| ATOM | 1208 | O | SER | B | 25 | −55.633 | 11.492 | −54.657 | 1.00 | 84.68 | B |
| ATOM | 1209 | N | PRO | B | 26 | −54.749 | 11.614 | −56.730 | 1.00 | 85.80 | B |
| ATOM | 1210 | CD | PRO | B | 26 | −53.769 | 11.287 | −57.779 | 1.00 | 85.92 | B |
| ATOM | 1211 | CA | PRO | B | 26 | −55.793 | 12.500 | −57.254 | 1.00 | 87.16 | B |
| ATOM | 1212 | CB | PRO | B | 26 | −55.212 | 12.950 | −58.588 | 1.00 | 86.58 | B |
| ATOM | 1213 | CG | PRO | B | 26 | −54.482 | 11.736 | −59.038 | 1.00 | 86.26 | B |
| ATOM | 1214 | C | PRO | B | 26 | −57.166 | 11.837 | −57.407 | 1.00 | 88.81 | B |
| ATOM | 1215 | O | PRO | B | 26 | −58.139 | 12.487 | −57.795 | 1.00 | 89.06 | B |
| ATOM | 1216 | N | PHE | B | 27 | −57.242 | 10.544 | −57.108 | 1.00 | 89.93 | B |
| ATOM | 1217 | CA | PHE | B | 27 | −58.507 | 9.823 | −57.207 | 1.00 | 91.46 | B |
| ATOM | 1218 | CB | PHE | B | 27 | −58.359 | 8.550 | −58.053 | 1.00 | 91.94 | B |
| ATOM | 1219 | CG | PHE | B | 27 | −57.967 | 8.801 | −59.482 | 1.00 | 91.42 | B |
| ATOM | 1220 | CD1 | PHE | B | 27 | −56.659 | 9.137 | −59.811 | 1.00 | 91.14 | B |

TABLE 5-continued

Atomic coordinates of rSIFN-co (SEQ ID NO: 1)

| ATOM | 1221 | CD2 | PHE | B | 27 | −58.909 | 8.695 | −60.498 | 1.00 | 90.75 | B |
| ATOM | 1222 | CE1 | PHE | B | 27 | −56.294 | 9.361 | −61.131 | 1.00 | 91.14 | B |
| ATOM | 1223 | CE2 | PHE | B | 27 | −58.555 | 8.917 | −61.820 | 1.00 | 91.00 | B |
| ATOM | 1224 | CZ  | PHE | B | 27 | −57.245 | 9.252 | −62.139 | 1.00 | 91.47 | B |
| ATOM | 1225 | C   | PHE | B | 27 | −58.989 | 9.426 | −55.820 | 1.00 | 92.32 | B |
| ATOM | 1226 | O   | PHE | B | 27 | −60.192 | 9.267 | −55.599 | 1.00 | 93.11 | B |
| ATOM | 1227 | N   | ALA | B | 28 | −58.035 | 9.269 | −54.900 | 1.00 | 92.92 | B |
| ATOM | 1228 | CA  | ALA | B | 28 | −58.295 | 8.864 | −53.516 | 1.00 | 92.18 | B |
| ATOM | 1229 | CB  | ALA | B | 28 | −56.996 | 8.915 | −52.706 | 1.00 | 91.40 | B |
| ATOM | 1230 | C   | ALA | B | 28 | −59.387 | 9.649 | −52.790 | 1.00 | 91.90 | B |
| ATOM | 1231 | O   | ALA | B | 28 | −60.199 | 9.057 | −52.074 | 1.00 | 91.57 | B |
| ATOM | 1232 | N   | CYS | B | 29 | −59.416 | 10.969 | −52.963 | 1.00 | 91.32 | B |
| ATOM | 1233 | CA  | CYS | B | 29 | −60.433 | 11.772 | −52.288 | 1.00 | 91.47 | B |
| ATOM | 1234 | C   | CYS | B | 29 | −61.450 | 12.374 | −53.243 | 1.00 | 92.66 | B |
| ATOM | 1235 | O   | CYS | B | 29 | −61.088 | 12.992 | −54.245 | 1.00 | 92.45 | B |
| ATOM | 1236 | CB  | CYS | B | 29 | −59.780 | 12.887 | −51.463 | 1.00 | 89.53 | B |
| ATOM | 1237 | SG  | CYS | B | 29 | −58.531 | 12.280 | −50.282 | 1.00 | 86.39 | B |
| ATOM | 1238 | N   | GLY | B | 30 | −62.727 | 12.178 | −52.926 | 1.00 | 93.98 | B |
| ATOM | 1239 | CA  | GLY | B | 30 | −63.784 | 12.716 | −53.758 | 1.00 | 95.70 | B |
| ATOM | 1240 | C   | GLY | B | 30 | −63.862 | 14.212 | −53.543 | 1.00 | 96.95 | B |
| ATOM | 1241 | O   | GLY | B | 30 | −63.276 | 14.727 | −52.592 | 1.00 | 97.62 | B |
| ATOM | 1242 | N   | GLY | B | 31 | −64.577 | 14.908 | −54.420 | 1.00 | 97.39 | B |
| ATOM | 1243 | CA  | GLY | B | 31 | −64.707 | 16.349 | −54.296 | 1.00 | 97.58 | B |
| ATOM | 1244 | C   | GLY | B | 31 | −65.411 | 16.803 | −53.027 | 1.00 | 97.64 | B |
| ATOM | 1245 | O   | GLY | B | 31 | −66.503 | 17.375 | −53.083 | 1.00 | 98.81 | B |
| ATOM | 1246 | N   | GLY | B | 32 | −64.787 | 16.546 | −51.880 | 1.00 | 96.79 | B |
| ATOM | 1247 | CA  | GLY | B | 32 | −65.360 | 16.951 | −50.609 | 1.00 | 94.95 | B |
| ATOM | 1248 | C   | GLY | B | 32 | −64.893 | 18.350 | −50.254 | 1.00 | 93.64 | B |
| ATOM | 1249 | O   | GLY | B | 32 | −64.396 | 18.597 | −49.150 | 1.00 | 93.49 | B |
| ATOM | 1250 | N   | GLY | B | 33 | −65.052 | 19.265 | −51.207 | 1.00 | 92.18 | B |
| ATOM | 1251 | CA  | GLY | B | 33 | −64.646 | 20.645 | −51.009 | 1.00 | 89.82 | B |
| ATOM | 1252 | C   | GLY | B | 33 | −65.345 | 21.318 | −49.846 | 1.00 | 88.28 | B |
| ATOM | 1253 | O   | GLY | B | 33 | −66.577 | 21.331 | −49.762 | 1.00 | 88.34 | B |
| ATOM | 1254 | N   | HIS | B | 34 | −64.544 | 21.878 | −48.943 | 1.00 | 85.84 | B |
| ATOM | 1255 | CA  | HIS | B | 34 | −65.053 | 22.571 | −47.762 | 1.00 | 82.36 | B |
| ATOM | 1256 | CB  | HIS | B | 34 | −64.630 | 21.808 | −46.496 | 1.00 | 80.60 | B |
| ATOM | 1257 | CG  | HIS | B | 34 | −65.146 | 22.398 | −45.220 | 1.00 | 78.05 | B |
| ATOM | 1258 | CD2 | HIS | B | 34 | −65.986 | 21.899 | −44.281 | 1.00 | 76.62 | B |
| ATOM | 1259 | ND1 | HIS | B | 34 | −64.766 | 23.644 | −44.763 | 1.00 | 77.24 | B |
| ATOM | 1260 | CE1 | HIS | B | 34 | −65.346 | 23.883 | −43.603 | 1.00 | 75.05 | B |
| ATOM | 1261 | NE2 | HIS | B | 34 | −66.092 | 22.838 | −43.287 | 1.00 | 75.00 | B |
| ATOM | 1262 | C   | HIS | B | 34 | −64.472 | 23.983 | −47.764 | 1.00 | 80.50 | B |
| ATOM | 1263 | O   | HIS | B | 34 | −63.349 | 24.198 | −48.226 | 1.00 | 81.27 | B |
| ATOM | 1264 | N   | ASP | B | 35 | −65.246 | 24.947 | −47.278 | 1.00 | 77.74 | B |
| ATOM | 1265 | CA  | ASP | B | 35 | −64.787 | 26.330 | −47.225 | 1.00 | 75.78 | B |
| ATOM | 1266 | CB  | ASP | B | 35 | −65.795 | 27.264 | −47.895 | 1.00 | 76.50 | B |
| ATOM | 1267 | CG  | ASP | B | 35 | −65.703 | 28.687 | −47.371 | 1.00 | 77.21 | B |
| ATOM | 1268 | OD1 | ASP | B | 35 | −64.578 | 29.227 | −47.288 | 1.00 | 77.48 | B |
| ATOM | 1269 | OD2 | ASP | B | 35 | −66.759 | 29.266 | −47.040 | 1.00 | 77.57 | B |
| ATOM | 1270 | C   | ASP | B | 35 | −64.579 | 26.767 | −45.784 | 1.00 | 73.69 | B |
| ATOM | 1271 | O   | ASP | B | 35 | −65.486 | 26.653 | −44.956 | 1.00 | 74.03 | B |
| ATOM | 1272 | N   | PHE | B | 36 | −63.390 | 27.282 | −45.484 | 1.00 | 69.71 | B |
| ATOM | 1273 | CA  | PHE | B | 36 | −63.097 | 27.707 | −44.125 | 1.00 | 65.47 | B |
| ATOM | 1274 | CB  | PHE | B | 36 | −61.694 | 27.260 | −43.724 | 1.00 | 63.29 | B |
| ATOM | 1275 | CG  | PHE | B | 36 | −61.484 | 25.780 | −43.842 | 1.00 | 61.40 | B |
| ATOM | 1276 | CD1 | PHE | B | 36 | −61.068 | 25.218 | −45.040 | 1.00 | 60.82 | B |
| ATOM | 1277 | CD2 | PHE | B | 36 | −61.722 | 24.942 | −42.762 | 1.00 | 59.30 | B |
| ATOM | 1278 | CE1 | PHE | B | 36 | −60.896 | 23.840 | −45.157 | 1.00 | 59.96 | B |
| ATOM | 1279 | CE2 | PHE | B | 36 | −61.554 | 23.568 | −42.873 | 1.00 | 58.76 | B |
| ATOM | 1280 | CZ  | PHE | B | 36 | −61.139 | 23.018 | −44.071 | 1.00 | 57.07 | B |
| ATOM | 1281 | C   | PHE | B | 36 | −63.254 | 29.195 | −43.882 | 1.00 | 63.46 | B |
| ATOM | 1282 | O   | PHE | B | 36 | −62.813 | 29.701 | −42.860 | 1.00 | 63.36 | B |
| ATOM | 1283 | N   | GLY | B | 37 | −63.892 | 29.889 | −44.816 | 1.00 | 61.85 | B |
| ATOM | 1284 | CA  | GLY | B | 37 | −64.105 | 31.317 | −44.657 | 1.00 | 60.22 | B |
| ATOM | 1285 | C   | GLY | B | 37 | −62.860 | 32.105 | −44.299 | 1.00 | 59.45 | B |
| ATOM | 1286 | O   | GLY | B | 37 | −62.897 | 32.984 | −43.436 | 1.00 | 59.52 | B |
| ATOM | 1287 | N   | PHE | B | 38 | −61.757 | 31.785 | −44.965 | 1.00 | 58.21 | B |
| ATOM | 1288 | CA  | PHE | B | 38 | −60.496 | 32.467 | −44.735 | 1.00 | 57.09 | B |
| ATOM | 1289 | CB  | PHE | B | 38 | −59.465 | 32.035 | −45.776 | 1.00 | 55.16 | B |
| ATOM | 1290 | CG  | PHE | B | 38 | −58.169 | 32.774 | −45.684 | 1.00 | 52.52 | B |
| ATOM | 1291 | CD1 | PHE | B | 38 | −57.409 | 32.728 | −44.523 | 1.00 | 51.16 | B |
| ATOM | 1292 | CD2 | PHE | B | 38 | −57.704 | 33.517 | −46.760 | 1.00 | 52.45 | B |
| ATOM | 1293 | CE1 | PHE | B | 38 | −56.201 | 33.414 | −44.433 | 1.00 | 50.89 | B |
| ATOM | 1294 | CE2 | PHE | B | 38 | −56.492 | 34.207 | −46.681 | 1.00 | 52.43 | B |
| ATOM | 1295 | CZ  | PHE | B | 38 | −55.741 | 34.152 | −45.511 | 1.00 | 51.93 | B |
| ATOM | 1296 | C   | PHE | B | 38 | −60.729 | 33.958 | −44.844 | 1.00 | 57.08 | B |
| ATOM | 1297 | O   | PHE | B | 38 | −61.224 | 34.434 | −45.853 | 1.00 | 56.69 | B |
| ATOM | 1298 | N   | PRO | B | 39 | −60.369 | 34.716 | −43.802 | 1.00 | 58.27 | B |

TABLE 5-continued

Atomic coordinates of rSIFN-co (SEQ ID NO: 1)

| ATOM | 1299 | CD | PRO | B | 39 | −59.687 | 34.259 | −42.581 | 1.00 | 58.11 | B |
|---|---|---|---|---|---|---|---|---|---|---|---|
| ATOM | 1300 | CA | PRO | B | 39 | −60.542 | 36.168 | −43.776 | 1.00 | 60.08 | B |
| ATOM | 1301 | CB | PRO | B | 39 | −60.253 | 36.511 | −42.323 | 1.00 | 59.19 | B |
| ATOM | 1302 | CG | PRO | B | 39 | −59.163 | 35.556 | −41.999 | 1.00 | 58.94 | B |
| ATOM | 1303 | C | PRO | B | 39 | −59.596 | 36.875 | −44.742 | 1.00 | 62.95 | B |
| ATOM | 1304 | O | PRO | B | 39 | −58.544 | 37.387 | −44.344 | 1.00 | 63.46 | B |
| ATOM | 1305 | N | GLN | B | 40 | −59.982 | 36.908 | −46.014 | 1.00 | 65.02 | B |
| ATOM | 1306 | CA | GLN | B | 40 | −59.163 | 37.545 | −47.031 | 1.00 | 66.34 | B |
| ATOM | 1307 | CB | GLN | B | 40 | −59.705 | 37.224 | −48.412 | 1.00 | 66.89 | B |
| ATOM | 1308 | CG | GLN | B | 40 | −58.720 | 37.527 | −49.510 | 1.00 | 69.39 | B |
| ATOM | 1309 | CD | GLN | B | 40 | −59.274 | 37.201 | −50.872 | 1.00 | 71.14 | B |
| ATOM | 1310 | OE1 | GLN | B | 40 | −59.732 | 36.084 | −51.121 | 1.00 | 71.05 | B |
| ATOM | 1311 | NE2 | GLN | B | 40 | −59.235 | 38.174 | −51.769 | 1.00 | 72.52 | B |
| ATOM | 1312 | C | GLN | B | 40 | −59.085 | 39.056 | −46.856 | 1.00 | 67.85 | B |
| ATOM | 1313 | O | GLN | B | 40 | −58.107 | 39.678 | −47.260 | 1.00 | 67.07 | B |
| ATOM | 1314 | N | GLU | B | 41 | −60.110 | 39.643 | −46.248 | 1.00 | 70.00 | B |
| ATOM | 1315 | CA | GLU | B | 41 | −60.135 | 41.085 | −46.029 | 1.00 | 73.07 | B |
| ATOM | 1316 | CB | GLU | B | 41 | −61.390 | 41.506 | −45.255 | 1.00 | 73.73 | B |
| ATOM | 1317 | CG | GLU | B | 41 | −62.623 | 40.648 | −45.473 | 1.00 | 75.45 | B |
| ATOM | 1318 | CD | GLU | B | 41 | −62.636 | 39.399 | −44.604 | 1.00 | 76.40 | B |
| ATOM | 1319 | OE1 | GLU | B | 41 | −62.528 | 39.534 | −43.363 | 1.00 | 75.97 | B |
| ATOM | 1320 | OE2 | GLU | B | 41 | −62.764 | 38.285 | −45.162 | 1.00 | 76.54 | B |
| ATOM | 1321 | C | GLU | B | 41 | −58.914 | 41.562 | −45.241 | 1.00 | 74.88 | B |
| ATOM | 1322 | O | GLU | B | 41 | −58.437 | 42.675 | −45.439 | 1.00 | 75.45 | B |
| ATOM | 1323 | N | GLU | B | 42 | −58.414 | 40.722 | −44.342 | 1.00 | 76.27 | B |
| ATOM | 1324 | CA | GLU | B | 42 | −57.272 | 41.091 | −43.515 | 1.00 | 76.77 | B |
| ATOM | 1325 | CB | GLU | B | 42 | −57.154 | 40.118 | −42.341 | 1.00 | 77.03 | B |
| ATOM | 1326 | CG | GLU | B | 42 | −58.484 | 39.812 | −41.670 | 1.00 | 76.96 | B |
| ATOM | 1327 | CD | GLU | B | 42 | −59.135 | 41.036 | −41.062 | 1.00 | 77.01 | B |
| ATOM | 1328 | OE1 | GLU | B | 42 | −60.354 | 40.980 | −40.783 | 1.00 | 76.54 | B |
| ATOM | 1329 | OE2 | GLU | B | 42 | −58.428 | 42.047 | −40.855 | 1.00 | 77.00 | B |
| ATOM | 1330 | C | GLU | B | 42 | −55.953 | 41.136 | −44.276 | 1.00 | 77.34 | B |
| ATOM | 1331 | O | GLU | B | 42 | −54.978 | 41.721 | −43.797 | 1.00 | 76.70 | B |
| ATOM | 1332 | N | PHE | B | 43 | −55.927 | 40.523 | −45.460 | 1.00 | 78.79 | B |
| ATOM | 1333 | CA | PHE | B | 43 | −54.716 | 40.481 | −46.282 | 1.00 | 79.57 | B |
| ATOM | 1334 | CB | PHE | B | 43 | −54.354 | 39.030 | −46.614 | 1.00 | 76.30 | B |
| ATOM | 1335 | CG | PHE | B | 43 | −54.174 | 38.158 | −45.407 | 1.00 | 73.38 | B |
| ATOM | 1336 | CD1 | PHE | B | 43 | −55.259 | 37.518 | −44.827 | 1.00 | 72.32 | B |
| ATOM | 1337 | CD2 | PHE | B | 43 | −52.918 | 37.982 | −44.846 | 1.00 | 72.34 | B |
| ATOM | 1338 | CE1 | PHE | B | 43 | −55.093 | 36.716 | −43.708 | 1.00 | 71.63 | B |
| ATOM | 1339 | CE2 | PHE | B | 43 | −52.743 | 37.182 | −43.727 | 1.00 | 71.80 | B |
| ATOM | 1340 | CZ | PHE | B | 43 | −53.832 | 36.547 | −43.158 | 1.00 | 71.86 | B |
| ATOM | 1341 | C | PHE | B | 43 | −54.830 | 41.274 | −47.584 | 1.00 | 81.78 | B |
| ATOM | 1342 | O | PHE | B | 43 | −54.032 | 42.171 | −47.855 | 1.00 | 82.37 | B |
| ATOM | 1343 | N | GLY | B | 44 | −55.825 | 40.932 | −48.391 | 1.00 | 84.35 | B |
| ATOM | 1344 | CA | GLY | B | 44 | −56.013 | 41.619 | −49.654 | 1.00 | 86.86 | B |
| ATOM | 1345 | C | GLY | B | 44 | −56.880 | 42.859 | −49.557 | 1.00 | 88.99 | B |
| ATOM | 1346 | O | GLY | B | 44 | −58.085 | 42.785 | −49.304 | 1.00 | 88.66 | B |
| ATOM | 1347 | N | GLY | B | 45 | −56.259 | 44.011 | −49.766 | 1.00 | 90.98 | B |
| ATOM | 1348 | CA | GLY | B | 45 | −56.995 | 45.256 | −49.708 | 1.00 | 93.31 | B |
| ATOM | 1349 | C | GLY | B | 45 | −56.073 | 46.453 | −49.679 | 1.00 | 95.02 | B |
| ATOM | 1350 | O | GLY | B | 45 | −54.874 | 46.323 | −49.413 | 1.00 | 95.65 | B |
| ATOM | 1351 | N | GLY | B | 46 | −56.633 | 47.624 | −49.967 | 1.00 | 95.75 | B |
| ATOM | 1352 | CA | GLY | B | 46 | −55.846 | 48.839 | −49.947 | 1.00 | 96.64 | B |
| ATOM | 1353 | C | GLY | B | 46 | −55.513 | 49.204 | −48.513 | 1.00 | 97.19 | B |
| ATOM | 1354 | O | GLY | B | 46 | −55.188 | 50.354 | −48.212 | 1.00 | 97.50 | B |
| ATOM | 1355 | N | GLY | B | 47 | −55.602 | 48.218 | −47.623 | 1.00 | 97.06 | B |
| ATOM | 1356 | CA | GLY | B | 47 | −55.307 | 48.454 | −46.223 | 1.00 | 97.22 | B |
| ATOM | 1357 | C | GLY | B | 47 | −54.088 | 49.337 | −46.029 | 1.00 | 97.43 | B |
| ATOM | 1358 | O | GLY | B | 47 | −54.193 | 50.430 | −45.463 | 1.00 | 97.59 | B |
| ATOM | 1359 | N | GLY | B | 48 | −52.935 | 48.868 | −46.508 | 1.00 | 96.90 | B |
| ATOM | 1360 | CA | GLY | B | 48 | −51.700 | 49.623 | −46.371 | 1.00 | 95.31 | B |
| ATOM | 1361 | C | GLY | B | 48 | −51.429 | 50.049 | −44.937 | 1.00 | 94.30 | B |
| ATOM | 1362 | O | GLY | B | 48 | −51.772 | 51.165 | −44.541 | 1.00 | 94.67 | B |
| ATOM | 1363 | N | ALA | B | 49 | −50.817 | 49.163 | −44.155 | 1.00 | 92.52 | B |
| ATOM | 1364 | CA | ALA | B | 49 | −50.508 | 49.455 | −42.756 | 1.00 | 90.44 | B |
| ATOM | 1365 | CB | ALA | B | 49 | −51.795 | 49.488 | −41.929 | 1.00 | 90.39 | B |
| ATOM | 1366 | C | ALA | B | 49 | −49.536 | 48.424 | −42.182 | 1.00 | 88.31 | B |
| ATOM | 1367 | O | ALA | B | 49 | −49.944 | 47.366 | −41.697 | 1.00 | 87.77 | B |
| ATOM | 1368 | N | GLY | B | 50 | −48.249 | 48.753 | −42.241 | 1.00 | 85.76 | B |
| ATOM | 1369 | CA | GLY | B | 50 | −47.214 | 47.865 | −41.742 | 1.00 | 82.69 | B |
| ATOM | 1370 | C | GLY | B | 50 | −47.476 | 47.214 | −40.396 | 1.00 | 80.16 | B |
| ATOM | 1371 | O | GLY | B | 50 | −46.976 | 46.125 | −40.130 | 1.00 | 80.60 | B |
| ATOM | 1372 | N | ALA | B | 51 | −48.256 | 47.867 | −39.543 | 1.00 | 77.39 | B |
| ATOM | 1373 | CA | ALA | B | 51 | −48.548 | 47.319 | −38.223 | 1.00 | 74.09 | B |
| ATOM | 1374 | CB | ALA | B | 51 | −48.967 | 48.433 | −37.273 | 1.00 | 74.25 | B |
| ATOM | 1375 | C | ALA | B | 51 | −49.631 | 46.252 | −38.287 | 1.00 | 71.65 | B |
| ATOM | 1376 | O | ALA | B | 51 | −49.622 | 45.307 | −37.499 | 1.00 | 70.67 | B |

TABLE 5-continued

Atomic coordinates of rSIFN-co (SEQ ID NO: 1)

| ATOM | 1377 | N | ALA | B | 52 | −50.568 | 46.412 | −39.220 | 1.00 | 68.72 | B |
|------|------|------|------|---|----|---------|--------|---------|------|-------|---|
| ATOM | 1378 | CA | ALA | B | 52 | −51.652 | 45.450 | −39.392 | 1.00 | 65.82 | B |
| ATOM | 1379 | CB | ALA | B | 52 | −52.784 | 46.066 | −40.204 | 1.00 | 65.58 | B |
| ATOM | 1380 | C | ALA | B | 52 | −51.102 | 44.226 | −40.111 | 1.00 | 63.64 | B |
| ATOM | 1381 | O | ALA | B | 52 | −51.346 | 43.086 | −39.713 | 1.00 | 63.09 | B |
| ATOM | 1382 | N | ALA | B | 53 | −50.351 | 44.472 | −41.175 | 1.00 | 60.70 | B |
| ATOM | 1383 | CA | ALA | B | 53 | −49.758 | 43.390 | −41.942 | 1.00 | 58.62 | B |
| ATOM | 1384 | CB | ALA | B | 53 | −48.812 | 43.959 | −42.994 | 1.00 | 57.63 | B |
| ATOM | 1385 | C | ALA | B | 53 | −49.003 | 42.443 | −41.014 | 1.00 | 56.79 | B |
| ATOM | 1386 | O | ALA | B | 53 | −49.350 | 41.271 | −40.897 | 1.00 | 56.46 | B |
| ATOM | 1387 | N | ILE | B | 54 | −47.977 | 42.971 | −40.350 | 1.00 | 55.35 | B |
| ATOM | 1388 | CA | ILE | B | 54 | −47.139 | 42.197 | −39.440 | 1.00 | 53.78 | B |
| ATOM | 1389 | CB | ILE | B | 54 | −46.178 | 43.100 | −38.678 | 1.00 | 53.66 | B |
| ATOM | 1390 | CG2 | ILE | B | 54 | −45.360 | 42.267 | −37.708 | 1.00 | 53.50 | B |
| ATOM | 1391 | CG1 | ILE | B | 54 | −45.275 | 43.848 | −39.665 | 1.00 | 54.89 | B |
| ATOM | 1392 | CD1 | ILE | B | 54 | −44.430 | 44.947 | −39.029 | 1.00 | 53.54 | B |
| ATOM | 1393 | C | ILE | B | 54 | −47.913 | 41.393 | −38.412 | 1.00 | 53.50 | B |
| ATOM | 1394 | O | ILE | B | 54 | −47.529 | 40.280 | −38.074 | 1.00 | 53.63 | B |
| ATOM | 1395 | N | SER | B | 55 | −48.999 | 41.965 | −37.916 | 1.00 | 53.54 | B |
| ATOM | 1396 | CA | SER | B | 55 | −49.820 | 41.306 | −36.922 | 1.00 | 53.69 | B |
| ATOM | 1397 | CB | SER | B | 55 | −50.764 | 42.312 | −36.277 | 1.00 | 55.26 | B |
| ATOM | 1398 | OG | SER | B | 55 | −50.023 | 43.376 | −35.708 | 1.00 | 58.90 | B |
| ATOM | 1399 | C | SER | B | 55 | −50.615 | 40.161 | −37.515 | 1.00 | 52.96 | B |
| ATOM | 1400 | O | SER | B | 55 | −50.797 | 39.142 | −36.867 | 1.00 | 54.85 | B |
| ATOM | 1401 | N | VAL | B | 56 | −51.098 | 40.307 | −38.738 | 1.00 | 51.44 | B |
| ATOM | 1402 | CA | VAL | B | 56 | −51.849 | 39.210 | −39.318 | 1.00 | 51.64 | B |
| ATOM | 1403 | CB | VAL | B | 56 | −52.798 | 39.692 | −40.431 | 1.00 | 51.99 | B |
| ATOM | 1404 | CG1 | VAL | B | 56 | −53.812 | 40.643 | −39.846 | 1.00 | 50.15 | B |
| ATOM | 1405 | CG2 | VAL | B | 56 | −52.020 | 40.360 | −41.536 | 1.00 | 51.94 | B |
| ATOM | 1406 | C | VAL | B | 56 | −50.924 | 38.115 | −39.849 | 1.00 | 51.00 | B |
| ATOM | 1407 | O | VAL | B | 56 | −51.165 | 36.937 | −39.613 | 1.00 | 50.59 | B |
| ATOM | 1408 | N | LEU | B | 57 | −49.867 | 38.489 | −40.560 | 1.00 | 50.84 | B |
| ATOM | 1409 | CA | LEU | B | 57 | −48.943 | 37.479 | −41.061 | 1.00 | 51.20 | B |
| ATOM | 1410 | CB | LEU | B | 57 | −47.755 | 38.107 | −41.798 | 1.00 | 51.55 | B |
| ATOM | 1411 | CG | LEU | B | 57 | −47.820 | 38.373 | −43.304 | 1.00 | 52.66 | B |
| ATOM | 1412 | CD1 | LEU | B | 57 | −48.796 | 37.400 | −43.946 | 1.00 | 52.07 | B |
| ATOM | 1413 | CD2 | LEU | B | 57 | −48.221 | 39.805 | −43.569 | 1.00 | 52.06 | B |
| ATOM | 1414 | C | LEU | B | 57 | −48.410 | 36.699 | −39.871 | 1.00 | 50.92 | B |
| ATOM | 1415 | O | LEU | B | 57 | −48.392 | 35.462 | −39.879 | 1.00 | 51.14 | B |
| ATOM | 1416 | N | HIS | B | 58 | −47.983 | 37.427 | −38.841 | 1.00 | 48.84 | B |
| ATOM | 1417 | CA | HIS | B | 58 | −47.433 | 36.786 | −37.649 | 1.00 | 48.56 | B |
| ATOM | 1418 | CB | HIS | B | 58 | −47.033 | 37.837 | −36.593 | 1.00 | 45.06 | B |
| ATOM | 1419 | CG | HIS | B | 58 | −46.150 | 37.292 | −35.510 | 1.00 | 41.60 | B |
| ATOM | 1420 | CD2 | HIS | B | 58 | −44.811 | 37.390 | −35.322 | 1.00 | 40.97 | B |
| ATOM | 1421 | ND1 | HIS | B | 58 | −46.620 | 36.470 | −34.511 | 1.00 | 41.10 | B |
| ATOM | 1422 | CE1 | HIS | B | 58 | −45.605 | 36.077 | −33.754 | 1.00 | 39.76 | B |
| ATOM | 1423 | NE2 | HIS | B | 58 | −44.500 | 36.619 | −34.225 | 1.00 | 38.18 | B |
| ATOM | 1424 | C | HIS | B | 58 | −48.405 | 35.769 | −37.035 | 1.00 | 47.89 | B |
| ATOM | 1425 | O | HIS | B | 58 | −48.000 | 34.667 | −36.652 | 1.00 | 47.61 | B |
| ATOM | 1426 | N | GLU | B | 59 | −49.682 | 36.125 | −36.955 | 1.00 | 44.67 | B |
| ATOM | 1427 | CA | GLU | B | 59 | −50.649 | 35.215 | −36.376 | 1.00 | 44.65 | B |
| ATOM | 1428 | CB | GLU | B | 59 | −51.992 | 35.911 | −36.156 | 1.00 | 45.09 | B |
| ATOM | 1429 | CG | GLU | B | 59 | −52.996 | 35.078 | −35.377 | 1.00 | 46.22 | B |
| ATOM | 1430 | CD | GLU | B | 59 | −52.491 | 34.750 | −33.994 | 1.00 | 48.75 | B |
| ATOM | 1431 | OE1 | GLU | B | 59 | −51.714 | 35.571 | −33.474 | 1.00 | 50.15 | B |
| ATOM | 1432 | OE2 | GLU | B | 59 | −52.860 | 33.696 | −33.422 | 1.00 | 48.92 | B |
| ATOM | 1433 | C | GLU | B | 59 | −50.857 | 33.998 | −37.257 | 1.00 | 44.41 | B |
| ATOM | 1434 | O | GLU | B | 59 | −51.033 | 32.892 | −36.757 | 1.00 | 44.67 | B |
| ATOM | 1435 | N | MET | B | 60 | −50.842 | 34.196 | −38.571 | 1.00 | 44.37 | B |
| ATOM | 1436 | CA | MET | B | 60 | −51.055 | 33.079 | −39.471 | 1.00 | 45.11 | B |
| ATOM | 1437 | CB | MET | B | 60 | −51.331 | 33.559 | −40.897 | 1.00 | 48.89 | B |
| ATOM | 1438 | CG | MET | B | 60 | −51.721 | 32.415 | −41.821 | 1.00 | 53.44 | B |
| ATOM | 1439 | SD | MET | B | 60 | −51.754 | 32.856 | −43.555 | 1.00 | 61.98 | B |
| ATOM | 1440 | CE | MET | B | 60 | −50.021 | 33.361 | −43.846 | 1.00 | 58.01 | B |
| ATOM | 1441 | C | MET | B | 60 | −49.864 | 32.128 | −39.465 | 1.00 | 43.04 | B |
| ATOM | 1442 | O | MET | B | 60 | −50.039 | 30.909 | −39.449 | 1.00 | 40.32 | B |
| ATOM | 1443 | N | ILE | B | 61 | −48.655 | 32.671 | −39.481 | 1.00 | 40.71 | B |
| ATOM | 1444 | CA | ILE | B | 61 | −47.500 | 31.802 | −39.457 | 1.00 | 42.41 | B |
| ATOM | 1445 | CB | ILE | B | 61 | −46.170 | 32.608 | −39.520 | 1.00 | 43.92 | B |
| ATOM | 1446 | CG2 | ILE | B | 61 | −44.975 | 31.667 | −39.434 | 1.00 | 44.05 | B |
| ATOM | 1447 | CG1 | ILE | B | 61 | −46.094 | 33.395 | −40.823 | 1.00 | 41.85 | B |
| ATOM | 1448 | CD1 | ILE | B | 61 | −46.283 | 32.551 | −42.028 | 1.00 | 45.99 | B |
| ATOM | 1449 | C | ILE | B | 61 | −47.557 | 30.991 | −38.153 | 1.00 | 43.11 | B |
| ATOM | 1450 | O | ILE | B | 61 | −47.413 | 29.762 | −38.158 | 1.00 | 43.91 | B |
| ATOM | 1451 | N | GLN | B | 62 | −47.795 | 31.690 | −37.049 | 1.00 | 42.04 | B |
| ATOM | 1452 | CA | GLN | B | 62 | −47.863 | 31.082 | −35.726 | 1.00 | 43.22 | B |
| ATOM | 1453 | CB | GLN | B | 62 | −48.229 | 32.140 | −34.685 | 1.00 | 46.41 | B |
| ATOM | 1454 | CG | GLN | B | 62 | −48.049 | 31.713 | −33.245 | 1.00 | 46.91 | B |

TABLE 5-continued

Atomic coordinates of rSIFN-co (SEQ ID NO: 1)

| ATOM | 1455 | CD | GLN | B | 62 | −46.596 | 31.663 | −32.837 | 1.00 | 52.53 | B |
|---|---|---|---|---|---|---|---|---|---|---|---|
| ATOM | 1456 | OE1 | GLN | B | 62 | −45.904 | 30.665 | −33.070 | 1.00 | 55.84 | B |
| ATOM | 1457 | NE2 | GLN | B | 62 | −46.113 | 32.748 | −32.228 | 1.00 | 54.09 | B |
| ATOM | 1458 | C | GLN | B | 62 | −48.880 | 29.960 | −35.663 | 1.00 | 43.47 | B |
| ATOM | 1459 | O | GLN | B | 62 | −48.587 | 28.870 | −35.152 | 1.00 | 44.07 | B |
| ATOM | 1460 | N | GLN | B | 63 | −50.083 | 30.228 | −36.163 | 1.00 | 42.32 | B |
| ATOM | 1461 | CA | GLN | B | 63 | −51.140 | 29.221 | −36.158 | 1.00 | 43.14 | B |
| ATOM | 1462 | CB | GLN | B | 63 | −52.456 | 29.812 | −36.653 | 1.00 | 43.36 | B |
| ATOM | 1463 | CG | GLN | B | 63 | −53.088 | 30.810 | −35.702 | 1.00 | 45.90 | B |
| ATOM | 1464 | CD | GLN | B | 63 | −53.432 | 30.220 | −34.339 | 1.00 | 44.57 | B |
| ATOM | 1465 | OE1 | GLN | B | 63 | −53.643 | 30.956 | −33.386 | 1.00 | 44.63 | B |
| ATOM | 1466 | NE2 | GLN | B | 63 | −53.497 | 28.896 | −34.250 | 1.00 | 44.30 | B |
| ATOM | 1467 | C | GLN | B | 63 | −50.796 | 28.018 | −37.017 | 1.00 | 43.72 | B |
| ATOM | 1468 | O | GLN | B | 63 | −51.089 | 26.880 | −36.649 | 1.00 | 44.40 | B |
| ATOM | 1469 | N | THR | B | 64 | −50.177 | 28.277 | −38.164 | 1.00 | 42.86 | B |
| ATOM | 1470 | CA | THR | B | 64 | −49.811 | 27.211 | −39.073 | 1.00 | 42.63 | B |
| ATOM | 1471 | CB | THR | B | 64 | −49.271 | 27.777 | −40.409 | 1.00 | 42.59 | B |
| ATOM | 1472 | OG1 | THR | B | 64 | −50.275 | 28.599 | −41.012 | 1.00 | 40.41 | B |
| ATOM | 1473 | CG2 | THR | B | 64 | −48.910 | 26.649 | −41.368 | 1.00 | 39.23 | B |
| ATOM | 1474 | C | THR | B | 64 | −48.762 | 26.343 | −38.405 | 1.00 | 43.08 | B |
| ATOM | 1475 | O | THR | B | 64 | −48.801 | 25.118 | −38.509 | 1.00 | 45.34 | B |
| ATOM | 1476 | N | PHE | B | 65 | −47.820 | 26.980 | −37.724 | 1.00 | 41.85 | B |
| ATOM | 1477 | CA | PHE | B | 65 | −46.781 | 26.245 | −37.026 | 1.00 | 41.65 | B |
| ATOM | 1478 | CB | PHE | B | 65 | −45.890 | 27.210 | −36.231 | 1.00 | 39.65 | B |
| ATOM | 1479 | CG | PHE | B | 65 | −44.753 | 26.533 | −35.514 | 1.00 | 37.50 | B |
| ATOM | 1480 | CD1 | PHE | B | 65 | −43.503 | 26.448 | −36.095 | 1.00 | 38.07 | B |
| ATOM | 1481 | CD2 | PHE | B | 65 | −44.952 | 25.931 | −34.285 | 1.00 | 38.71 | B |
| ATOM | 1482 | CE1 | PHE | B | 65 | −42.463 | 25.766 | −35.473 | 1.00 | 38.97 | B |
| ATOM | 1483 | CE2 | PHE | B | 65 | −43.927 | 25.247 | −33.651 | 1.00 | 40.75 | B |
| ATOM | 1484 | CZ | PHE | B | 65 | −42.674 | 25.163 | −34.252 | 1.00 | 41.00 | B |
| ATOM | 1485 | C | PHE | B | 65 | −47.459 | 25.268 | −36.062 | 1.00 | 42.95 | B |
| ATOM | 1486 | O | PHE | B | 65 | −47.199 | 24.067 | −36.077 | 1.00 | 41.78 | B |
| ATOM | 1487 | N | ASN | B | 66 | −48.346 | 25.797 | −35.228 | 1.00 | 44.10 | B |
| ATOM | 1488 | CA | ASN | B | 66 | −49.036 | 24.976 | −34.244 | 1.00 | 45.15 | B |
| ATOM | 1489 | CB | ASN | B | 66 | −50.014 | 25.836 | −33.444 | 1.00 | 45.22 | B |
| ATOM | 1490 | CG | ASN | B | 66 | −49.309 | 26.882 | −32.588 | 1.00 | 45.60 | B |
| ATOM | 1491 | OD1 | ASN | B | 66 | −49.917 | 27.866 | −32.179 | 1.00 | 47.81 | B |
| ATOM | 1492 | ND2 | ASN | B | 66 | −48.026 | 26.667 | −32.310 | 1.00 | 45.74 | B |
| ATOM | 1493 | C | ASN | B | 66 | −49.758 | 23.802 | −34.874 | 1.00 | 45.93 | B |
| ATOM | 1494 | O | ASN | B | 66 | −49.592 | 22.661 | −34.443 | 1.00 | 46.70 | B |
| ATOM | 1495 | N | LEU | B | 67 | −50.545 | 24.087 | −35.906 | 1.00 | 46.78 | B |
| ATOM | 1496 | CA | LEU | B | 67 | −51.314 | 23.072 | −36.614 | 1.00 | 45.25 | B |
| ATOM | 1497 | CB | LEU | B | 67 | −52.027 | 23.708 | −37.802 | 1.00 | 44.17 | B |
| ATOM | 1498 | CG | LEU | B | 67 | −52.943 | 22.848 | −38.673 | 1.00 | 44.83 | B |
| ATOM | 1499 | CD1 | LEU | B | 67 | −54.221 | 22.524 | −37.908 | 1.00 | 43.33 | B |
| ATOM | 1500 | CD2 | LEU | B | 67 | −53.269 | 23.609 | −39.950 | 1.00 | 43.75 | B |
| ATOM | 1501 | C | LEU | B | 67 | −50.465 | 21.914 | −37.109 | 1.00 | 46.02 | B |
| ATOM | 1502 | O | LEU | B | 67 | −50.888 | 20.763 | −37.037 | 1.00 | 47.59 | B |
| ATOM | 1503 | N | PHE | B | 68 | −49.270 | 22.209 | −37.606 | 1.00 | 45.93 | B |
| ATOM | 1504 | CA | PHE | B | 68 | −48.407 | 21.165 | −38.142 | 1.00 | 48.01 | B |
| ATOM | 1505 | CB | PHE | B | 68 | −47.690 | 21.674 | −39.400 | 1.00 | 47.07 | B |
| ATOM | 1506 | CG | PHE | B | 68 | −48.573 | 21.725 | −40.623 | 1.00 | 47.28 | B |
| ATOM | 1507 | CD1 | PHE | B | 68 | −49.374 | 22.834 | −40.879 | 1.00 | 47.40 | B |
| ATOM | 1508 | CD2 | PHE | B | 68 | −48.629 | 20.643 | −41.497 | 1.00 | 45.54 | B |
| ATOM | 1509 | CE1 | PHE | B | 68 | −50.217 | 22.863 | −41.985 | 1.00 | 45.20 | B |
| ATOM | 1510 | CE2 | PHE | B | 68 | −49.463 | 20.660 | −42.598 | 1.00 | 45.58 | B |
| ATOM | 1511 | CZ | PHE | B | 68 | −50.261 | 21.772 | −42.843 | 1.00 | 45.21 | B |
| ATOM | 1512 | C | PHE | B | 68 | −47.385 | 20.564 | −37.174 | 1.00 | 50.56 | B |
| ATOM | 1513 | O | PHE | B | 68 | −46.660 | 19.625 | −37.519 | 1.00 | 50.22 | B |
| ATOM | 1514 | N | SER | B | 69 | −47.333 | 21.093 | −35.959 | 1.00 | 52.03 | B |
| ATOM | 1515 | CA | SER | B | 69 | −46.397 | 20.592 | −34.963 | 1.00 | 51.91 | B |
| ATOM | 1516 | CB | SER | B | 69 | −45.844 | 21.762 | −34.145 | 1.00 | 50.79 | B |
| ATOM | 1517 | OG | SER | B | 69 | −46.861 | 22.698 | −33.850 | 1.00 | 50.68 | B |
| ATOM | 1518 | C | SER | B | 69 | −47.098 | 19.559 | −34.071 | 1.00 | 52.49 | B |
| ATOM | 1519 | O | SER | B | 69 | −46.471 | 18.877 | −33.263 | 1.00 | 51.65 | B |
| ATOM | 1520 | N | THR | B | 70 | −48.406 | 19.437 | −34.256 | 1.00 | 53.35 | B |
| ATOM | 1521 | CA | THR | B | 70 | −49.220 | 18.485 | −33.519 | 1.00 | 54.95 | B |
| ATOM | 1522 | CB | THR | B | 70 | −50.715 | 18.667 | −33.892 | 1.00 | 54.32 | B |
| ATOM | 1523 | OG1 | THR | B | 70 | −51.292 | 19.672 | −33.051 | 1.00 | 53.43 | B |
| ATOM | 1524 | CG2 | THR | B | 70 | −51.491 | 17.378 | −33.749 | 1.00 | 53.28 | B |
| ATOM | 1525 | C | THR | B | 70 | −48.816 | 17.024 | −33.764 | 1.00 | 57.60 | B |
| ATOM | 1526 | O | THR | B | 70 | −48.196 | 16.683 | −34.775 | 1.00 | 56.59 | B |
| ATOM | 1527 | N | ARG | B | 71 | −49.183 | 16.177 | −32.806 | 1.00 | 60.45 | B |
| ATOM | 1528 | CA | ARG | B | 71 | −48.931 | 14.739 | −32.839 | 1.00 | 63.09 | B |
| ATOM | 1529 | CB | ARG | B | 71 | −49.445 | 14.131 | −31.527 | 1.00 | 66.17 | B |
| ATOM | 1530 | CG | ARG | B | 71 | −50.748 | 14.806 | −31.033 | 1.00 | 71.66 | B |
| ATOM | 1531 | CD | ARG | B | 71 | −50.651 | 15.471 | −29.626 | 1.00 | 74.28 | B |
| ATOM | 1532 | NE | ARG | B | 71 | −49.626 | 16.519 | −29.495 | 1.00 | 75.60 | B |

TABLE 5-continued

Atomic coordinates of rSIFN-co (SEQ ID NO: 1)

| ATOM | 1533 | CZ | ARG | B | 71 | −48.406 | 16.325 | −28.982 | 1.00 | 76.64 | B |
|---|---|---|---|---|---|---|---|---|---|---|---|
| ATOM | 1534 | NH1 | ARG | B | 71 | −48.039 | 15.122 | −28.548 | 1.00 | 76.04 | B |
| ATOM | 1535 | NH2 | ARG | B | 71 | −47.551 | 17.338 | −28.891 | 1.00 | 75.84 | B |
| ATOM | 1536 | C | ARG | B | 71 | −49.654 | 14.119 | −34.046 | 1.00 | 62.93 | B |
| ATOM | 1537 | O | ARG | B | 71 | −49.156 | 13.186 | −34.684 | 1.00 | 62.66 | B |
| ATOM | 1538 | N | ASP | B | 72 | −50.834 | 14.654 | −34.344 | 1.00 | 62.27 | B |
| ATOM | 1539 | CA | ASP | B | 72 | −51.642 | 14.201 | −35.465 | 1.00 | 61.32 | B |
| ATOM | 1540 | CB | ASP | B | 72 | −53.017 | 14.844 | −35.398 | 1.00 | 63.05 | B |
| ATOM | 1541 | CG | ASP | B | 72 | −53.745 | 14.517 | −34.121 | 1.00 | 65.14 | B |
| ATOM | 1542 | OD1 | ASP | B | 72 | −54.164 | 13.350 | −33.973 | 1.00 | 66.97 | B |
| ATOM | 1543 | OD2 | ASP | B | 72 | −53.894 | 15.425 | −33.270 | 1.00 | 65.14 | B |
| ATOM | 1544 | C | ASP | B | 72 | −50.973 | 14.600 | −36.768 | 1.00 | 60.42 | B |
| ATOM | 1545 | O | ASP | B | 72 | −51.034 | 13.882 | −37.762 | 1.00 | 61.00 | B |
| ATOM | 1546 | N | SER | B | 73 | −50.341 | 15.762 | −36.758 | 1.00 | 59.06 | B |
| ATOM | 1547 | CA | SER | B | 73 | −49.657 | 16.238 | −37.938 | 1.00 | 58.72 | B |
| ATOM | 1548 | CB | SER | B | 73 | −49.126 | 17.654 | −37.704 | 1.00 | 57.83 | B |
| ATOM | 1549 | OG | SER | B | 73 | −48.578 | 18.194 | −38.892 | 1.00 | 58.48 | B |
| ATOM | 1550 | C | SER | B | 73 | −48.509 | 15.281 | −38.262 | 1.00 | 58.75 | B |
| ATOM | 1551 | O | SER | B | 73 | −48.355 | 14.859 | −39.408 | 1.00 | 58.86 | B |
| ATOM | 1552 | N | SER | B | 74 | −47.718 | 14.927 | −37.250 | 1.00 | 57.50 | B |
| ATOM | 1553 | CA | SER | B | 74 | −46.582 | 14.026 | −37.443 | 1.00 | 56.83 | B |
| ATOM | 1554 | CB | SER | B | 74 | −45.849 | 13.794 | −36.127 | 1.00 | 55.68 | B |
| ATOM | 1555 | OG | SER | B | 74 | −45.131 | 14.949 | −35.737 | 1.00 | 59.88 | B |
| ATOM | 1556 | C | SER | B | 74 | −47.000 | 12.686 | −38.020 | 1.00 | 55.92 | B |
| ATOM | 1557 | O | SER | B | 74 | −46.286 | 12.097 | −38.837 | 1.00 | 54.81 | B |
| ATOM | 1558 | N | ALA | B | 75 | −48.154 | 12.201 | −37.583 | 1.00 | 54.52 | B |
| ATOM | 1559 | CA | ALA | B | 75 | −48.658 | 10.929 | −38.069 | 1.00 | 54.44 | B |
| ATOM | 1560 | CB | ALA | B | 75 | −49.870 | 10.520 | −37.268 | 1.00 | 53.67 | B |
| ATOM | 1561 | C | ALA | B | 75 | −49.029 | 11.043 | −39.540 | 1.00 | 54.05 | B |
| ATOM | 1562 | O | ALA | B | 75 | −48.835 | 10.114 | −40.323 | 1.00 | 53.83 | B |
| ATOM | 1563 | N | ALA | B | 76 | −49.542 | 12.211 | −39.905 | 1.00 | 53.41 | B |
| ATOM | 1564 | CA | ALA | B | 76 | −49.996 | 12.477 | −41.255 | 1.00 | 52.31 | B |
| ATOM | 1565 | CB | ALA | B | 76 | −51.042 | 13.580 | −41.208 | 1.00 | 52.11 | B |
| ATOM | 1566 | C | ALA | B | 76 | −48.946 | 12.810 | −42.315 | 1.00 | 52.55 | B |
| ATOM | 1567 | O | ALA | B | 76 | −49.114 | 12.443 | −43.477 | 1.00 | 52.41 | B |
| ATOM | 1568 | N | TRP | B | 77 | −47.862 | 13.481 | −41.941 | 1.00 | 51.98 | B |
| ATOM | 1569 | CA | TRP | B | 77 | −46.879 | 13.868 | −42.947 | 1.00 | 51.34 | B |
| ATOM | 1570 | CB | TRP | B | 77 | −46.887 | 15.391 | −43.126 | 1.00 | 50.88 | B |
| ATOM | 1571 | CG | TRP | B | 77 | −48.248 | 15.994 | −43.099 | 1.00 | 52.09 | B |
| ATOM | 1572 | CD2 | TRP | B | 77 | −49.187 | 16.052 | −44.178 | 1.00 | 53.10 | B |
| ATOM | 1573 | CE2 | TRP | B | 77 | −50.347 | 16.691 | −43.689 | 1.00 | 53.99 | B |
| ATOM | 1574 | CE3 | TRP | B | 77 | −49.163 | 15.624 | −45.512 | 1.00 | 52.69 | B |
| ATOM | 1575 | CD1 | TRP | B | 77 | −48.858 | 16.579 | −42.032 | 1.00 | 53.81 | B |
| ATOM | 1576 | NE1 | TRP | B | 77 | −50.119 | 17.002 | −42.375 | 1.00 | 54.33 | B |
| ATOM | 1577 | CZ2 | TRP | B | 77 | −51.476 | 16.916 | −44.490 | 1.00 | 54.45 | B |
| ATOM | 1578 | CZ3 | TRP | B | 77 | −50.287 | 15.845 | −46.309 | 1.00 | 50.90 | B |
| ATOM | 1579 | CH2 | TRP | B | 77 | −51.427 | 16.486 | −45.794 | 1.00 | 51.54 | B |
| ATOM | 1580 | C | TRP | B | 77 | −45.450 | 13.425 | −42.722 | 1.00 | 50.67 | B |
| ATOM | 1581 | O | TRP | B | 77 | −45.053 | 13.094 | −41.620 | 1.00 | 49.80 | B |
| ATOM | 1582 | N | ASP | B | 78 | −44.672 | 13.436 | −43.796 | 1.00 | 52.39 | B |
| ATOM | 1583 | CA | ASP | B | 78 | −43.278 | 13.064 | −43.711 | 1.00 | 53.40 | B |
| ATOM | 1584 | CB | ASP | B | 78 | −42.578 | 13.257 | −45.050 | 1.00 | 55.50 | B |
| ATOM | 1585 | CG | ASP | B | 78 | −41.104 | 12.936 | −44.966 | 1.00 | 59.62 | B |
| ATOM | 1586 | OD1 | ASP | B | 78 | −40.273 | 13.875 | −45.018 | 1.00 | 62.42 | B |
| ATOM | 1587 | OD2 | ASP | B | 78 | −40.777 | 11.738 | −44.820 | 1.00 | 59.99 | B |
| ATOM | 1588 | C | ASP | B | 78 | −42.602 | 13.933 | −42.663 | 1.00 | 53.04 | B |
| ATOM | 1589 | O | ASP | B | 78 | −42.706 | 15.160 | −42.700 | 1.00 | 53.12 | B |
| ATOM | 1590 | N | ALA | B | 79 | −41.901 | 13.287 | −41.738 | 1.00 | 52.08 | B |
| ATOM | 1591 | CA | ALA | B | 79 | −41.220 | 13.983 | −40.662 | 1.00 | 52.01 | B |
| ATOM | 1592 | CB | ALA | B | 79 | −40.643 | 12.968 | −39.675 | 1.00 | 50.85 | B |
| ATOM | 1593 | C | ALA | B | 79 | −40.128 | 14.917 | −41.179 | 1.00 | 51.80 | B |
| ATOM | 1594 | O | ALA | B | 79 | −40.008 | 16.050 | −40.723 | 1.00 | 52.56 | B |
| ATOM | 1595 | N | SER | B | 80 | −39.341 | 14.453 | −42.138 | 1.00 | 51.82 | B |
| ATOM | 1596 | CA | SER | B | 80 | −38.273 | 15.277 | −42.687 | 1.00 | 51.59 | B |
| ATOM | 1597 | CB | SER | B | 80 | −37.511 | 14.507 | −43.764 | 1.00 | 53.55 | B |
| ATOM | 1598 | OG | SER | B | 80 | −36.317 | 15.188 | −44.120 | 1.00 | 57.70 | B |
| ATOM | 1599 | C | SER | B | 80 | −38.818 | 16.577 | −43.280 | 1.00 | 50.52 | B |
| ATOM | 1600 | O | SER | B | 80 | −38.223 | 17.649 | −43.113 | 1.00 | 51.02 | B |
| ATOM | 1601 | N | LEU | B | 81 | −39.937 | 16.487 | −43.990 | 1.00 | 47.40 | B |
| ATOM | 1602 | CA | LEU | B | 81 | −40.521 | 17.684 | −44.574 | 1.00 | 46.68 | B |
| ATOM | 1603 | CB | LEU | B | 81 | −41.665 | 17.327 | −45.531 | 1.00 | 44.63 | B |
| ATOM | 1604 | CG | LEU | B | 81 | −41.253 | 16.605 | −46.824 | 1.00 | 43.12 | B |
| ATOM | 1605 | CD1 | LEU | B | 81 | −42.433 | 16.565 | −47.792 | 1.00 | 40.61 | B |
| ATOM | 1606 | CD2 | LEU | B | 81 | −40.080 | 17.329 | −47.467 | 1.00 | 38.50 | B |
| ATOM | 1607 | C | LEU | B | 81 | −41.021 | 18.607 | −43.464 | 1.00 | 47.01 | B |
| ATOM | 1608 | O | LEU | B | 81 | −40.806 | 19.823 | −43.507 | 1.00 | 46.43 | B |
| ATOM | 1609 | N | LEU | B | 82 | −41.668 | 18.019 | −42.462 | 1.00 | 45.79 | B |
| ATOM | 1610 | CA | LEU | B | 82 | −42.184 | 18.790 | −41.344 | 1.00 | 44.38 | B |

TABLE 5-continued

Atomic coordinates of rSIFN-co (SEQ ID NO: 1)

| ATOM | 1611 | CB | LEU | B | 82 | −42.915 | 17.881 | −40.355 | 1.00 | 43.65 | B |
|------|------|------|-----|---|----|---------|--------|---------|------|-------|---|
| ATOM | 1612 | CG | LEU | B | 82 | −44.350 | 17.506 | −40.712 | 1.00 | 42.39 | B |
| ATOM | 1613 | CD1 | LEU | B | 82 | −44.969 | 16.779 | −39.542 | 1.00 | 41.48 | B |
| ATOM | 1614 | CD2 | LEU | B | 82 | −45.148 | 18.764 | −41.040 | 1.00 | 40.02 | B |
| ATOM | 1615 | C | LEU | B | 82 | −41.106 | 19.579 | −40.608 | 1.00 | 43.60 | B |
| ATOM | 1616 | O | LEU | B | 82 | −41.306 | 20.748 | −40.294 | 1.00 | 43.44 | B |
| ATOM | 1617 | N | ALA | B | 83 | −39.968 | 18.958 | −40.326 | 1.00 | 41.84 | B |
| ATOM | 1618 | CA | ALA | B | 83 | −38.920 | 19.686 | −39.617 | 1.00 | 42.47 | B |
| ATOM | 1619 | CB | ALA | B | 83 | −37.732 | 18.749 | −39.241 | 1.00 | 42.87 | B |
| ATOM | 1620 | C | ALA | B | 83 | −38.442 | 20.857 | −40.466 | 1.00 | 40.93 | B |
| ATOM | 1621 | O | ALA | B | 83 | −38.074 | 21.898 | −39.930 | 1.00 | 41.51 | B |
| ATOM | 1622 | N | LYS | B | 84 | −38.458 | 20.693 | −41.785 | 1.00 | 39.80 | B |
| ATOM | 1623 | CA | LYS | B | 84 | −38.041 | 21.770 | −42.680 | 1.00 | 40.20 | B |
| ATOM | 1624 | CB | LYS | B | 84 | −37.916 | 21.257 | −44.121 | 1.00 | 42.21 | B |
| ATOM | 1625 | CG | LYS | B | 84 | −36.919 | 20.117 | −44.326 | 1.00 | 44.38 | B |
| ATOM | 1626 | CD | LYS | B | 84 | −36.542 | 20.019 | −45.799 | 1.00 | 45.90 | B |
| ATOM | 1627 | CE | LYS | B | 84 | −35.545 | 18.920 | −46.068 | 1.00 | 45.47 | B |
| ATOM | 1628 | NZ | LYS | B | 84 | −36.209 | 17.606 | −45.922 | 1.00 | 49.90 | B |
| ATOM | 1629 | C | LYS | B | 84 | −39.076 | 22.902 | −42.631 | 1.00 | 39.06 | B |
| ATOM | 1630 | O | LYS | B | 84 | −38.743 | 24.087 | −42.678 | 1.00 | 39.36 | B |
| ATOM | 1631 | N | PHE | B | 85 | −40.338 | 22.512 | −42.539 | 1.00 | 37.58 | B |
| ATOM | 1632 | CA | PHE | B | 85 | −41.449 | 23.442 | −42.475 | 1.00 | 38.00 | B |
| ATOM | 1633 | CB | PHE | B | 85 | −42.749 | 22.644 | −42.492 | 1.00 | 38.99 | B |
| ATOM | 1634 | CG | PHE | B | 85 | −43.959 | 23.458 | −42.811 | 1.00 | 39.63 | B |
| ATOM | 1635 | CD1 | PHE | B | 85 | −43.942 | 24.366 | −43.866 | 1.00 | 38.44 | B |
| ATOM | 1636 | CD2 | PHE | B | 85 | −45.137 | 23.276 | −42.099 | 1.00 | 38.81 | B |
| ATOM | 1637 | CE1 | PHE | B | 85 | −45.076 | 25.079 | −44.211 | 1.00 | 39.59 | B |
| ATOM | 1638 | CE2 | PHE | B | 85 | −46.288 | 23.986 | −42.439 | 1.00 | 41.20 | B |
| ATOM | 1639 | CZ | PHE | B | 85 | −46.255 | 24.891 | −43.501 | 1.00 | 41.17 | B |
| ATOM | 1640 | C | PHE | B | 85 | −41.387 | 24.331 | −41.223 | 1.00 | 38.99 | B |
| ATOM | 1641 | O | PHE | B | 85 | −41.419 | 25.557 | −41.334 | 1.00 | 39.44 | B |
| ATOM | 1642 | N | TYR | B | 86 | −41.299 | 23.709 | −40.044 | 1.00 | 38.21 | B |
| ATOM | 1643 | CA | TYR | B | 86 | −41.217 | 24.435 | −38.769 | 1.00 | 37.40 | B |
| ATOM | 1644 | CB | TYR | B | 86 | −40.998 | 23.493 | −37.574 | 1.00 | 35.90 | B |
| ATOM | 1645 | CG | TYR | B | 86 | −41.920 | 22.311 | −37.450 | 1.00 | 33.12 | B |
| ATOM | 1646 | CD1 | TYR | B | 86 | −43.276 | 22.428 | −37.721 | 1.00 | 32.96 | B |
| ATOM | 1647 | CE1 | TYR | B | 86 | −44.138 | 21.343 | −37.563 | 1.00 | 35.08 | B |
| ATOM | 1648 | CD2 | TYR | B | 86 | −41.435 | 21.077 | −37.019 | 1.00 | 30.36 | B |
| ATOM | 1649 | CE2 | TYR | B | 86 | −42.276 | 19.992 | −36.861 | 1.00 | 30.76 | B |
| ATOM | 1650 | CZ | TYR | B | 86 | −43.628 | 20.133 | −37.129 | 1.00 | 34.57 | B |
| ATOM | 1651 | OH | TYR | B | 86 | −44.491 | 19.085 | −36.932 | 1.00 | 37.86 | B |
| ATOM | 1652 | C | TYR | B | 86 | −40.044 | 25.403 | −38.776 | 1.00 | 38.65 | B |
| ATOM | 1653 | O | TYR | B | 86 | −40.156 | 26.527 | −38.300 | 1.00 | 40.78 | B |
| ATOM | 1654 | N | THR | B | 87 | −38.905 | 24.948 | −39.289 | 1.00 | 38.79 | B |
| ATOM | 1655 | CA | THR | B | 87 | −37.712 | 25.778 | −39.347 | 1.00 | 38.38 | B |
| ATOM | 1656 | CB | THR | B | 87 | −36.538 | 25.026 | −39.984 | 1.00 | 35.81 | B |
| ATOM | 1657 | OG1 | THR | B | 87 | −36.316 | 23.803 | −39.276 | 1.00 | 35.27 | B |
| ATOM | 1658 | CG2 | THR | B | 87 | −35.280 | 25.870 | −39.946 | 1.00 | 28.02 | B |
| ATOM | 1659 | C | THR | B | 87 | −37.976 | 27.029 | −40.165 | 1.00 | 40.34 | B |
| ATOM | 1660 | O | THR | B | 87 | −37.600 | 28.136 | −39.768 | 1.00 | 42.58 | B |
| ATOM | 1661 | N | GLU | B | 88 | −38.629 | 26.849 | −41.308 | 1.00 | 41.62 | B |
| ATOM | 1662 | CA | GLU | B | 88 | −38.948 | 27.962 | −42.196 | 1.00 | 41.56 | B |
| ATOM | 1663 | CB | GLU | B | 88 | −39.541 | 27.428 | −43.498 | 1.00 | 41.09 | B |
| ATOM | 1664 | CG | GLU | B | 88 | −39.850 | 28.487 | −44.526 | 1.00 | 43.87 | B |
| ATOM | 1665 | CD | GLU | B | 88 | −38.622 | 29.295 | −44.906 | 1.00 | 47.13 | B |
| ATOM | 1666 | OE1 | GLU | B | 88 | −37.542 | 28.689 | −45.046 | 1.00 | 48.15 | B |
| ATOM | 1667 | OE2 | GLU | B | 88 | −38.728 | 30.528 | −45.078 | 1.00 | 48.87 | B |
| ATOM | 1668 | C | GLU | B | 88 | −39.941 | 28.907 | −41.523 | 1.00 | 41.37 | B |
| ATOM | 1669 | O | GLU | B | 88 | −39.719 | 30.120 | −41.441 | 1.00 | 42.84 | B |
| ATOM | 1670 | N | LEU | B | 89 | −41.037 | 28.342 | −41.032 | 1.00 | 39.06 | B |
| ATOM | 1671 | CA | LEU | B | 89 | −42.049 | 29.144 | −40.380 | 1.00 | 38.27 | B |
| ATOM | 1672 | CB | LEU | B | 89 | −43.214 | 28.255 | −39.938 | 1.00 | 34.88 | B |
| ATOM | 1673 | CG | LEU | B | 89 | −43.971 | 27.575 | −41.087 | 1.00 | 32.56 | B |
| ATOM | 1674 | CD1 | LEU | B | 89 | −45.074 | 26.700 | −40.540 | 1.00 | 29.69 | B |
| ATOM | 1675 | CD2 | LEU | B | 89 | −44.519 | 28.629 | −42.014 | 1.00 | 29.86 | B |
| ATOM | 1676 | C | LEU | B | 89 | −41.475 | 29.923 | −39.199 | 1.00 | 39.22 | B |
| ATOM | 1677 | O | LEU | B | 89 | −41.707 | 31.125 | −39.070 | 1.00 | 38.24 | B |
| ATOM | 1678 | N | TYR | B | 90 | −40.703 | 29.257 | −38.351 | 1.00 | 39.74 | B |
| ATOM | 1679 | CA | TYR | B | 90 | −40.153 | 29.951 | −37.214 | 1.00 | 41.05 | B |
| ATOM | 1680 | CB | TYR | B | 90 | −39.453 | 28.987 | −36.256 | 1.00 | 43.39 | B |
| ATOM | 1681 | CG | TYR | B | 90 | −39.363 | 29.572 | −34.863 | 1.00 | 45.73 | B |
| ATOM | 1682 | CD1 | TYR | B | 90 | −40.479 | 29.577 | −34.019 | 1.00 | 44.72 | B |
| ATOM | 1683 | CE1 | TYR | B | 90 | −40.446 | 30.218 | −32.789 | 1.00 | 46.68 | B |
| ATOM | 1684 | CD2 | TYR | B | 90 | −38.203 | 30.219 | −34.429 | 1.00 | 45.13 | B |
| ATOM | 1685 | CE2 | TYR | B | 90 | −38.160 | 30.863 | −33.193 | 1.00 | 46.07 | B |
| ATOM | 1686 | CZ | TYR | B | 90 | −39.287 | 30.863 | −32.379 | 1.00 | 46.81 | B |
| ATOM | 1687 | OH | TYR | B | 90 | −39.272 | 31.538 | −31.177 | 1.00 | 46.41 | B |
| ATOM | 1688 | C | TYR | B | 90 | −39.193 | 31.047 | −37.639 | 1.00 | 42.36 | B |

TABLE 5-continued

Atomic coordinates of rSIFN-co (SEQ ID NO: 1)

| ATOM | 1689 | O | TYR | B | 90 | −39.092 | 32.086 | −36.986 | 1.00 | 43.93 | B |
|---|---|---|---|---|---|---|---|---|---|---|---|
| ATOM | 1690 | N | GLN | B | 91 | −38.487 | 30.831 | −38.738 | 1.00 | 43.52 | B |
| ATOM | 1691 | CA | GLN | B | 91 | −37.557 | 31.844 | −39.217 | 1.00 | 45.08 | B |
| ATOM | 1692 | CB | GLN | B | 91 | −36.684 | 31.262 | −40.330 | 1.00 | 44.47 | B |
| ATOM | 1693 | CG | GLN | B | 91 | −35.262 | 31.826 | −40.377 | 1.00 | 48.72 | B |
| ATOM | 1694 | CD | GLN | B | 91 | −34.471 | 31.656 | −39.068 | 1.00 | 49.14 | B |
| ATOM | 1695 | OE1 | GLN | B | 91 | −34.568 | 30.634 | −38.385 | 1.00 | 49.61 | B |
| ATOM | 1696 | NE2 | GLN | B | 91 | −33.669 | 32.660 | −38.735 | 1.00 | 49.34 | B |
| ATOM | 1697 | C | GLN | B | 91 | −38.382 | 33.040 | −39.721 | 1.00 | 45.99 | B |
| ATOM | 1698 | O | GLN | B | 91 | −38.042 | 34.204 | −39.472 | 1.00 | 44.12 | B |
| ATOM | 1699 | N | GLN | B | 92 | −39.482 | 32.753 | −40.412 | 1.00 | 45.91 | B |
| ATOM | 1700 | CA | GLN | B | 92 | −40.340 | 33.821 | −40.904 | 1.00 | 47.21 | B |
| ATOM | 1701 | CB | GLN | B | 92 | −41.514 | 33.244 | −41.698 | 1.00 | 47.99 | B |
| ATOM | 1702 | CG | GLN | B | 92 | −41.191 | 32.841 | −43.123 | 1.00 | 51.32 | B |
| ATOM | 1703 | CD | GLN | B | 92 | −42.447 | 32.523 | −43.905 | 1.00 | 55.62 | B |
| ATOM | 1704 | OE1 | GLN | B | 92 | −43.411 | 33.290 | −43.885 | 1.00 | 57.55 | B |
| ATOM | 1705 | NE2 | GLN | B | 92 | −42.448 | 31.390 | −44.602 | 1.00 | 56.89 | B |
| ATOM | 1706 | C | GLN | B | 92 | −40.873 | 34.654 | −39.733 | 1.00 | 47.67 | B |
| ATOM | 1707 | O | GLN | B | 92 | −41.157 | 35.838 | −39.880 | 1.00 | 48.06 | B |
| ATOM | 1708 | N | LEU | B | 93 | −41.011 | 34.017 | −38.575 | 1.00 | 48.22 | B |
| ATOM | 1709 | CA | LEU | B | 93 | −41.502 | 34.663 | −37.366 | 1.00 | 46.33 | B |
| ATOM | 1710 | CB | LEU | B | 93 | −41.793 | 33.606 | −36.312 | 1.00 | 44.07 | B |
| ATOM | 1711 | CG | LEU | B | 93 | −43.211 | 33.418 | −35.790 | 1.00 | 42.19 | B |
| ATOM | 1712 | CD1 | LEU | B | 93 | −44.271 | 33.719 | −36.855 | 1.00 | 40.20 | B |
| ATOM | 1713 | CD2 | LEU | B | 93 | −43.303 | 31.992 | −35.296 | 1.00 | 38.45 | B |
| ATOM | 1714 | C | LEU | B | 93 | −40.454 | 35.629 | −36.848 | 1.00 | 47.84 | B |
| ATOM | 1715 | O | LEU | B | 93 | −40.772 | 36.740 | −36.439 | 1.00 | 47.68 | B |
| ATOM | 1716 | N | ASN | B | 94 | −39.196 | 35.201 | −36.857 | 1.00 | 49.68 | B |
| ATOM | 1717 | CA | ASN | B | 94 | −38.118 | 36.067 | −36.396 | 1.00 | 50.86 | B |
| ATOM | 1718 | CB | ASN | B | 94 | −36.797 | 35.295 | −36.302 | 1.00 | 49.93 | B |
| ATOM | 1719 | CG | ASN | B | 94 | −36.741 | 34.372 | −35.097 | 1.00 | 49.12 | B |
| ATOM | 1720 | OD1 | ASN | B | 94 | −37.613 | 34.402 | −34.228 | 1.00 | 48.85 | B |
| ATOM | 1721 | ND2 | ASN | B | 94 | −35.699 | 33.555 | −35.035 | 1.00 | 50.25 | B |
| ATOM | 1722 | C | ASN | B | 94 | −37.957 | 37.256 | −37.339 | 1.00 | 52.00 | B |
| ATOM | 1723 | O | ASN | B | 94 | −37.673 | 38.362 | −36.902 | 1.00 | 52.28 | B |
| ATOM | 1724 | N | ASP | B | 95 | −38.144 | 37.038 | −38.635 | 1.00 | 54.31 | B |
| ATOM | 1725 | CA | ASP | B | 95 | −38.016 | 38.147 | −39.574 | 1.00 | 55.94 | B |
| ATOM | 1726 | CB | ASP | B | 95 | −38.055 | 37.651 | −41.021 | 1.00 | 56.73 | B |
| ATOM | 1727 | CG | ASP | B | 95 | −36.892 | 36.737 | −41.344 | 1.00 | 59.74 | B |
| ATOM | 1728 | OD1 | ASP | B | 95 | −35.823 | 36.923 | −40.721 | 1.00 | 60.29 | B |
| ATOM | 1729 | OD2 | ASP | B | 95 | −37.037 | 35.844 | −42.216 | 1.00 | 60.62 | B |
| ATOM | 1730 | C | ASP | B | 95 | −39.114 | 39.167 | −39.340 | 1.00 | 55.97 | B |
| ATOM | 1731 | O | ASP | B | 95 | −38.849 | 40.357 | −39.328 | 1.00 | 55.88 | B |
| ATOM | 1732 | N | LEU | B | 96 | −40.343 | 38.701 | −39.145 | 1.00 | 57.37 | B |
| ATOM | 1733 | CA | LEU | B | 96 | −41.460 | 39.602 | −38.898 | 1.00 | 59.48 | B |
| ATOM | 1734 | CB | LEU | B | 96 | −42.762 | 38.813 | −38.735 | 1.00 | 57.57 | B |
| ATOM | 1735 | CG | LEU | B | 96 | −43.302 | 38.114 | −39.984 | 1.00 | 56.36 | B |
| ATOM | 1736 | CD1 | LEU | B | 96 | −44.553 | 37.313 | −39.654 | 1.00 | 53.91 | B |
| ATOM | 1737 | CD2 | LEU | B | 96 | −43.607 | 39.163 | −41.034 | 1.00 | 57.46 | B |
| ATOM | 1738 | C | LEU | B | 96 | −41.201 | 40.436 | −37.644 | 1.00 | 62.45 | B |
| ATOM | 1739 | O | LEU | B | 96 | −41.511 | 41.628 | −37.601 | 1.00 | 62.77 | B |
| ATOM | 1740 | N | GLU | B | 97 | −40.628 | 39.812 | −36.622 | 1.00 | 65.05 | B |
| ATOM | 1741 | CA | GLU | B | 97 | −40.338 | 40.528 | −35.392 | 1.00 | 68.23 | B |
| ATOM | 1742 | CB | GLU | B | 97 | −39.952 | 39.540 | −34.277 | 1.00 | 68.89 | B |
| ATOM | 1743 | CG | GLU | B | 97 | −41.097 | 38.626 | −33.830 | 1.00 | 71.87 | B |
| ATOM | 1744 | CD | GLU | B | 97 | −40.668 | 37.539 | −32.849 | 1.00 | 73.15 | B |
| ATOM | 1745 | OE1 | GLU | B | 97 | −40.181 | 37.886 | −31.756 | 1.00 | 76.25 | B |
| ATOM | 1746 | OE2 | GLU | B | 97 | −40.820 | 36.337 | −33.164 | 1.00 | 72.83 | B |
| ATOM | 1747 | C | GLU | B | 97 | −39.214 | 41.532 | −35.651 | 1.00 | 70.40 | B |
| ATOM | 1748 | O | GLU | B | 97 | −39.135 | 42.571 | −34.998 | 1.00 | 71.54 | B |
| ATOM | 1749 | N | ALA | B | 98 | −38.349 | 41.229 | −36.614 | 1.00 | 73.00 | B |
| ATOM | 1750 | CA | ALA | B | 98 | −37.248 | 42.128 | −36.952 | 1.00 | 75.20 | B |
| ATOM | 1751 | CB | ALA | B | 98 | −36.322 | 41.474 | −37.970 | 1.00 | 75.82 | B |
| ATOM | 1752 | C | ALA | B | 98 | −37.808 | 43.423 | −37.523 | 1.00 | 76.99 | B |
| ATOM | 1753 | O | ALA | B | 98 | −37.160 | 44.467 | −37.448 | 1.00 | 77.06 | B |
| ATOM | 1754 | N | CYS | B | 99 | −39.015 | 43.337 | −38.088 | 1.00 | 79.24 | B |
| ATOM | 1755 | CA | CYS | B | 99 | −39.711 | 44.478 | −38.691 | 1.00 | 81.14 | B |
| ATOM | 1756 | CB | CYS | B | 99 | −40.765 | 44.002 | −39.695 | 1.00 | 81.56 | B |
| ATOM | 1757 | SG | CYS | B | 99 | −40.126 | 43.247 | −41.210 | 1.00 | 84.65 | B |
| ATOM | 1758 | C | CYS | B | 99 | −40.397 | 45.359 | −37.658 | 1.00 | 82.14 | B |
| ATOM | 1759 | O | CYS | B | 99 | −40.290 | 46.582 | −37.715 | 1.00 | 82.34 | B |
| ATOM | 1760 | N | VAL | B | 100 | −41.116 | 44.740 | −36.725 | 1.00 | 83.70 | B |
| ATOM | 1761 | CA | VAL | B | 100 | −41.814 | 45.493 | −35.684 | 1.00 | 85.68 | B |
| ATOM | 1762 | CB | VAL | B | 100 | −42.619 | 44.556 | −34.740 | 1.00 | 85.07 | B |
| ATOM | 1763 | CG1 | VAL | B | 100 | −41.688 | 43.602 | −34.020 | 1.00 | 84.36 | B |
| ATOM | 1764 | CG2 | VAL | B | 100 | −43.405 | 45.381 | −33.741 | 1.00 | 85.62 | B |
| ATOM | 1765 | C | VAL | B | 100 | −40.801 | 46.287 | −34.863 | 1.00 | 87.06 | B |
| ATOM | 1766 | O | VAL | B | 100 | −41.162 | 47.202 | −34.115 | 1.00 | 87.20 | B |

TABLE 5-continued

| Atomic coordinates of rSIFN-co (SEQ ID NO: 1) | | | | | | | | | |
|---|---|---|---|---|---|---|---|---|---|
| ATOM | 1767 | N | ALA | B | 101 | −39.529 | 45.927 | −35.023 | 1.00 88.22 B |
| ATOM | 1768 | CA | ALA | B | 101 | −38.434 | 46.582 | −34.323 | 1.00 89.09 B |
| ATOM | 1769 | CB | ALA | B | 101 | −37.497 | 45.533 | −33.730 | 1.00 88.54 B |
| ATOM | 1770 | C | ALA | B | 101 | −37.666 | 47.498 | −35.276 | 1.00 89.84 B |
| ATOM | 1771 | O | ALA | B | 101 | −37.324 | 48.626 | −34.925 | 1.00 90.61 B |
| ATOM | 1772 | N | GLY | B | 102 | −37.401 | 47.010 | −36.484 | 1.00 90.46 B |
| ATOM | 1773 | CA | GLY | B | 102 | −36.678 | 47.808 | −37.457 | 1.00 91.07 B |
| ATOM | 1774 | C | GLY | B | 102 | −37.577 | 48.761 | −38.223 | 1.00 92.05 B |
| ATOM | 1775 | O | GLY | B | 102 | −37.266 | 49.135 | −39.351 | 1.00 92.33 B |
| ATOM | 1776 | N | GLY | B | 103 | −38.692 | 49.157 | −37.612 | 1.00 92.84 B |
| ATOM | 1777 | CA | GLY | B | 103 | −39.616 | 50.069 | −38.266 | 1.00 92.74 B |
| ATOM | 1778 | C | GLY | B | 103 | −40.887 | 50.291 | −37.465 | 1.00 92.62 B |
| ATOM | 1779 | O | GLY | B | 103 | −41.047 | 51.321 | −36.807 | 1.00 92.47 B |
| ATOM | 1780 | N | ALA | B | 111 | −51.414 | 47.696 | −31.869 | 1.00 93.96 B |
| ATOM | 1781 | CA | ALA | B | 111 | −51.666 | 47.368 | −33.267 | 1.00 93.85 B |
| ATOM | 1782 | CB | ALA | B | 111 | −51.378 | 45.889 | −33.516 | 1.00 92.71 B |
| ATOM | 1783 | C | ALA | B | 111 | −53.105 | 47.697 | −33.661 | 1.00 93.95 B |
| ATOM | 1784 | O | ALA | B | 111 | −53.906 | 46.792 | −33.916 | 1.00 94.29 B |
| ATOM | 1785 | N | GLY | B | 112 | −53.424 | 48.993 | −33.708 | 1.00 92.98 B |
| ATOM | 1786 | CA | GLY | B | 112 | −54.760 | 49.429 | −34.080 | 1.00 91.20 B |
| ATOM | 1787 | C | GLY | B | 112 | −55.854 | 48.615 | −33.416 | 1.00 90.66 B |
| ATOM | 1788 | O | GLY | B | 112 | −56.271 | 48.924 | −32.298 | 1.00 91.11 B |
| ATOM | 1789 | N | ASN | B | 113 | −56.328 | 47.575 | −34.101 | 1.00 88.98 B |
| ATOM | 1790 | CA | ASN | B | 113 | −57.368 | 46.715 | −33.546 | 1.00 86.63 B |
| ATOM | 1791 | CB | ASN | B | 113 | −58.702 | 46.922 | −34.275 | 1.00 88.02 B |
| ATOM | 1792 | CG | ASN | B | 113 | −58.597 | 46.693 | −35.770 | 1.00 88.87 B |
| ATOM | 1793 | OD1 | ASN | B | 113 | −57.973 | 45.729 | −36.226 | 1.00 88.93 B |
| ATOM | 1794 | ND2 | ASN | B | 113 | −59.225 | 47.573 | −36.545 | 1.00 89.31 B |
| ATOM | 1795 | C | ASN | B | 113 | −56.988 | 45.237 | −33.586 | 1.00 84.10 B |
| ATOM | 1796 | O | ASN | B | 113 | −56.396 | 44.750 | −34.559 | 1.00 82.68 B |
| ATOM | 1797 | N | ALA | B | 114 | −57.333 | 44.538 | −32.507 | 1.00 80.69 B |
| ATOM | 1798 | CA | ALA | B | 114 | −57.053 | 43.117 | −32.365 | 1.00 77.04 B |
| ATOM | 1799 | CB | ALA | B | 114 | −57.060 | 42.734 | −30.885 | 1.00 74.97 B |
| ATOM | 1800 | C | ALA | B | 114 | −58.094 | 42.307 | −33.129 | 1.00 75.04 B |
| ATOM | 1801 | O | ALA | B | 114 | −58.167 | 41.092 | −32.987 | 1.00 75.09 B |
| ATOM | 1802 | N | ASP | B | 115 | −58.898 | 42.993 | −33.935 | 1.00 73.04 B |
| ATOM | 1803 | CA | ASP | B | 115 | −59.940 | 42.354 | −34.739 | 1.00 71.39 B |
| ATOM | 1804 | CB | ASP | B | 115 | −60.755 | 43.408 | −35.493 | 1.00 75.02 B |
| ATOM | 1805 | CG | ASP | B | 115 | −61.440 | 44.387 | −34.573 | 1.00 77.51 B |
| ATOM | 1806 | OD1 | ASP | B | 115 | −61.719 | 45.520 | −35.022 | 1.00 77.99 B |
| ATOM | 1807 | OD2 | ASP | B | 115 | −61.707 | 44.019 | −33.408 | 1.00 80.45 B |
| ATOM | 1808 | C | ASP | B | 115 | −59.318 | 41.429 | −35.766 | 1.00 68.05 B |
| ATOM | 1809 | O | ASP | B | 115 | −59.626 | 40.245 | −35.834 | 1.00 67.22 B |
| ATOM | 1810 | N | SER | B | 116 | −58.451 | 42.002 | −36.585 | 1.00 65.47 B |
| ATOM | 1811 | CA | SER | B | 116 | −57.775 | 41.259 | −37.628 | 1.00 62.95 B |
| ATOM | 1812 | CB | SER | B | 116 | −56.707 | 42.137 | −38.277 | 1.00 63.58 B |
| ATOM | 1813 | OG | SER | B | 116 | −57.268 | 43.350 | −38.753 | 1.00 63.46 B |
| ATOM | 1814 | C | SER | B | 116 | −57.140 | 39.998 | −37.062 | 1.00 61.42 B |
| ATOM | 1815 | O | SER | B | 116 | −57.296 | 38.917 | −37.626 | 1.00 62.05 B |
| ATOM | 1816 | N | ILE | B | 117 | −56.430 | 40.137 | −35.946 | 1.00 58.31 B |
| ATOM | 1817 | CA | ILE | B | 117 | −55.772 | 38.999 | −35.313 | 1.00 54.83 B |
| ATOM | 1818 | CB | ILE | B | 117 | −54.966 | 39.423 | −34.076 | 1.00 53.03 B |
| ATOM | 1819 | CG2 | ILE | B | 117 | −54.366 | 38.202 | −33.414 | 1.00 51.47 B |
| ATOM | 1820 | CG1 | ILE | B | 117 | −53.871 | 40.404 | −34.477 | 1.00 52.17 B |
| ATOM | 1821 | CD1 | ILE | B | 117 | −53.280 | 41.161 | −33.307 | 1.00 50.94 B |
| ATOM | 1822 | C | ILE | B | 117 | −56.772 | 37.944 | −34.870 | 1.00 54.11 B |
| ATOM | 1823 | O | ILE | B | 117 | −56.565 | 36.761 | −35.091 | 1.00 56.60 B |
| ATOM | 1824 | N | LEU | B | 118 | −57.854 | 38.370 | −34.235 | 1.00 52.88 B |
| ATOM | 1825 | CA | LEU | B | 118 | −58.862 | 37.430 | −33.766 | 1.00 50.60 B |
| ATOM | 1826 | CB | LEU | B | 118 | −59.955 | 38.167 | −32.984 | 1.00 51.65 B |
| ATOM | 1827 | CG | LEU | B | 118 | −61.046 | 37.271 | −32.391 | 1.00 54.03 B |
| ATOM | 1828 | CD1 | LEU | B | 118 | −60.591 | 36.760 | −31.040 | 1.00 54.61 B |
| ATOM | 1829 | CD2 | LEU | B | 118 | −62.343 | 38.044 | −32.249 | 1.00 53.11 B |
| ATOM | 1830 | C | LEU | B | 118 | −59.470 | 36.716 | −34.966 | 1.00 49.21 B |
| ATOM | 1831 | O | LEU | B | 118 | −59.797 | 35.534 | −34.900 | 1.00 47.90 B |
| ATOM | 1832 | N | ALA | B | 119 | −59.611 | 37.436 | −36.072 | 1.00 48.72 B |
| ATOM | 1833 | CA | ALA | B | 119 | −60.183 | 36.852 | −37.278 | 1.00 49.24 B |
| ATOM | 1834 | CB | ALA | B | 119 | −60.323 | 37.916 | −38.343 | 1.00 48.04 B |
| ATOM | 1835 | C | ALA | B | 119 | −59.339 | 35.674 | −37.793 | 1.00 50.65 B |
| ATOM | 1836 | O | ALA | B | 119 | −59.884 | 34.667 | −38.270 | 1.00 51.27 B |
| ATOM | 1837 | N | VAL | B | 120 | −58.016 | 35.795 | −37.691 | 1.00 49.50 B |
| ATOM | 1838 | CA | VAL | B | 120 | −57.130 | 34.727 | −38.130 | 1.00 50.37 B |
| ATOM | 1839 | CB | VAL | B | 120 | −55.657 | 35.188 | −38.178 | 1.00 49.79 B |
| ATOM | 1840 | CG1 | VAL | B | 120 | −54.746 | 33.979 | −38.348 | 1.00 47.60 B |
| ATOM | 1841 | CG2 | VAL | B | 120 | −55.455 | 36.190 | −39.315 | 1.00 47.48 B |
| ATOM | 1842 | C | VAL | B | 120 | −57.235 | 33.546 | −37.170 | 1.00 52.26 B |
| ATOM | 1843 | O | VAL | B | 120 | −57.177 | 32.377 | −37.582 | 1.00 51.97 B |
| ATOM | 1844 | N | LYS | B | 121 | −57.382 | 33.855 | −35.883 | 1.00 53.62 B |

TABLE 5-continued

Atomic coordinates of rSIFN-co (SEQ ID NO: 1)

| ATOM | 1845 | CA | LYS | B | 121 | −57.501 | 32.811 | −34.875 | 1.00 | 54.59 | B |
|---|---|---|---|---|---|---|---|---|---|---|---|
| ATOM | 1846 | CB | LYS | B | 121 | −57.508 | 33.413 | −33.475 | 1.00 | 54.64 | B |
| ATOM | 1847 | CG | LYS | B | 121 | −56.148 | 33.911 | −33.017 | 1.00 | 58.06 | B |
| ATOM | 1848 | CD | LYS | B | 121 | −56.232 | 34.584 | −31.650 | 1.00 | 60.35 | B |
| ATOM | 1849 | CE | LYS | B | 121 | −54.864 | 35.021 | −31.140 | 1.00 | 60.35 | B |
| ATOM | 1850 | NZ | LYS | B | 121 | −53.990 | 33.861 | −30.842 | 1.00 | 61.51 | B |
| ATOM | 1851 | C | LYS | B | 121 | −58.769 | 32.005 | −35.108 | 1.00 | 55.58 | B |
| ATOM | 1852 | O | LYS | B | 121 | −58.744 | 30.780 | −35.065 | 1.00 | 55.57 | B |
| ATOM | 1853 | N | LYS | B | 122 | −59.876 | 32.689 | −35.378 | 1.00 | 56.77 | B |
| ATOM | 1854 | CA | LYS | B | 122 | −61.140 | 31.997 | −35.618 | 1.00 | 58.18 | B |
| ATOM | 1855 | CB | LYS | B | 122 | −62.275 | 33.014 | −35.811 | 1.00 | 60.88 | B |
| ATOM | 1856 | CG | LYS | B | 122 | −62.628 | 33.807 | −34.545 | 1.00 | 63.85 | B |
| ATOM | 1857 | CD | LYS | B | 122 | −63.785 | 34.770 | −34.784 | 1.00 | 67.04 | B |
| ATOM | 1858 | CE | LYS | B | 122 | −65.079 | 34.020 | −35.089 | 1.00 | 70.23 | B |
| ATOM | 1859 | NZ | LYS | B | 122 | −66.260 | 34.925 | −35.259 | 1.00 | 71.84 | B |
| ATOM | 1860 | C | LYS | B | 122 | −61.036 | 31.078 | −36.835 | 1.00 | 57.34 | B |
| ATOM | 1861 | O | LYS | B | 122 | −61.588 | 29.975 | −36.846 | 1.00 | 57.39 | B |
| ATOM | 1862 | N | TYR | B | 123 | −60.316 | 31.540 | −37.852 | 1.00 | 55.98 | B |
| ATOM | 1863 | CA | TYR | B | 123 | −60.117 | 30.774 | −39.080 | 1.00 | 54.34 | B |
| ATOM | 1864 | CB | TYR | B | 123 | −59.252 | 31.593 | −40.050 | 1.00 | 54.18 | B |
| ATOM | 1865 | CG | TYR | B | 123 | −58.689 | 30.830 | −41.226 | 1.00 | 53.30 | B |
| ATOM | 1866 | CD1 | TYR | B | 123 | −59.524 | 30.175 | −42.130 | 1.00 | 53.39 | B |
| ATOM | 1867 | CE1 | TYR | B | 123 | −59.001 | 29.474 | −43.217 | 1.00 | 53.48 | B |
| ATOM | 1868 | CD2 | TYR | B | 123 | −57.315 | 30.767 | −41.436 | 1.00 | 53.09 | B |
| ATOM | 1869 | CE2 | TYR | B | 123 | −56.781 | 30.069 | −42.518 | 1.00 | 53.78 | B |
| ATOM | 1870 | CZ | TYR | B | 123 | −57.627 | 29.426 | −43.404 | 1.00 | 53.93 | B |
| ATOM | 1871 | OH | TYR | B | 123 | −57.097 | 28.736 | −44.471 | 1.00 | 52.16 | B |
| ATOM | 1872 | C | TYR | B | 123 | −59.458 | 29.430 | −38.773 | 1.00 | 53.07 | B |
| ATOM | 1873 | O | TYR | B | 123 | −59.994 | 28.369 | −39.100 | 1.00 | 51.67 | B |
| ATOM | 1874 | N | PHE | B | 124 | −58.296 | 29.487 | −38.133 | 1.00 | 52.86 | B |
| ATOM | 1875 | CA | PHE | B | 124 | −57.555 | 28.283 | −37.775 | 1.00 | 53.45 | B |
| ATOM | 1876 | CB | PHE | B | 124 | −56.200 | 28.665 | −37.186 | 1.00 | 50.18 | B |
| ATOM | 1877 | CG | PHE | B | 124 | −55.177 | 29.018 | −38.228 | 1.00 | 48.40 | B |
| ATOM | 1878 | CD1 | PHE | B | 124 | −54.460 | 28.019 | −38.880 | 1.00 | 43.87 | B |
| ATOM | 1879 | CD2 | PHE | B | 124 | −54.958 | 30.345 | −38.590 | 1.00 | 46.73 | B |
| ATOM | 1880 | CE1 | PHE | B | 124 | −53.553 | 28.327 | −39.865 | 1.00 | 41.12 | B |
| ATOM | 1881 | CE2 | PHE | B | 124 | −54.040 | 30.659 | −39.587 | 1.00 | 44.49 | B |
| ATOM | 1882 | CZ | PHE | B | 124 | −53.338 | 29.641 | −40.223 | 1.00 | 41.38 | B |
| ATOM | 1883 | C | PHE | B | 124 | −58.336 | 27.440 | −36.796 | 1.00 | 55.05 | B |
| ATOM | 1884 | O | PHE | B | 124 | −58.134 | 26.234 | −36.695 | 1.00 | 54.37 | B |
| ATOM | 1885 | N | GLN | B | 125 | −59.238 | 28.094 | −36.076 | 1.00 | 59.25 | B |
| ATOM | 1886 | CA | GLN | B | 125 | −60.081 | 27.421 | −35.106 | 1.00 | 60.57 | B |
| ATOM | 1887 | CB | GLN | B | 125 | −60.883 | 28.445 | −34.307 | 1.00 | 64.50 | B |
| ATOM | 1888 | CG | GLN | B | 125 | −61.759 | 27.839 | −33.227 | 1.00 | 70.78 | B |
| ATOM | 1889 | CD | GLN | B | 125 | −60.960 | 27.038 | −32.212 | 1.00 | 74.51 | B |
| ATOM | 1890 | OE1 | GLN | B | 125 | −60.071 | 27.575 | −31.540 | 1.00 | 76.71 | B |
| ATOM | 1891 | NE2 | GLN | B | 125 | −61.272 | 25.744 | −32.095 | 1.00 | 75.37 | B |
| ATOM | 1892 | C | GLN | B | 125 | −61.014 | 26.525 | −35.894 | 1.00 | 59.74 | B |
| ATOM | 1893 | O | GLN | B | 125 | −61.124 | 25.336 | −35.608 | 1.00 | 60.48 | B |
| ATOM | 1894 | N | ARG | B | 126 | −61.672 | 27.096 | −36.901 | 1.00 | 58.55 | B |
| ATOM | 1895 | CA | ARG | B | 126 | −62.591 | 26.332 | −37.740 | 1.00 | 58.45 | B |
| ATOM | 1896 | CB | ARG | B | 126 | −63.192 | 27.230 | −38.819 | 1.00 | 58.22 | B |
| ATOM | 1897 | CG | ARG | B | 126 | −64.322 | 28.135 | −38.334 | 1.00 | 56.82 | B |
| ATOM | 1898 | CD | ARG | B | 126 | −64.632 | 29.227 | −39.348 | 1.00 | 55.96 | B |
| ATOM | 1899 | NE | ARG | B | 126 | −64.100 | 30.523 | −38.925 | 1.00 | 56.75 | B |
| ATOM | 1900 | CZ | ARG | B | 126 | −63.490 | 31.379 | −39.738 | 1.00 | 57.05 | B |
| ATOM | 1901 | NH1 | ARG | B | 126 | −63.333 | 31.072 | −41.013 | 1.00 | 56.86 | B |
| ATOM | 1902 | NH2 | ARG | B | 126 | −63.039 | 32.541 | −39.282 | 1.00 | 57.49 | B |
| ATOM | 1903 | C | ARG | B | 126 | −61.874 | 25.151 | −38.384 | 1.00 | 59.08 | B |
| ATOM | 1904 | O | ARG | B | 126 | −62.406 | 24.043 | −38.425 | 1.00 | 58.89 | B |
| ATOM | 1905 | N | ILE | B | 127 | −60.667 | 25.396 | −38.888 | 1.00 | 59.70 | B |
| ATOM | 1906 | CA | ILE | B | 127 | −59.862 | 24.351 | −39.514 | 1.00 | 59.95 | B |
| ATOM | 1907 | CB | ILE | B | 127 | −58.472 | 24.891 | −39.914 | 1.00 | 59.73 | B |
| ATOM | 1908 | CG2 | ILE | B | 127 | −57.508 | 23.745 | −40.190 | 1.00 | 57.13 | B |
| ATOM | 1909 | CG1 | ILE | B | 127 | −58.609 | 25.809 | −41.126 | 1.00 | 60.37 | B |
| ATOM | 1910 | CD1 | ILE | B | 127 | −57.338 | 26.563 | −41.468 | 1.00 | 62.06 | B |
| ATOM | 1911 | C | ILE | B | 127 | −59.675 | 23.199 | −38.538 | 1.00 | 60.89 | B |
| ATOM | 1912 | O | ILE | B | 127 | −59.904 | 22.041 | −38.884 | 1.00 | 60.80 | B |
| ATOM | 1913 | N | THR | B | 128 | −59.264 | 23.543 | −37.319 | 1.00 | 61.84 | B |
| ATOM | 1914 | CA | THR | B | 128 | −59.012 | 22.583 | −36.241 | 1.00 | 63.43 | B |
| ATOM | 1915 | CB | THR | B | 128 | −58.598 | 23.320 | −34.940 | 1.00 | 64.67 | B |
| ATOM | 1916 | OG1 | THR | B | 128 | −57.481 | 24.172 | −35.212 | 1.00 | 67.07 | B |
| ATOM | 1917 | CG2 | THR | B | 128 | −58.204 | 22.331 | −33.853 | 1.00 | 65.28 | B |
| ATOM | 1918 | C | THR | B | 128 | −60.209 | 21.690 | −35.918 | 1.00 | 63.22 | B |
| ATOM | 1919 | O | THR | B | 128 | −60.045 | 20.515 | −35.585 | 1.00 | 61.95 | B |
| ATOM | 1920 | N | LEU | B | 129 | −61.407 | 22.256 | −36.008 | 1.00 | 64.24 | B |
| ATOM | 1921 | CA | LEU | B | 129 | −62.630 | 21.524 | −35.716 | 1.00 | 66.29 | B |
| ATOM | 1922 | CB | LEU | B | 129 | −63.771 | 22.505 | −35.454 | 1.00 | 66.59 | B |

TABLE 5-continued

Atomic coordinates of rSIFN-co (SEQ ID NO: 1)

| ATOM | 1923 | CG | LEU | B | 129 | −64.722 | 22.138 | −34.313 | 1.00 | 67.84 | B |
|------|------|-----|-----|---|-----|---------|--------|---------|------|-------|---|
| ATOM | 1924 | CD1 | LEU | B | 129 | −65.736 | 23.255 | −34.140 | 1.00 | 67.06 | B |
| ATOM | 1925 | CD2 | LEU | B | 129 | −65.409 | 20.796 | −34.595 | 1.00 | 67.62 | B |
| ATOM | 1926 | C | LEU | B | 129 | −62.986 | 20.619 | −36.886 | 1.00 | 68.37 | B |
| ATOM | 1927 | O | LEU | B | 129 | −63.672 | 19.613 | −36.720 | 1.00 | 70.05 | B |
| ATOM | 1928 | N | TYR | B | 130 | −62.530 | 20.994 | −38.077 | 1.00 | 69.17 | B |
| ATOM | 1929 | CA | TYR | B | 130 | −62.780 | 20.208 | −39.273 | 1.00 | 68.74 | B |
| ATOM | 1930 | CB | TYR | B | 130 | −62.296 | 20.973 | −40.507 | 1.00 | 69.94 | B |
| ATOM | 1931 | CG | TYR | B | 130 | −62.397 | 20.200 | −41.803 | 1.00 | 71.43 | B |
| ATOM | 1932 | CD1 | TYR | B | 130 | −63.627 | 19.990 | −42.425 | 1.00 | 71.95 | B |
| ATOM | 1933 | CE1 | TYR | B | 130 | −63.719 | 19.273 | −43.624 | 1.00 | 72.25 | B |
| ATOM | 1934 | CD2 | TYR | B | 130 | −61.258 | 19.671 | −42.409 | 1.00 | 72.21 | B |
| ATOM | 1935 | CE2 | TYR | B | 130 | −61.340 | 18.950 | −43.607 | 1.00 | 72.56 | B |
| ATOM | 1936 | CZ | TYR | B | 130 | −62.571 | 18.756 | −44.207 | 1.00 | 72.07 | B |
| ATOM | 1937 | OH | TYR | B | 130 | −62.649 | 18.044 | −45.383 | 1.00 | 71.77 | B |
| ATOM | 1938 | C | TYR | B | 130 | −61.996 | 18.911 | −39.115 | 1.00 | 69.00 | B |
| ATOM | 1939 | O | TYR | B | 130 | −62.556 | 17.821 | −39.175 | 1.00 | 68.44 | B |
| ATOM | 1940 | N | LEU | B | 131 | −60.691 | 19.044 | −38.896 | 1.00 | 68.64 | B |
| ATOM | 1941 | CA | LEU | B | 131 | −59.821 | 17.890 | −38.724 | 1.00 | 68.04 | B |
| ATOM | 1942 | CB | LEU | B | 131 | −58.422 | 18.345 | −38.310 | 1.00 | 66.02 | B |
| ATOM | 1943 | CG | LEU | B | 131 | −57.471 | 18.856 | −39.391 | 1.00 | 65.04 | B |
| ATOM | 1944 | CD1 | LEU | B | 131 | −56.264 | 19.481 | −38.719 | 1.00 | 63.94 | B |
| ATOM | 1945 | CD2 | LEU | B | 131 | −57.043 | 17.716 | −40.313 | 1.00 | 63.38 | B |
| ATOM | 1946 | C | LEU | B | 131 | −60.347 | 16.891 | −37.698 | 1.00 | 68.93 | B |
| ATOM | 1947 | O | LEU | B | 131 | −60.523 | 15.714 | −38.006 | 1.00 | 68.61 | B |
| ATOM | 1948 | N | THR | B | 132 | −60.594 | 17.363 | −36.478 | 1.00 | 70.61 | B |
| ATOM | 1949 | CA | THR | B | 132 | −61.083 | 16.495 | −35.406 | 1.00 | 71.92 | B |
| ATOM | 1950 | CB | THR | B | 132 | −60.841 | 17.131 | −34.008 | 1.00 | 71.89 | B |
| ATOM | 1951 | OG1 | THR | B | 132 | −61.250 | 16.214 | −32.987 | 1.00 | 70.43 | B |
| ATOM | 1952 | CG2 | THR | B | 132 | −61.623 | 18.429 | −33.860 | 1.00 | 72.59 | B |
| ATOM | 1953 | C | THR | B | 132 | −62.565 | 16.161 | −35.562 | 1.00 | 72.74 | B |
| ATOM | 1954 | O | THR | B | 132 | −63.170 | 15.549 | −34.683 | 1.00 | 73.16 | B |
| ATOM | 1955 | N | GLY | B | 133 | −63.141 | 16.576 | −36.687 | 1.00 | 73.71 | B |
| ATOM | 1956 | CA | GLY | B | 133 | −64.539 | 16.301 | −36.968 | 1.00 | 73.91 | B |
| ATOM | 1957 | C | GLY | B | 133 | −64.582 | 15.208 | −38.019 | 1.00 | 74.32 | B |
| ATOM | 1958 | O | GLY | B | 133 | −65.606 | 14.556 | −38.236 | 1.00 | 74.32 | B |
| ATOM | 1959 | N | LYS | B | 134 | −63.442 | 15.015 | −38.676 | 1.00 | 74.07 | B |
| ATOM | 1960 | CA | LYS | B | 134 | −63.296 | 14.001 | −39.708 | 1.00 | 73.57 | B |
| ATOM | 1961 | CB | LYS | B | 134 | −62.847 | 14.629 | −41.028 | 1.00 | 72.93 | B |
| ATOM | 1962 | CG | LYS | B | 134 | −63.976 | 14.926 | −42.004 | 1.00 | 73.33 | B |
| ATOM | 1963 | CD | LYS | B | 134 | −64.905 | 16.035 | −41.525 | 1.00 | 74.01 | B |
| ATOM | 1964 | CE | LYS | B | 134 | −65.972 | 16.349 | −42.583 | 1.00 | 74.15 | B |
| ATOM | 1965 | NZ | LYS | B | 134 | −66.745 | 17.600 | −42.317 | 1.00 | 72.79 | B |
| ATOM | 1966 | C | LYS | B | 134 | −62.282 | 12.962 | −39.262 | 1.00 | 73.93 | B |
| ATOM | 1967 | O | LYS | B | 134 | −61.676 | 12.278 | −40.082 | 1.00 | 72.76 | B |
| ATOM | 1968 | N | LYS | B | 135 | −62.093 | 12.867 | −37.951 | 1.00 | 75.07 | B |
| ATOM | 1969 | CA | LYS | B | 135 | −61.184 | 11.890 | −37.367 | 1.00 | 76.77 | B |
| ATOM | 1970 | CB | LYS | B | 135 | −61.808 | 10.496 | −37.485 | 1.00 | 77.37 | B |
| ATOM | 1971 | CG | LYS | B | 135 | −63.245 | 10.428 | −36.990 | 1.00 | 78.83 | B |
| ATOM | 1972 | CD | LYS | B | 135 | −63.856 | 9.057 | −37.231 | 1.00 | 81.28 | B |
| ATOM | 1973 | CE | LYS | B | 135 | −63.278 | 8.000 | −36.295 | 1.00 | 83.54 | B |
| ATOM | 1974 | NZ | LYS | B | 135 | −63.708 | 8.200 | −34.876 | 1.00 | 84.34 | B |
| ATOM | 1975 | C | LYS | B | 135 | −59.773 | 11.878 | −37.967 | 1.00 | 77.31 | B |
| ATOM | 1976 | O | LYS | B | 135 | −59.174 | 10.815 | −38.135 | 1.00 | 78.04 | B |
| ATOM | 1977 | N | TYR | B | 136 | −59.246 | 13.056 | −38.283 | 1.00 | 77.23 | B |
| ATOM | 1978 | CA | TYR | B | 136 | −57.902 | 13.181 | −38.845 | 1.00 | 76.63 | B |
| ATOM | 1979 | CB | TYR | B | 136 | −56.861 | 12.989 | −37.748 | 1.00 | 78.09 | B |
| ATOM | 1980 | CG | TYR | B | 136 | −57.053 | 13.907 | −36.564 | 1.00 | 82.10 | B |
| ATOM | 1981 | CD1 | TYR | B | 136 | −58.076 | 13.685 | −35.638 | 1.00 | 83.03 | B |
| ATOM | 1982 | CE1 | TYR | B | 136 | −58.244 | 14.522 | −34.529 | 1.00 | 84.37 | B |
| ATOM | 1983 | CD2 | TYR | B | 136 | −56.204 | 14.992 | −36.359 | 1.00 | 83.46 | B |
| ATOM | 1984 | CE2 | TYR | B | 136 | −56.362 | 15.837 | −35.255 | 1.00 | 85.30 | B |
| ATOM | 1985 | CZ | TYR | B | 136 | −57.382 | 15.596 | −34.341 | 1.00 | 85.81 | B |
| ATOM | 1986 | OH | TYR | B | 136 | −57.524 | 16.419 | −33.237 | 1.00 | 85.88 | B |
| ATOM | 1987 | C | TYR | B | 136 | −57.615 | 12.202 | −39.980 | 1.00 | 75.70 | B |
| ATOM | 1988 | O | TYR | B | 136 | −56.528 | 11.625 | −40.057 | 1.00 | 74.43 | B |
| ATOM | 1989 | N | SER | B | 137 | −58.592 | 12.039 | −40.867 | 1.00 | 75.24 | B |
| ATOM | 1990 | CA | SER | B | 137 | −58.477 | 11.131 | −42.001 | 1.00 | 74.25 | B |
| ATOM | 1991 | CB | SER | B | 137 | −59.860 | 10.845 | −42.580 | 1.00 | 73.68 | B |
| ATOM | 1992 | OG | SER | B | 137 | −60.451 | 12.033 | −43.072 | 1.00 | 73.31 | B |
| ATOM | 1993 | C | SER | B | 137 | −57.578 | 11.668 | −43.106 | 1.00 | 74.57 | B |
| ATOM | 1994 | O | SER | B | 137 | −57.476 | 12.880 | −43.312 | 1.00 | 73.85 | B |
| ATOM | 1995 | N | PRO | B | 138 | −56.921 | 10.758 | −43.842 | 1.00 | 74.56 | B |
| ATOM | 1996 | CD | PRO | B | 138 | −56.984 | 9.296 | −43.668 | 1.00 | 74.19 | B |
| ATOM | 1997 | CA | PRO | B | 138 | −56.021 | 11.103 | −44.940 | 1.00 | 74.13 | B |
| ATOM | 1998 | CB | PRO | B | 138 | −55.832 | 9.771 | −45.643 | 1.00 | 73.66 | B |
| ATOM | 1999 | CG | PRO | B | 138 | −55.810 | 8.822 | −44.486 | 1.00 | 73.91 | B |
| ATOM | 2000 | C | PRO | B | 138 | −56.579 | 12.177 | −45.859 | 1.00 | 74.15 | B |

TABLE 5-continued

Atomic coordinates of rSIFN-co (SEQ ID NO: 1)

| ATOM | 2001 | O | PRO | B | 138 | −55.832 | 13.016 | −46.362 | 1.00 | 74.48 | B |
|---|---|---|---|---|---|---|---|---|---|---|---|
| ATOM | 2002 | N | CYS | B | 139 | −57.887 | 12.156 | −46.081 | 1.00 | 74.19 | B |
| ATOM | 2003 | CA | CYS | B | 139 | −58.488 | 13.163 | −46.943 | 1.00 | 75.46 | B |
| ATOM | 2004 | C | CYS | B | 139 | −58.702 | 14.457 | −46.178 | 1.00 | 74.04 | B |
| ATOM | 2005 | O | CYS | B | 139 | −58.472 | 15.545 | −46.705 | 1.00 | 73.77 | B |
| ATOM | 2006 | CB | CYS | B | 139 | −59.814 | 12.665 | −47.538 | 1.00 | 79.16 | B |
| ATOM | 2007 | SG | CYS | B | 139 | −59.600 | 11.373 | −48.809 | 1.00 | 82.68 | B |
| ATOM | 2008 | N | ALA | B | 140 | −59.136 | 14.342 | −44.930 | 1.00 | 72.55 | B |
| ATOM | 2009 | CA | ALA | B | 140 | −59.346 | 15.529 | −44.115 | 1.00 | 71.12 | B |
| ATOM | 2010 | CB | ALA | B | 140 | −59.704 | 15.128 | −42.704 | 1.00 | 71.98 | B |
| ATOM | 2011 | C | ALA | B | 140 | −58.063 | 16.364 | −44.117 | 1.00 | 70.40 | B |
| ATOM | 2012 | O | ALA | B | 140 | −58.104 | 17.576 | −44.354 | 1.00 | 70.21 | B |
| ATOM | 2013 | N | TRP | B | 141 | −56.929 | 15.706 | −43.862 | 1.00 | 68.06 | B |
| ATOM | 2014 | CA | TRP | B | 141 | −55.630 | 16.379 | −43.839 | 1.00 | 66.09 | B |
| ATOM | 2015 | CB | TRP | B | 141 | −54.511 | 15.405 | −43.429 | 1.00 | 65.31 | B |
| ATOM | 2016 | CG | TRP | B | 141 | −54.188 | 15.447 | −41.954 | 1.00 | 64.66 | B |
| ATOM | 2017 | CD2 | TRP | B | 141 | −53.698 | 16.570 | −41.215 | 1.00 | 63.91 | B |
| ATOM | 2018 | CE2 | TRP | B | 141 | −53.587 | 16.171 | −39.868 | 1.00 | 63.61 | B |
| ATOM | 2019 | CE3 | TRP | B | 141 | −53.333 | 17.879 | −41.564 | 1.00 | 63.30 | B |
| ATOM | 2020 | CD1 | TRP | B | 141 | −54.351 | 14.438 | −41.046 | 1.00 | 64.31 | B |
| ATOM | 2021 | NE1 | TRP | B | 141 | −53.995 | 14.864 | −39.793 | 1.00 | 63.47 | B |
| ATOM | 2022 | CZ2 | TRP | B | 141 | −53.140 | 17.031 | −38.864 | 1.00 | 63.01 | B |
| ATOM | 2023 | CZ3 | TRP | B | 141 | −52.887 | 18.735 | −40.566 | 1.00 | 63.15 | B |
| ATOM | 2024 | CH2 | TRP | B | 141 | −52.792 | 18.305 | −39.231 | 1.00 | 62.58 | B |
| ATOM | 2025 | C | TRP | B | 141 | −55.293 | 16.999 | −45.190 | 1.00 | 65.08 | B |
| ATOM | 2026 | O | TRP | B | 141 | −54.775 | 18.118 | −45.263 | 1.00 | 64.05 | B |
| ATOM | 2027 | N | GLU | B | 142 | −55.592 | 16.268 | −46.259 | 1.00 | 63.17 | B |
| ATOM | 2028 | CA | GLU | B | 142 | −55.324 | 16.750 | −47.603 | 1.00 | 60.88 | B |
| ATOM | 2029 | CB | GLU | B | 142 | −55.801 | 15.725 | −48.635 | 1.00 | 59.86 | B |
| ATOM | 2030 | CG | GLU | B | 142 | −55.595 | 16.126 | −50.094 | 1.00 | 58.69 | B |
| ATOM | 2031 | CD | GLU | B | 142 | −54.176 | 16.583 | −50.414 | 1.00 | 57.82 | B |
| ATOM | 2032 | OE1 | GLU | B | 142 | −53.198 | 15.912 | −50.004 | 1.00 | 58.06 | B |
| ATOM | 2033 | OE2 | GLU | B | 142 | −54.045 | 17.617 | −51.096 | 1.00 | 54.99 | B |
| ATOM | 2034 | C | GLU | B | 142 | −56.005 | 18.092 | −47.825 | 1.00 | 60.14 | B |
| ATOM | 2035 | O | GLU | B | 142 | −55.367 | 19.042 | −48.265 | 1.00 | 61.06 | B |
| ATOM | 2036 | N | VAL | B | 143 | −57.288 | 18.184 | −47.505 | 1.00 | 58.83 | B |
| ATOM | 2037 | CA | VAL | B | 143 | −58.006 | 19.437 | −47.692 | 1.00 | 60.46 | B |
| ATOM | 2038 | CB | VAL | B | 143 | −59.473 | 19.312 | −47.217 | 1.00 | 63.38 | B |
| ATOM | 2039 | CG1 | VAL | B | 143 | −60.189 | 20.652 | −47.353 | 1.00 | 64.93 | B |
| ATOM | 2040 | CG2 | VAL | B | 143 | −60.194 | 18.259 | −48.044 | 1.00 | 62.82 | B |
| ATOM | 2041 | C | VAL | B | 143 | −57.324 | 20.584 | −46.937 | 1.00 | 60.05 | B |
| ATOM | 2042 | O | VAL | B | 143 | −57.199 | 21.703 | −47.453 | 1.00 | 60.09 | B |
| ATOM | 2043 | N | VAL | B | 144 | −56.881 | 20.301 | −45.716 | 1.00 | 58.84 | B |
| ATOM | 2044 | CA | VAL | B | 144 | −56.207 | 21.307 | −44.905 | 1.00 | 56.80 | B |
| ATOM | 2045 | CB | VAL | B | 144 | −55.901 | 20.779 | −43.475 | 1.00 | 56.37 | B |
| ATOM | 2046 | CG1 | VAL | B | 144 | −54.933 | 21.720 | −42.756 | 1.00 | 53.83 | B |
| ATOM | 2047 | CG2 | VAL | B | 144 | −57.195 | 20.655 | −42.688 | 1.00 | 53.78 | B |
| ATOM | 2048 | C | VAL | B | 144 | −54.907 | 21.723 | −45.570 | 1.00 | 55.71 | B |
| ATOM | 2049 | O | VAL | B | 144 | −54.580 | 22.907 | −45.619 | 1.00 | 56.30 | B |
| ATOM | 2050 | N | ARG | B | 145 | −54.166 | 20.748 | −46.083 | 1.00 | 54.57 | B |
| ATOM | 2051 | CA | ARG | B | 145 | −52.904 | 21.039 | −46.746 | 1.00 | 53.98 | B |
| ATOM | 2052 | CB | ARG | B | 145 | −52.290 | 19.755 | −47.301 | 1.00 | 54.48 | B |
| ATOM | 2053 | CG | ARG | B | 145 | −50.776 | 19.805 | −47.398 | 1.00 | 57.53 | B |
| ATOM | 2054 | CD | ARG | B | 145 | −50.189 | 18.656 | −48.226 | 1.00 | 59.32 | B |
| ATOM | 2055 | NE | ARG | B | 145 | −50.007 | 19.028 | −49.627 | 1.00 | 60.85 | B |
| ATOM | 2056 | CZ | ARG | B | 145 | −51.000 | 19.146 | −50.497 | 1.00 | 61.21 | B |
| ATOM | 2057 | NH1 | ARG | B | 145 | −52.245 | 18.912 | −50.113 | 1.00 | 63.40 | B |
| ATOM | 2058 | NH2 | ARG | B | 145 | −50.750 | 19.516 | −51.741 | 1.00 | 61.96 | B |
| ATOM | 2059 | C | ARG | B | 145 | −53.163 | 22.034 | −47.884 | 1.00 | 53.44 | B |
| ATOM | 2060 | O | ARG | B | 145 | −52.508 | 23.072 | −47.982 | 1.00 | 51.98 | B |
| ATOM | 2061 | N | ALA | B | 146 | −54.141 | 21.724 | −48.729 | 1.00 | 52.37 | B |
| ATOM | 2062 | CA | ALA | B | 146 | −54.474 | 22.596 | −49.844 | 1.00 | 52.73 | B |
| ATOM | 2063 | CB | ALA | B | 146 | −55.476 | 21.927 | −50.752 | 1.00 | 53.23 | B |
| ATOM | 2064 | C | ALA | B | 146 | −55.013 | 23.937 | −49.375 | 1.00 | 52.70 | B |
| ATOM | 2065 | O | ALA | B | 146 | −54.678 | 24.964 | −49.964 | 1.00 | 53.35 | B |
| ATOM | 2066 | N | GLU | B | 147 | −55.841 | 23.937 | −48.328 | 1.00 | 52.05 | B |
| ATOM | 2067 | CA | GLU | B | 147 | −56.401 | 25.191 | −47.799 | 1.00 | 51.29 | B |
| ATOM | 2068 | CB | GLU | B | 147 | −57.351 | 24.913 | −46.626 | 1.00 | 52.80 | B |
| ATOM | 2069 | CG | GLU | B | 147 | −57.846 | 26.161 | −45.865 | 1.00 | 56.59 | B |
| ATOM | 2070 | CD | GLU | B | 147 | −58.780 | 27.066 | −46.685 | 1.00 | 60.42 | B |
| ATOM | 2071 | OE1 | GLU | B | 147 | −59.760 | 26.554 | −47.274 | 1.00 | 63.21 | B |
| ATOM | 2072 | OE2 | GLU | B | 147 | −58.546 | 28.294 | −46.732 | 1.00 | 61.56 | B |
| ATOM | 2073 | C | GLU | B | 147 | −55.295 | 26.129 | −47.325 | 1.00 | 50.23 | B |
| ATOM | 2074 | O | GLU | B | 147 | −55.338 | 27.332 | −47.575 | 1.00 | 48.90 | B |
| ATOM | 2075 | N | ILE | B | 148 | −54.308 | 25.561 | −46.638 | 1.00 | 49.88 | B |
| ATOM | 2076 | CA | ILE | B | 148 | −53.187 | 26.320 | −46.099 | 1.00 | 48.21 | B |
| ATOM | 2077 | CB | ILE | B | 148 | −52.368 | 25.443 | −45.110 | 1.00 | 47.14 | B |
| ATOM | 2078 | CG2 | ILE | B | 148 | −51.030 | 26.118 | −44.755 | 1.00 | 44.12 | B |

TABLE 5-continued

Atomic coordinates of rSIFN-co (SEQ ID NO: 1)

| ATOM | 2079 | CG1 | ILE | B | 148 | −53.223 | 25.162 | −43.870 | 1.00 | 44.09 | B |
|---|---|---|---|---|---|---|---|---|---|---|---|
| ATOM | 2080 | CD1 | ILE | B | 148 | −53.734 | 26.429 | −43.164 | 1.00 | 42.93 | B |
| ATOM | 2081 | C | ILE | B | 148 | −52.292 | 26.883 | −47.196 | 1.00 | 48.42 | B |
| ATOM | 2082 | O | ILE | B | 148 | −51.653 | 27.925 | −47.014 | 1.00 | 47.29 | B |
| ATOM | 2083 | N | MET | B | 149 | −52.243 | 26.199 | −48.335 | 1.00 | 49.13 | B |
| ATOM | 2084 | CA | MET | B | 149 | −51.442 | 26.686 | −49.452 | 1.00 | 51.23 | B |
| ATOM | 2085 | CB | MET | B | 149 | −51.230 | 25.600 | −50.494 | 1.00 | 51.00 | B |
| ATOM | 2086 | CG | MET | B | 149 | −49.910 | 24.895 | −50.350 | 1.00 | 53.30 | B |
| ATOM | 2087 | SD | MET | B | 149 | −49.527 | 23.955 | −51.813 | 1.00 | 56.01 | B |
| ATOM | 2088 | CE | MET | B | 149 | −50.453 | 22.505 | −51.485 | 1.00 | 54.85 | B |
| ATOM | 2089 | C | MET | B | 149 | −52.176 | 27.855 | −50.082 | 1.00 | 51.95 | B |
| ATOM | 2090 | O | MET | B | 149 | −51.568 | 28.851 | −50.492 | 1.00 | 52.45 | B |
| ATOM | 2091 | N | ARG | B | 150 | −53.495 | 27.724 | −50.150 | 1.00 | 51.47 | B |
| ATOM | 2092 | CA | ARG | B | 150 | −54.333 | 28.767 | −50.707 | 1.00 | 52.51 | B |
| ATOM | 2093 | CB | ARG | B | 150 | −55.790 | 28.312 | −50.658 | 1.00 | 55.92 | B |
| ATOM | 2094 | CG | ARG | B | 150 | −56.784 | 29.125 | −51.454 | 1.00 | 60.87 | B |
| ATOM | 2095 | CD | ARG | B | 150 | −58.038 | 28.271 | −51.662 | 1.00 | 67.39 | B |
| ATOM | 2096 | NE | ARG | B | 150 | −59.207 | 29.025 | −52.117 | 1.00 | 73.67 | B |
| ATOM | 2097 | CZ | ARG | B | 150 | −59.231 | 29.827 | −53.180 | 1.00 | 76.78 | B |
| ATOM | 2098 | NH1 | ARG | B | 150 | −58.140 | 30.001 | −53.922 | 1.00 | 78.58 | B |
| ATOM | 2099 | NH2 | ARG | B | 150 | −60.354 | 30.456 | −53.506 | 1.00 | 77.37 | B |
| ATOM | 2100 | C | ARG | B | 150 | −54.109 | 30.009 | −49.851 | 1.00 | 51.57 | B |
| ATOM | 2101 | O | ARG | B | 150 | −53.689 | 31.046 | −50.355 | 1.00 | 52.44 | B |
| ATOM | 2102 | N | SER | B | 151 | −54.354 | 29.887 | −48.549 | 1.00 | 50.14 | B |
| ATOM | 2103 | CA | SER | B | 151 | −54.168 | 30.999 | −47.633 | 1.00 | 49.46 | B |
| ATOM | 2104 | CB | SER | B | 151 | −54.458 | 30.559 | −46.207 | 1.00 | 48.27 | B |
| ATOM | 2105 | OG | SER | B | 151 | −55.742 | 29.986 | −46.112 | 1.00 | 48.71 | B |
| ATOM | 2106 | C | SER | B | 151 | −52.760 | 31.574 | −47.705 | 1.00 | 50.79 | B |
| ATOM | 2107 | O | SER | B | 151 | −52.584 | 32.791 | −47.687 | 1.00 | 50.33 | B |
| ATOM | 2108 | N | PHE | B | 152 | −51.749 | 30.716 | −47.778 | 1.00 | 52.18 | B |
| ATOM | 2109 | CA | PHE | B | 152 | −50.380 | 31.225 | −47.861 | 1.00 | 55.34 | B |
| ATOM | 2110 | CB | PHE | B | 152 | −49.365 | 30.087 | −47.739 | 1.00 | 55.53 | B |
| ATOM | 2111 | CG | PHE | B | 152 | −48.768 | 29.954 | −46.366 | 1.00 | 54.12 | B |
| ATOM | 2112 | CD1 | PHE | B | 152 | −49.502 | 29.406 | −45.320 | 1.00 | 54.49 | B |
| ATOM | 2113 | CD2 | PHE | B | 152 | −47.476 | 30.391 | −46.114 | 1.00 | 53.65 | B |
| ATOM | 2114 | CE1 | PHE | B | 152 | −48.954 | 29.297 | −44.039 | 1.00 | 53.70 | B |
| ATOM | 2115 | CE2 | PHE | B | 152 | −46.925 | 30.286 | −44.834 | 1.00 | 55.29 | B |
| ATOM | 2116 | CZ | PHE | B | 152 | −47.668 | 29.737 | −43.799 | 1.00 | 53.15 | B |
| ATOM | 2117 | C | PHE | B | 152 | −50.095 | 32.024 | −49.145 | 1.00 | 55.94 | B |
| ATOM | 2118 | O | PHE | B | 152 | −49.423 | 33.062 | −49.115 | 1.00 | 54.62 | B |
| ATOM | 2119 | N | ALA | B | 153 | −50.603 | 31.541 | −50.271 | 1.00 | 57.38 | B |
| ATOM | 2120 | CA | ALA | B | 153 | −50.381 | 32.238 | −51.526 | 1.00 | 59.97 | B |
| ATOM | 2121 | CB | ALA | B | 153 | −50.910 | 31.408 | −52.700 | 1.00 | 59.69 | B |
| ATOM | 2122 | C | ALA | B | 153 | −51.083 | 33.587 | −51.460 | 1.00 | 61.25 | B |
| ATOM | 2123 | O | ALA | B | 153 | −50.514 | 34.607 | −51.841 | 1.00 | 62.94 | B |
| ATOM | 2124 | N | LEU | B | 154 | −52.312 | 33.588 | −50.953 | 1.00 | 62.12 | B |
| ATOM | 2125 | CA | LEU | B | 154 | −53.112 | 34.804 | −50.833 | 1.00 | 63.13 | B |
| ATOM | 2126 | CB | LEU | B | 154 | −54.510 | 34.437 | −50.340 | 1.00 | 60.76 | B |
| ATOM | 2127 | CG | LEU | B | 154 | −55.360 | 33.639 | −51.331 | 1.00 | 59.42 | B |
| ATOM | 2128 | CD1 | LEU | B | 154 | −56.627 | 33.136 | −50.660 | 1.00 | 58.68 | B |
| ATOM | 2129 | CD2 | LEU | B | 154 | −55.698 | 34.523 | −52.513 | 1.00 | 57.64 | B |
| ATOM | 2130 | C | LEU | B | 154 | −52.518 | 35.899 | −49.932 | 1.00 | 65.86 | B |
| ATOM | 2131 | O | LEU | B | 154 | −52.951 | 37.052 | −49.982 | 1.00 | 65.99 | B |
| ATOM | 2132 | N | SER | B | 155 | −51.525 | 35.546 | −49.121 | 1.00 | 68.63 | B |
| ATOM | 2133 | CA | SER | B | 155 | −50.899 | 36.509 | −48.219 | 1.00 | 71.66 | B |
| ATOM | 2134 | CB | SER | B | 155 | −50.675 | 35.871 | −46.845 | 1.00 | 71.59 | B |
| ATOM | 2135 | OG | SER | B | 155 | −49.726 | 34.820 | −46.920 | 1.00 | 71.04 | B |
| ATOM | 2136 | C | SER | B | 155 | −49.562 | 37.032 | −48.750 | 1.00 | 74.34 | B |
| ATOM | 2137 | O | SER | B | 155 | −48.873 | 37.802 | −48.071 | 1.00 | 74.13 | B |
| ATOM | 2138 | N | THR | B | 156 | −49.193 | 36.611 | −49.958 | 1.00 | 76.74 | B |
| ATOM | 2139 | CA | THR | B | 156 | −47.930 | 37.037 | −50.556 | 1.00 | 78.25 | B |
| ATOM | 2140 | CB | THR | B | 156 | −47.659 | 36.302 | −51.909 | 1.00 | 78.41 | B |
| ATOM | 2141 | OG1 | THR | B | 156 | −48.703 | 36.602 | −52.847 | 1.00 | 78.59 | B |
| ATOM | 2142 | CG2 | THR | B | 156 | −47.600 | 34.791 | −51.697 | 1.00 | 77.83 | B |
| ATOM | 2143 | C | THR | B | 156 | −47.930 | 38.547 | −50.784 | 1.00 | 78.96 | B |
| ATOM | 2144 | O | THR | B | 156 | −46.955 | 39.233 | −50.479 | 1.00 | 77.97 | B |
| ATOM | 2145 | N | ASN | B | 157 | −49.035 | 39.062 | −51.313 | 1.00 | 80.60 | B |
| ATOM | 2146 | CA | ASN | B | 157 | −49.146 | 40.489 | −51.576 | 1.00 | 82.39 | B |
| ATOM | 2147 | CB | ASN | B | 157 | −50.574 | 40.847 | −52.011 | 1.00 | 83.54 | B |
| ATOM | 2148 | CG | ASN | B | 157 | −50.923 | 40.286 | −53.382 | 1.00 | 85.98 | B |
| ATOM | 2149 | OD1 | ASN | B | 157 | −50.166 | 40.449 | −54.344 | 1.00 | 86.88 | B |
| ATOM | 2150 | ND2 | ASN | B | 157 | −52.075 | 39.628 | −53.481 | 1.00 | 87.40 | B |
| ATOM | 2151 | C | ASN | B | 157 | −48.752 | 41.307 | −50.351 | 1.00 | 82.41 | B |
| ATOM | 2152 | O | ASN | B | 157 | −48.015 | 42.290 | −50.459 | 1.00 | 83.08 | B |
| ATOM | 2153 | N | LEU | B | 158 | −49.234 | 40.889 | −49.185 | 1.00 | 81.77 | B |
| ATOM | 2154 | CA | LEU | B | 158 | −48.936 | 41.585 | −47.941 | 1.00 | 80.56 | B |
| ATOM | 2155 | CB | LEU | B | 158 | −49.732 | 40.974 | −46.785 | 1.00 | 80.09 | B |
| ATOM | 2156 | CG | LEU | B | 158 | −50.412 | 41.950 | −45.821 | 1.00 | 79.10 | B |

TABLE 5-continued

Atomic coordinates of rSIFN-co (SEQ ID NO: 1)

| ATOM | 2157 | CD1 | LEU | B | 158 | −51.452 | 42.765 | −46.569 | 1.00 | 79.09 | B |
|---|---|---|---|---|---|---|---|---|---|---|---|
| ATOM | 2158 | CD2 | LEU | B | 158 | −51.078 | 41.183 | −44.702 | 1.00 | 79.49 | B |
| ATOM | 2159 | C | LEU | B | 158 | −47.447 | 41.501 | −47.647 | 1.00 | 80.15 | B |
| ATOM | 2160 | O | LEU | B | 158 | −46.772 | 42.520 | −47.568 | 1.00 | 80.43 | B |
| ATOM | 2161 | N | GLN | B | 159 | −46.935 | 40.286 | −47.494 | 1.00 | 80.14 | B |
| ATOM | 2162 | CA | GLN | B | 159 | −45.519 | 40.095 | −47.210 | 1.00 | 81.12 | B |
| ATOM | 2163 | CB | GLN | B | 159 | −45.171 | 38.603 | −47.275 | 1.00 | 81.69 | B |
| ATOM | 2164 | CG | GLN | B | 159 | −45.683 | 37.807 | −46.067 | 1.00 | 83.74 | B |
| ATOM | 2165 | CD | GLN | B | 159 | −45.782 | 36.306 | −46.320 | 1.00 | 84.02 | B |
| ATOM | 2166 | OE1 | GLN | B | 159 | −46.586 | 35.853 | −47.141 | 1.00 | 84.95 | B |
| ATOM | 2167 | NE2 | GLN | B | 159 | −44.969 | 35.531 | −45.611 | 1.00 | 81.86 | B |
| ATOM | 2168 | C | GLN | B | 159 | −44.662 | 40.899 | −48.189 | 1.00 | 81.34 | B |
| ATOM | 2169 | O | GLN | B | 159 | −43.627 | 41.459 | −47.813 | 1.00 | 80.91 | B |
| ATOM | 2170 | N | GLY | B | 160 | −45.115 | 40.973 | −49.438 | 1.00 | 81.50 | B |
| ATOM | 2171 | CA | GLY | B | 160 | −44.389 | 41.716 | −50.453 | 1.00 | 82.03 | B |
| ATOM | 2172 | C | GLY | B | 160 | −44.444 | 43.224 | −50.261 | 1.00 | 82.52 | B |
| ATOM | 2173 | O | GLY | B | 160 | −43.401 | 43.875 | −50.197 | 1.00 | 83.21 | B |
| ATOM | 2174 | N | ALA | B | 161 | −45.652 | 43.783 | −50.174 | 1.00 | 82.63 | B |
| ATOM | 2175 | CA | ALA | B | 161 | −45.832 | 45.225 | −49.989 | 1.00 | 82.61 | B |
| ATOM | 2176 | CB | ALA | B | 161 | −47.318 | 45.575 | −49.991 | 1.00 | 81.89 | B |
| ATOM | 2177 | C | ALA | B | 161 | −45.193 | 45.672 | −48.681 | 1.00 | 82.81 | B |
| ATOM | 2178 | O | ALA | B | 161 | −44.989 | 46.865 | −48.444 | 1.00 | 82.18 | B |
| ATOM | 2179 | N | LEU | B | 162 | −44.892 | 44.691 | −47.836 | 1.00 | 83.61 | B |
| ATOM | 2180 | CA | LEU | B | 162 | −44.262 | 44.918 | −46.542 | 1.00 | 83.73 | B |
| ATOM | 2181 | CB | LEU | B | 162 | −44.569 | 43.741 | −45.608 | 1.00 | 81.75 | B |
| ATOM | 2182 | CG | LEU | B | 162 | −44.375 | 43.877 | −44.097 | 1.00 | 80.23 | B |
| ATOM | 2183 | CD1 | LEU | B | 162 | −44.889 | 42.617 | −43.433 | 1.00 | 79.72 | B |
| ATOM | 2184 | CD2 | LEU | B | 162 | −42.912 | 44.096 | −43.755 | 1.00 | 80.03 | B |
| ATOM | 2185 | C | LEU | B | 162 | −42.760 | 45.014 | −46.802 | 1.00 | 84.64 | B |
| ATOM | 2186 | O | LEU | B | 162 | −42.053 | 45.804 | −46.167 | 1.00 | 84.99 | B |
| ATOM | 2187 | N | GLY | B | 163 | −42.288 | 44.206 | −47.752 | 1.00 | 84.65 | B |
| ATOM | 2188 | CA | GLY | B | 163 | −40.881 | 44.207 | −48.107 | 1.00 | 84.77 | B |
| ATOM | 2189 | C | GLY | B | 163 | −40.469 | 45.480 | −48.828 | 1.00 | 85.10 | B |
| ATOM | 2190 | O | GLY | B | 163 | −39.592 | 46.201 | −48.300 | 1.00 | 84.53 | B |
| ATOM | 2191 | OXT | GLY | B | 163 | −41.021 | 45.762 | −49.918 | 1.00 | 84.32 | B |
| ATOM | 2192 | S | CXS | $ | 1001 | −37.007 | 7.286 | −12.909 | 1.00 | 89.60 | $ |
| ATOM | 2193 | O1 | CXS | $ | 1001 | −37.722 | 7.642 | −11.758 | 1.00 | 90.92 | $ |
| ATOM | 2194 | O2 | CXS | $ | 1001 | −37.206 | 7.283 | −14.330 | 1.00 | 90.52 | $ |
| ATOM | 2195 | O3 | CXS | $ | 1001 | −35.476 | 7.404 | −12.678 | 1.00 | 90.21 | $ |
| ATOM | 2196 | C1 | CXS | $ | 1001 | −36.878 | 9.113 | −13.140 | 1.00 | 86.35 | $ |
| ATOM | 2197 | C2 | CXS | $ | 1001 | −38.280 | 9.714 | −13.449 | 1.00 | 82.21 | $ |
| ATOM | 2198 | C3 | CXS | $ | 1001 | −38.308 | 11.211 | −13.660 | 1.00 | 78.87 | $ |
| ATOM | 2199 | N | CXS | $ | 1001 | −39.730 | 11.610 | −13.907 | 1.00 | 74.83 | $ |
| ATOM | 2200 | C4 | CXS | $ | 1001 | −39.806 | 13.069 | −14.118 | 1.00 | 72.04 | $ |
| ATOM | 2201 | C5 | CXS | $ | 1001 | −38.946 | 13.813 | −13.094 | 1.00 | 71.28 | $ |
| ATOM | 2202 | C6 | CXS | $ | 1001 | −38.989 | 15.336 | −13.308 | 1.00 | 70.38 | $ |
| ATOM | 2203 | C7 | CXS | $ | 1001 | −38.608 | 15.704 | −14.767 | 1.00 | 70.92 | $ |
| ATOM | 2204 | C8 | CXS | $ | 1001 | −39.501 | 14.945 | −15.785 | 1.00 | 69.52 | $ |
| ATOM | 2205 | C9 | CXS | $ | 1001 | −39.379 | 13.417 | −15.567 | 1.00 | 71.02 | $ |
| ATOM | 2206 | S | CXS | $ | 1002 | −33.172 | 31.213 | −33.664 | 1.00 | 59.12 | $ |
| ATOM | 2207 | O1 | CXS | $ | 1002 | −33.303 | 31.719 | −34.982 | 1.00 | 61.00 | $ |
| ATOM | 2208 | O2 | CXS | $ | 1002 | −31.915 | 30.813 | −33.130 | 1.00 | 59.84 | $ |
| ATOM | 2209 | O3 | CXS | $ | 1002 | −33.679 | 32.294 | −32.738 | 1.00 | 61.33 | $ |
| ATOM | 2210 | C1 | CXS | $ | 1002 | −34.407 | 29.954 | −33.375 | 1.00 | 56.21 | $ |
| ATOM | 2211 | C2 | CXS | $ | 1002 | −34.146 | 28.753 | −34.253 | 1.00 | 51.82 | $ |
| ATOM | 2212 | C3 | CXS | $ | 1002 | −35.236 | 27.757 | −33.951 | 1.00 | 52.23 | $ |
| ATOM | 2213 | N | CXS | $ | 1002 | −35.098 | 26.561 | −34.782 | 1.00 | 53.07 | $ |
| ATOM | 2214 | C4 | CXS | $ | 1002 | −36.180 | 25.616 | −34.422 | 1.00 | 50.12 | $ |
| ATOM | 2215 | C5 | CXS | $ | 1002 | −37.574 | 26.289 | −34.439 | 1.00 | 47.85 | $ |
| ATOM | 2216 | C6 | CXS | $ | 1002 | −38.645 | 25.266 | −34.045 | 1.00 | 47.93 | $ |
| ATOM | 2217 | C7 | CXS | $ | 1002 | −38.644 | 24.095 | −35.046 | 1.00 | 49.65 | $ |
| ATOM | 2218 | C8 | CXS | $ | 1002 | −37.263 | 23.410 | −35.077 | 1.00 | 49.27 | $ |
| ATOM | 2219 | C9 | CXS | $ | 1002 | −36.157 | 24.435 | −35.413 | 1.00 | 50.51 | $ |
| ATOM | 2220 | O | HOH | S | 1 | −55.089 | 30.721 | −29.788 | 1.00 | 42.32 | S |
| ATOM | 2221 | O | HOH | S | 2 | −51.354 | 16.117 | −54.214 | 1.00 | 66.49 | S |
| ATOM | 2222 | O | HOH | S | 3 | −35.292 | 43.228 | −45.412 | 1.00 | 70.66 | S |
| ATOM | 2223 | O | HOH | S | 6 | −36.194 | 33.341 | −31.023 | 1.00 | 62.49 | S |
| ATOM | 2224 | O | HOH | S | 8 | −42.460 | 34.031 | −31.211 | 1.00 | 52.51 | S |
| ATOM | 2225 | O | HOH | S | 11 | −51.117 | 14.500 | −24.316 | 1.00 | 63.19 | S |
| ATOM | 2226 | O | HOH | S | 13 | −34.186 | 35.241 | −31.749 | 1.00 | 69.73 | S |
| ATOM | 2227 | O | HOH | S | 14 | −46.886 | 23.354 | −15.063 | 1.00 | 62.91 | S |
| ATOM | 2228 | O | HOH | S | 15 | −67.379 | 16.745 | −38.051 | 1.00 | 74.92 | S |
| ATOM | 2229 | O | HOH | S | 16 | −48.149 | 52.600 | −41.809 | 1.00 | 65.55 | S |
| ATOM | 2230 | O | HOH | S | 20 | −37.533 | 46.814 | −44.158 | 1.00 | 63.62 | S |
| ATOM | 2231 | O | HOH | S | 23 | −26.090 | 20.564 | −40.954 | 1.00 | 64.92 | S |
| ATOM | 2232 | O | HOH | S | 33 | −66.641 | 27.143 | −35.990 | 1.00 | 64.70 | S |
| ATOM | 2233 | O | HOH | S | 34 | −34.278 | 43.389 | −42.980 | 1.00 | 66.36 | S |
| ATOM | 2234 | O | HOH | S | 35 | −40.575 | 14.233 | −23.786 | 1.00 | 68.23 | S |

TABLE 5-continued

Atomic coordinates of rSIFN-co (SEQ ID NO: 1)

| ATOM | 2235 | O | HOH | S | 36 | −26.941 | 28.813 | −12.491 | 1.00 | 61.13 | S |
|---|---|---|---|---|---|---|---|---|---|---|---|
| ATOM | 2236 | O | HOH | S | 37 | −30.827 | 27.593 | −14.316 | 1.00 | 59.11 | S |
| ATOM | 2237 | O | HOH | S | 39 | −44.040 | 36.979 | −30.178 | 1.00 | 56.62 | S |
| ATOM | 2238 | O | HOH | S | 40 | −33.347 | 44.688 | −11.256 | 1.00 | 77.43 | S |
| ATOM | 2239 | O | HOH | S | 42 | −64.966 | 36.711 | −39.384 | 1.00 | 64.46 | S |
| ATOM | 2240 | O | HOH | S | 43 | −14.994 | 28.360 | −34.554 | 1.00 | 79.56 | S |
| ATOM | 2241 | O | HOH | S | 45 | −58.115 | 31.298 | −30.300 | 1.00 | 73.59 | S |
| ATOM | 2242 | O | HOH | S | 46 | −36.924 | 25.549 | −50.937 | 1.00 | 62.92 | S |
| ATOM | 2243 | O | HOH | S | 49 | −20.930 | 37.291 | −14.901 | 1.00 | 62.70 | S |
| ATOM | 2244 | O | HOH | S | 55 | −35.088 | 9.503 | −41.169 | 1.00 | 56.66 | S |
| ATOM | 2245 | O | HOH | S | 58 | −45.523 | 36.927 | −10.019 | 1.00 | 53.41 | S |
| ATOM | 2246 | O | HOH | S | 60 | −24.940 | 43.426 | −34.908 | 1.00 | 64.11 | S |
| ATOM | 2247 | O | HOH | S | 61 | −43.094 | 16.769 | −33.268 | 1.00 | 88.80 | S |
| ATOM | 2248 | O | HOH | S | 64 | −52.392 | 52.632 | −34.025 | 1.00 | 92.27 | S |
| ATOM | 2249 | O | HOH | S | 66 | −14.474 | 29.522 | −20.678 | 1.00 | 73.76 | S |
| ATOM | 2250 | O | HOH | S | 67 | −61.923 | 12.568 | −56.894 | 1.00 | 71.78 | S |
| ATOM | 2251 | O | HOH | S | 68 | −17.930 | 11.026 | −27.010 | 1.00 | 57.62 | S |
| ATOM | 2252 | O | HOH | S | 69 | −26.009 | 23.821 | −38.215 | 1.00 | 56.83 | S |
| ATOM | 2253 | O | HOH | S | 70 | −34.979 | 17.848 | −41.915 | 1.00 | 57.66 | S |
| ATOM | 2254 | O | HOH | S | 73 | −53.375 | 25.113 | −34.332 | 1.00 | 67.17 | S |
| ATOM | 2255 | O | HOH | S | 78 | −3.369 | 14.903 | −39.536 | 1.00 | 76.47 | S |
| ATOM | 2256 | O | HOH | S | 79 | −49.809 | 52.012 | −53.024 | 1.00 | 74.16 | S |
| ATOM | 2257 | O | HOH | S | 80 | −52.873 | 32.569 | −23.870 | 1.00 | 59.72 | S |
| ATOM | 2258 | O | HOH | S | 81 | −69.907 | 24.040 | −37.219 | 1.00 | 59.30 | S |
| ATOM | 2259 | O | HOH | S | 82 | −42.669 | 56.555 | −30.390 | 1.00 | 65.30 | S |
| ATOM | 2260 | O | HOH | S | 85 | −29.842 | 34.315 | −33.948 | 1.00 | 62.56 | S |
| ATOM | 2261 | O | HOH | S | 96 | −54.795 | 49.118 | −60.472 | 1.00 | 72.94 | S |
| ATOM | 2262 | O | HOH | S | 100 | −16.120 | 34.824 | −29.084 | 1.00 | 73.72 | S |
| ATOM | 2263 | O | HOH | S | 103 | −41.801 | 10.188 | −41.652 | 1.00 | 59.23 | S |
| ATOM | 2264 | O | HOH | S | 108 | −72.826 | 20.167 | −44.484 | 1.00 | 75.51 | S |
| ATOM | 2265 | O | HOH | S | 111 | −31.210 | 25.257 | −37.321 | 1.00 | 71.53 | S |
| ATOM | 2266 | O | HOH | S | 113 | −35.456 | 11.432 | −29.314 | 1.00 | 64.29 | S |
| ATOM | 2267 | O | HOH | S | 114 | −14.615 | 14.030 | −42.236 | 1.00 | 64.98 | S |
| ATOM | 2268 | O | HOH | S | 116 | −30.150 | 46.628 | −35.936 | 1.00 | 67.88 | S |
| ATOM | 2269 | O | HOH | S | 117 | −33.711 | 52.716 | −21.422 | 1.00 | 75.50 | S |
| ATOM | 2270 | O | HOH | S | 122 | −42.524 | 31.582 | −56.165 | 1.00 | 60.35 | S |
| ATOM | 2271 | O | HOH | S | 124 | −57.788 | 19.390 | −20.057 | 1.00 | 80.05 | S |
| ATOM | 2272 | O | HOH | S | 127 | −8.352 | 21.156 | −33.703 | 1.00 | 72.60 | S |
| ATOM | 2273 | O | HOH | S | 131 | −65.658 | 4.703 | −48.301 | 1.00 | 67.75 | S |
| ATOM | 2274 | O | HOH | S | 136 | −31.961 | 29.091 | −37.073 | 1.00 | 65.98 | S |
| ATOM | 2275 | O | HOH | S | 144 | −32.295 | 17.761 | −36.053 | 1.00 | 61.82 | S |
| ATOM | 2276 | O | HOH | S | 145 | −16.099 | 20.782 | −27.246 | 1.00 | 62.57 | S |
| ATOM | 2277 | O | HOH | S | 152 | −40.098 | 47.171 | −61.867 | 1.00 | 70.18 | S |
| ATOM | 2278 | O | HOH | S | 153 | −16.949 | 16.723 | −30.701 | 1.00 | 72.82 | S |
| ATOM | 2279 | O | HOH | S | 154 | −49.102 | 54.760 | −44.857 | 1.00 | 74.87 | S |
| ATOM | 2280 | O | HOH | S | 155 | −33.241 | 36.181 | −28.893 | 1.00 | 53.26 | S |
| ATOM | 2281 | O | HOH | S | 157 | −28.846 | 4.566 | −28.970 | 1.00 | 65.48 | S |
| ATOM | 2282 | O | HOH | S | 159 | −18.078 | 6.979 | −32.388 | 1.00 | 62.25 | S |
| ATOM | 2283 | O | HOH | S | 160 | −49.927 | 12.224 | −25.999 | 1.00 | 83.57 | S |
| ATOM | 2284 | O | HOH | S | 161 | −35.384 | 38.748 | −45.921 | 1.00 | 78.38 | S |
| ATOM | 2285 | O | HOH | S | 164 | −19.431 | 9.631 | −42.561 | 1.00 | 83.75 | S |
| ATOM | 2286 | O | HOH | S | 165 | −24.757 | 7.452 | −28.428 | 1.00 | 62.83 | S |
| ATOM | 2287 | O | HOH | S | 166 | −26.095 | 40.110 | −19.029 | 1.00 | 71.51 | S |
| ATOM | 2288 | O | HOH | S | 167 | −33.517 | 28.875 | −11.950 | 1.00 | 65.15 | S |
| ATOM | 2289 | O | HOH | S | 169 | −23.559 | 26.637 | −34.978 | 1.00 | 69.82 | S |
| ATOM | 2290 | O | HOH | S | 171 | −35.911 | 32.089 | −11.426 | 1.00 | 70.81 | S |
| ATOM | 2291 | O | HOH | S | 173 | −29.541 | 39.675 | −27.861 | 1.00 | 73.58 | S |
| ATOM | 2292 | O | HOH | S | 174 | −42.366 | 9.773 | −12.564 | 1.00 | 75.10 | S |
| ATOM | 2293 | O | HOH | S | 179 | −37.615 | 36.321 | −6.575 | 1.00 | 60.84 | S |
| ATOM | 2294 | O | HOH | S | 185 | −37.396 | 54.966 | −35.497 | 1.00 | 66.51 | S |
| ATOM | 2295 | O | HOH | S | 186 | −34.811 | 40.197 | −42.025 | 1.00 | 78.57 | S |
| ATOM | 2296 | O | HOH | S | 189 | −41.472 | 38.031 | −56.357 | 1.00 | 76.56 | S |
| ATOM | 2297 | O | HOH | S | 193 | −31.145 | 43.929 | −38.718 | 1.00 | 64.82 | S |
| ATOM | 2298 | O | HOH | S | 197 | −44.621 | 37.091 | −53.919 | 1.00 | 74.57 | S |
| ATOM | 2299 | O | HOH | S | 200 | −26.601 | 47.858 | −27.412 | 1.00 | 73.60 | S |
| ATOM | 2300 | O | HOH | S | 204 | −34.070 | 22.759 | −42.394 | 1.00 | 64.86 | S |
| ATOM | 2301 | O | HOH | S | 206 | −56.104 | 23.451 | −54.858 | 1.00 | 63.95 | S |
| ATOM | 2302 | O | HOH | S | 207 | −42.623 | 14.939 | −36.850 | 1.00 | 58.12 | S |
| ATOM | 2303 | O | HOH | S | 215 | −57.916 | 20.611 | −53.534 | 1.00 | 65.65 | S |
| ATOM | 2304 | O | HOH | S | 217 | −68.703 | 19.492 | −32.308 | 1.00 | 66.71 | S |
| ATOM | 2305 | O | HOH | S | 218 | −34.288 | 47.462 | −17.190 | 1.00 | 87.83 | S |
| ATOM | 2306 | O | HOH | S | 219 | −47.023 | 49.480 | −49.463 | 1.00 | 80.36 | S |
| ATOM | 2307 | O | HOH | S | 221 | −36.167 | 35.091 | −46.526 | 1.00 | 82.36 | S |
| ATOM | 2308 | O | HOH | S | 229 | −5.120 | 14.056 | −34.382 | 1.00 | 80.88 | S |
| ATOM | 2309 | O | HOH | S | 234 | −61.102 | 28.009 | −56.501 | 1.00 | 73.87 | S |
| ATOM | 2310 | O | HOH | S | 236 | −50.038 | 53.208 | −31.379 | 1.00 | 80.66 | S |
| ATOM | 2311 | O | HOH | S | 238 | −63.210 | 5.594 | −33.656 | 1.00 | 73.31 | S |
| ATOM | 2312 | O | HOH | S | 239 | −18.979 | 25.474 | −40.262 | 1.00 | 65.13 | S |

TABLE 5-continued

Atomic coordinates of rSIFN-co (SEQ ID NO: 1)

| ATOM | 2313 | O | HOH | S | 241 | −9.247 | 22.473 | −40.473 | 1.00 | 62.01 | S |
|------|------|---|-----|---|-----|--------|--------|---------|------|-------|---|
| ATOM | 2314 | O | HOH | S | 242 | −23.581 | 0.874 | −22.639 | 1.00 | 79.48 | S |
| ATOM | 2315 | O | HOH | S | 244 | −37.921 | 9.795 | −41.267 | 1.00 | 71.07 | S |
| ATOM | 2316 | O | HOH | S | 245 | −68.213 | 16.294 | −47.338 | 1.00 | 66.37 | S |
| ATOM | 2317 | O | HOH | S | 259 | −54.297 | 15.702 | −29.864 | 1.00 | 69.25 | S |
| ATOM | 2318 | O | HOH | S | 260 | −53.332 | 29.741 | −10.004 | 1.00 | 79.52 | S |
| ATOM | 2319 | O | HOH | S | 261 | −58.281 | 47.179 | −58.668 | 1.00 | 71.63 | S |
| ATOM | 2320 | O | HOH | S | 262 | −61.633 | 19.952 | −25.923 | 1.00 | 74.21 | S |
| ATOM | 2321 | O | HOH | S | 264 | −59.854 | 24.019 | −57.410 | 1.00 | 84.87 | S |
| ATOM | 2322 | O | HOH | S | 265 | −34.910 | 13.726 | −35.043 | 1.00 | 75.92 | S |
| ATOM | 2323 | O | HOH | S | 266 | −65.206 | −1.041 | −22.378 | 1.00 | 67.71 | S |
| ATOM | 2324 | O | HOH | S | 267 | −30.825 | 12.386 | −15.339 | 1.00 | 53.22 | S |
| ATOM | 2325 | O | HOH | S | 268 | −23.141 | 25.046 | −40.085 | 1.00 | 77.62 | S |
| ATOM | 2326 | O | HOH | S | 273 | −64.261 | 24.028 | −29.410 | 1.00 | 61.30 | S |
| ATOM | 2327 | O | HOH | S | 281 | −45.175 | 18.432 | −30.051 | 1.00 | 88.80 | S |
| ATOM | 2328 | O | HOH | S | 285 | −44.514 | 56.451 | −43.099 | 1.00 | 73.84 | S |
| ATOM | 2329 | O | HOH | S | 298 | −41.747 | 37.900 | −7.567 | 1.00 | 67.96 | S |
| ATOM | 2330 | O | HOH | S | 301 | −51.187 | 22.922 | −27.202 | 1.00 | 59.87 | S |
| ATOM | 2331 | O | HOH | S | 308 | −56.697 | 51.798 | −45.311 | 1.00 | 76.39 | S |
| ATOM | 2332 | O | HOH | S | 310 | −30.921 | 48.271 | −19.130 | 1.00 | 67.15 | S |
| ATOM | 2333 | O | HOH | S | 315 | −26.247 | 3.171 | −24.345 | 1.00 | 70.11 | S |
| ATOM | 2334 | O | HOH | S | 317 | −7.989 | 11.928 | −10.219 | 1.00 | 69.93 | S |
| ATOM | 2335 | O | HOH | S | 323 | −67.469 | 1.840 | −28.352 | 1.00 | 73.34 | S |
| ATOM | 2336 | O | HOH | S | 327 | −1.519 | 7.683 | −30.620 | 1.00 | 68.63 | S |
| ATOM | 2337 | O | HOH | S | 330 | −13.341 | 11.540 | −27.689 | 1.00 | 66.95 | S |
| ATOM | 2338 | O | HOH | S | 334 | −31.782 | 46.438 | −31.042 | 1.00 | 84.75 | S |
| ATOM | 2339 | O | HOH | S | 337 | −14.963 | 25.917 | −41.978 | 1.00 | 64.34 | S |
| ATOM | 2340 | O | HOH | S | 341 | −55.975 | 23.392 | −31.423 | 1.00 | 74.05 | S |
| ATOM | 2341 | O | HOH | S | 347 | −30.795 | 46.682 | −44.519 | 1.00 | 85.03 | S |
| ATOM | 2342 | O | HOH | S | 348 | −40.398 | 44.400 | −17.941 | 1.00 | 78.54 | S |
| ATOM | 2343 | O | HOH | S | 351 | −63.588 | 34.580 | −53.000 | 1.00 | 64.83 | S |
| ATOM | 2344 | O | HOH | S | 352 | −52.859 | 26.925 | −10.393 | 1.00 | 76.36 | S |
| ATOM | 2345 | O | HOH | S | 360 | −66.994 | 13.614 | −58.601 | 1.00 | 80.08 | S |
| ATOM | 2346 | O | HOH | S | 362 | −6.728 | 7.392 | −14.487 | 1.00 | 66.11 | S |
| ATOM | 2347 | O | HOH | S | 363 | −45.315 | 52.345 | −44.599 | 1.00 | 70.94 | S |
| ATOM | 2348 | O | HOH | S | 364 | −27.723 | 55.681 | −25.949 | 1.00 | 80.92 | S |
| ATOM | 2349 | O | HOH | S | 365 | −0.192 | 8.761 | −14.858 | 1.00 | 65.43 | S |
| ATOM | 2350 | O | HOH | S | 366 | −33.943 | 48.435 | −9.023 | 1.00 | 73.21 | S |
| ATOM | 2351 | O | HOH | S | 369 | −23.185 | 39.615 | −20.816 | 1.00 | 75.14 | S |
| ATOM | 2352 | O | HOH | S | 371 | −47.369 | 8.811 | −24.333 | 1.00 | 90.58 | S |
| ATOM | 2353 | O | HOH | S | 378 | −72.215 | 16.093 | −37.276 | 1.00 | 79.02 | S |
| ATOM | 2354 | O | HOH | S | 382 | −62.101 | 39.118 | −53.345 | 1.00 | 91.47 | S |
| ATOM | 2355 | O | HOH | S | 399 | −5.346 | 7.993 | −18.480 | 1.00 | 82.98 | S |
| ATOM | 2356 | O | HOH | S | 404 | −48.898 | 52.763 | −34.937 | 1.00 | 79.67 | S |
| ATOM | 2357 | O | HOH | S | 408 | −58.332 | 50.605 | −57.798 | 1.00 | 73.84 | S |
| ATOM | 2358 | O | HOH | S | 414 | −16.594 | 33.677 | −18.292 | 1.00 | 67.72 | S |
| ATOM | 2359 | O | HOH | S | 421 | −14.075 | 7.273 | −31.446 | 1.00 | 75.74 | S |
| ATOM | 2360 | O | HOH | S | 425 | −52.456 | 25.670 | −30.099 | 1.00 | 68.36 | S |
| ATOM | 2361 | O | HOH | S | 429 | −34.829 | 54.773 | −17.284 | 1.00 | 73.77 | S |
| ATOM | 2362 | O | HOH | S | 438 | −25.176 | 29.403 | −40.958 | 1.00 | 77.48 | S |
| ATOM | 2363 | O | HOH | S | 444 | −42.956 | 49.806 | −10.829 | 1.00 | 87.00 | S |
| ATOM | 2364 | O | HOH | S | 458 | −70.377 | 23.808 | −46.086 | 1.00 | 78.30 | S |
| ATOM | 2365 | O | HOH | S | 476 | −33.612 | 35.694 | −43.631 | 1.00 | 66.61 | S |
| ATOM | 2366 | O | HOH | S | 488 | −43.909 | 38.988 | −59.269 | 1.00 | 90.04 | S |
| ATOM | 2367 | O | HOH | S | 490 | −55.112 | 12.025 | −28.305 | 1.00 | 69.08 | S |
| ATOM | 2368 | O | HOH | S | 497 | −52.018 | 36.590 | −59.300 | 1.00 | 73.00 | S |
| ATOM | 2369 | O | HOH | S | 498 | −67.080 | 8.456 | −47.025 | 1.00 | 77.54 | S |
| ATOM | 2370 | O | HOH | S | 501 | −33.375 | 45.638 | −46.606 | 1.00 | 67.04 | S |
| ATOM | 2371 | O | HOH | S | 504 | −17.519 | 40.287 | −29.824 | 1.00 | 75.48 | S |
| ATOM | 2372 | O | HOH | S | 508 | −38.469 | 54.630 | −22.566 | 1.00 | 81.92 | S |
| ATOM | 2373 | O | HOH | S | 548 | −7.619 | 13.490 | −18.323 | 1.00 | 80.70 | S |
| ATOM | 2374 | O | HOH | S | 562 | −52.127 | 9.380 | −31.442 | 1.00 | 93.77 | S |
| ATOM | 2375 | O | HOH | S | 574 | −71.476 | 15.001 | −51.047 | 1.00 | 83.08 | S |
| ATOM | 2376 | O | HOH | S | 581 | −35.133 | 54.715 | −54.265 | 1.00 | 79.21 | S |
| ATOM | 2377 | O | HOH | S | 598 | −38.686 | 54.511 | −51.645 | 1.00 | 83.16 | S |

What is claimed is:

1. A crystalline recombinant interferon polypeptide consisting of the amino acid sequence of SEQ ID NO:1, wherein the space group of the crystal is $P3_121$, and the unit cell parameters of the crystal are a=b=77.92 Å, c=125.935 Å, $\alpha=\beta=90°$, and $\gamma=120°$.

2. The crystalline interferon of claim 1, wherein said crystal contains two molecules in an asymmetric unit.

3. The crystalline interferon of claim 1, wherein the crystal further comprises covalently or non-covalently bound metal ions.

4. A composition comprising the crystalline interferon of claim 1.

5. The composition of claim 4, wherein the composition is a pharmaceutical composition.

6. The composition of claim 5, further comprising a pharmaceutically acceptable carrier.

* * * * *

SEQUENCE LISTING

<160> NUMBER OF SEQ ID NOS: 15

<210> SEQ ID NO 1
<211> LENGTH: 167

```
<212> TYPE: PRT
<213> ORGANISM: Artificial Sequence
<220> FEATURE:
<223> OTHER INFORMATION: Amino acid sequence of recombinant interferon

<400> SEQUENCE: 1

Met Cys Asp Leu Pro Gln Thr His Ser Leu Gly Asn Arg Arg Ala Leu
1               5                   10                  15

Ile Leu Leu Ala Gln Met Arg Arg Ile Ser Pro Phe Ser Cys Leu Lys
            20                  25                  30

Asp Arg His Asp Phe Gly Phe Pro Gln Glu Glu Phe Asp Gly Asn Gln
        35                  40                  45

Phe Gln Lys Ala Gln Ala Ile Ser Val Leu His Glu Met Ile Gln Gln
    50                  55                  60

Thr Phe Asn Leu Phe Ser Thr Lys Asp Ser Ser Ala Ala Trp Asp Glu
65                  70                  75                  80

Ser Leu Leu Glu Lys Phe Tyr Thr Glu Leu Tyr Gln Gln Leu Asn Asp
                85                  90                  95

Leu Glu Ala Cys Val Ile Gln Glu Val Gly Val Glu Glu Thr Pro Leu
            100                 105                 110

Met Asn Val Asp Ser Ile Leu Ala Val Lys Lys Tyr Phe Gln Arg Ile
        115                 120                 125

Thr Leu Tyr Leu Thr Glu Lys Lys Tyr Ser Pro Cys Ala Trp Glu Val
    130                 135                 140

Val Arg Ala Glu Ile Met Arg Ser Phe Ser Leu Ser Thr Asn Leu Gln
145                 150                 155                 160

Glu Arg Leu Arg Arg Lys Glu
                165

<210> SEQ ID NO 2
<211> LENGTH: 504
<212> TYPE: DNA
<213> ORGANISM: Artificial Sequence
<220> FEATURE:
<223> OTHER INFORMATION: Nucleotide sequence encoding recombinant
      interferon

<400> SEQUENCE: 2
atgtgcgacc tgccgcagac ccactccctg ggtaaccgtc gtgctctgat cctgctggct      60
cagatgcgtc gtatctcccc gttctcctgc ctgaaagacc gtcacgactt cggtttcccg     120
caggaagaat cgacggtaa ccagttccag aaagctcagg ctatctccgt tctgcacgaa      180
atgatccagc agaccttcaa cctgttctcc accaaagact cctccgctgc ttgggacgaa     240
tccctgctgg aaaaattcta caccgaactg taccagcagc tgaacgacct ggaagcttgc     300
gttatccagg aagttggtgt tgaagaaacc ccgctgatga acgttgactc catcctggct     360
gttaaaaaat acttccagcg tatcaccctg tacctgaccg aaaaaaaata ctccccgtgc     420
gcttgggaag ttgttcgtgc tgaaatcatg cgttccttct ccctgtccac caacctgcag     480
gaacgtctgc gtcgtaaaga ataa                                            504

<210> SEQ ID NO 3
<211> LENGTH: 504
<212> TYPE: DNA
<213> ORGANISM: Artificial Sequence
<220> FEATURE:
<223> OTHER INFORMATION: Nucleotide sequence encoding recombinant
      interferon

<400> SEQUENCE: 3
```

```
tacacgctgg acggcgtctg ggtgagggac ccattggcag cacgagacta ggacgaccga    60
gtctacgcag catagagggg caagaggacg gactttctgg cagtgctgaa gccaaagggc   120
gtccttctta agctgccatt ggtcaaggtc tttcgagtcc gatagaggca agacgtgctt   180
tactaggtcg tctggaagtt ggacaagagg tggtttctga ggaggcgacg aaccctgctt   240
agggacgacc tttttaagat gtggcttgac atggtcgtcg acttgctgga ccttcgaacg   300
caataggtcc ttcaaccaca acttctttgg ggcgactact tgcaactgag gtaggaccga   360 caattttta tgaaggtcgc atagtgggac atggactggc ttttttttat gaggggcacg    420
cgaacccttc aacaagcacg actttagtac gcaaggaaga gggacaggtg gttggacgtc   480
cttgcagacg cagcatttct tatt                                          504

<210> SEQ ID NO 4
<211> LENGTH: 9
<212> TYPE: PRT
<213> ORGANISM: Artificial Sequence
<220> FEATURE:
<223> OTHER INFORMATION: Amino acid sequence of AB loop

<400> SEQUENCE: 4

Ser Pro Phe Ser Cys Leu Lys Asp Arg
1               5

<210> SEQ ID NO 5
<211> LENGTH: 9
<212> TYPE: PRT
<213> ORGANISM: Artificial Sequence
<220> FEATURE:
<223> OTHER INFORMATION: Amino acid sequence of BC loop

<400> SEQUENCE: 5

Asp Gly Asn Gln Phe Gln Lys Ala Gln
1               5

<210> SEQ ID NO 6
<211> LENGTH: 108
<212> TYPE: DNA
<213> ORGANISM: Artificial Sequence
<220> FEATURE:
<223> OTHER INFORMATION: Chemically synthesized

<400> SEQUENCE: 6
atgtgcgacc tgccgcagac ccactccctg ggtaaccgtc gtgctctgat cctgctggct    60
cagatgcgtc gtatctcccc gttctcctgc ctgaaagacc gtcacgac                108

<210> SEQ ID NO 7
<211> LENGTH: 108
<212> TYPE: DNA
<213> ORGANISM: Artificial Sequence
<220> FEATURE:
<223> OTHER INFORMATION: Chemically synthesized

<400> SEQUENCE: 7
ctgaaagacc gtcacgactt cggtttcccg caggagaggt tcgacggtaa ccagttccag    60
aaagctcagg ctatctccgt tctgcacgaa atgatccagc agaccttc                108

<210> SEQ ID NO 8
<211> LENGTH: 103
<212> TYPE: DNA
<213> ORGANISM: Artificial Sequence
<220> FEATURE:
<223> OTHER INFORMATION: Chemically synthesized
```

<400> SEQUENCE: 8
gctgctggta cagttcggtg tagaattttt ccagcaggga ttcgtcccaa gcagcggagg    60
agtctttggt ggagaacagg ttgaaggtct gctggatcat ttc                     103

<210> SEQ ID NO 9
<211> LENGTH: 103
<212> TYPE: DNA
<213> ORGANISM: Artificial Sequence
<220> FEATURE:
<223> OTHER INFORMATION: Chemically synthesized

<400> SEQUENCE: 9
atccctgctg gaaaaattct acaccgaact gtaccagcag ctgaacgacc tggaagcttg    60
cgttatccag gaagttggtg ttgaagaaac cccgctgatg aac                     103

<210> SEQ ID NO 10
<211> LENGTH: 106
<212> TYPE: DNA
<213> ORGANISM: Artificial Sequence
<220> FEATURE:
<223> OTHER INFORMATION: Chemically synthesized

<400> SEQUENCE: 10
gaagaaaccc cgctgatgaa cgttgactcc atcctggctg ttaaaaaata cttccagcgt    60
atcaccctgt acctgaccga aaaaaaatac tccccgtgcg cttggg                  106

<210> SEQ ID NO 11
<211> LENGTH: 112
<212> TYPE: DNA
<213> ORGANISM: Artificial Sequence
<220> FEATURE:
<223> OTHER INFORMATION: Chemically synthesized

<400> SEQUENCE: 11
ttattcttta cgacgcagac gttcctgcag gttggtggac agggagaagg aacgcatgat    60
ttcagcacga acaacttccc aagcgcacgg ggagtatttt ttttcggtca gg           112

<210> SEQ ID NO 12
<211> LENGTH: 31
<212> TYPE: DNA
<213> ORGANISM: Artificial Sequence
<220> FEATURE:
<223> OTHER INFORMATION: Chemically synthesized

<400> SEQUENCE: 12
atcggccata tgtgcgacct gccgcagacc c                                   31

<210> SEQ ID NO 13
<211> LENGTH: 40
<212> TYPE: DNA
<213> ORGANISM: Artificial Sequence
<220> FEATURE:
<223> OTHER INFORMATION: Chemically synthesized

<400> SEQUENCE: 13
actgccaggc tgcagttatt ctttacgacg cagacgttcc                          40

<210> SEQ ID NO 14
<211> LENGTH: 15
<212> TYPE: PRT
<213> ORGANISM: Artificial Sequence
<220> FEATURE:
<223> OTHER INFORMATION: Synthetic Construct

```
<400> SEQUENCE: 14

Cys Asp Leu Pro Gln Thr His Ser Leu Gly Asn Arg Arg Ala Leu
1               5                   10                  15

<210> SEQ ID NO 15
<211> LENGTH: 4
<212> TYPE: PRT
<213> ORGANISM: Artificial Sequence
<220> FEATURE:
<223> OTHER INFORMATION: Synthetic Construct

<400> SEQUENCE: 15

Arg Arg Lys Glu
1
```